United States Patent
Linge et al.

(10) Patent No.: US 11,578,063 B2
(45) Date of Patent: Feb. 14, 2023

(54) MATERIALS FOR ORGANIC ELECTROLUMINESCENT DEVICES

(71) Applicant: Merck Patent GmbH, Darmstadt (DE)

(72) Inventors: Rouven Linge, Darmstadt (DE); Sebastian Meyer, Frankfurt am Main (DE); Lara-Isabel Rodriguez, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 300 days.

(21) Appl. No.: 16/756,824

(22) PCT Filed: Oct. 15, 2018

(86) PCT No.: PCT/EP2018/078011
§ 371 (c)(1),
(2) Date: Apr. 16, 2020

(87) PCT Pub. No.: WO2019/076789
PCT Pub. Date: Apr. 25, 2019

(65) Prior Publication Data
US 2020/0277284 A1 Sep. 3, 2020

(30) Foreign Application Priority Data

Oct. 17, 2017 (EP) .................................. 17196902
Jun. 26, 2018 (CN) ......................... 201810670515.0

(51) Int. Cl.
*H01L 51/00* (2006.01)
*C07D 407/12* (2006.01)

(52) U.S. Cl.
CPC ........ *C07D 407/12* (2013.01); *H01L 51/0061* (2013.01); *H01L 51/0073* (2013.01)

(58) Field of Classification Search
CPC .. C07D 407/12; C07D 493/04; C07D 307/93; C07D 307/94; H01L 51/0061; H01L 51/0073; H01L 51/5012; H01L 51/0052; H01L 51/50; Y02E 10/549; C09K 11/06; C09K 2211/1007; C09K 2211/1011; C09K 2211/1014; C09K 2211/1022; C09K 2211/1088; H05B 33/14; H05B 33/20
USPC .......................................................... 257/40
See application file for complete search history.

(56) References Cited

U.S. PATENT DOCUMENTS

| | | | |
|---|---|---|---|
| 4,539,507 A | 9/1985 | VanSlyke et al. | |
| 8,932,732 B2 * | 1/2015 | Buesing | C07C 25/24 548/440 |
| 9,028,978 B2 * | 5/2015 | Kim | H05B 33/10 564/429 |
| 10,381,570 B2 * | 8/2019 | Lim | C07D 213/74 |
| 10,930,853 B2 * | 2/2021 | Kim | H01L 51/0094 |
| 2012/0112174 A1 | 5/2012 | Lee et al. | |
| 2012/0326133 A1 * | 12/2012 | Kim | C07C 255/58 548/440 |
| 2015/0280136 A1 | 10/2015 | Ryu et al. | |
| 2016/0351820 A1 | 12/2016 | Shin et al. | |
| 2017/0012214 A1 | 1/2017 | Pyo et al. | |
| 2017/0155048 A1 * | 6/2017 | Kim | H01L 51/0073 |
| 2017/0207395 A1 | 7/2017 | Hayashi et al. | |

FOREIGN PATENT DOCUMENTS

| | | |
|---|---|---|
| CN | 102007194 A | 4/2011 |
| CN | 102558121 A | 7/2012 |
| CN | 104903421 A | 9/2015 |
| CN | 106892914 A | 6/2017 |
| CN | 107573308 A | 1/2018 |
| EP | 2902463 A1 | 8/2015 |
| JP | 2003277305 A | 10/2003 |
| JP | 2016-502500 A | 1/2016 |
| JP | 2017-515817 A | 6/2017 |
| WO | 2004/037887 A2 | 5/2004 |
| WO | 2010/097155 A1 | 9/2010 |
| WO | 2011021803 A2 | 2/2011 |
| WO | 2016/027938 A1 | 2/2016 |
| WO | 2016068450 A1 | 5/2016 |
| WO | 2017/012687 A1 | 1/2017 |

OTHER PUBLICATIONS

International Search Report dated Dec. 2, 2019 in International Application No. PCT/EP2018/078011.

(Continued)

*Primary Examiner* — Vu A Vu

(74) *Attorney, Agent, or Firm* — Faegre Drinker Biddle & Reath LLP

(57) ABSTRACT

The present invention relates to compounds of formula (1) which are suitable for use in electronic devices:

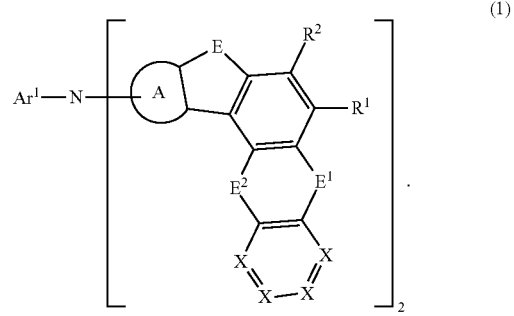

18 Claims, No Drawings

(56) References Cited

OTHER PUBLICATIONS

Zhao, et al., "Horizontal molecular orientation in solution-processed organic light-emitting diodes," Applied Physics Letters, 106, 063301 (2015).
Arnold et al., "Direct vapor jet printing of three color segment organic light emitting devices for white light illumination", Appl Phys. Lett., vol. 92, 053301, 2008, 4 pages.

* cited by examiner

MATERIALS FOR ORGANIC ELECTROLUMINESCENT DEVICES

RELATED APPLICATIONS

This application is a national stage application (under 35 U.S.C. § 371) of PCT/EP2018/078011, filed Oct. 15, 2018, which claims benefit of European Application No. 17196902.5, filed Oct. 17, 2017, and Chinese Patent Application No. 201810670515.0 both of which are incorporated herein by reference in their entirety.

BACKGROUND OF THE INVENTION

(1) Field of the Invention

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

(2) Description of Related Art

The development of functional compounds for use in electronic devices is currently the subject of intensive research. The aim is, in particular, the development of compounds with which improved properties of electronic devices in one or more relevant points can be achieved, such as, for example, power efficiency and lifetime of the device as well as colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, for example, in U.S. Pat. No. 4,539,507.

Further improvements are still necessary with respect to the performance data of OLEDs, in particular with a view to broad commercial use, for example in display devices or as light sources. Of particular importance in this connection are the lifetime, the efficiency and the operating voltage of the OLEDs and as well as the colour values achieved. In particular, in case of blue-emitting OLEDs, there is potential for improvement with respect to the lifetime and the efficiency of the devices.

An important starting point for achieving the said improvements is the choice of the emitter compound and of the host compound employed in the electronic device.

Blue-fluorescent emitters known from the prior art are a multiplicity of compounds. Arylamines containing one or more condensed aryl are known from the prior. Arylamines containing dibenzofuran groups (for example in US 2017/0012214) are also known from the prior art.

However, there is still a need for further fluorescent emitters, especially blue-fluorescent emitters, which may be employed in OLEDs and lead to OLEDs having very good properties in terms of lifetime, color emission and efficiency. More particularly, there is a need for blue-fluorescent emitters combining very high efficiencies, very good life time and suitable color coordinates.

Furthermore, it is known that an OLED may comprise different layers, which may be applied either by vapour deposition in a vacuum chamber or by processing from a solution. The processes based on vapour deposition lead to good results but such processes are complex and expensive. Therefore, there is a need for OLED materials that can be easily and reliably processed from solution. In this case, the materials should have good solubility properties in the solution that comprises them. Additionally, the OLED materials that are processed from a solution should be able to orientate themselves in the deposited film to improve the overall efficiency of the OLED. The term orientation means here the horizontal molecular orientation of the compounds, as explained in Zhao et al., Horizontal molecular orientation in solution-processed organic light-emitting diodes, Appl. Phys. Lett. 106063301, 2015.

BRIEF SUMMARY OF THE INVENTION

The present invention is thus based on the technical object of providing compounds which are suitable for use in electronic devices, such as OLEDs, more particularly as blue-fluorescent emitters or matrix materials and, which are suitable for vacuum processing or for solution processing.

In investigations on novel compounds for use in electronic devices, it has now been found, that compounds of formula (1) as defined below are eminently suitable for use in electronic devices. In particular, they achieve one or more, preferably all, of the above-mentioned technical objects.

The invention thus relates to compounds of formula (1),

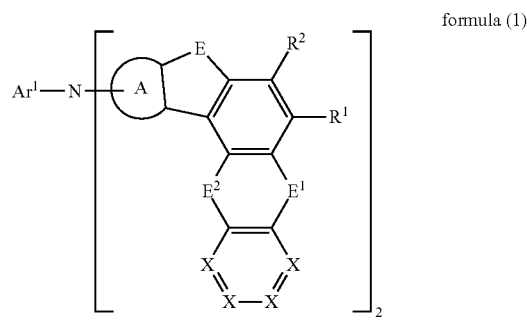

formula (1)

where the following applies to the symbols and indices used:

A stands on each occurrence, identically or differently, for an aromatic or heteroaromatic ring system having 5 to 60 aromatic ring atoms, which may in each case be substituted by one or more radicals $R^3$; wherein the ring A is condensed on the five-membered ring comprising E via two adjacent carbon atoms, as depicted in formula (1);

$Ar^1$ stands for:

an aromatic or heteroaromatic ring system having 5 to 60 aromatic ring atoms, which may in each case be substituted by one or more radicals $R^4$;

a group of formula (Ar1-1),

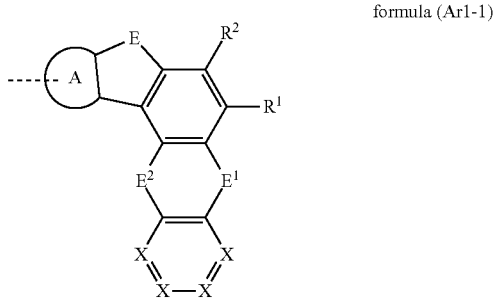

formula (Ar1-1)

where the dashed bond indicates the bonding to the nitrogen atom as depicted in formula (1); or
a group ArL;
ArL stands for a group of formula (ArL-1),

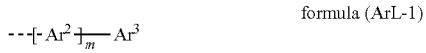

formula (ArL-1)

where the dashed bond in formula (ArL-1) indicates the bonding to the structure of formula (1);
X stands on each occurrence, identically or differently, for $CR^3$ or N;
E is on each occurrence, identically or differently, selected from —$BR^0$, —$C(R^0)_2$—, —$C(R^0)_2$—$C(R^0)_2$—, —$C(R^0)_2$—O—, —$C(R^0)_2$—S—, —$R^0C$=$CR^0$—, —$R^0C$=N—, $Si(R^0)_2$, —$Si(R^0)_2$—$Si(R^0)_2$—, —C(=O)—, —C(=$NR^0$)—, —C(=C($R^0)_2$)—, —O—, —S—, —S(=O)—, —$SO_2$—, —N($R^0$)—, —P($R^0$)— and —P((=O)$R^0$)—; or E is a group of formula (E-1),

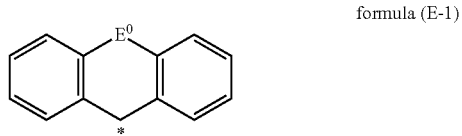

formula (E-1)

where the symbol * in formula (E-1) indicates the corresponding group E in formula (1); and
$E^0$ is identically or differently on each occurrence, selected from the group consisting of a single bond, —$BR^0$—, —$C(R^0)_2$—, —$C(R^0)_2$—$C(R^0)_2$—, —$C(R^0)_2$—O—, —$C(R^0)_2$—S—, —$R^0C$=$CR^0$—, —$R^0C$=N—, $Si(R^0)_2$, —$Si(R^0)_2$—$Si(R^0)_2$—, —C(=O)—, —C(=$NR^0$)—, —C(=C($R^0)_2$)—, —O—, —S—, —S(=O)—, —$SO_2$—, —N($R^0$)—, —P($R^0$)— and —P((=O)$R^0$)—;
$E^1$, $E^2$ are identically or differently on each occurrence, selected from the group consisting of a single bond, —$C(R^0)_2$—, $Si(R^0)_2$, —O— and —S—; with the proviso that, in a ring comprising the groups $E^1$ and $E^2$, one of the group $E^1$ and $E^2$, is a single bond, —$C(R^0)_2$— or $Si(R^0)_2$, and the other group is O or S;
$R^0$, $R^1$, $R^2$, $R^3$, $R^4$ stand on each occurrence, identically or differently, for:
H, D, F, Cl, Br, I, CHO, CN, $N(Ar)_2$, C(=O)Ar, P(=O)$(Ar)_2$, S(=O)Ar, S(=O)$_2$Ar, $NO_2$, $Si(R)_3$, $B(OR)_2$ or $OSO_2R$; or
a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals R, where in each case one or more non-adjacent $CH_2$ groups may be replaced by RC=CR, C≡C, $Si(R)_2$, $Ge(R)_2$, $Sn(R)_2$, C=O, C=S, C=Se, P(=O)(R), SO, $SO_2$, O, S or CONR and where one or more H atoms may be replaced by D, F, Cl, Br, I, CN or $NO_2$; or
an aromatic or heteroaromatic ring systems having 5 to 60 aromatic ring atoms, which may in each case be substituted by one or more radicals R, or an aryloxy groups having 5 to 40 aromatic ring atoms, which may be substituted by one or more radicals R; or
for a group ArL, which may be substituted by one or more radicals R; and where two adjacent substituents $R^0$, two adjacent substituents $R^1$ and $R^2$, two adjacent substituents $R^3$ and/or two adjacent substituents $R^4$, may form a mono- or polycyclic, aliphatic ring system or aromatic ring system, which may be substituted by one or more radicals R;
$Ar^2$, $Ar^3$ stand on each occurrence, identically or differently, for an aromatic or heteroaromatic ring systems having 5 to 60 aromatic ring atoms, which may in each case be substituted by one or more radicals R;
m is an integer selected from 1 to 10;
R stands on each occurrence, identically or differently, for H, D, F, Cl, Br, I, CHO, CN, $N(Ar)_2$, C(=O)Ar, P(=O)$(Ar)_2$, S(=O)Ar, S(=O)$_2$Ar, $NO_2$, $Si(R')_3$, $B(OR')_2$, $OSO_2R'$, a straight-chain alkyl, alkoxy or thioalkyl groups having 1 to 40 C atoms or branched or cyclic alkyl, alkoxy or thioalkyl groups having 3 to 40 C atoms, each of which may be substituted by one or more radicals R', where in each case one or more non-adjacent $CH_2$ groups may be replaced by R'C=CR', C≡C, $Si(R')_2$, $Ge(R')_2$, $Sn(R')_2$, C=O, C=S, C=Se, P(=O)(R'), SO, $SO_2$, O, S or CONR' and where one or more H atoms may be replaced by D, F, Cl, Br, I, CN or $NO_2$, an aromatic or heteroaromatic ring systems having 5 to 60 aromatic ring atoms, which may in each case be substituted by one or more radicals R', or an aryloxy group having 5 to 60 aromatic ring atoms, which may be substituted by one or more radicals R', where two adjacent substituents R may form a mono- or polycyclic, aliphatic ring system or aromatic ring system, which may be substituted by one or more radicals R';
Ar is an aromatic or heteroaromatic ring system having 5 to 24 aromatic ring atoms, which may in each case also be substituted by one or more radicals R';
R' stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 C atoms;
with the proviso that, when the ring A stands for a benzene ring, then the group $R^1$ or the group $R^2$ is selected from an aromatic or heteroaromatic ring systems having 5 to 60 aromatic ring atoms, which may in each case be substituted by one or more radicals R.

DETAILED DESCRIPTION OF THE INVENTION

Preferably, when the ring A stands for a benzene ring, then the group $R^1$ is selected from an aromatic or heteroaromatic ring systems having 5 to 60 aromatic ring atoms, which may in each case be substituted by one or more radicals R.

Adjacent substituents in the sense of the present invention are substituents which are bonded to atoms which are linked directly to one another or which are bonded to the same atom.

Furthermore, the following definitions of chemical groups apply for the purposes of the present application:

An aryl group in the sense of this invention contains 6 to 60 aromatic ring atoms, preferably 6 to 40 aromatic ring atoms, more preferably 6 to 20 aromatic ring atoms; a heteroaryl group in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system, preferably 6 to 40 C atoms, more preferably 6 to 20 C atoms. A heteroaromatic ring system in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

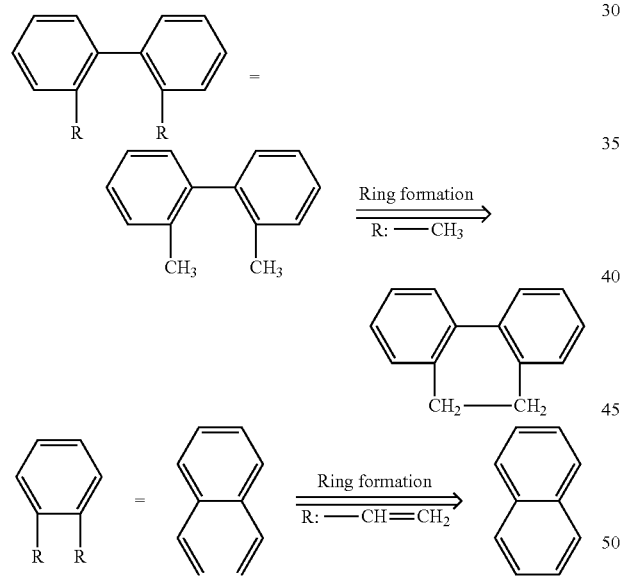

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

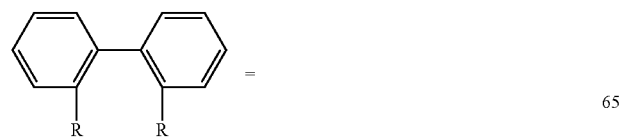

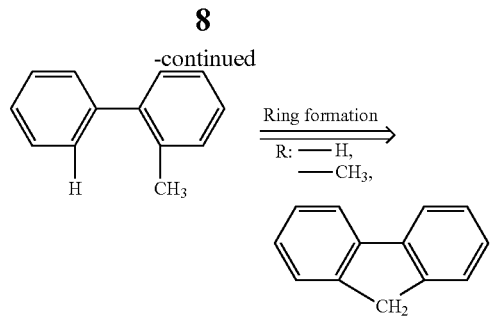

In accordance with a preferred embodiment, the ring A is selected from the group consisting of phenyl, naphthyl, anthracene, phenanthrene, fluorene, dibenzothiophene, dibenzofurane or carbazole, which may in each case be substituted by one or more radicals $R^3$.

Preferably, $Ar^1$ stands for:
an aromatic or heteroaromatic ring system having 5 to 40, preferably 5 to 30, more preferably 5 to 30, particularly preferably 6 to 18 aromatic ring atoms, which may in each case be substituted by one or more radicals $R^4$;
a group of formula (Ar1-1) as depicted above; or
a group ArL.

Very preferably, $Ar^1$ stands for:
phenyl, biphenyl, fluorene, spirobifluorene, naphthalene, phenanthrene, dibenzofuran, dibenzothiophene, carbazole, pyridine, pyrimidine, pyrazine, pyridazine, triazine, benzopyridine, benzopyridazine, benzopyrimidine or quinazoline, or a combination of of two or three of these groups, each of which may be substituted by one or more radicals $R^4$;
a group of formula (Ar1-1) as depicted above; or
a group ArL.

Particularly preferably, $Ar^1$ stands for:
phenyl, biphenyl, fluorene, spirobifluorene, naphthalene, phenanthrene, dibenzofuran, dibenzothiophene, carbazole or a combination of two or three of these groups, each of which may be substituted by one or more radicals $R^4$;
a group of formula (Ar1-1) as depicted above; or
a group ArL.

Very particularly preferably, $Ar^1$ stands for:
an aromatic or heteroaromatic ring system of one of the formulae (Ar-1) to (Ar-9) as depicted below;
a group of formula (Ar1-1) as depicted above; or
a group ArL.

Structure of the aromatic or heteroaromatic ring systems of formulae (Ar-1) to (Ar-9) are represented in the table below:

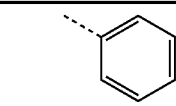

(Ar-1)

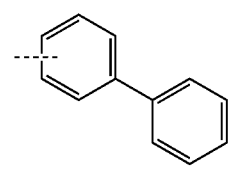

(Ar-2)

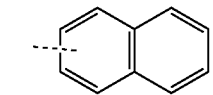

(Ar-3)

-continued (Ar-4)
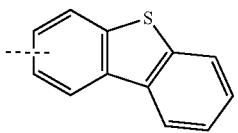

(Ar-5)
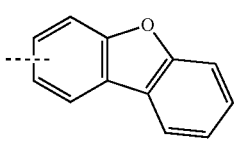

(Ar-6)
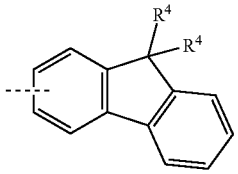

(Ar-7)
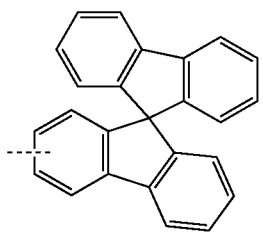

(Ar-8)
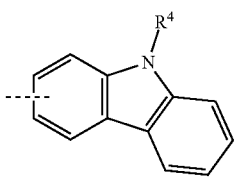

(Ar-9)
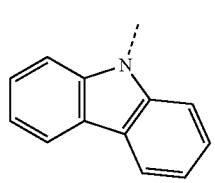

In formulae (Ar-1) to (Ar-9), the dashed bond indicates the bonding to the nitrogen of the structure of formula (1); and the groups of formulae (Ar-1) to (Ar-9) may be substituted at each free position by a group $R^4$, which has the same meaning as above.

Preferably, the compounds of formula (1) are selected from the compounds of formulae (2) to (41),

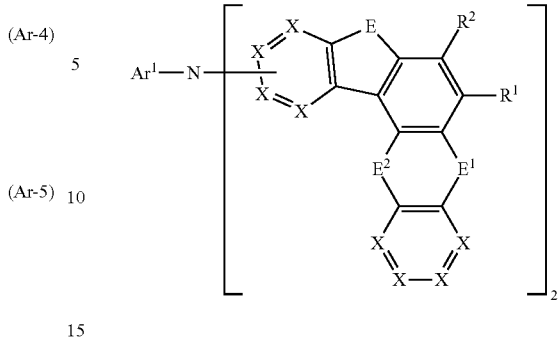
formula (2)

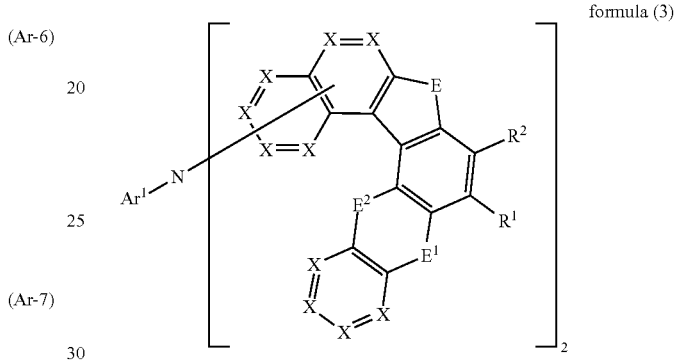
formula (3)

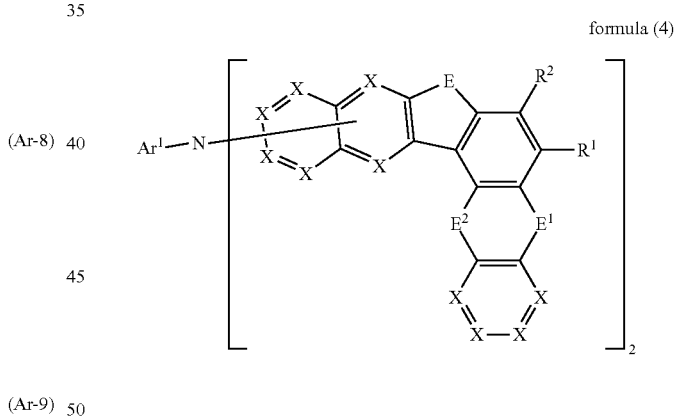
formula (4)

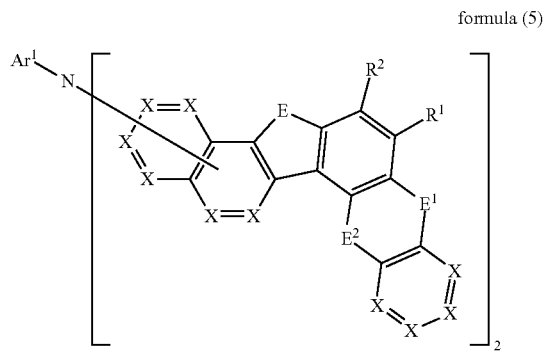
formula (5)

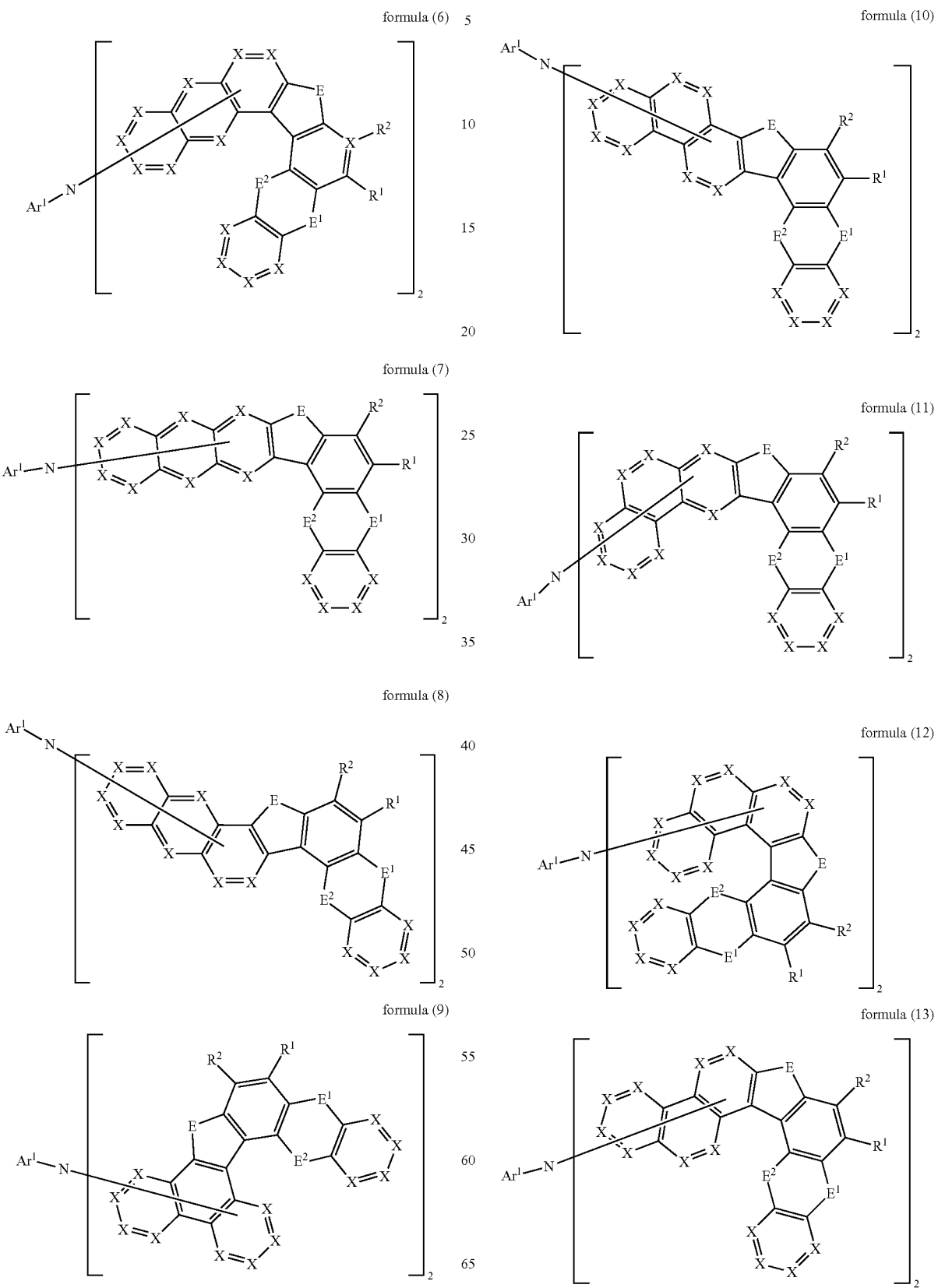

formula (14)
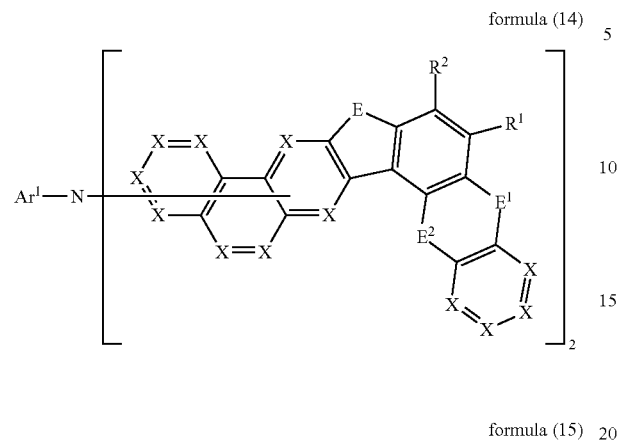
formula (15)
formula (16)
formula (17)
formula (18)
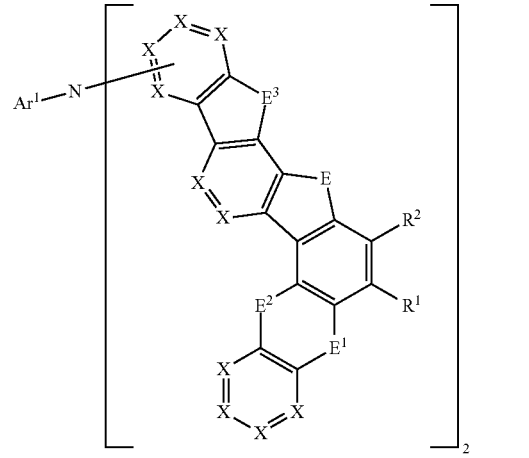
formula (19)
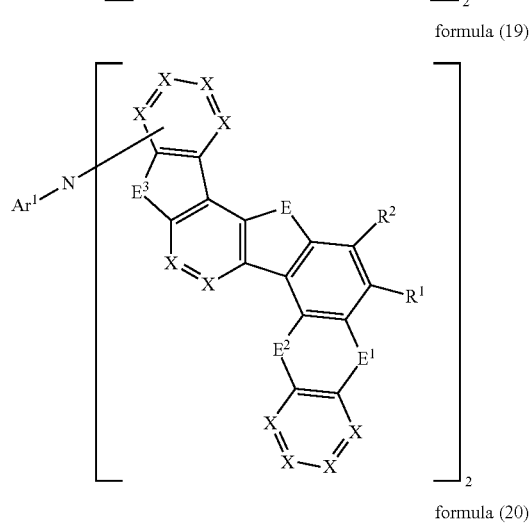
formula (20)
formula (21)
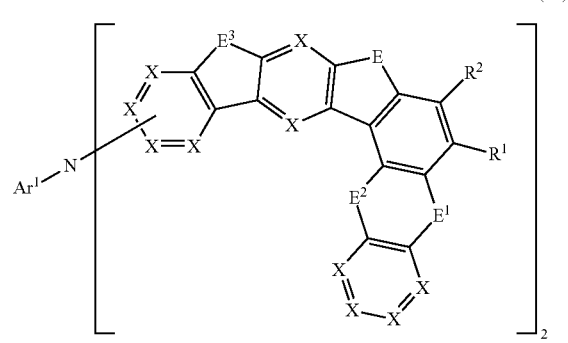

-continued
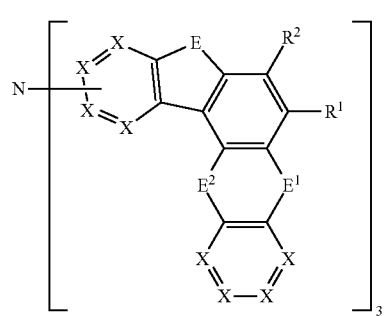
formula (22)
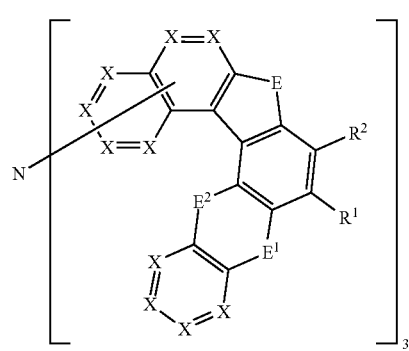
formula (23)
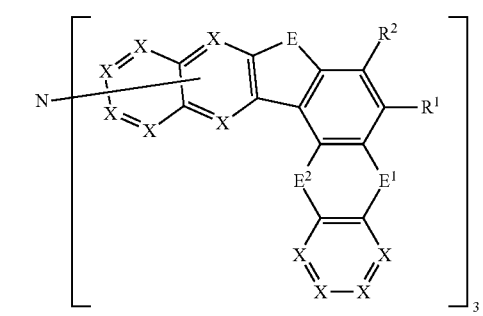
formula (24)
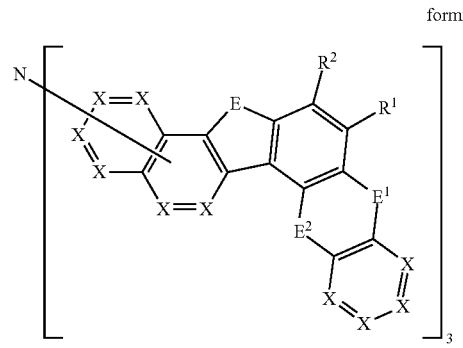
formula (25)
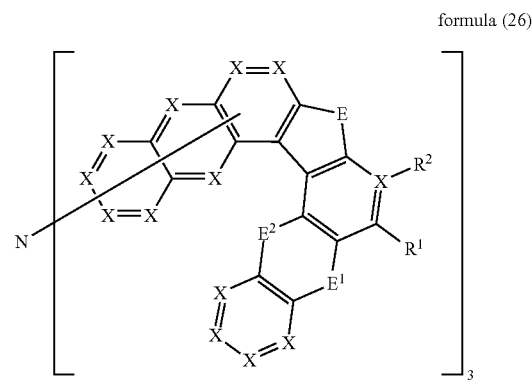
formula (26)
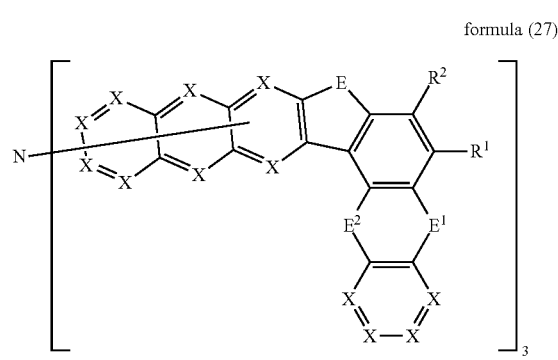
formula (27)
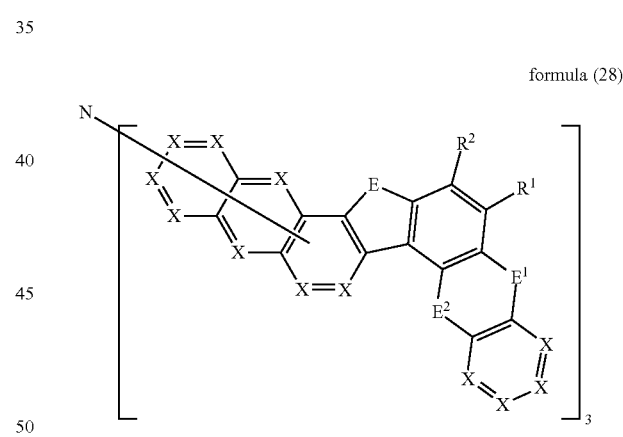
formula (28)
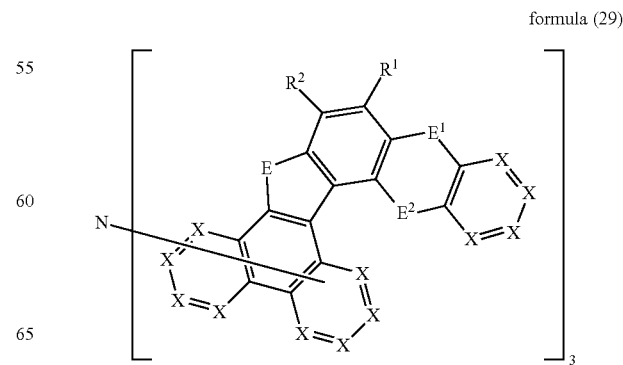
formula (29)

formula (30)
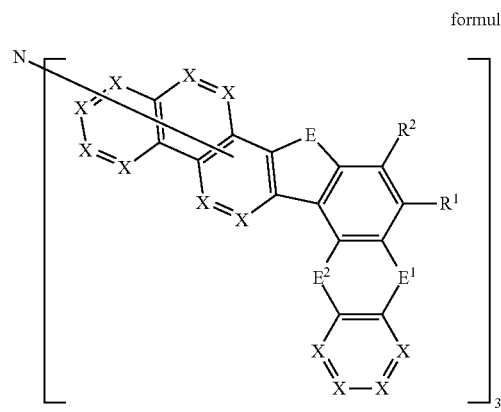
formula (31)
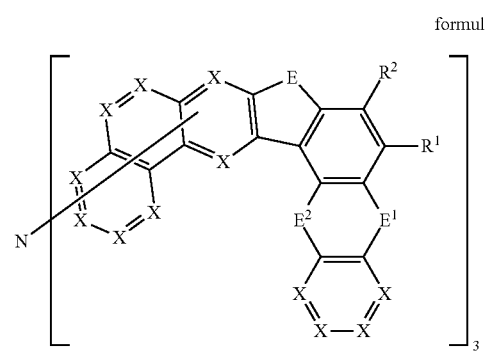
formula (32)
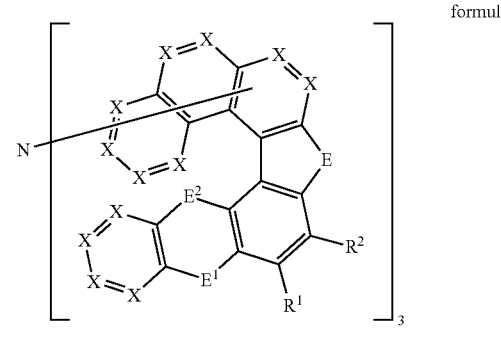
formula (33)
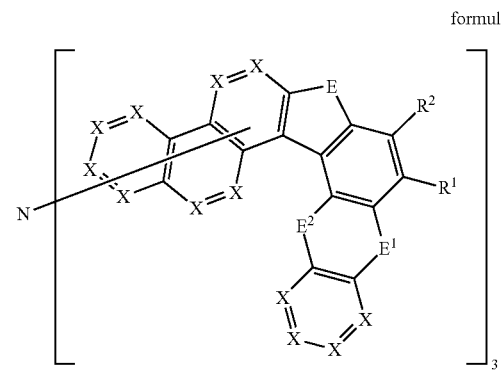
formula (34)
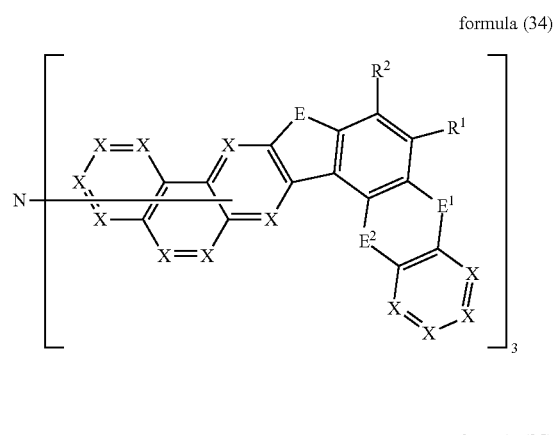
formula (35)
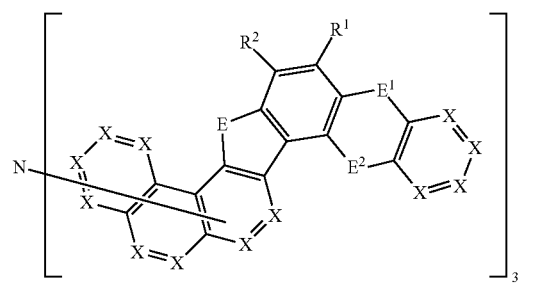
formula (36)
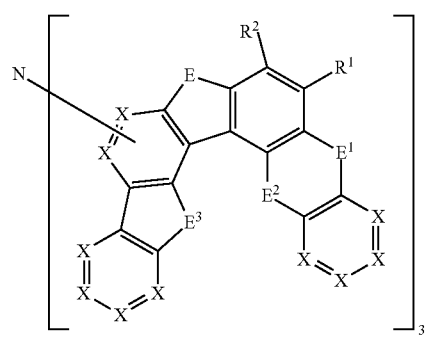
formula (37)
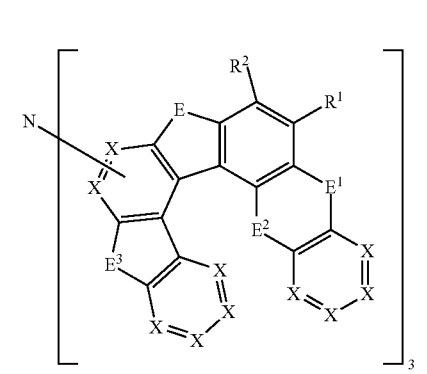

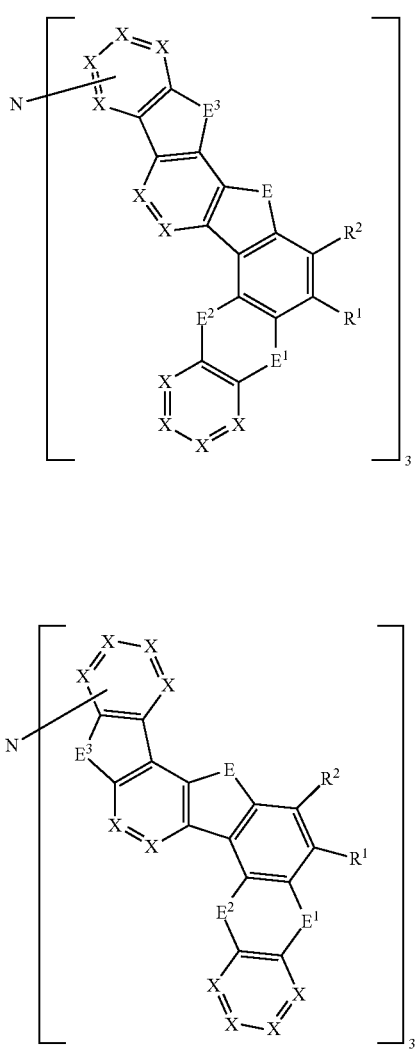

formula (38)

formula (39)

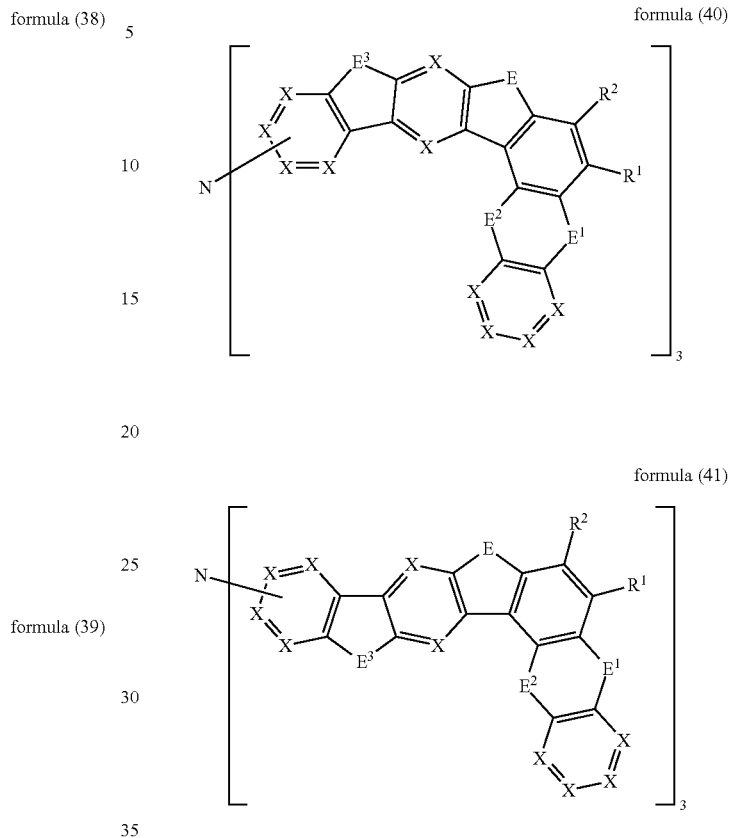

formula (40)

formula (41)

where the symbols Ar$^1$, E, E$^1$, E$^2$, R$^1$ and R$^2$ have the same meaning as above; and where X is CR$^2$ or N; or X stands for C if a group —NAr$^1$ is bonded to X; and E$^3$ is on each occurrence, identically or differently, selected from —C(R$^0$)$_2$—, —O—, —S— or —N(R$^0$)—; wherein R$^0$ has the same meaning as above.

Preferably, E$^3$ stands for —C(R$^0$)$_2$—.

Very preferably, the compounds of formula (1) are selected from the compounds of formulae (2-1) to (41-1),

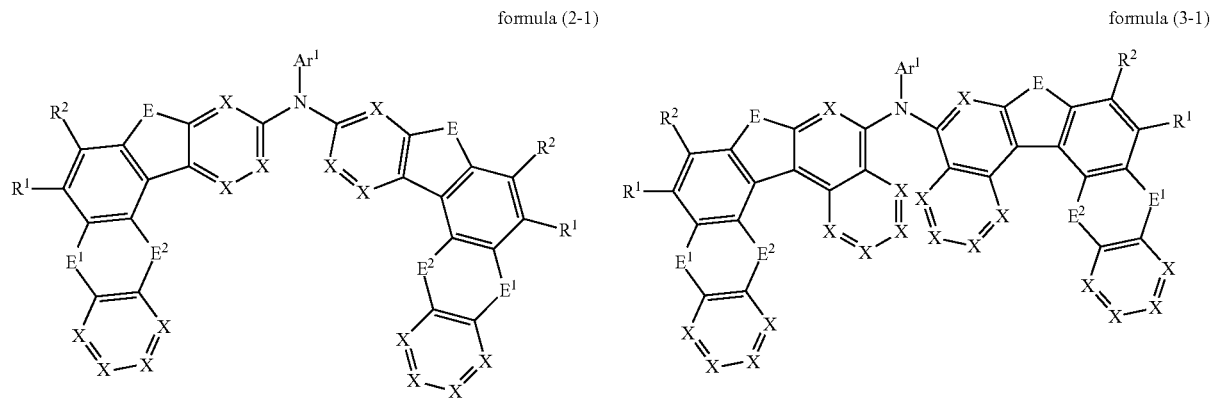

formula (2-1)

formula (3-1)

formula (4-1)
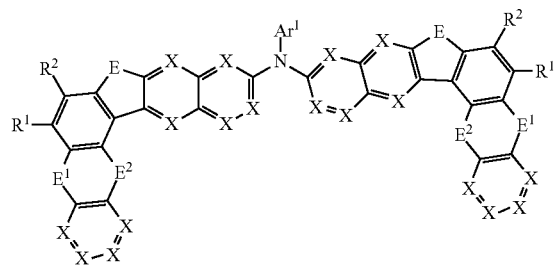
formula (5-1)
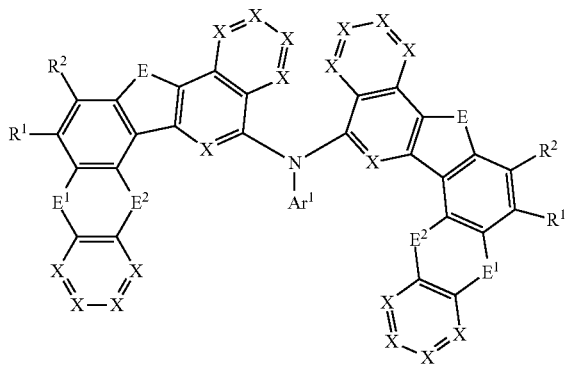
formula (6-1)
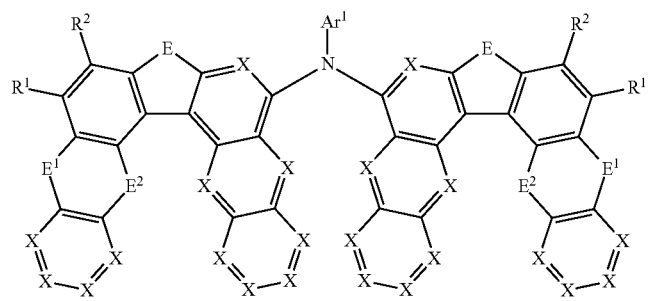
formula (7-1)
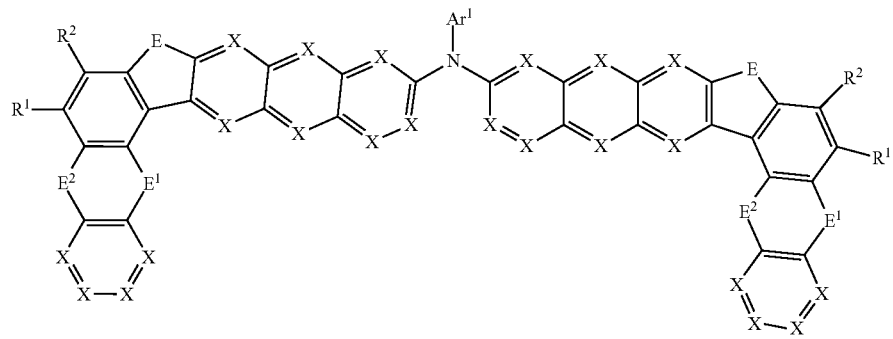
formula (8-1)
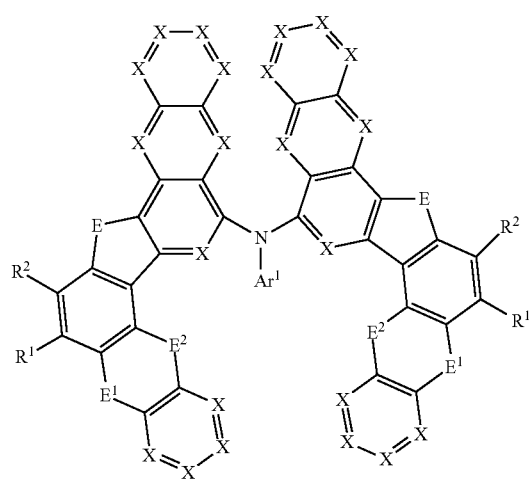
formula (9-1)
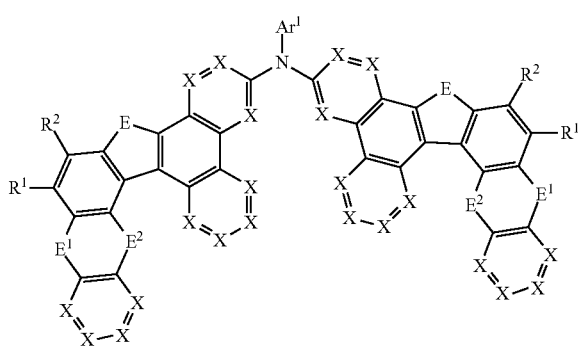

-continued
formula (10-1)
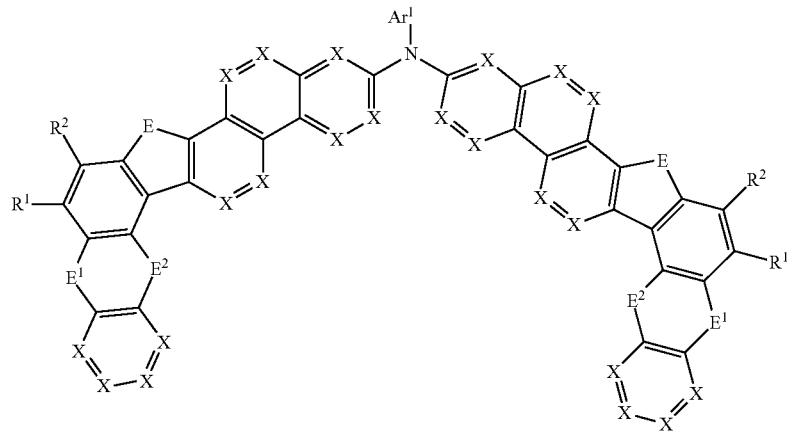
formula (11-1)
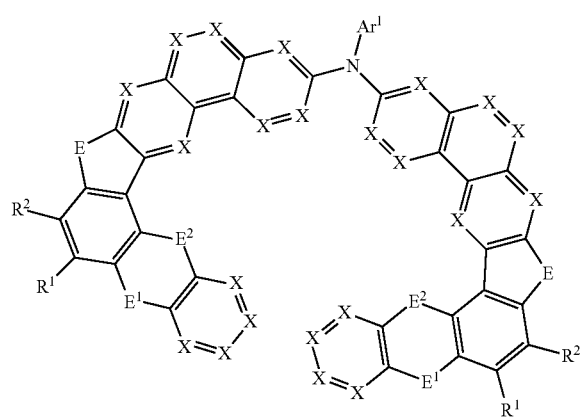
formula (12-1)
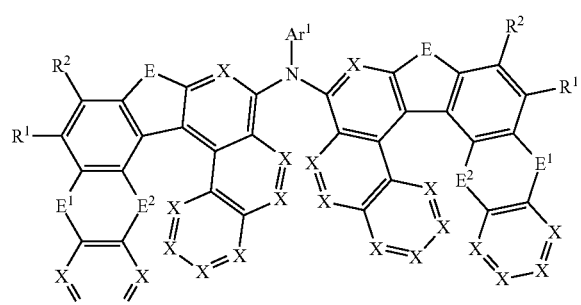
formula (13-1)
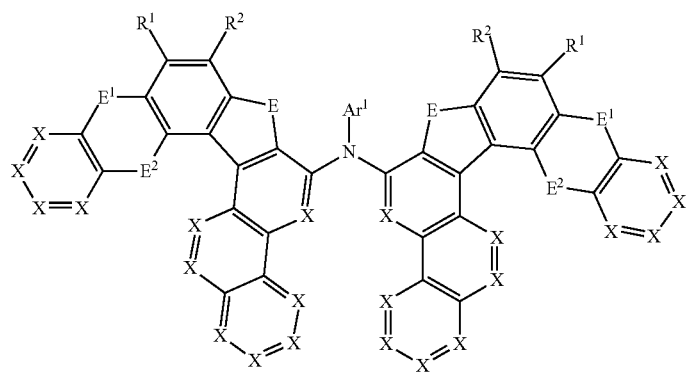
formula (14-1)
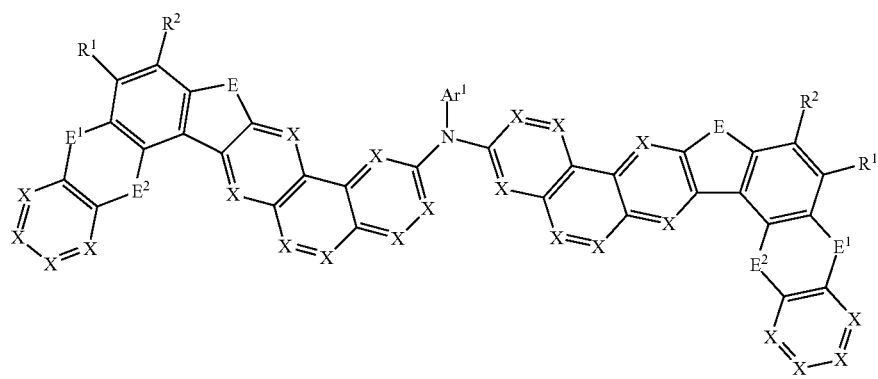

-continued
formula (15-1)
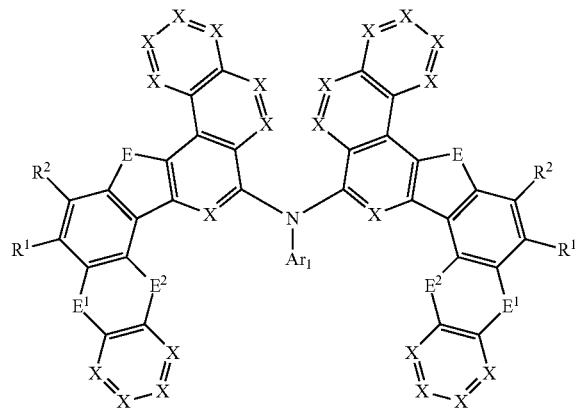
formula (16-1)
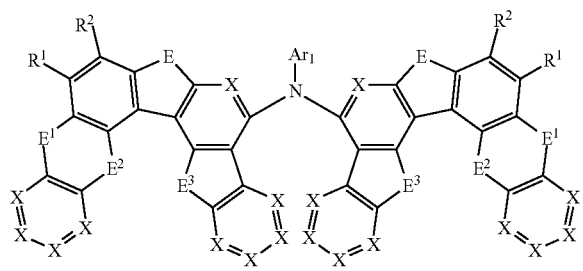
formula (17-1)
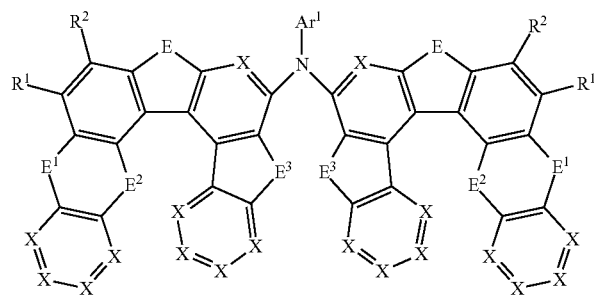
formula (18-1)
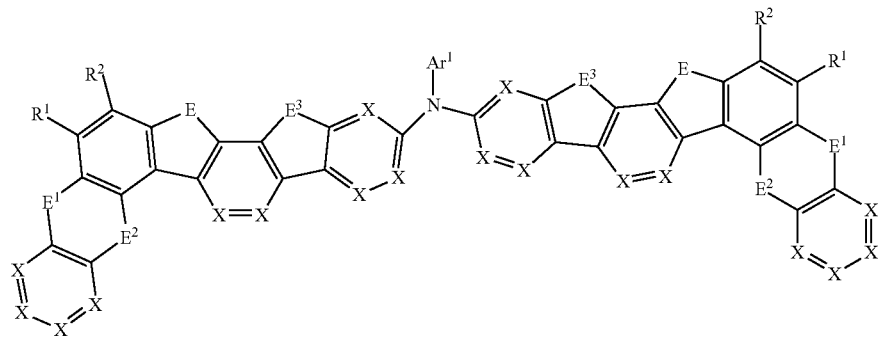
formula (19-1)
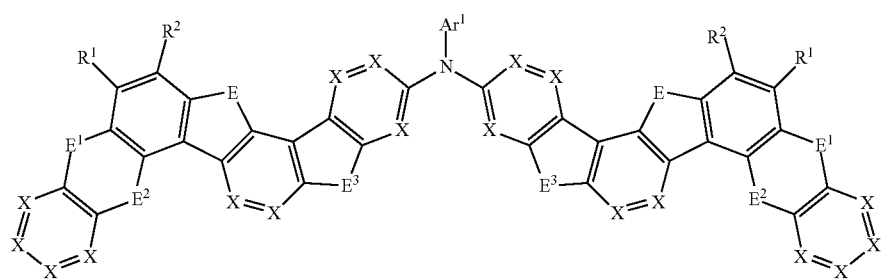

formula (20-1)
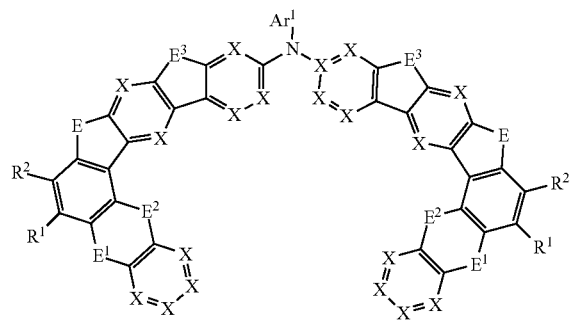
formula (21-1)
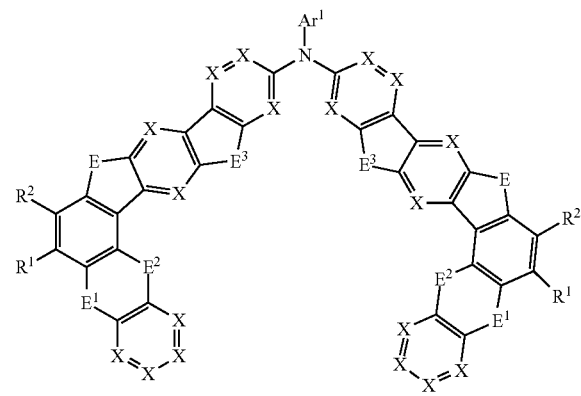
formula (22-1)
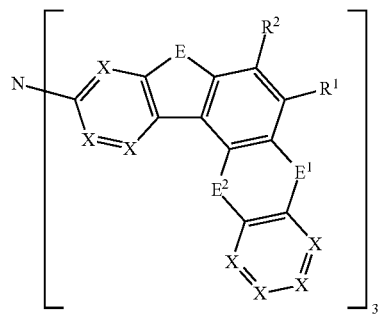
formula (23-1)
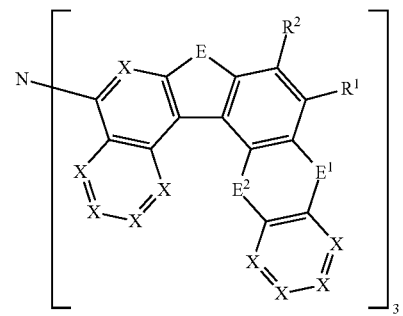
formula (24-1)
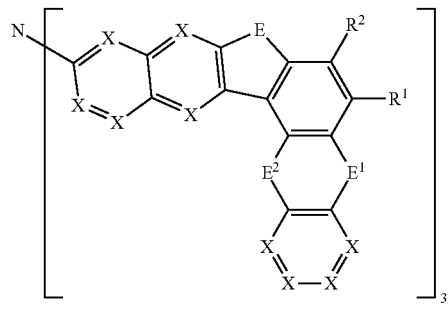
formula (25-1)
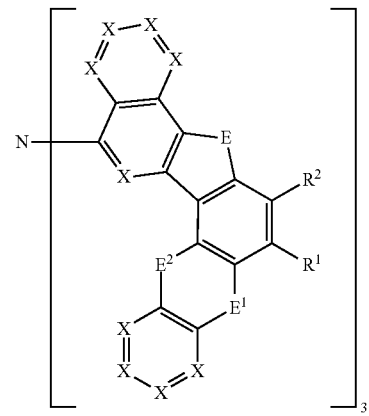
formula (26-1)
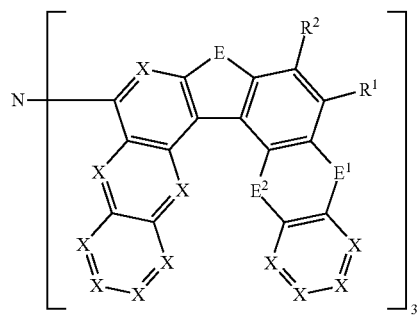
formula (27-1)
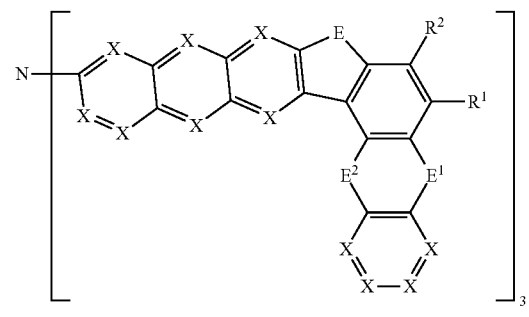

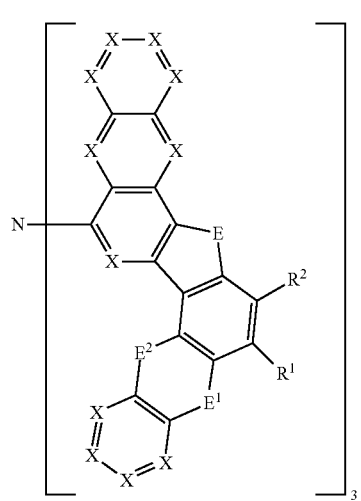
formula (28-1)
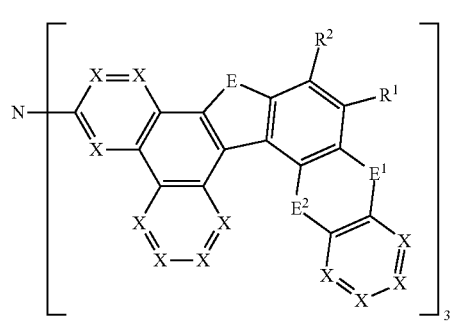
formula (29-1)
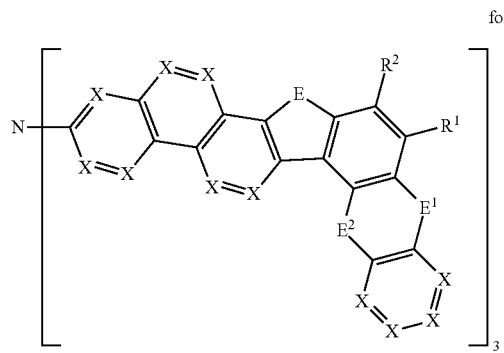
formula (30-1)
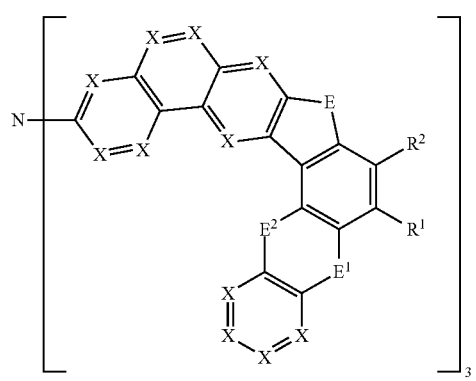
formula (31-1)
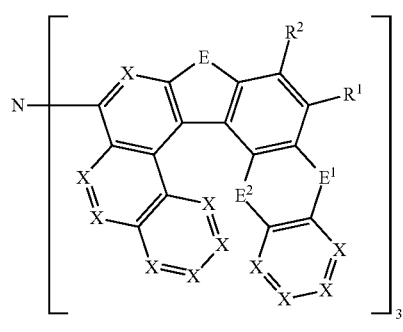
formula (32-1)
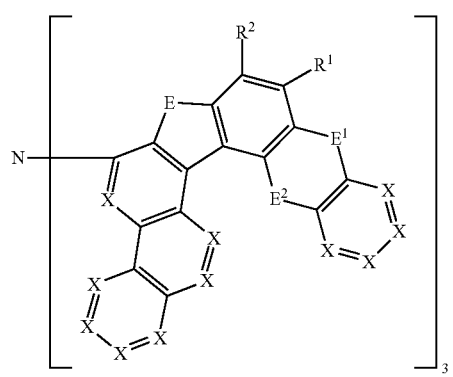
formula (33-1)

formula (34-1)
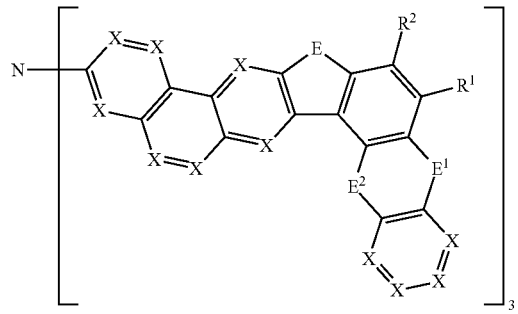
formula (35-1)
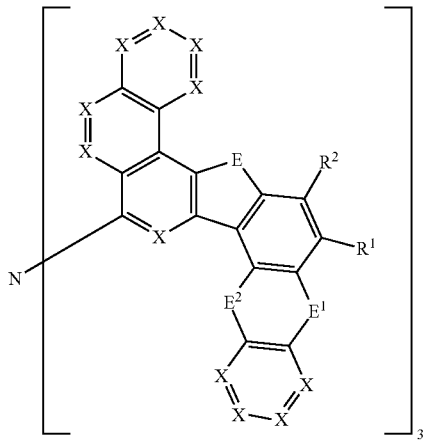
formula (36-1)
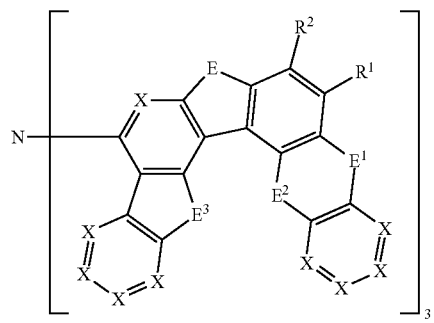
formula (37-1)
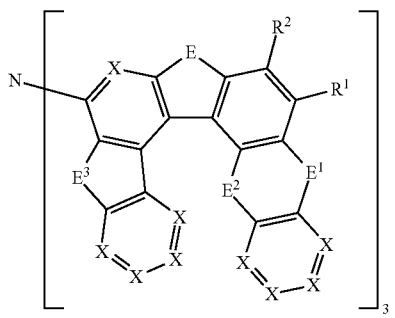
formula (38-1)
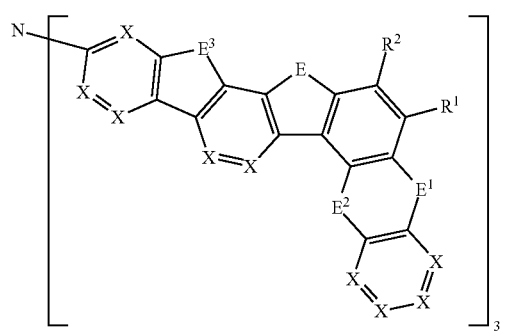
formula (39-1)
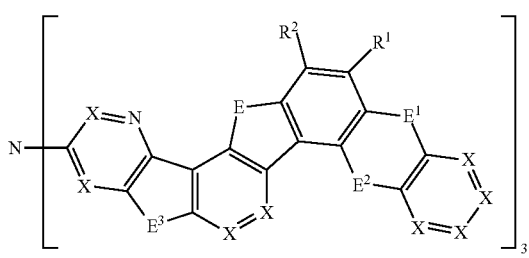
formula (40-1)
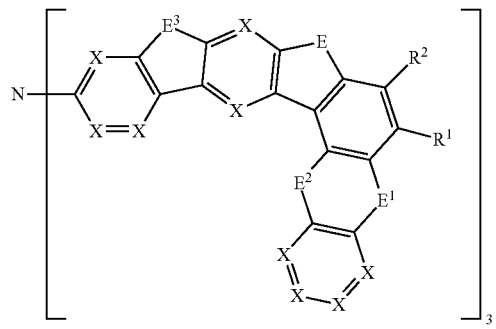
formula (41-1)
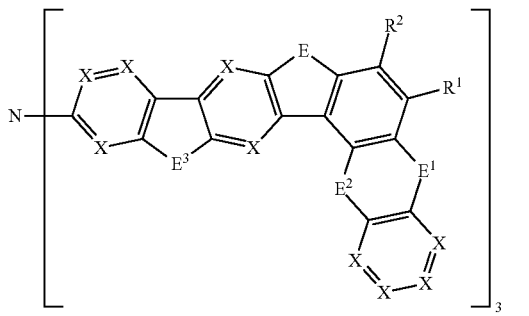
where the symbols X, $Ar^1$, E, $E^1$, $E^2$, $E^3$, $R^1$ and $R^2$ have the same meaning as above.

Particularly preferably, the compounds of formula (1) are selected from the compounds of formulae (2-2) to (41-2),
formula (2-2)
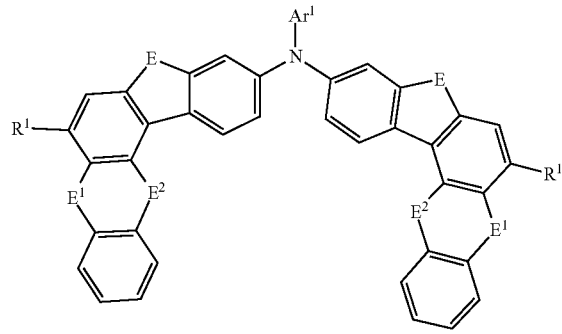
formula (3-2)
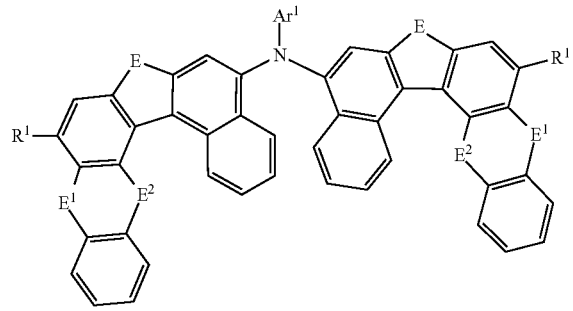
formula (4-2)
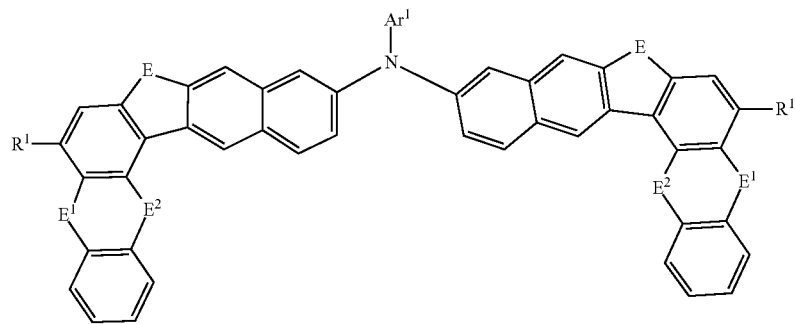
formula (5-2)
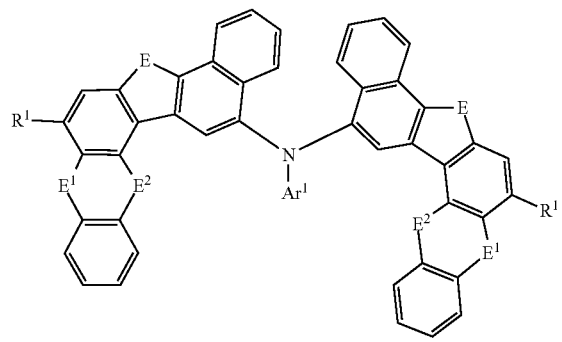
formula (6-2)
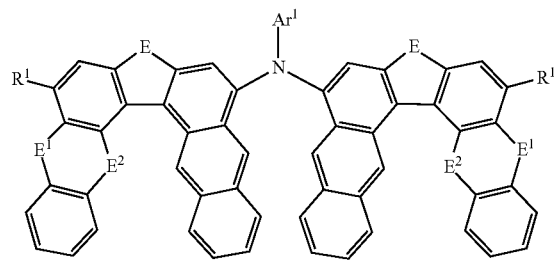
formula (7-2)
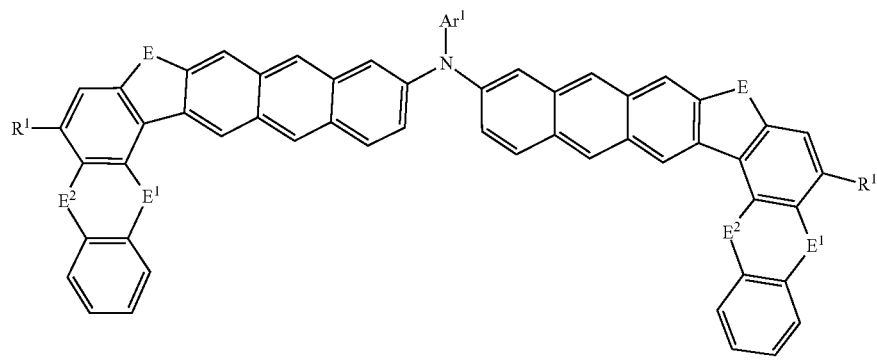

formula (8-2)
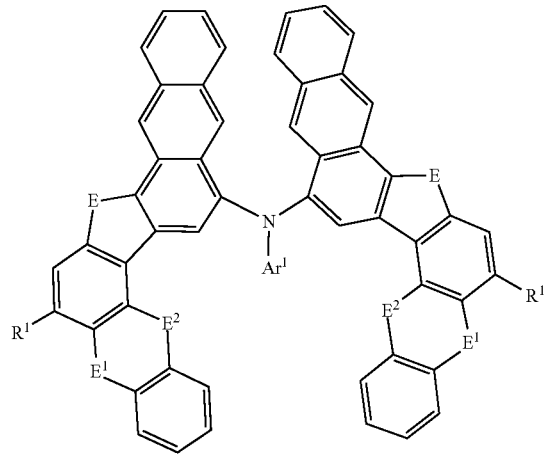
formula (9-2)
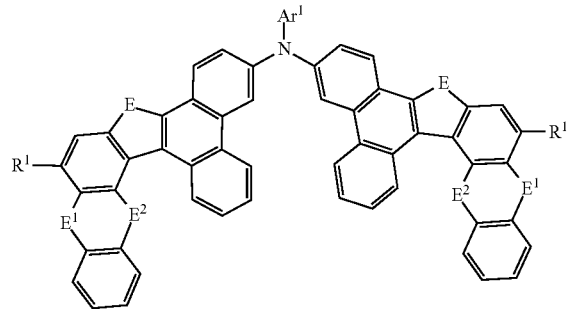
formula (10-2)
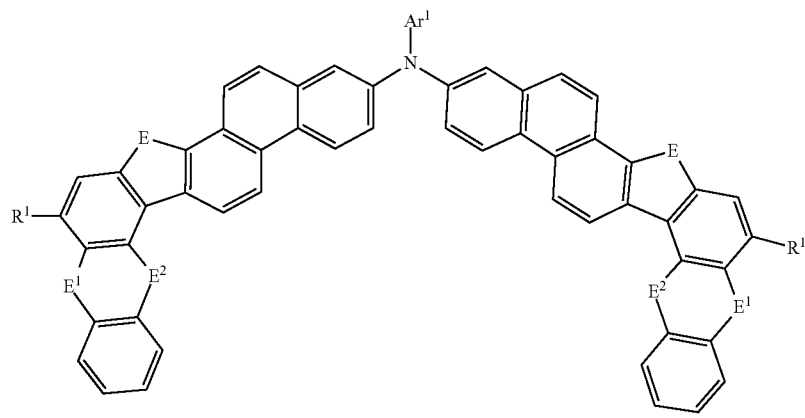
formula (11-2)
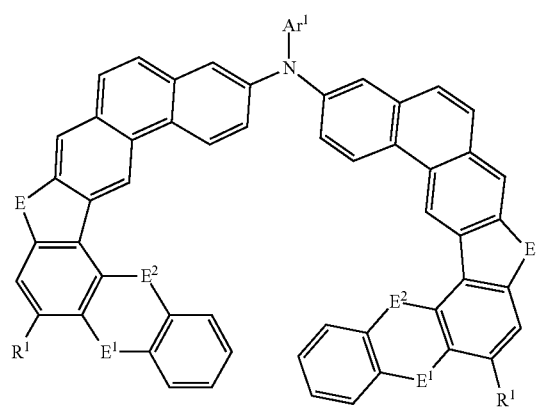
formula (12-2)
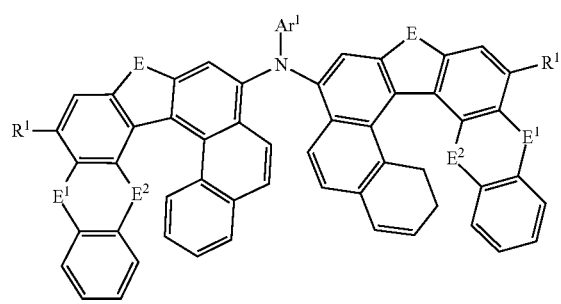

formula (13-2)
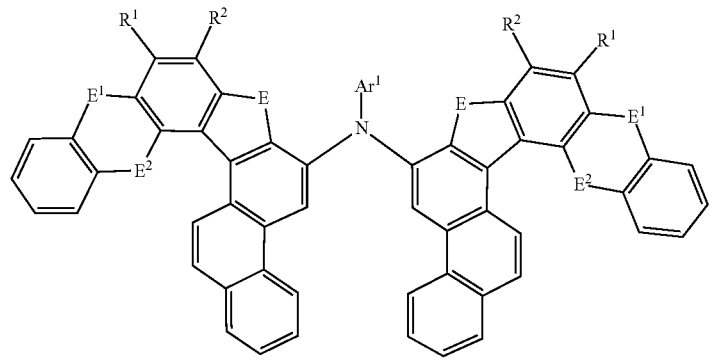
formula (14-2)
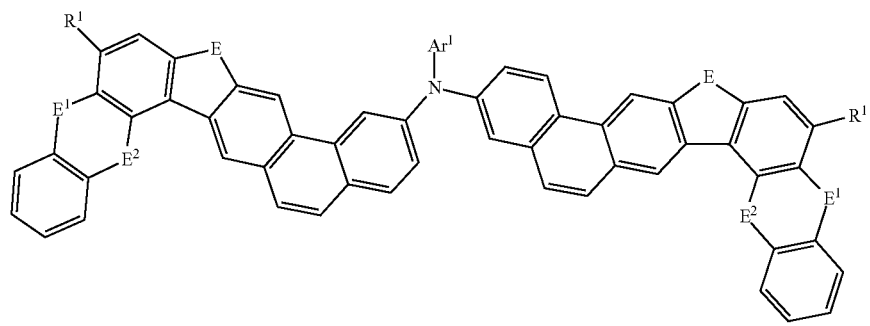
formula (15-2)
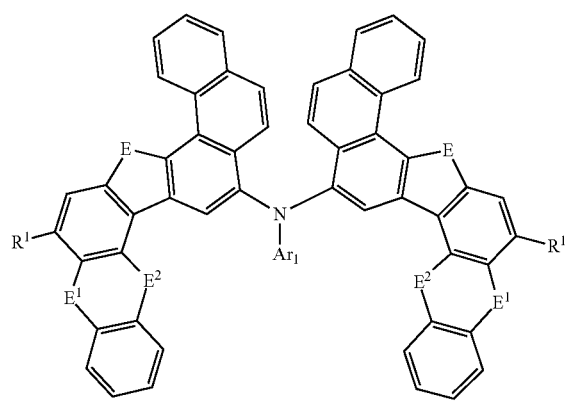
formula (16-2)
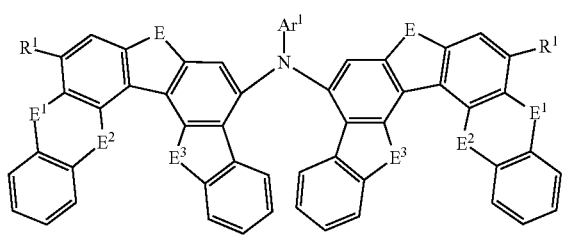
formula (17-2)
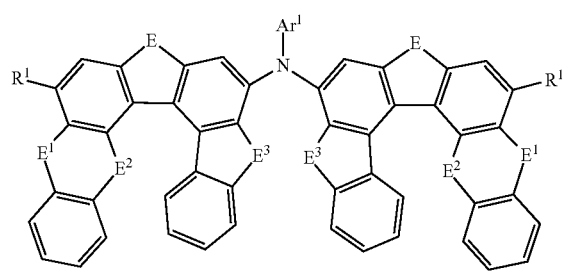

formula (18-2)
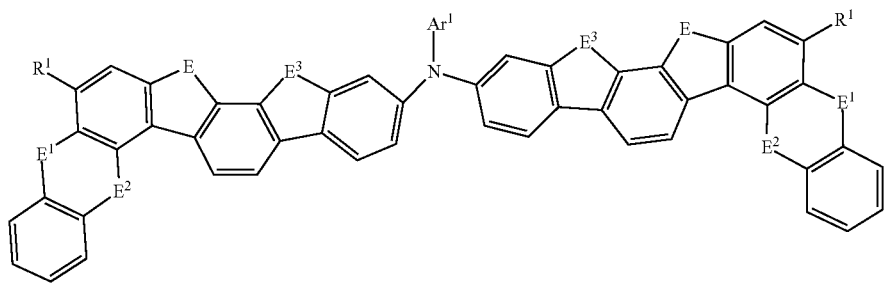
formula (19-2)
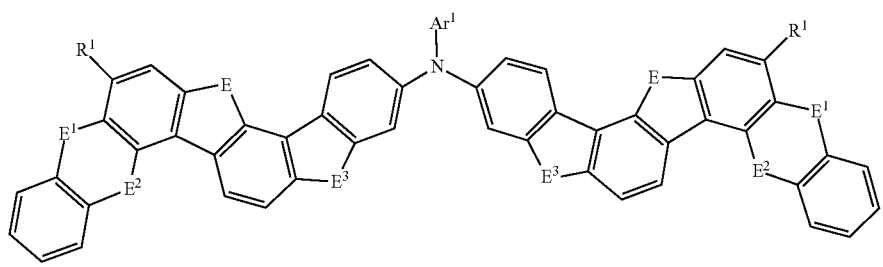
formula (20-2)
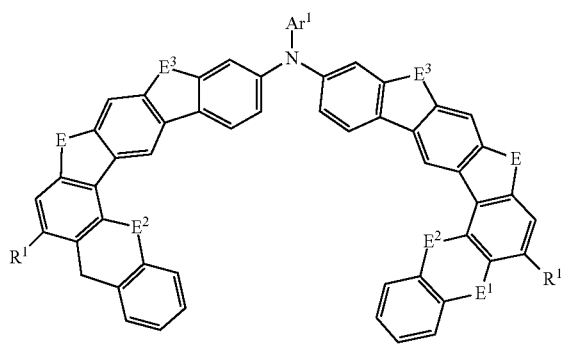
formula (21-2)
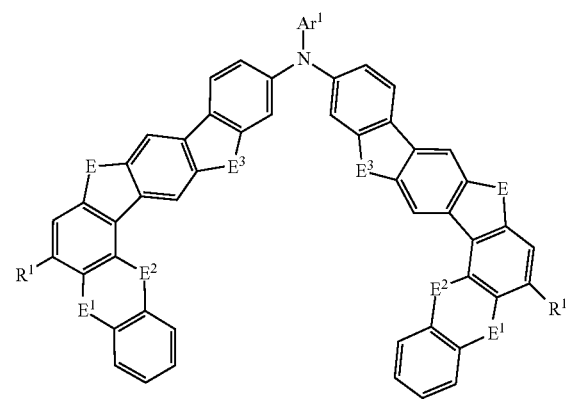
formula (22-2)
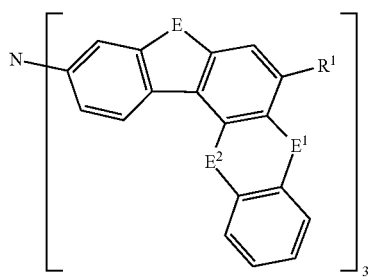
formula (23-2)
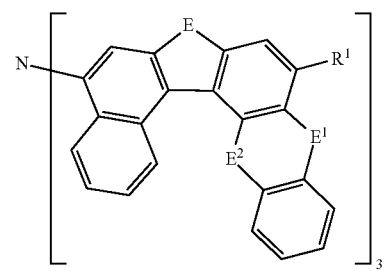
formula (24-2)
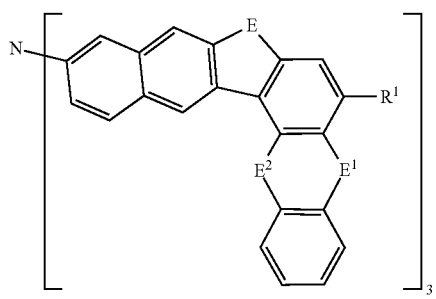
formula (25-2)
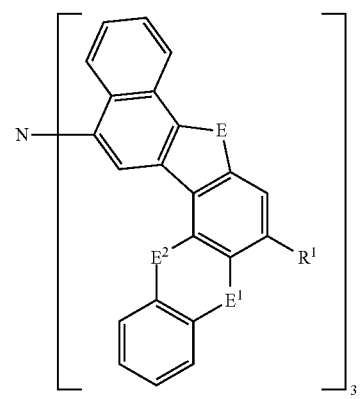

-continued
formula (26-2)
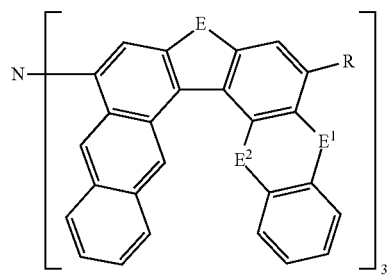
formula (27-2)
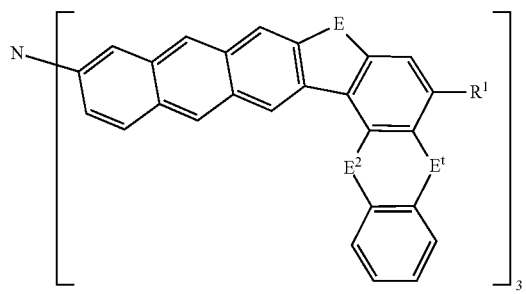
formula (28-2)
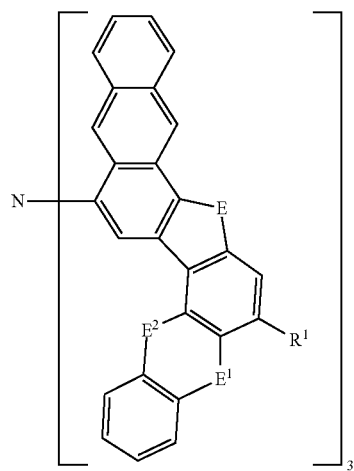
formula (29-2)
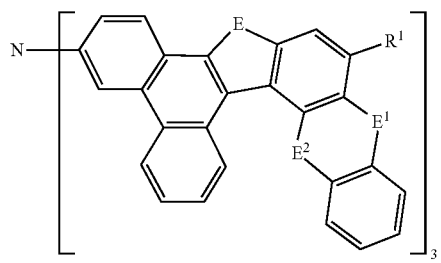
formula (30-2)
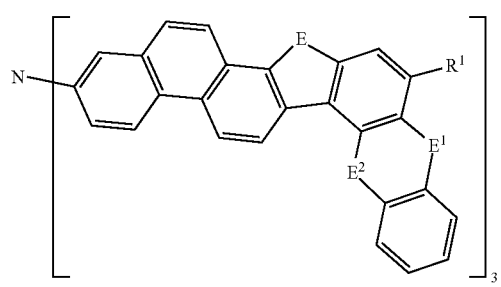
formula (31-2)
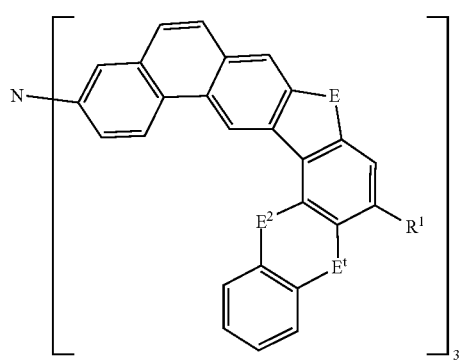
formula (32-2)
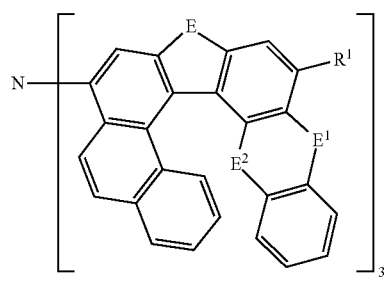
formula (33-2)
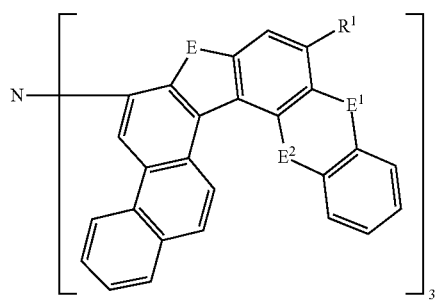

formula (34-2)
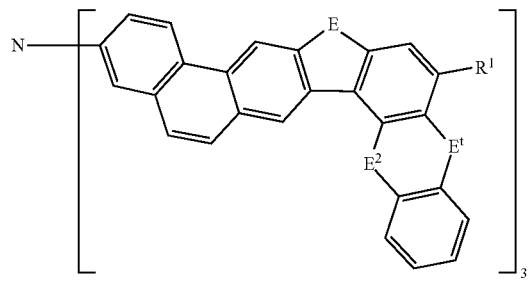

formula (35-2)
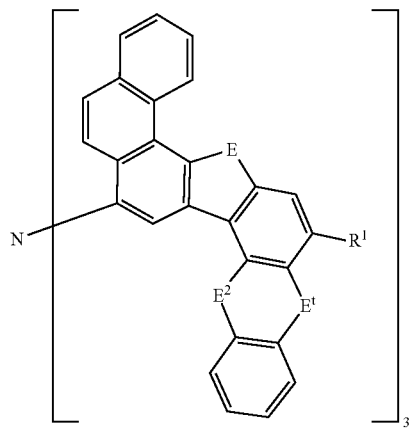

formula (36-2)
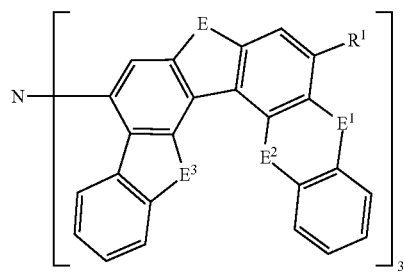

formula (37-2)
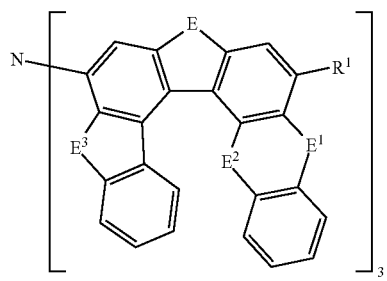

formula (38-2)
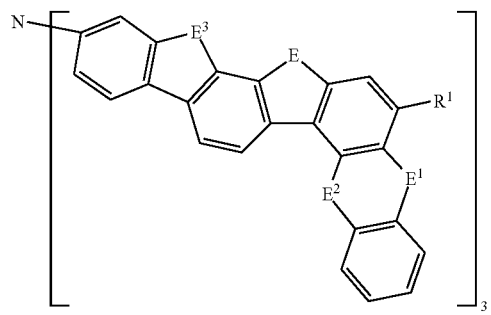

formula (39-2)
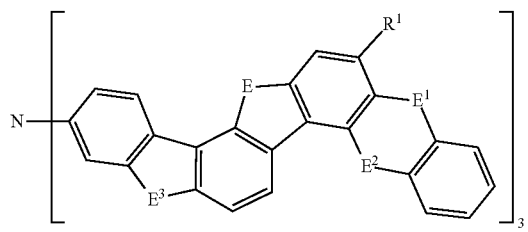

formula (40-2)
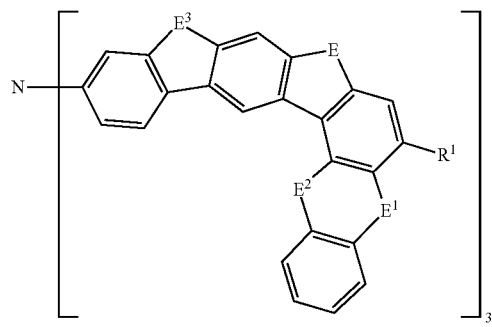

formula (41-2)
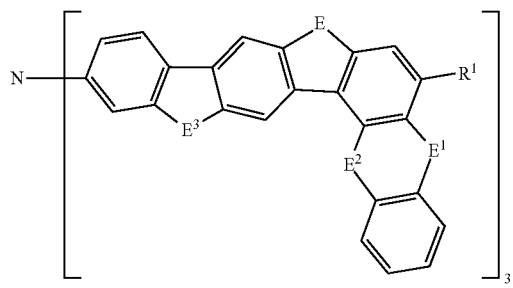

where the symbols X, $Ar^1$, E, E, $E^2$, $E^3$ and $R^1$ have the same meaning as above.

Preferably, $R^1$, $R^2$, $R^3$, $R^4$ stand on each occurrence, identically or differently, for:

H, D, F, $N(Ar)_2$, $Si(R)_3$; or a straight-chain alkyl or alkoxy groups having 1 to 20, preferably 1 to 10 C atoms or branched or a cyclic alkyl or alkoxy groups having 3 to 20, preferably 3 to 10 C atoms, each of which may be substituted by one or more radicals R, where in each case one or more non-adjacent $CH_2$ groups may be replaced by RC=CR, O or S and where one or more H atoms may be replaced by D or F; or an aromatic or heteroaromatic ring systems having 5 to 40, preferably 5 to 20 aromatic ring atoms, which may in each case be substituted by one or more radicals R; or for a group ArL as defined above, which may be substituted by one or more radicals R;

and where two adjacent substituents $R^1$ and $R^2$, two adjacent substituents $R^3$ and/or two adjacent substituents $R^4$, may form a mono- or polycyclic, aliphatic ring system or aromatic ring system, which may be substituted by one or more radicals R;

More preferably, $R^1$ and $R^2$ stand on each occurrence, identically or differently, for H, D, F, a straight-chain alkyl group having 1 to 10 C atoms or a branched or a cyclic alkyl group having 3 to 10 C atoms, each of which may be substituted by one or more radicals R, an aromatic or heteroaromatic ring systems having 5 to 18 aromatic ring atoms, which may in each case be substituted by one or more radicals R, or for a group ArL, which may be substituted by one or more radicals R, where ArL stands for a group of formula (ArL-1) as defined above.

In accordance with a preferred embodiment, the groups $R^1$ and $R^2$ are on each occurrence, identically or differently, selected from H, a straight-chain alkyl group having 1 to 10 C atoms, an aromatic or heteroaromatic ring systems having 5 to 18 aromatic ring atoms, which may in each case be substituted by one or more radicals R, or a group ArL of formula (ArL-1) as defined above.

In accordance with a very preferred embodiment, at least one of the groups $R^1$ and $R^2$ present in the same ring corresponds to a group ArL of formula (ArL-1) as defined above.

In accordance with a particularly preferred embodiment, the group $R^1$ corresponds to a group ArL of formula (ArL-1) as defined above.

In accordance with a preferred embodiment, $R^3$, $R^4$ stand on each occurrence, identically or differently, for H, D, F, a straight-chain alkyl group having 1 to 10 C atoms or branched or a cyclic alkyl having 3 to 10 C atoms, each of which may be substituted by one or more radicals R, where one or more H atoms may be replaced by D or F; or an aromatic or heteroaromatic ring systems having 5 to 18 aromatic ring atoms, which may in each case be substituted by one or more radicals R; where two adjacent substituents $R^3$ and/or two adjacent substituents $R^4$, may form a mono- or polycyclic, aliphatic ring system or aromatic ring system, which may be substituted by one or more radicals R.

In accordance with a preferred embodiment, R stands on each occurrence, identically or differently, for H, D, F, Cl, Br, I, CN, a straight-chain alkyl or alkoxy groups having 1 to 20, preferably 1 to 10 C atoms or branched or cyclic alkyl or alkoxy groups having 3 to 20, preferably 3 to 10 C atoms, each of which may be substituted by one or more radicals R', where one or more H atoms may be replaced by D or F, an aromatic or heteroaromatic ring systems having 5 to 40, preferably 5 to 20 aromatic ring atoms, which may in each case be substituted by one or more radicals R'. More preferably, R stands on each occurrence, identically or differently, for H, a straight-chain alkyl having 1 to 10 C atoms or branched or cyclic alkyl group having 3 to 10 C atoms, each of which may be substituted by one or more radicals R', an aromatic or heteroaromatic ring systems having 5 to 18 aromatic ring atoms, which may in each case be substituted by one or more radicals R'.

In accordance with a preferred embodiment, R stands on each occurrence, identically or differently, for H, D, F, Cl, Br, I, CN, a straight-chain alkyl group having 1 to 10 C atoms or branched or cyclic alkyl group having 3 to 10 C atoms, or an aromatic or heteroaromatic ring system having 5 to 18 C atoms.

In accordance with a preferred embodiment, the groups $E^1$, $E^2$ are, identically or differently, on each occurrence, selected from the group consisting of a single bond, —O— and —S—; with the proviso that, in a ring comprising the groups $E^1$ and $E^2$, one of the group $E^1$ and $E^2$ is a single bond, and the other group is O or S. Very preferably, in a ring comprising the groups $E^1$ and $E^2$, $E^1$ is O and $E^2$ is a single bond or $E^1$ is a single bond and $E^2$ is O.

In accordance with a preferred embodiment, the group E is on each occurrence, identically or differently, selected from —C(R⁰)$_2$—, —Si(R⁰)$_2$—, —O—, —S—, —N(R⁰)—; or E is a group of formula (E-1),

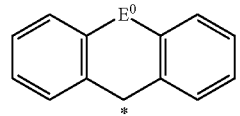

formula (E-1)

where the symbol * in formula (E-1) indicates the corresponding group E in formula (1) and where E⁰ has the same meaning as above.

In accordance with a very preferred embodiment, the group E stands for C(R⁰)$_2$—.

In accordance with another very preferred embodiment, the group E stands for a group of formula (E-1) where, E⁰ stands for a single bond or —C(R⁰)$_2$—.

In accordance with the invention, the group ArL stands for a group of the following formula (ArL-1),

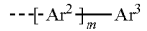

formula (ArL-1)

where the dashed bond in formula (ArL-1) indicates the bonding to the structure of formula (1).

Preferably, m is an integer selected from 1 to 6, very preferably from 1 to 4.

In formula (ArL-1), it is preferred that the group Ar² is selected from the groups of formulae (Ar2-1) to (Ar2-25),

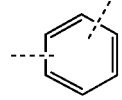

(Ar2-1)

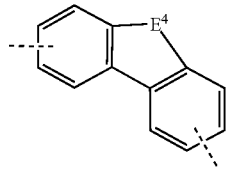

(Ar2-2)

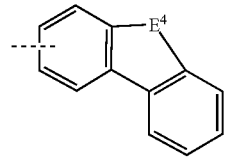

(Ar2-3)

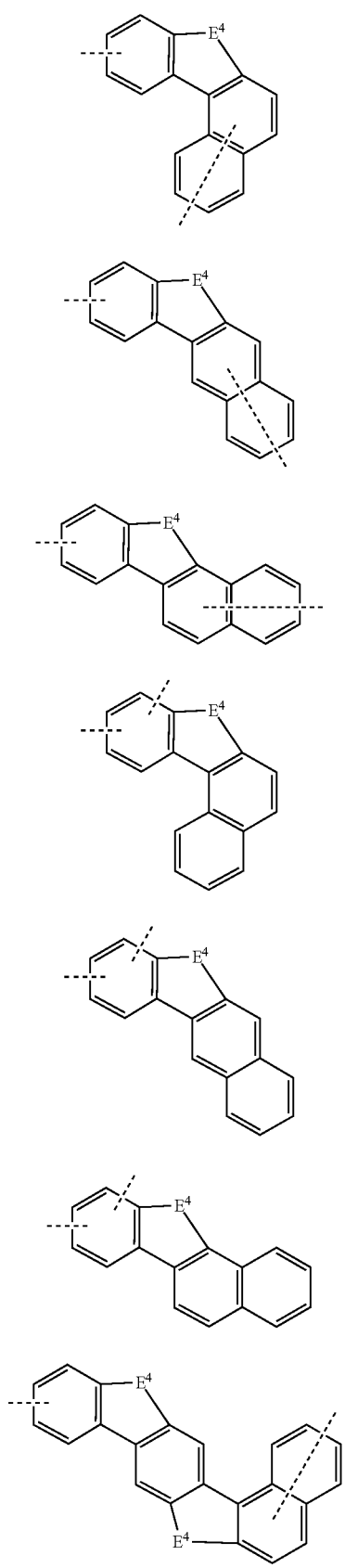
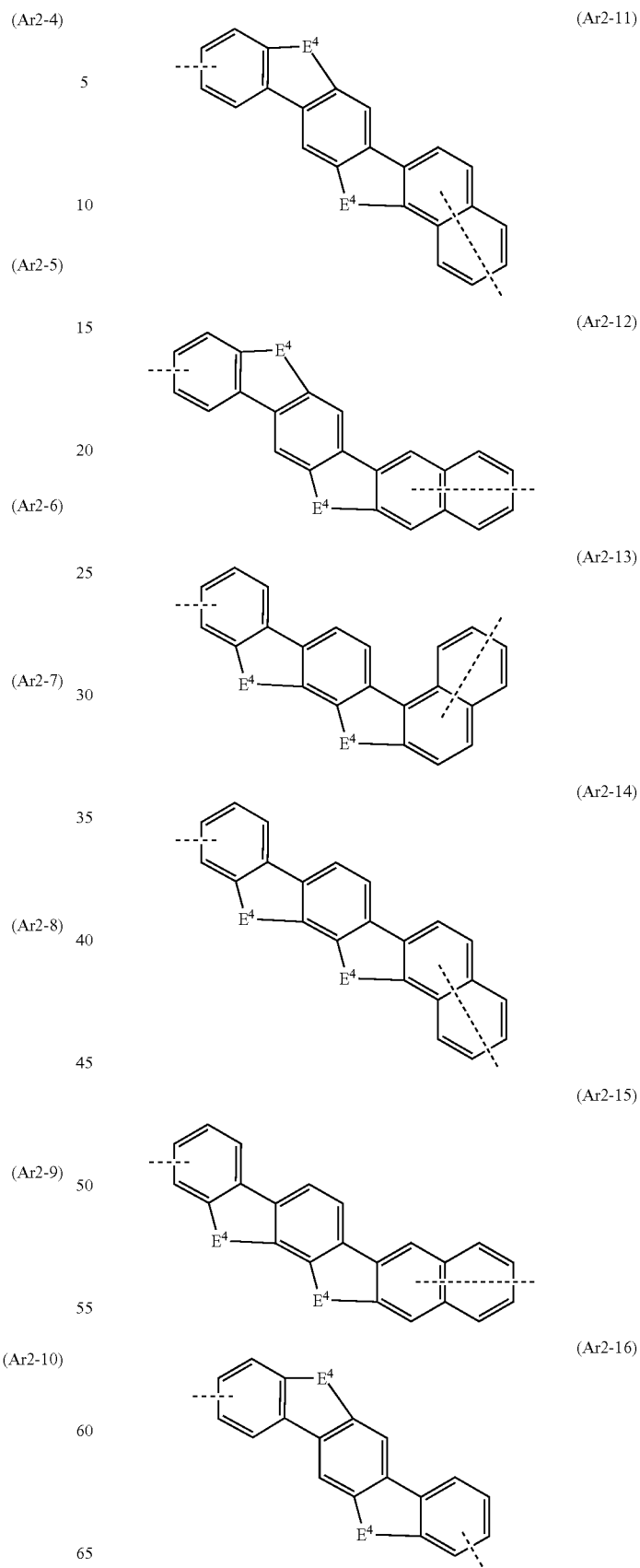

(Ar2-17) 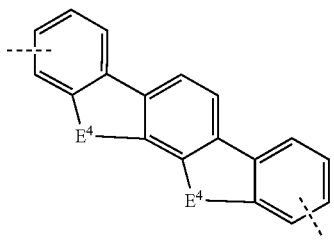

(Ar2-18) 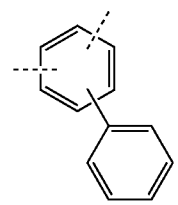

(Ar2-19) 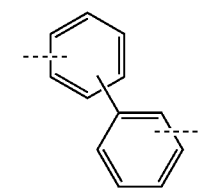

(Ar2-20) 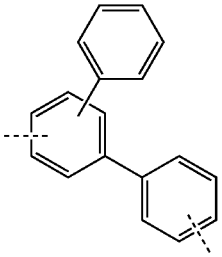

(Ar2-21) 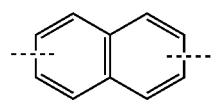

(Ar2-22) 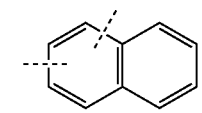

(Ar2-23) 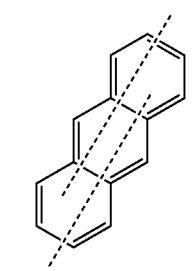

(Ar2-24) 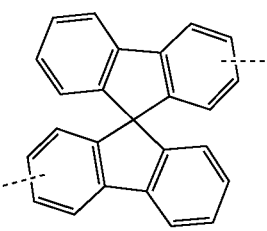

(Ar2-25) 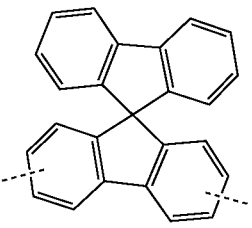

where the dashed bonds indicate the bonding to the structure of formula (1) and to a group $Ar^2$ or $Ar^3$ and the groups of formulae (Ar2-1) to (Ar2-25) may be substituted at each free position by a group R, which has the same meaning as above and where $E^4$ is selected from —B($R^0$)—, —C($R^0$)$_2$—, —C($R^0$)$_2$—C($R^0$)$_2$—, —Si($R^0$)$_2$—, —C(=O)—, —C(=N$R^0$)—, —C=(C($R^0$))$_2$—, —O—, —S—, —S(=O)—, —SO$_2$—, —N($R^0$)—, —P($R^0$)— and —P((=O)$R^0$)—, where the substituent $R^0$ has the same meaning as above.

Preferably, $E^4$ is selected from —C($R^0$)$_2$—, —Si($R^0$)$_2$, —O—, —S— or —N($R^0$)—, where the substituent $R^0$ has the same meaning as above Among formulae (Ar2-1) to (Ar2-25), following formulae are preferred: (Ar2-1), (Ar2-2), (Ar2-3), (Ar2-18), (Ar2-19), (Ar2-20), (Ar2-21), (Ar2-22) and (Ar2-25).

Furthermore, in formula (ArL-1), it is preferred that $Ar^3$ is on each occurrence, identically or differently, selected from the group consisting of the groups of formulae (Ar3-1) to (Ar3-27), (Ar3-1) 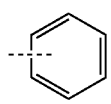

(Ar3-2) 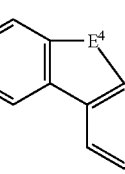

(Ar3-3) 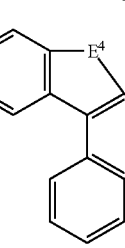

(Ar3-4) 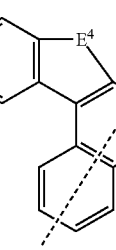

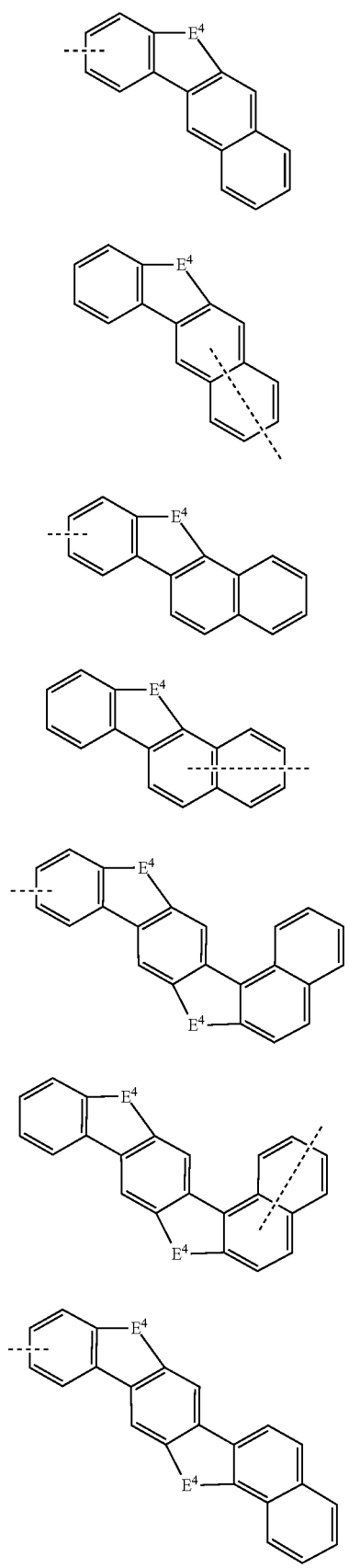
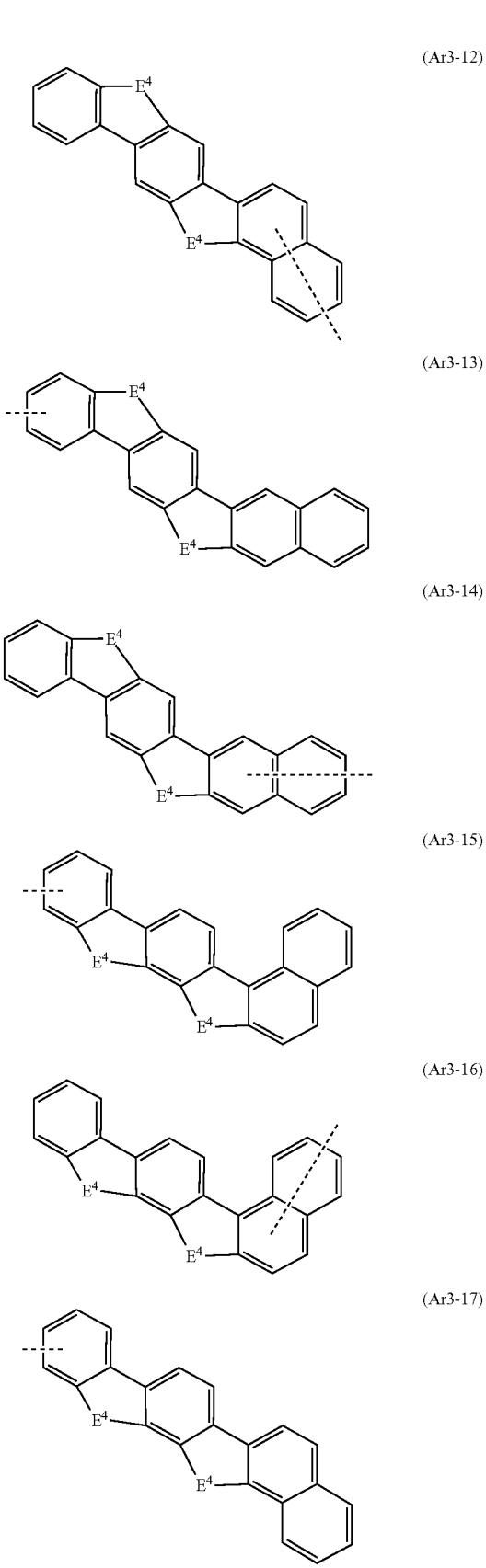

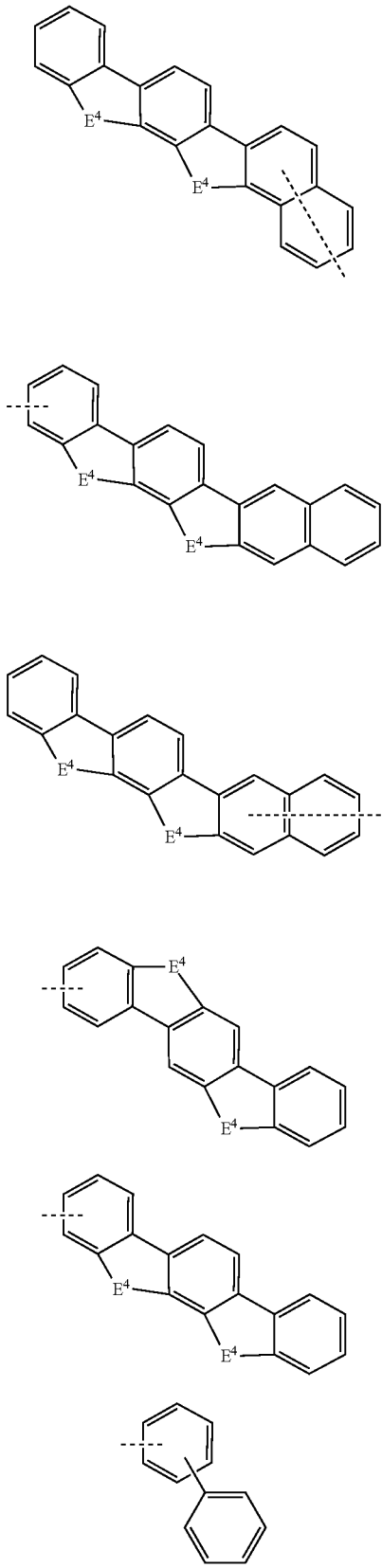

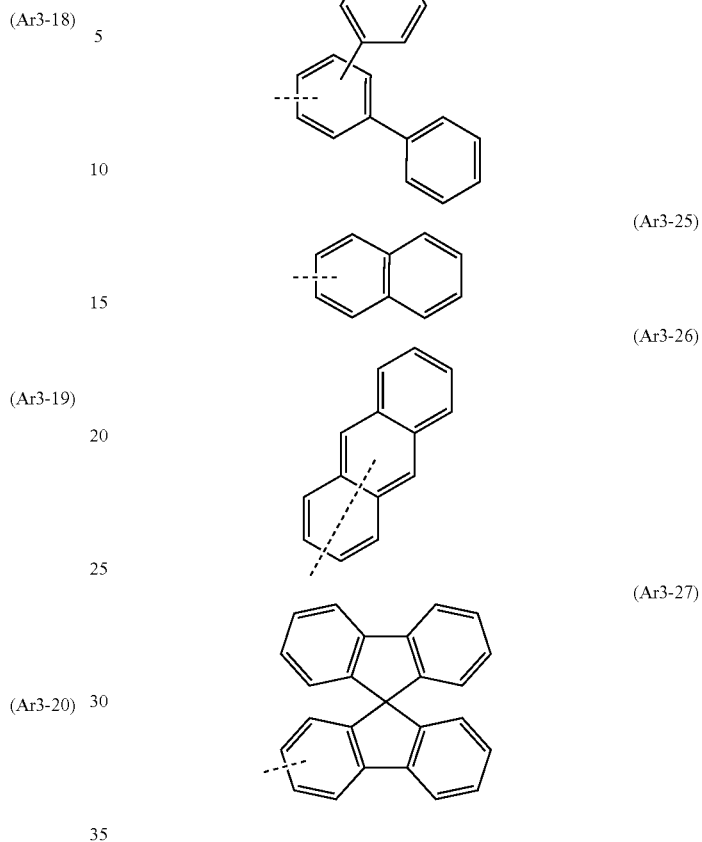

where the dashed bond indicates the bonding to Ar² and where E⁴ has the same meaning as above and the groups of formulae (Ar3-1) to (Ar3-27) may be substituted at each free position by a group R, which has the same meaning as above.

Among formulae (Ar3-1) to (Ar2-27), following formulae are preferred: (Ar3-1), (Ar3-2), (Ar3-23), (Ar3-24), (Ar3-25) and (Ar3-27).

In accordance with a preferred embodiment at least one group Ar² stands for a group of formula (Ar2-2) and/or at least one group Ar³ stands for a group of formula (Ar3-2),

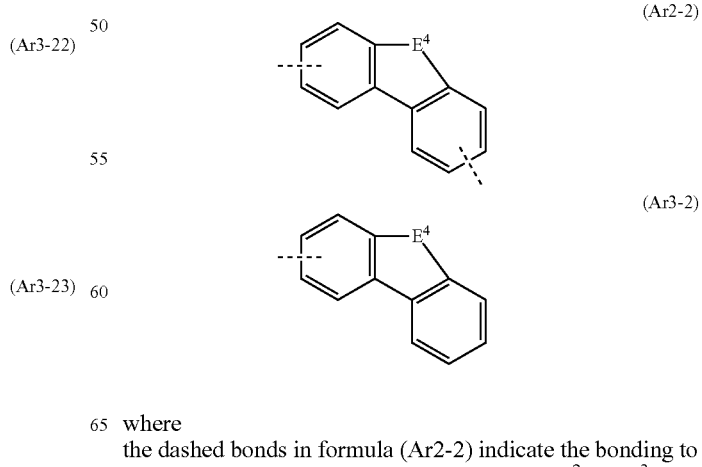

where
the dashed bonds in formula (Ar2-2) indicate the bonding to the structure of formula (1) and to a group Ar² or Ar³; and the dashed bond in formula (Ar3-2) indicates the bonding to Ar²; and E⁴ has the same meaning as in above; and the groups of formulae (Ar2-2) and (Ar3-2) may be substituted at each free position by a group R, which has the same meaning as above.

In accordance with a very preferred embodiment, at least one group Ar² stands for a group of formula (Ar2-2-1) and/or at least one group Ar³ stands for a group of formula (Ar3-2-1),

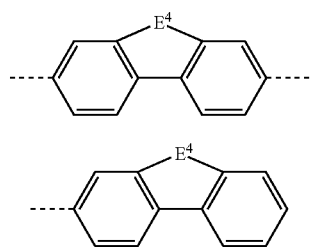

where
the dashed bonds in formula (Ar2-2-1) indicate the bonding to the structure of formula (1) and to a group Ar² or Ar³;
the dashed bond in formula (Ar3-2-1) indicates the bonding to Ar²;
E⁴ has the same meaning as above; and
the groups of formulae (Ar2-2-1) and (Ar3-2-1) may be substituted at each free position by a group R, which has the same meaning as above.

In accordance with a particularly preferred embodiment, at least one group Ar² stands for a group of formula (Ar2-2-1 b) and/or at least one group Ar³ stands for a group of formula (Ar3-2-1 b),

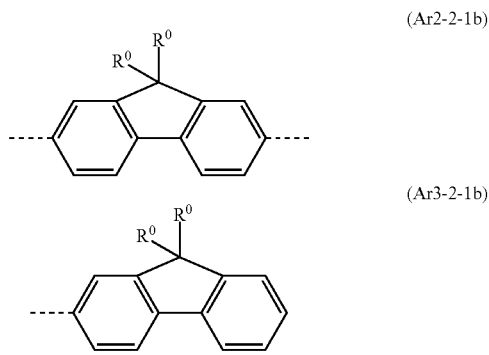

where
the dashed bonds in formula (Ar2-2-1b) indicate the bonding to the structure of formula (1) and to a group Ar² or Ar³;
the dashed bond in formula (Ar3-2-1b) indicates the bonding to Ar²; R⁰ has the same meaning as above; and
the groups of formulae (Ar2-2-1 b) and (Ar3-2-1 b) may be substituted at each free position by a group R, which has the same meaning as above.

The following compounds are examples of compounds of formula (1):

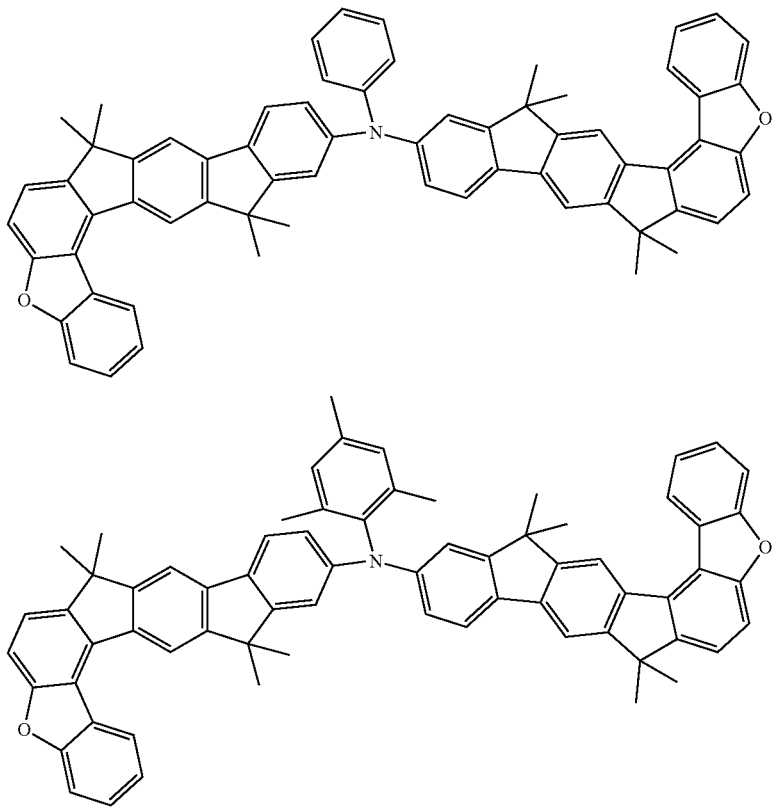

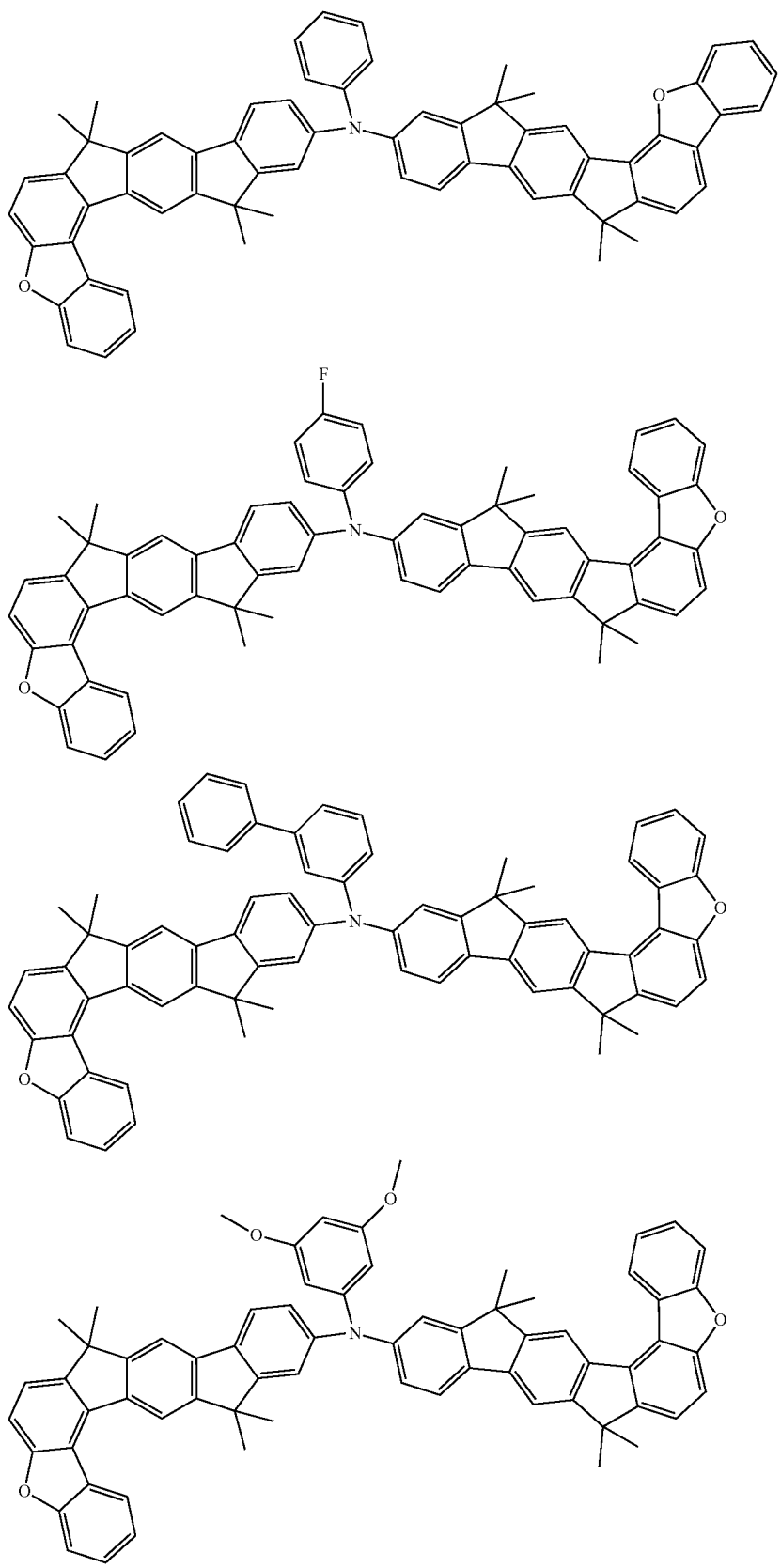

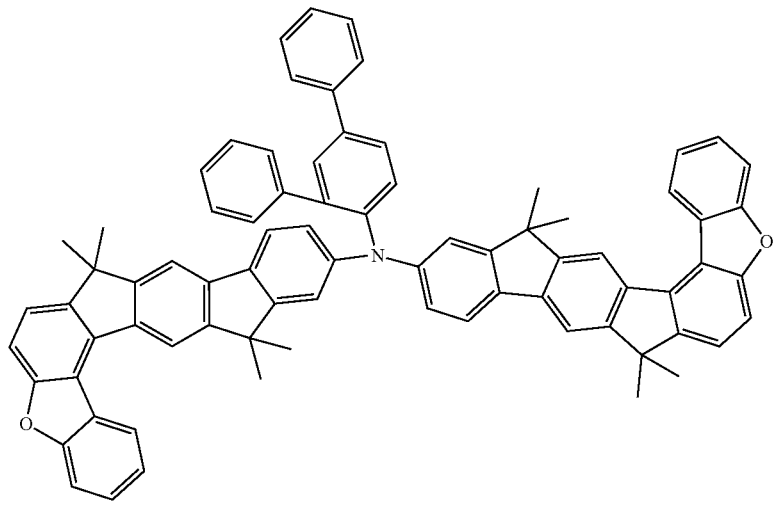
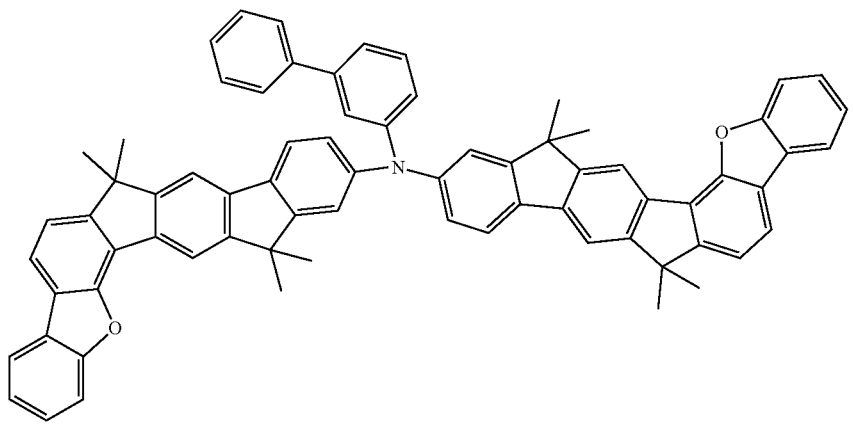
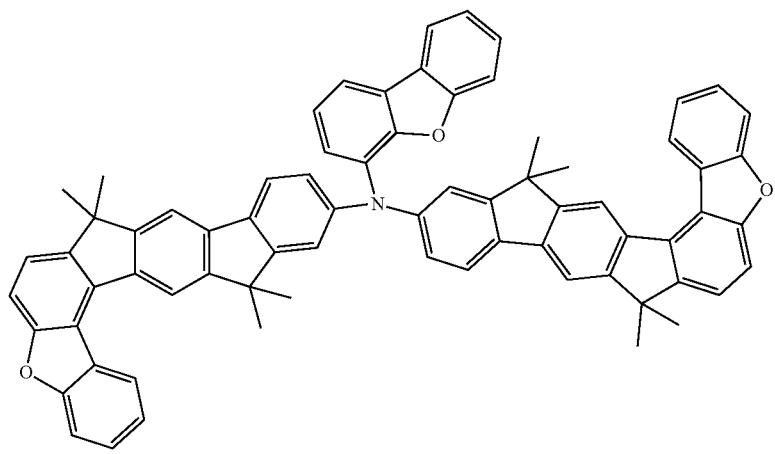

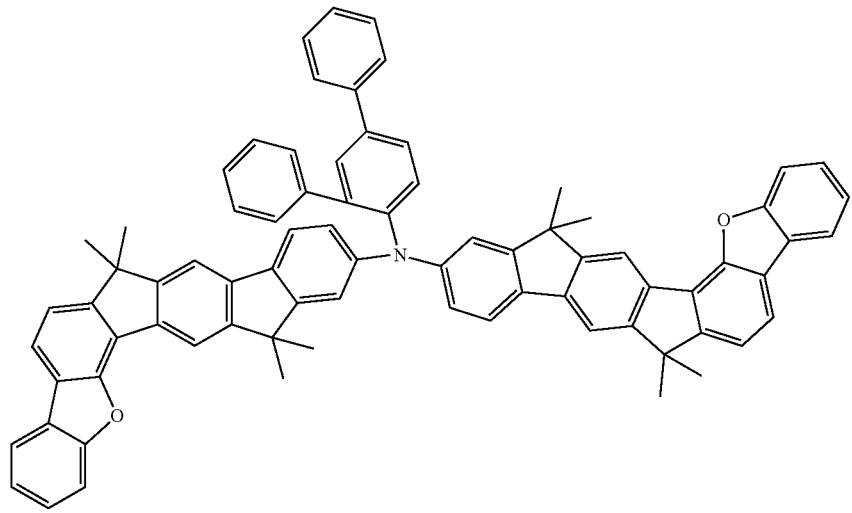
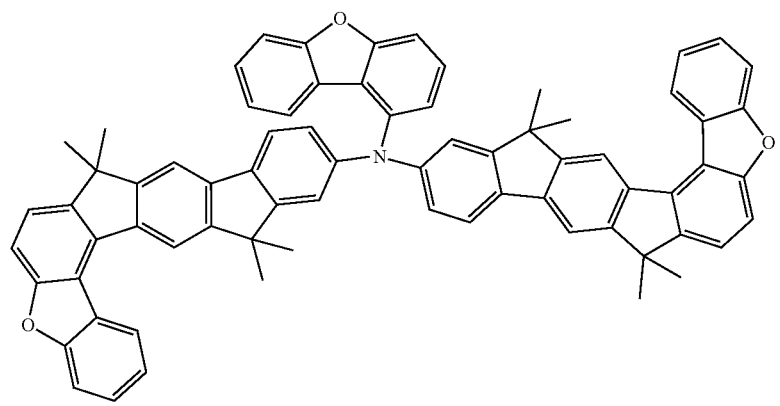
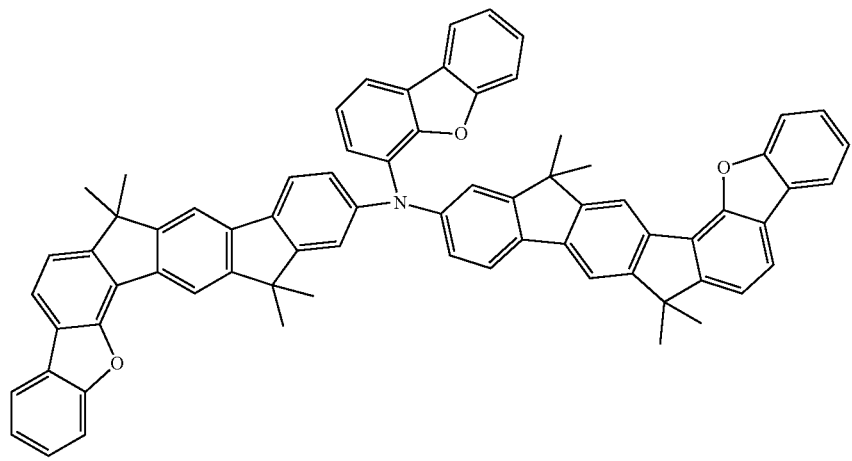

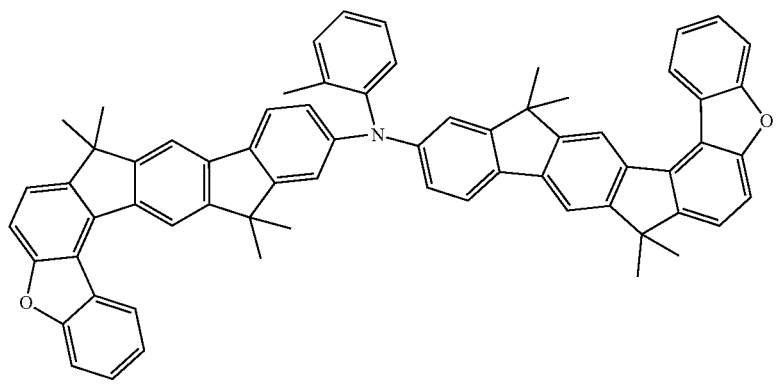
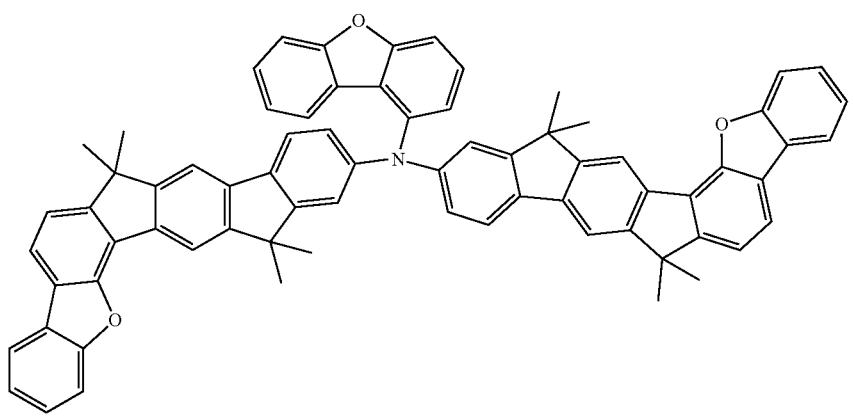
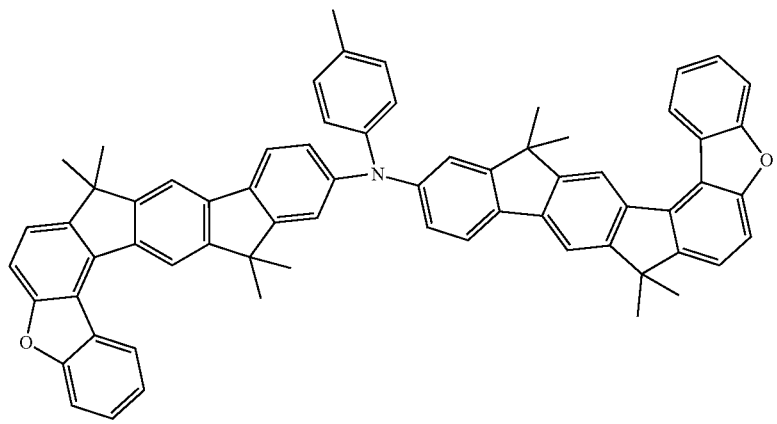
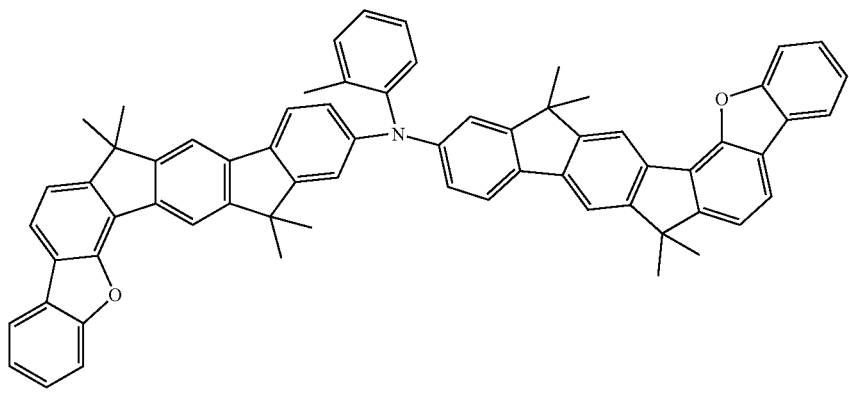

-continued
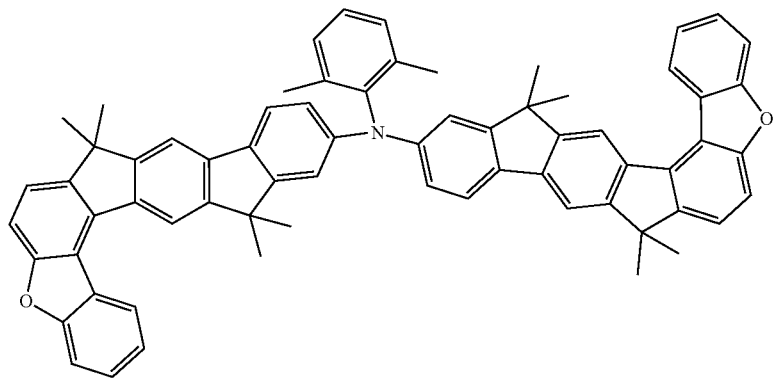
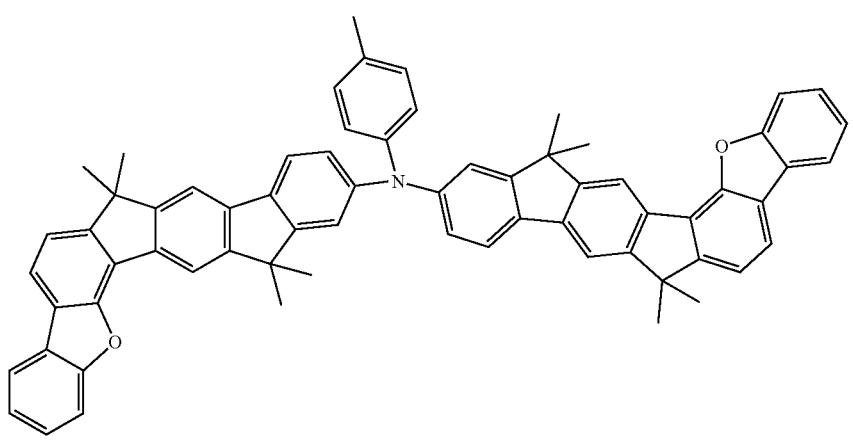
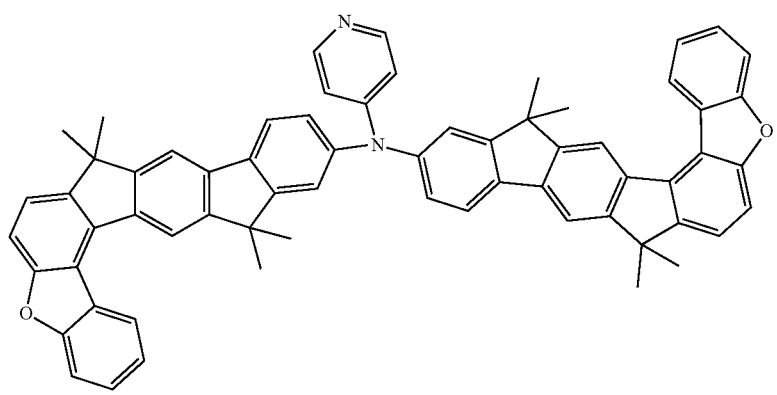
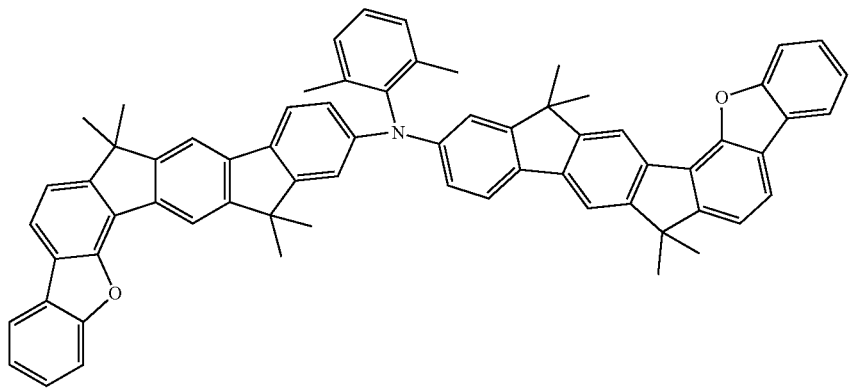

-continued
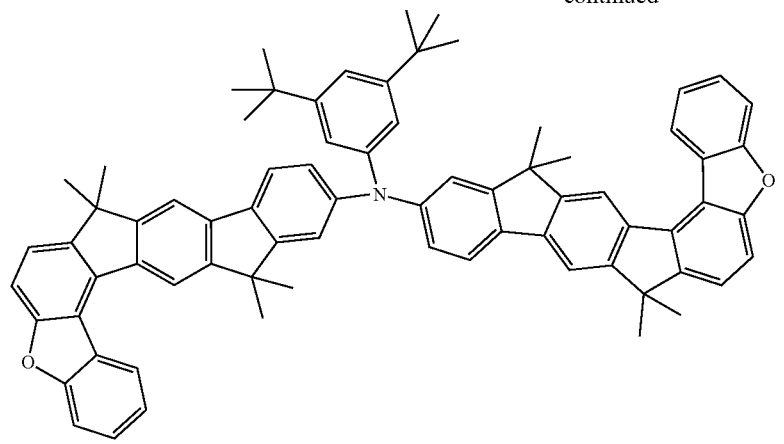
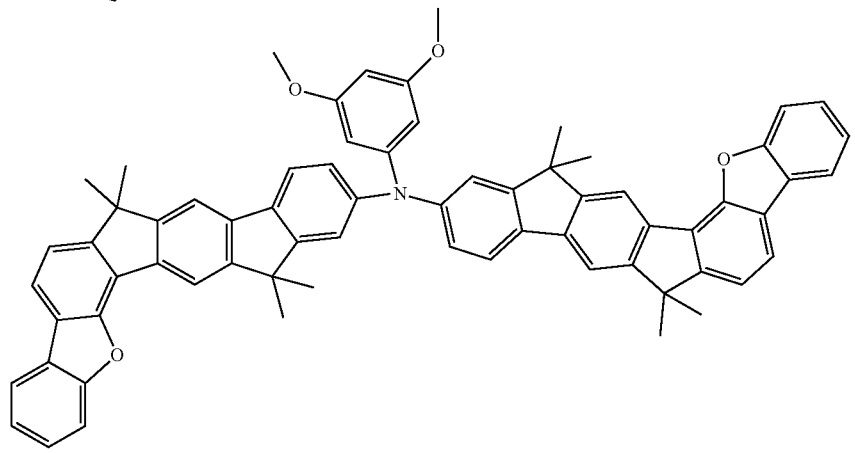
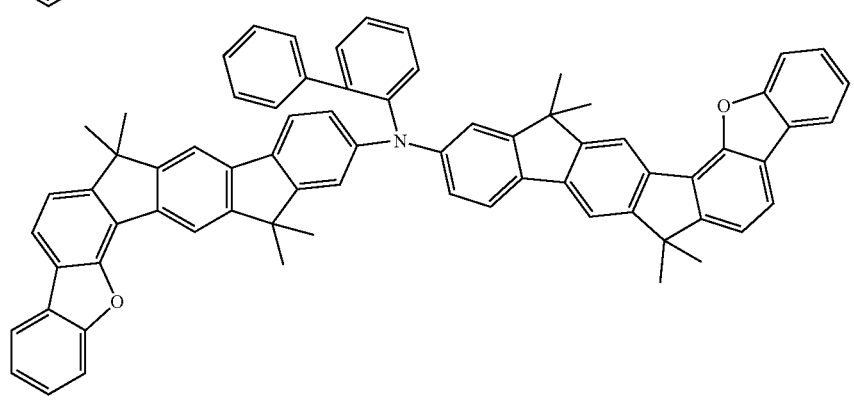
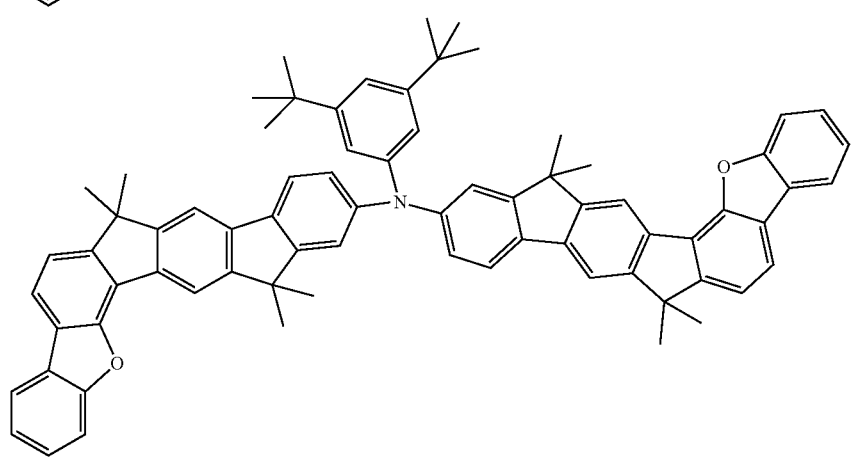

-continued
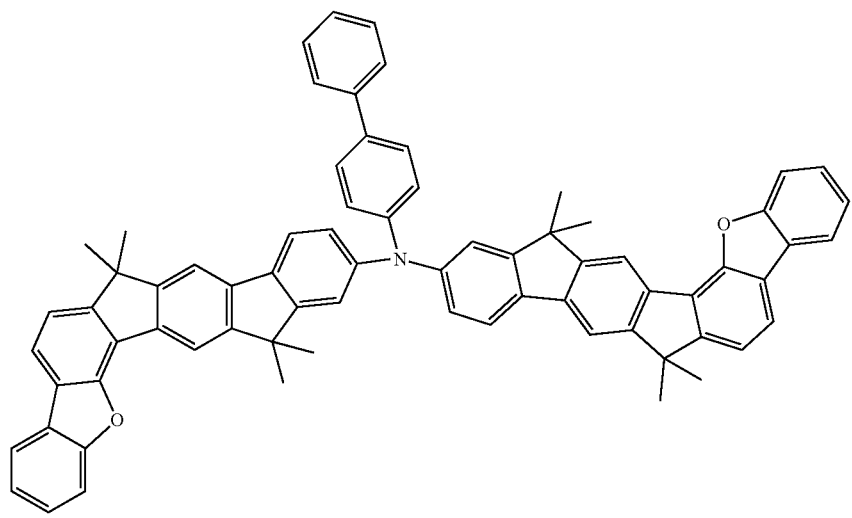
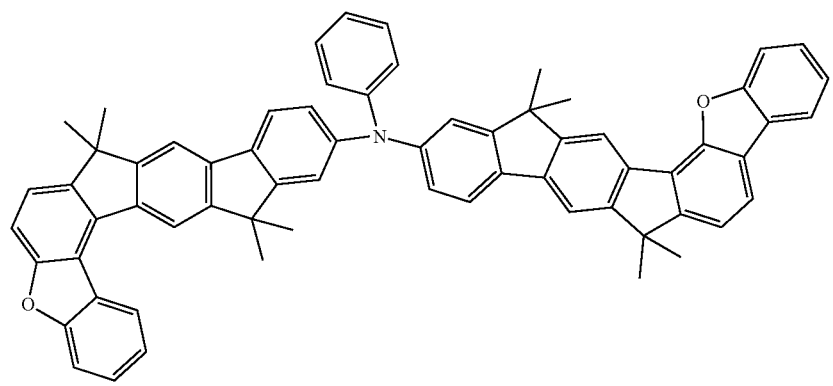
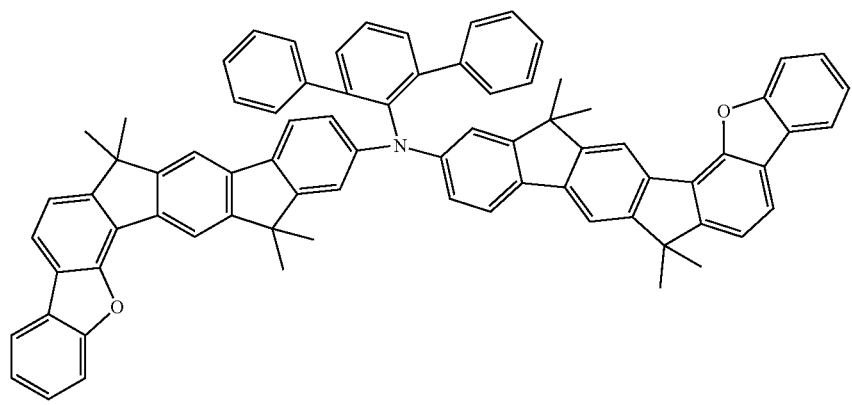
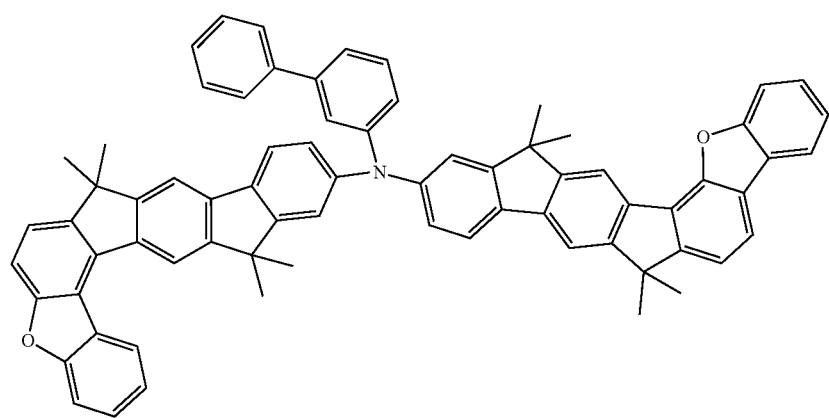

-continued
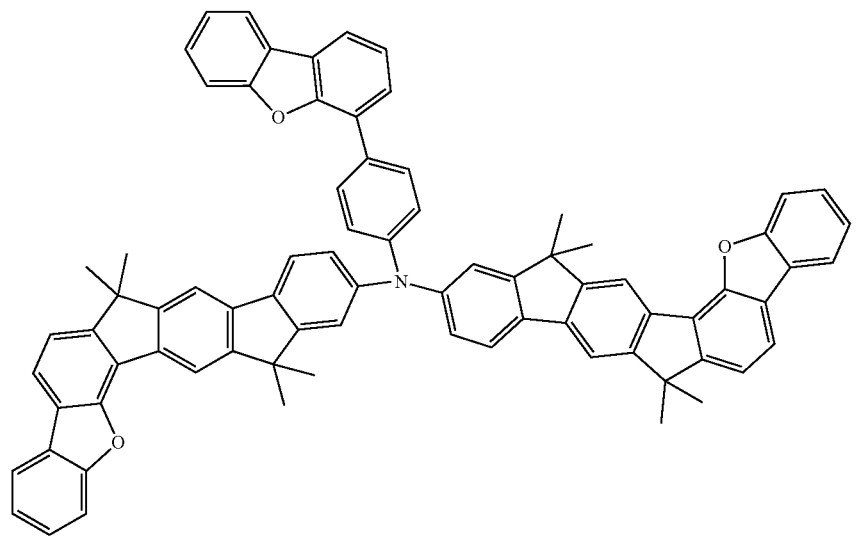
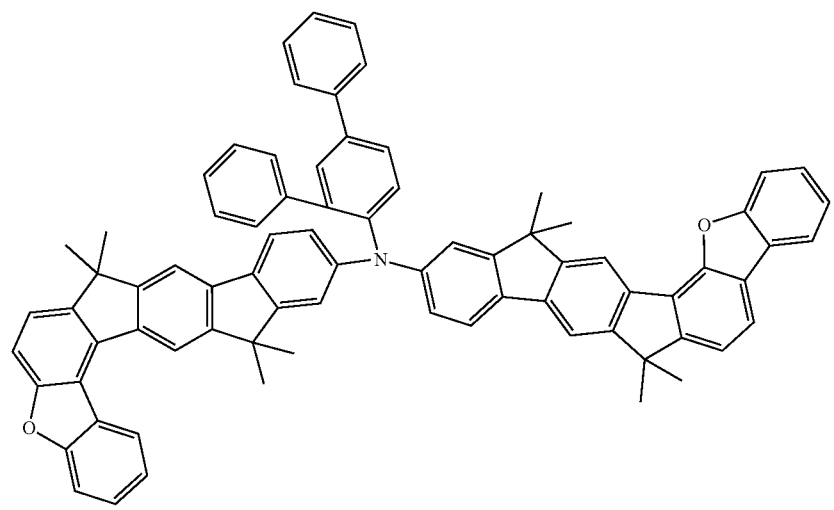
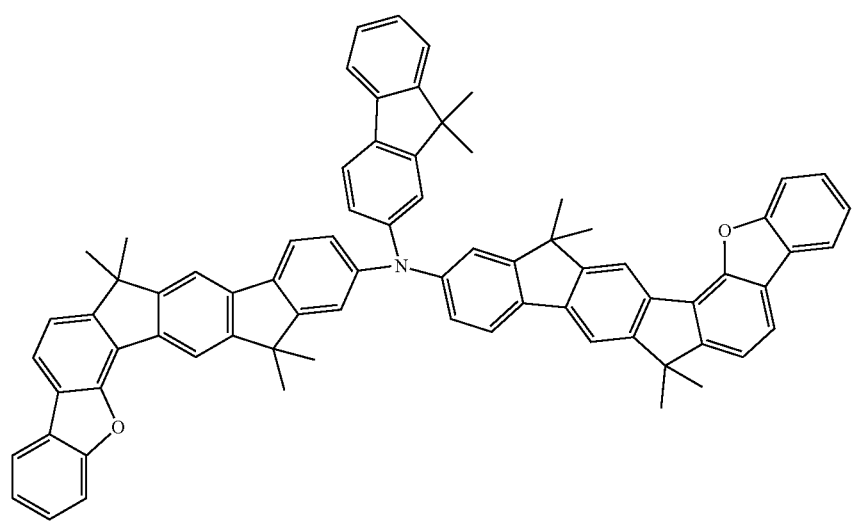

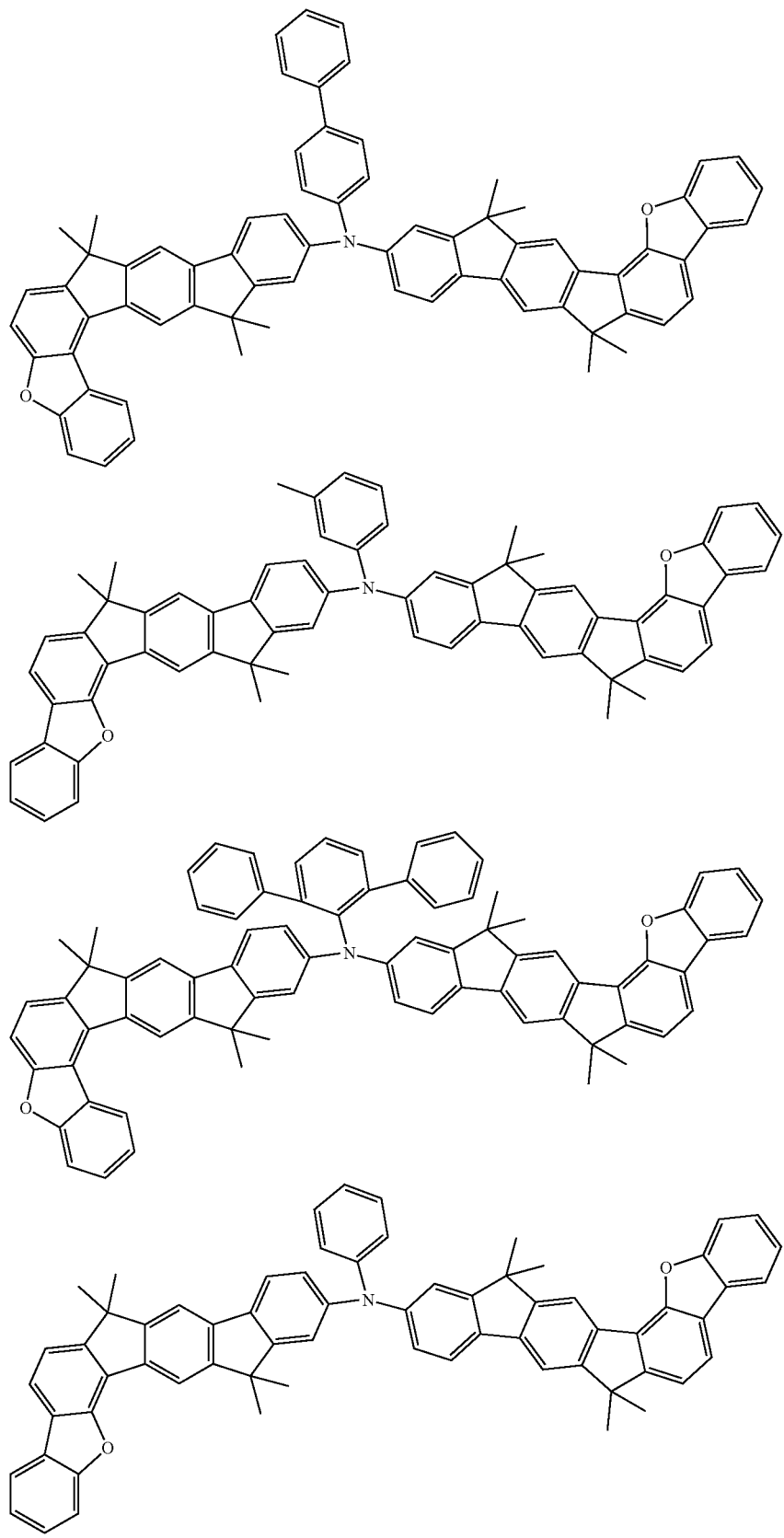

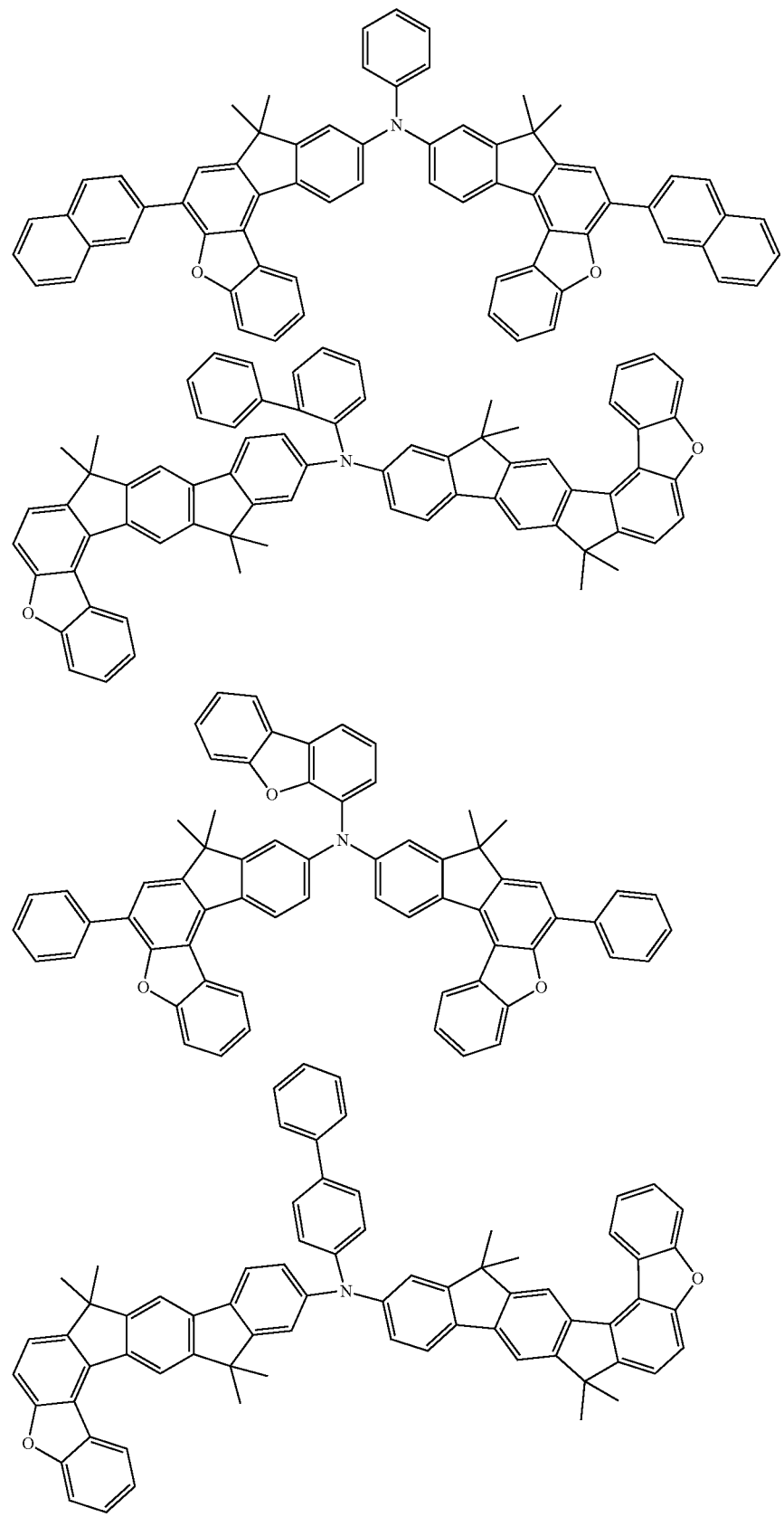

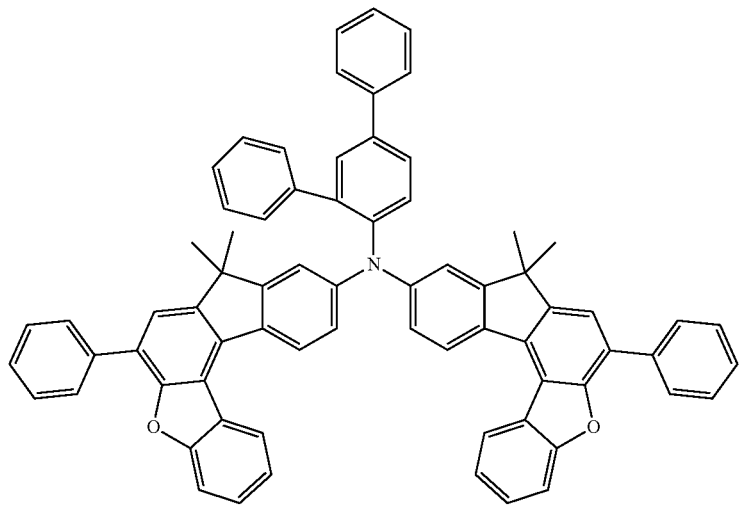
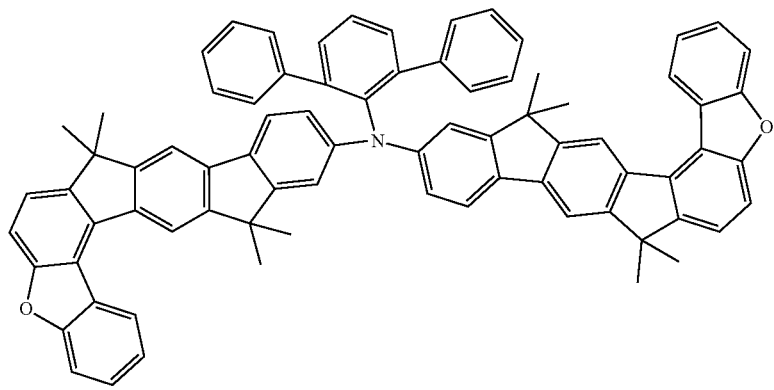
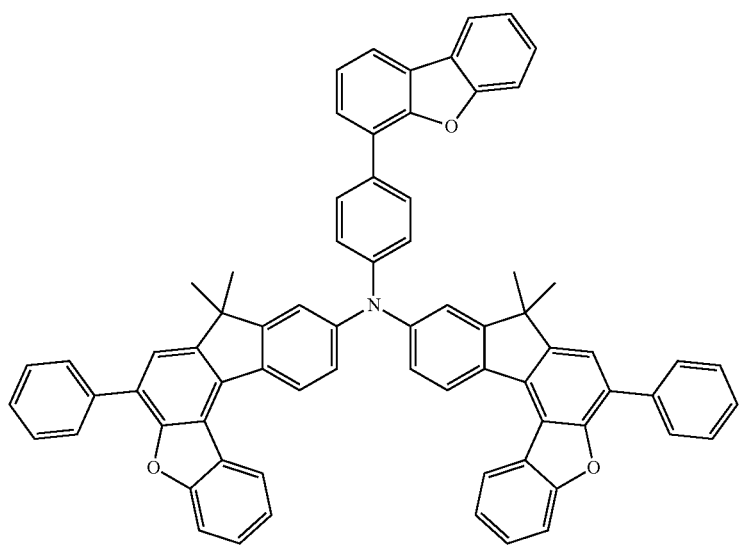

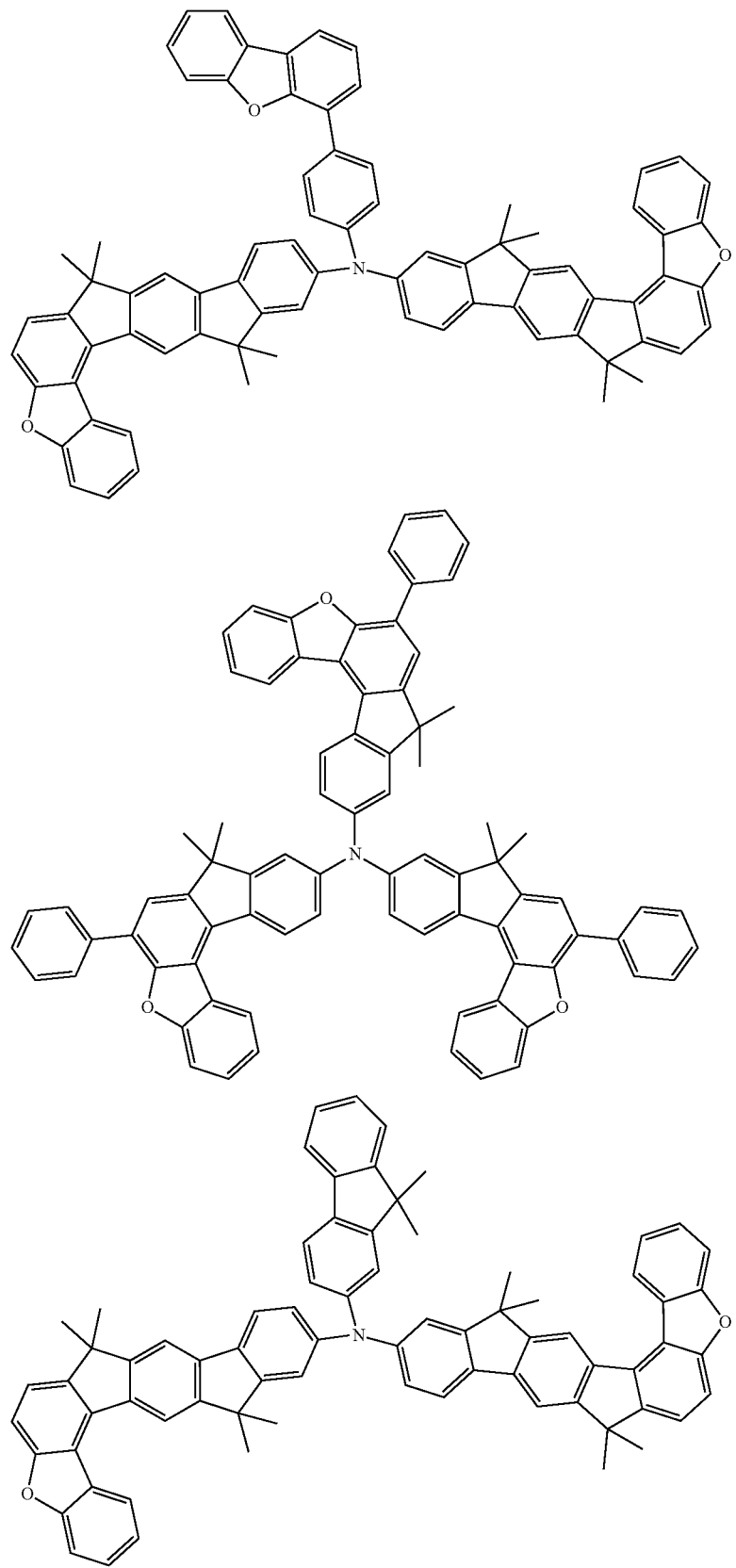

-continued
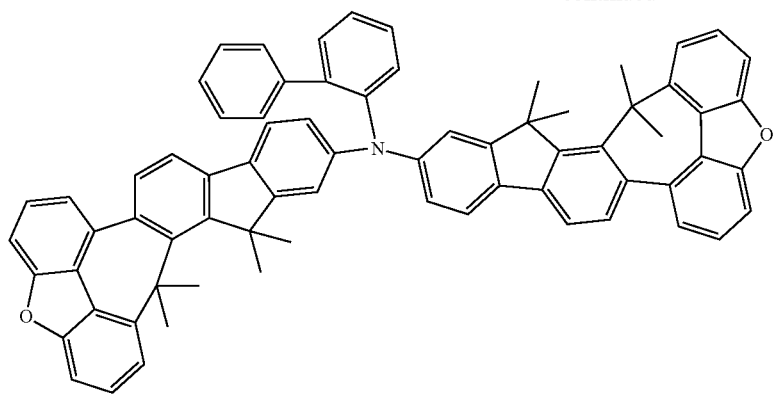
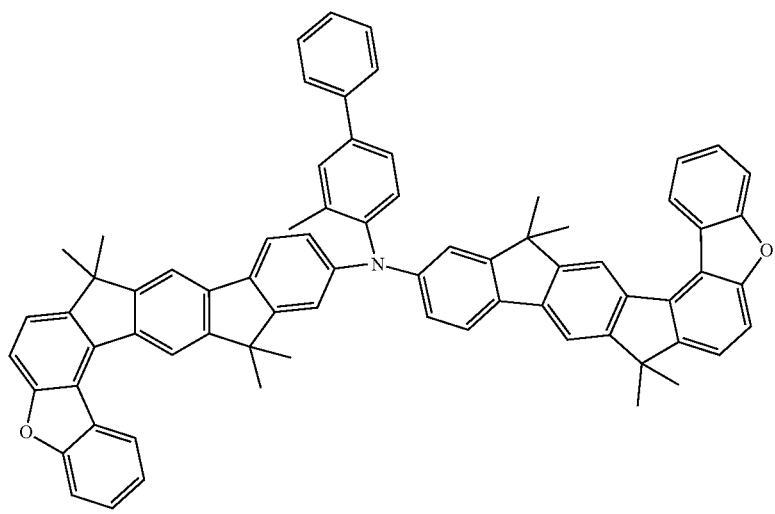
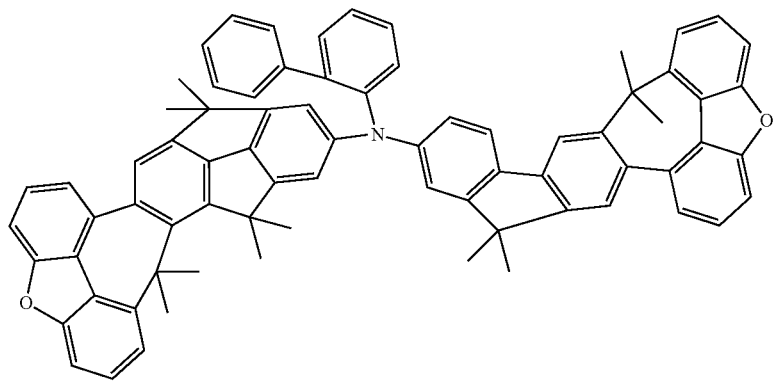
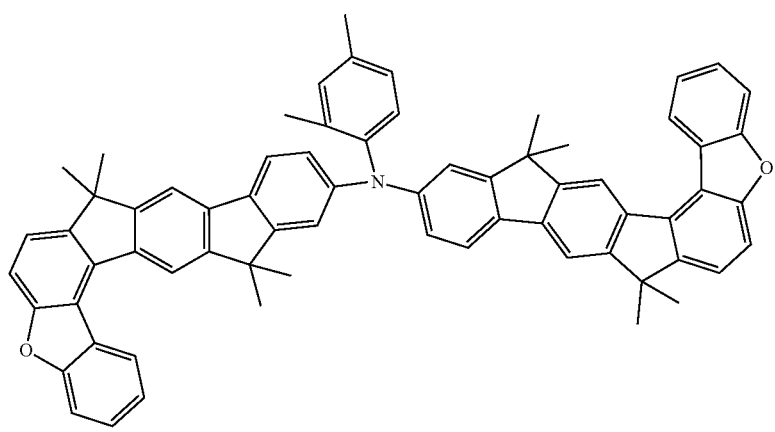

-continued
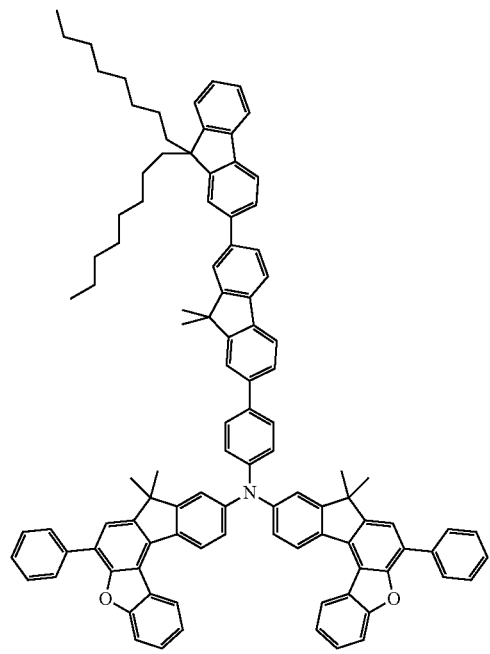
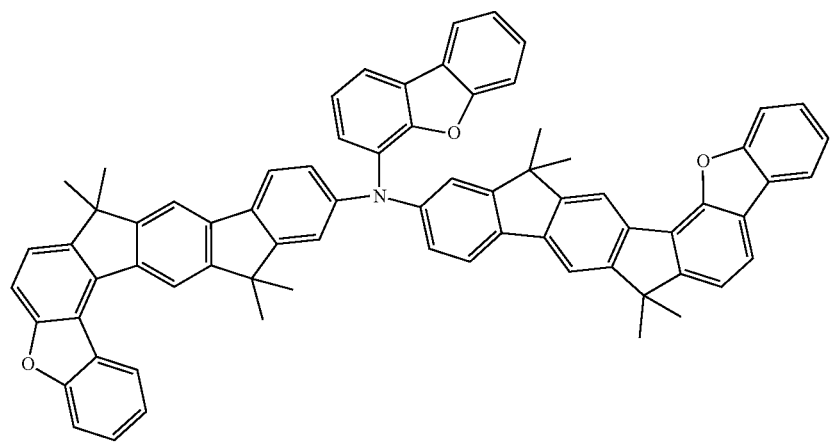
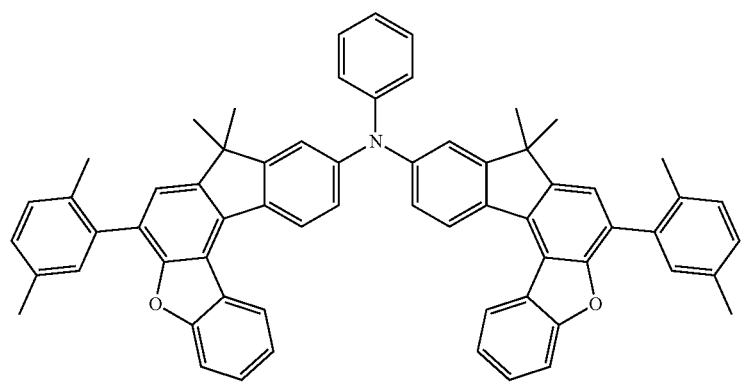

-continued
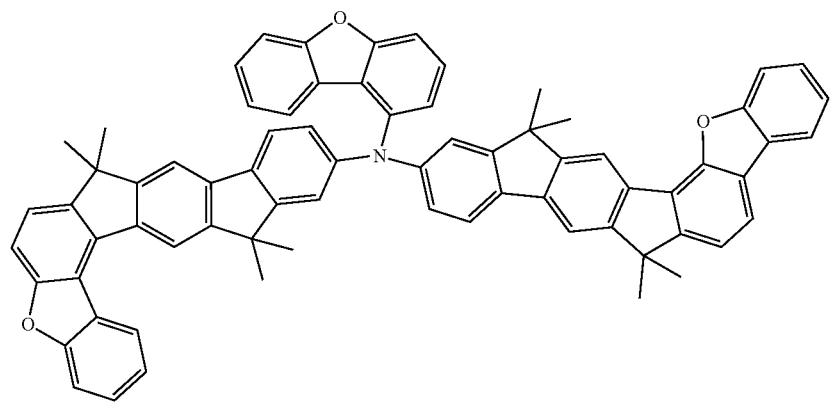
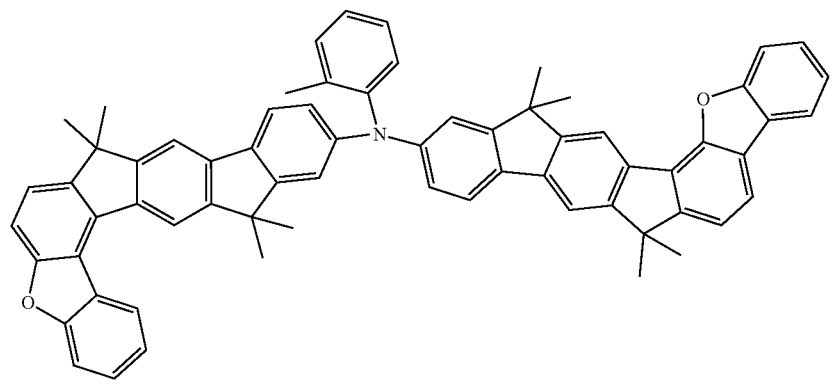
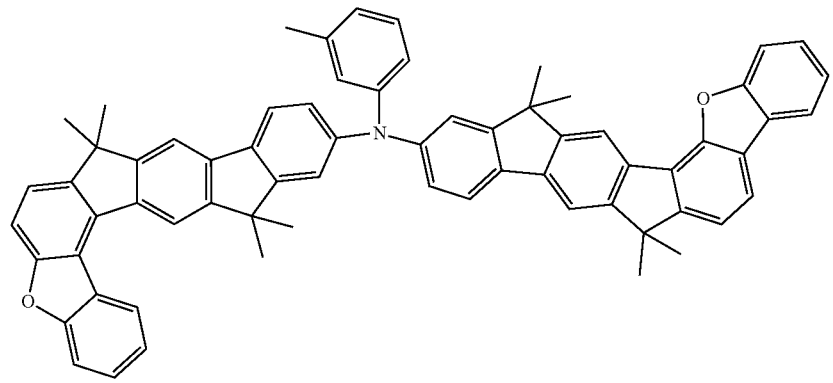
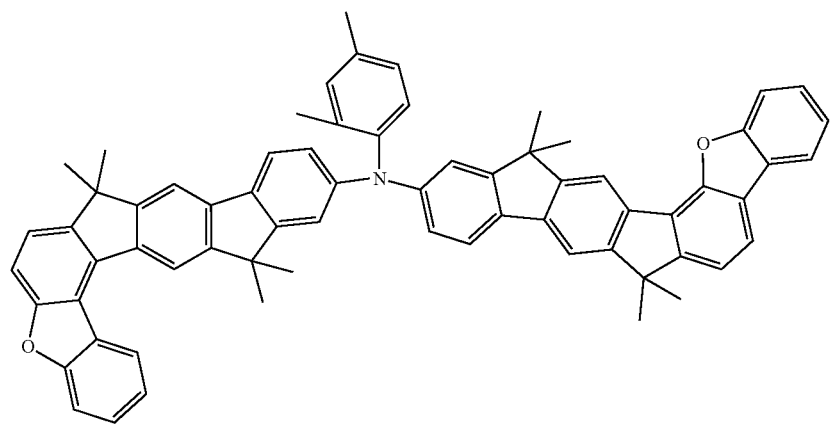

-continued
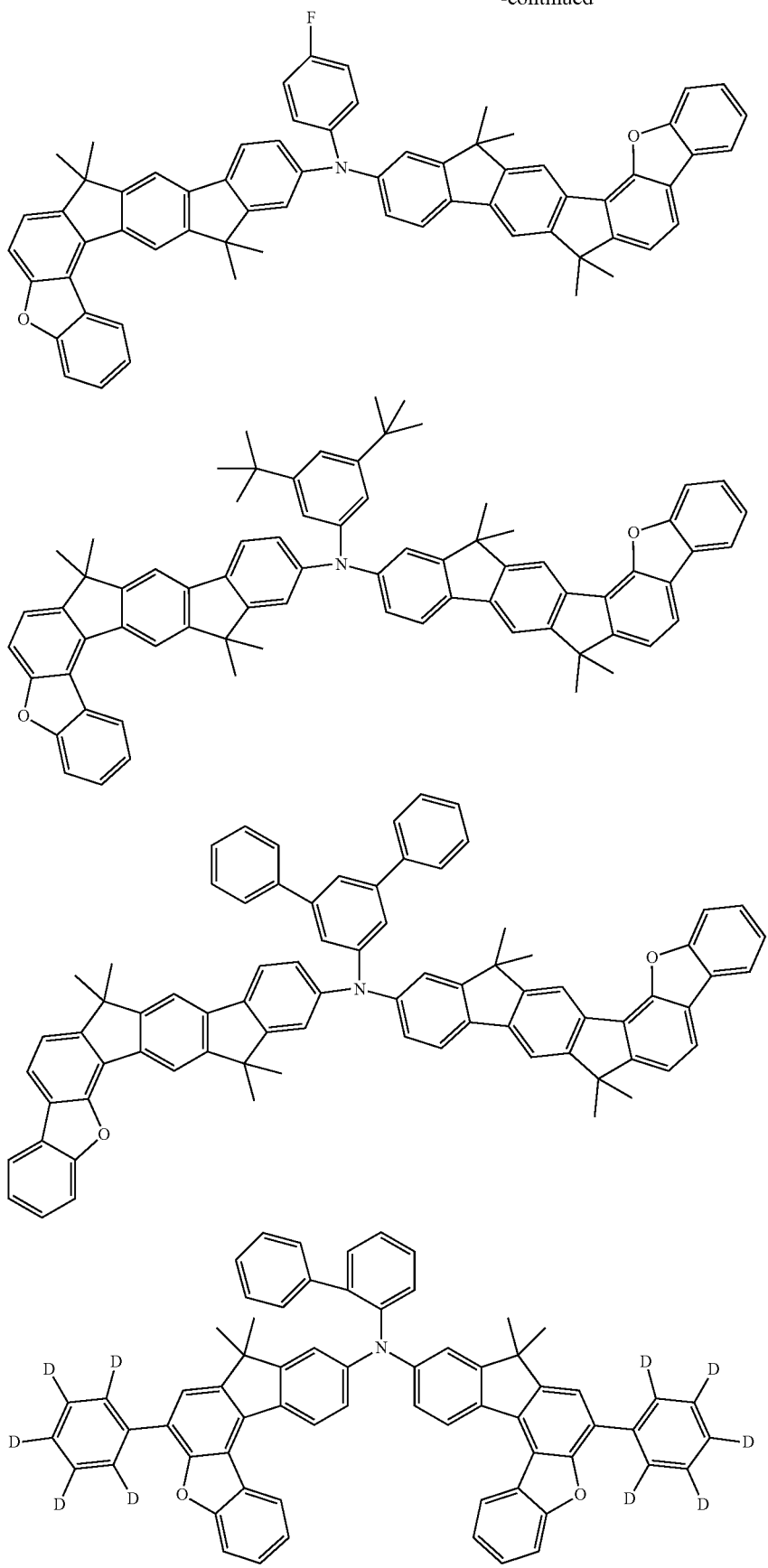

-continued
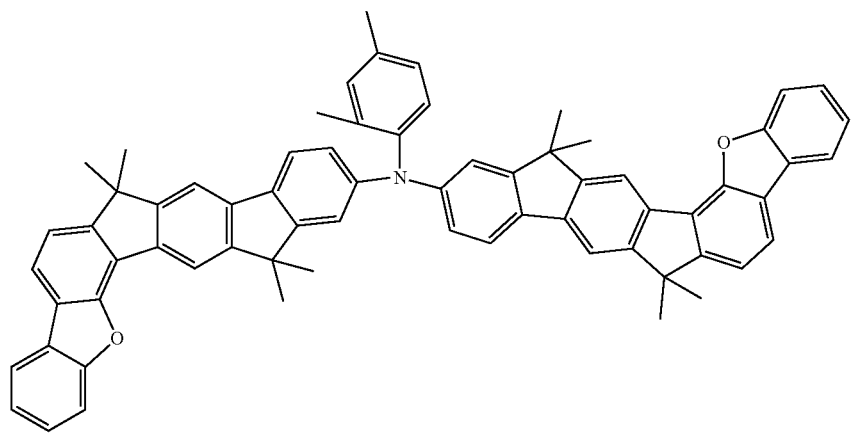
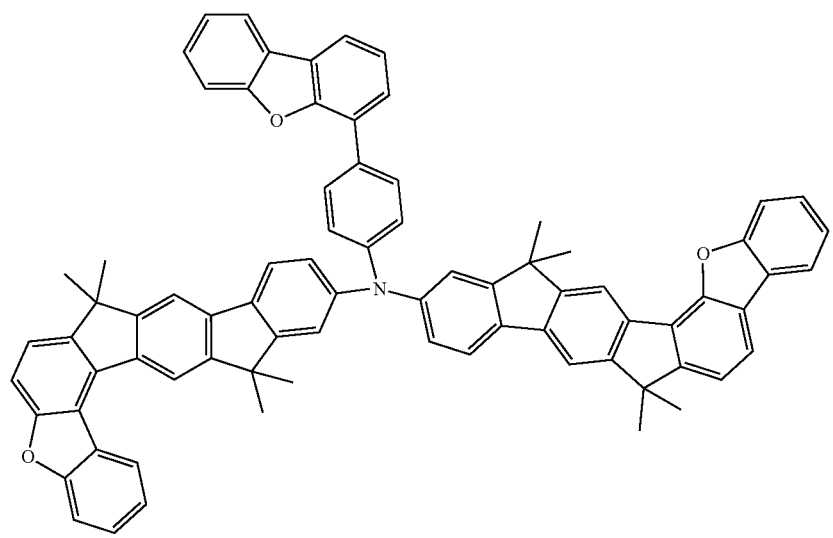
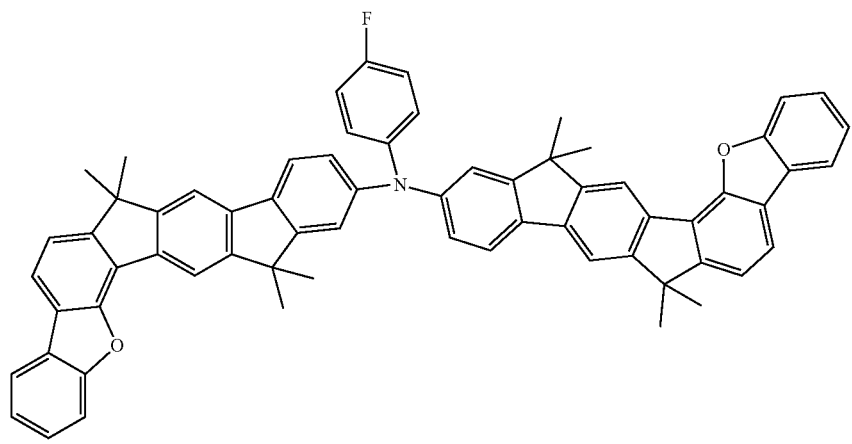

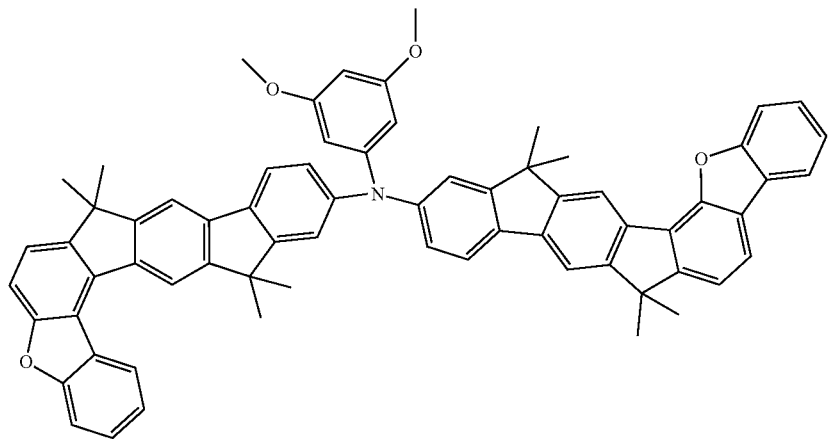
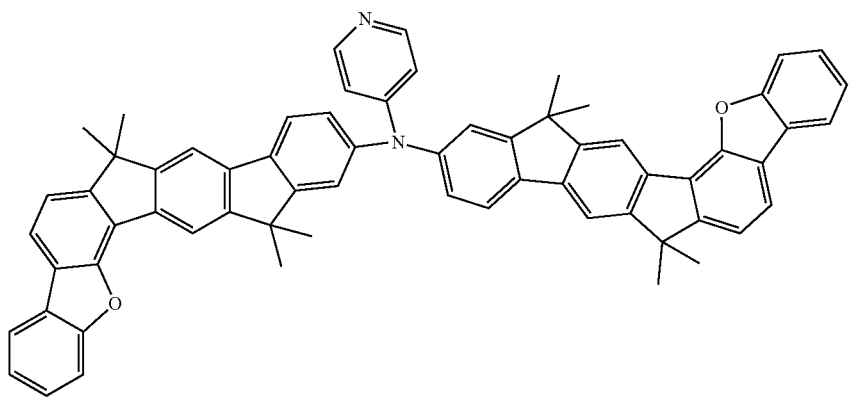
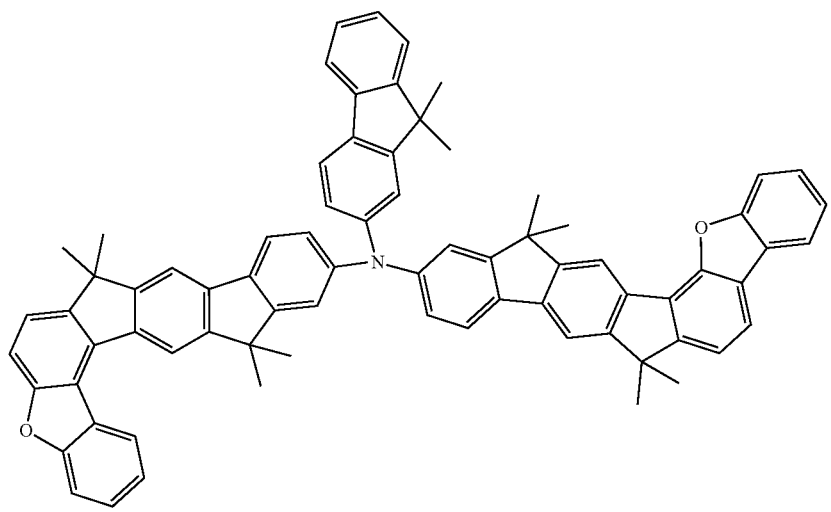

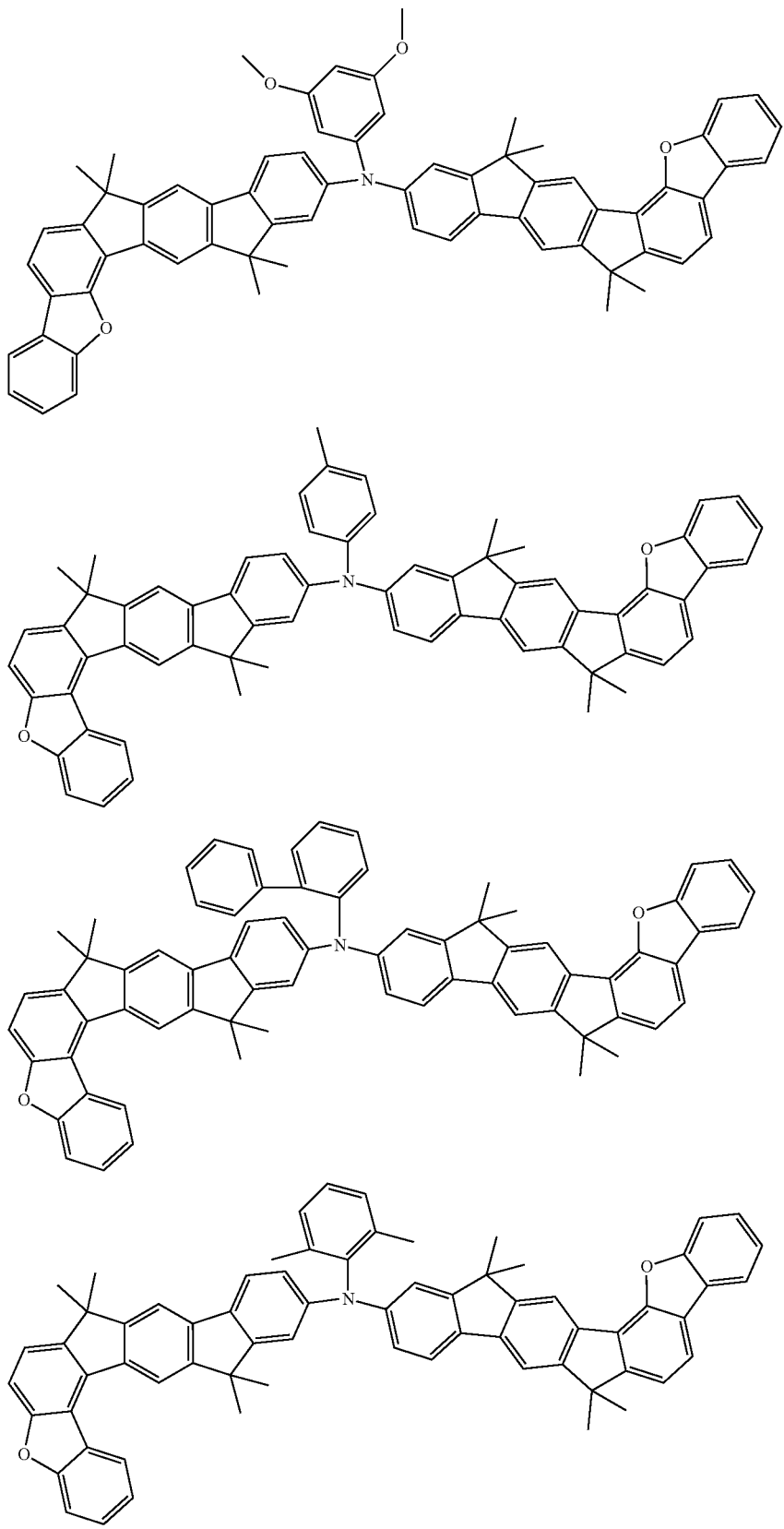

-continued
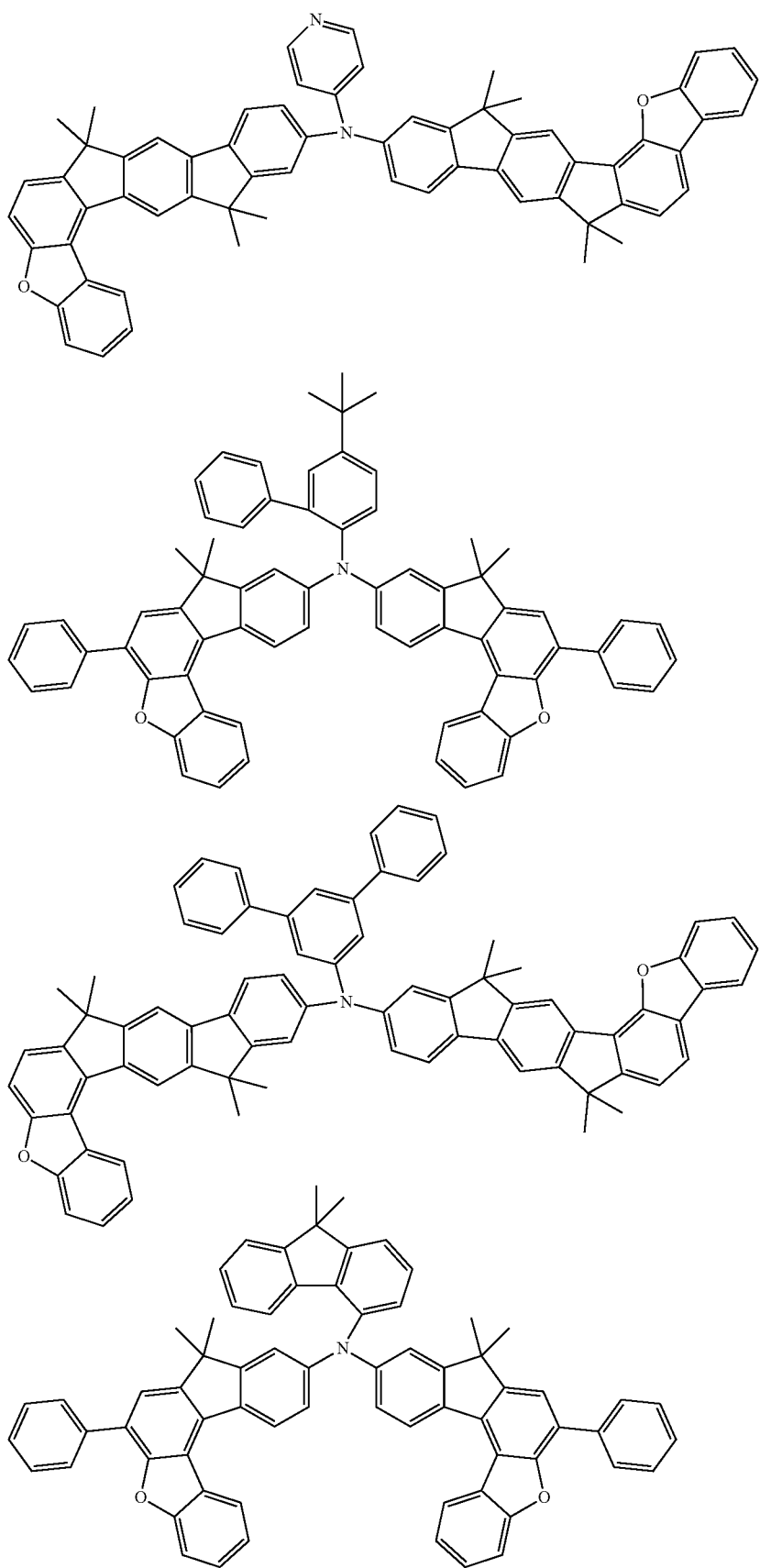

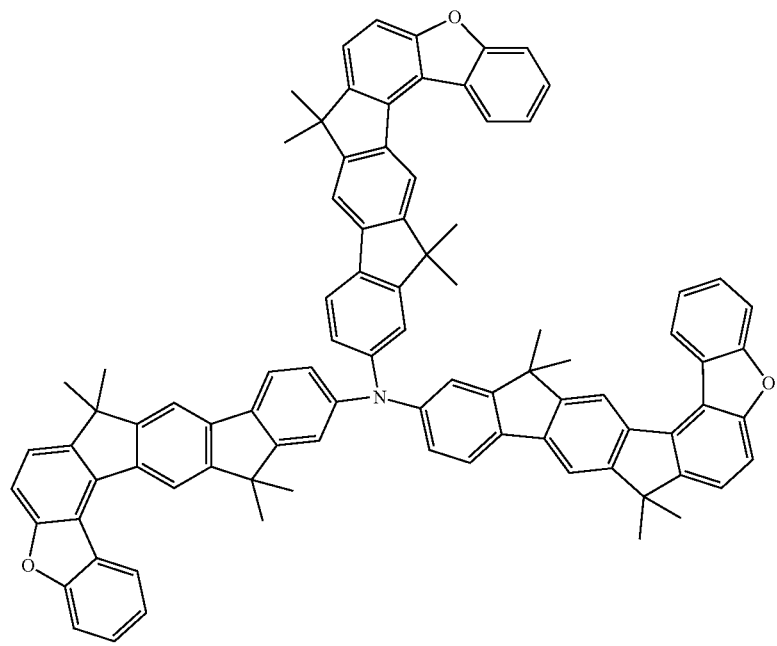
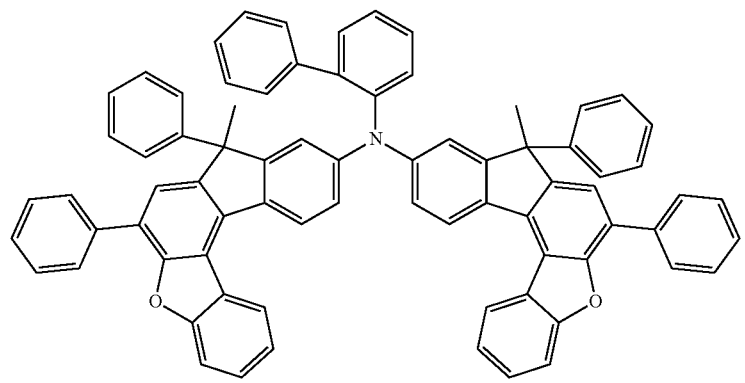
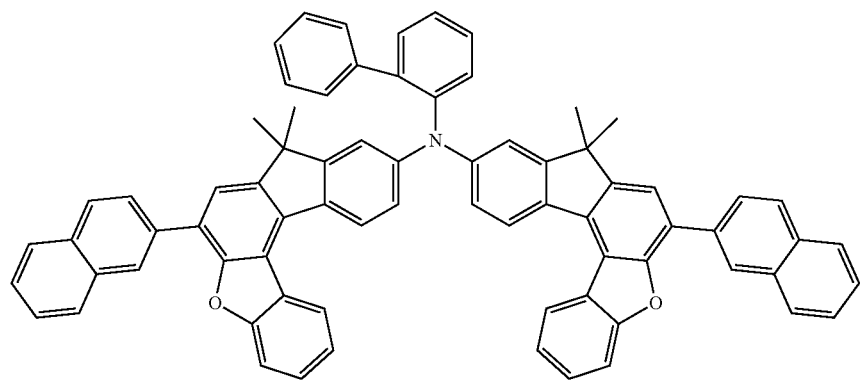

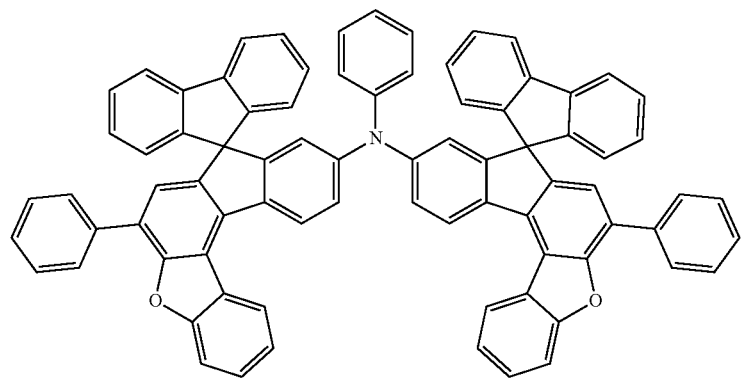
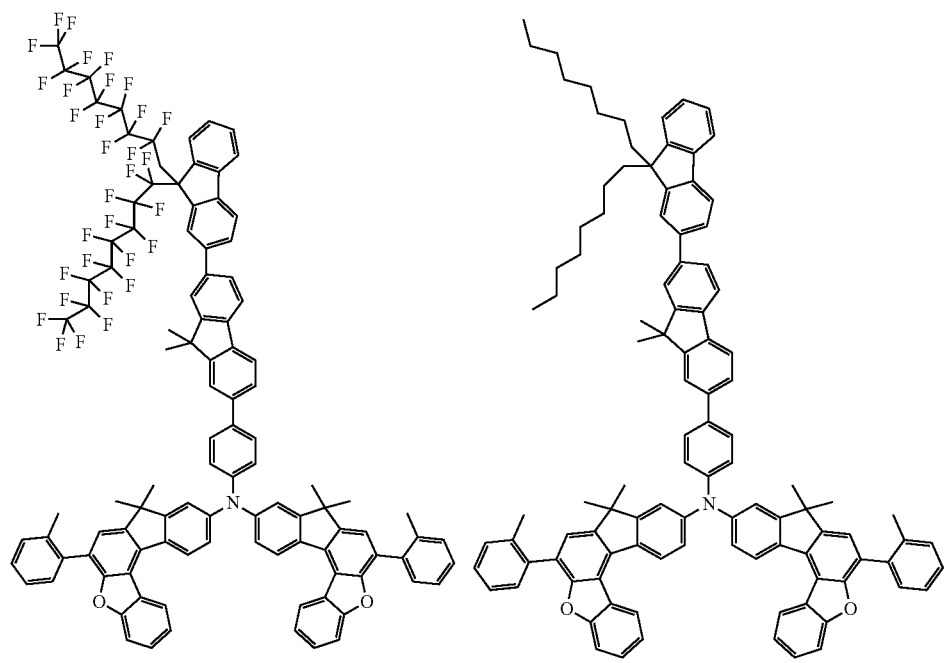
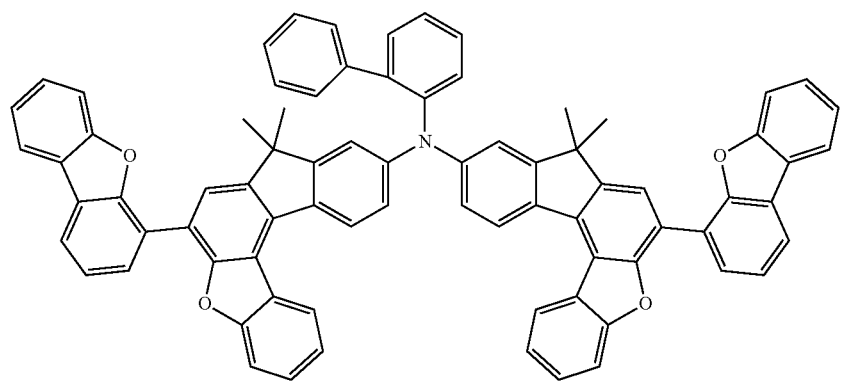

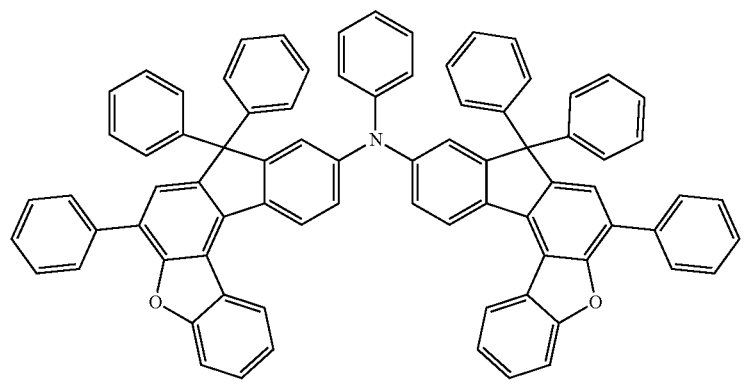
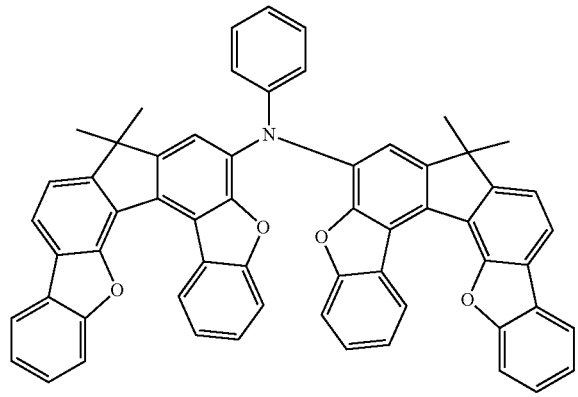
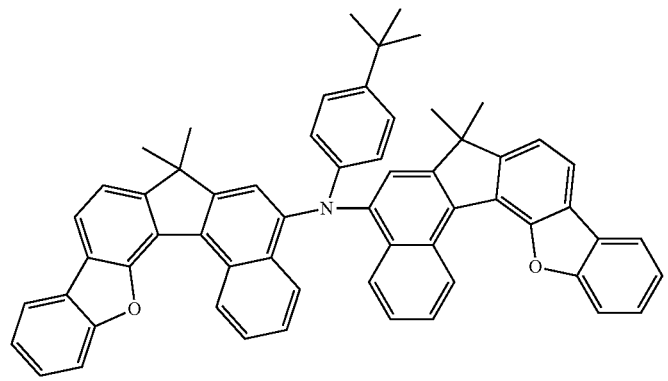
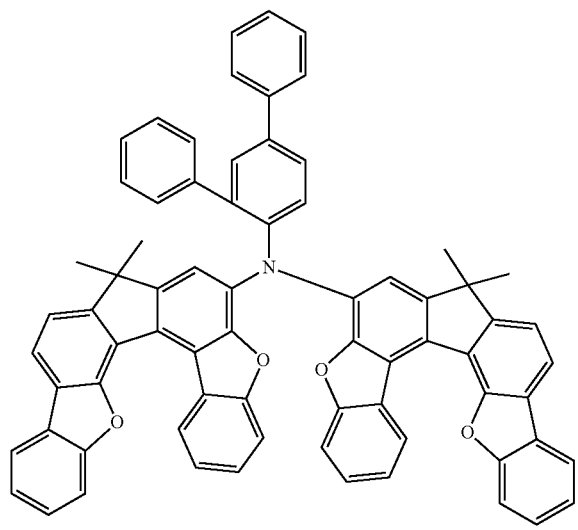

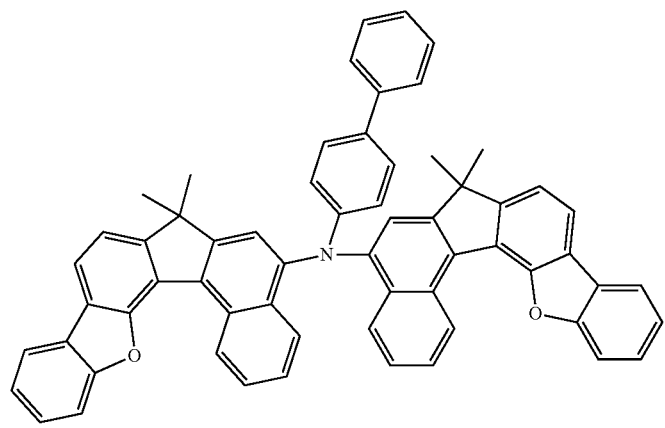
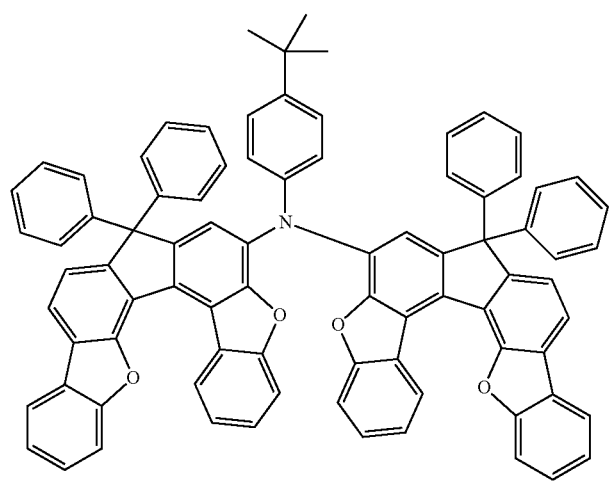
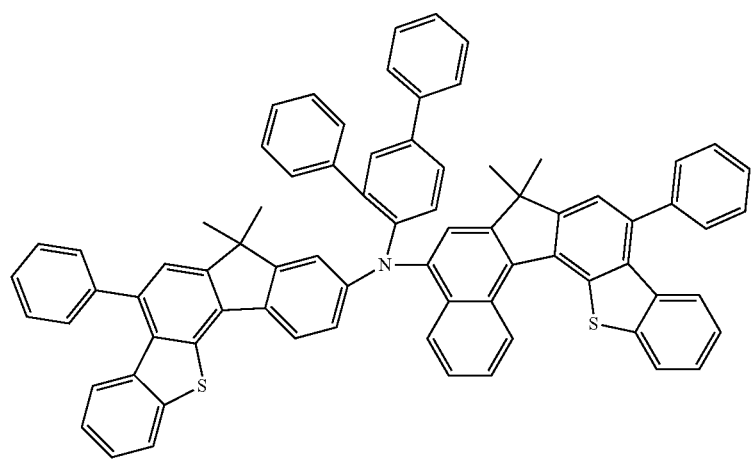

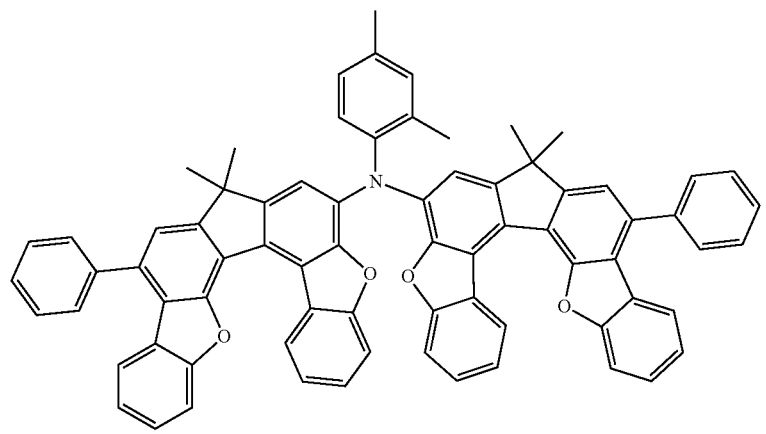
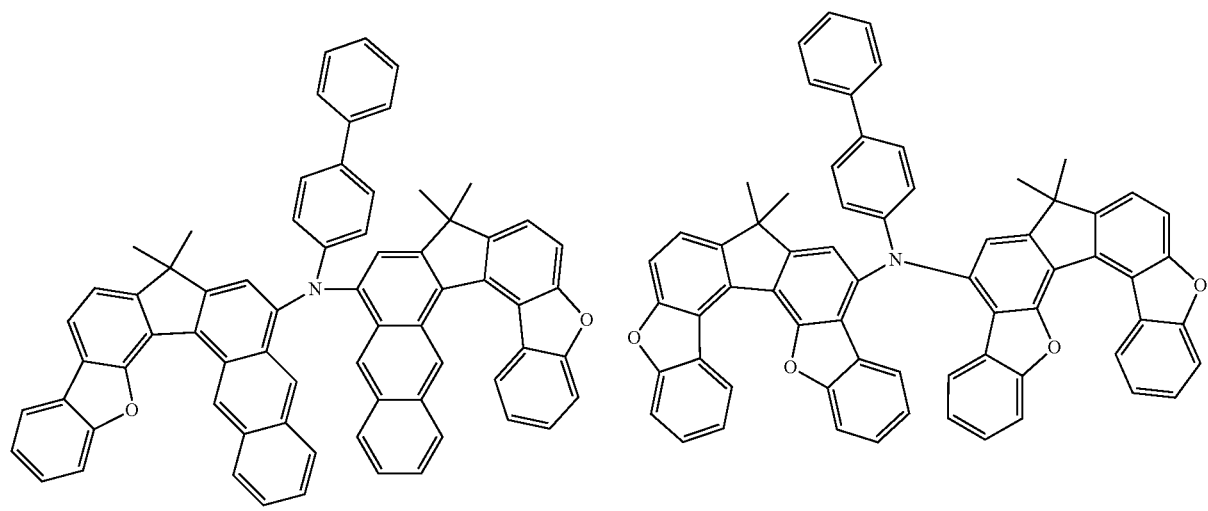
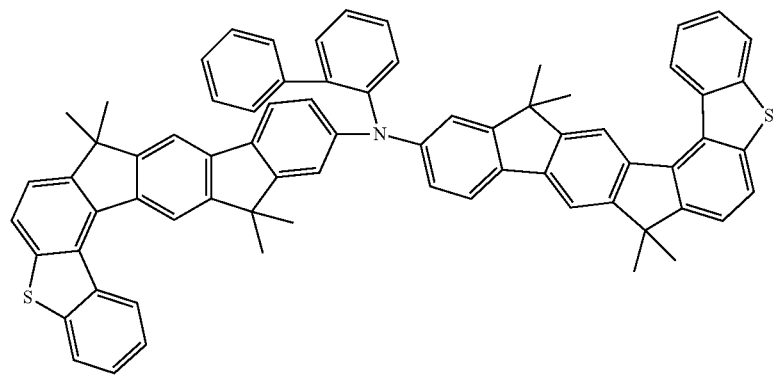

-continued
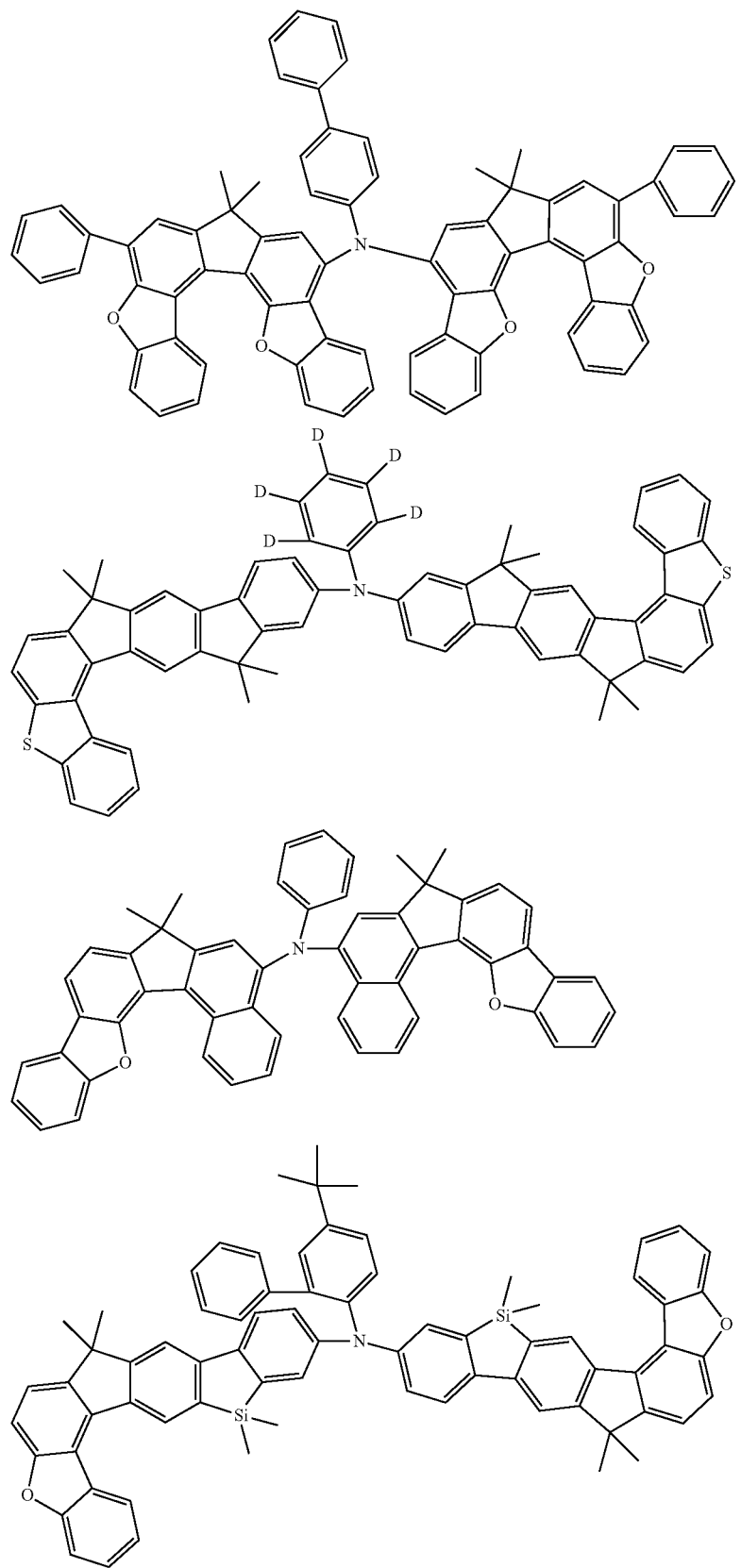

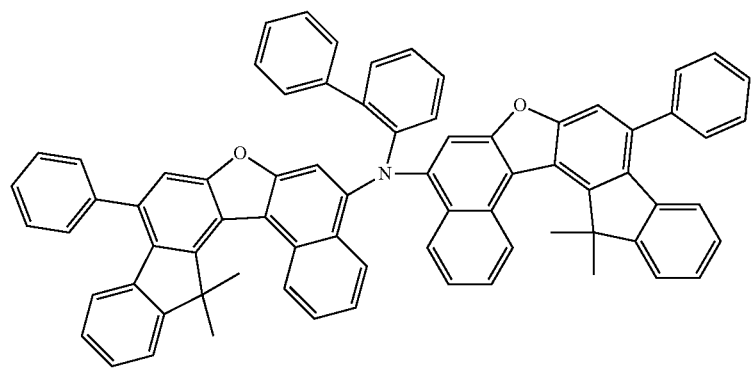
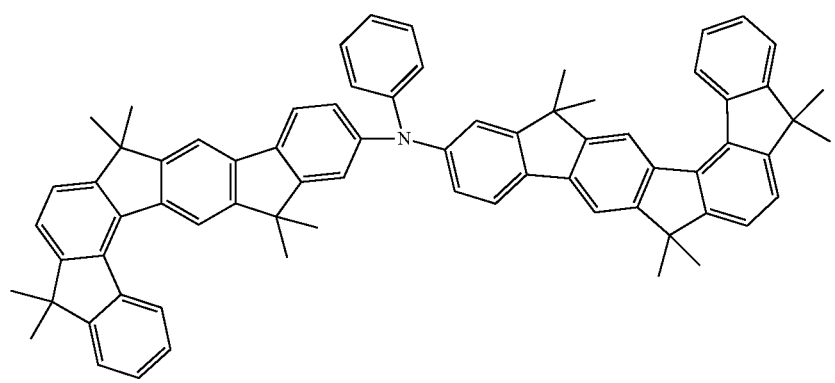
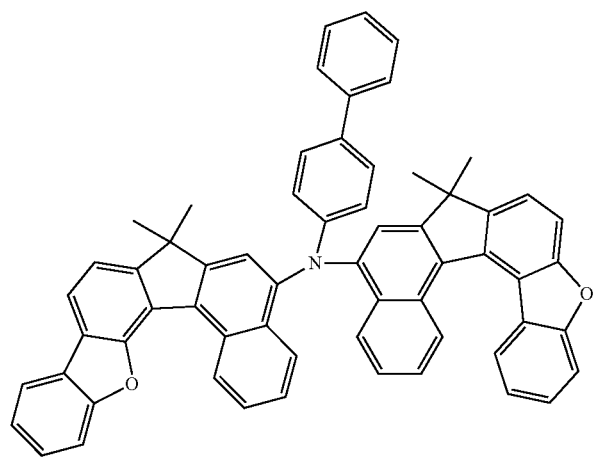
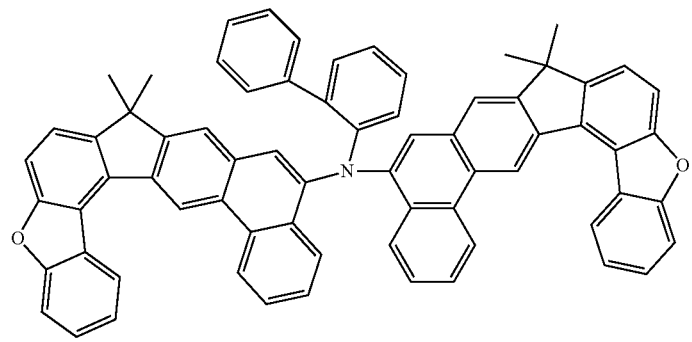

-continued
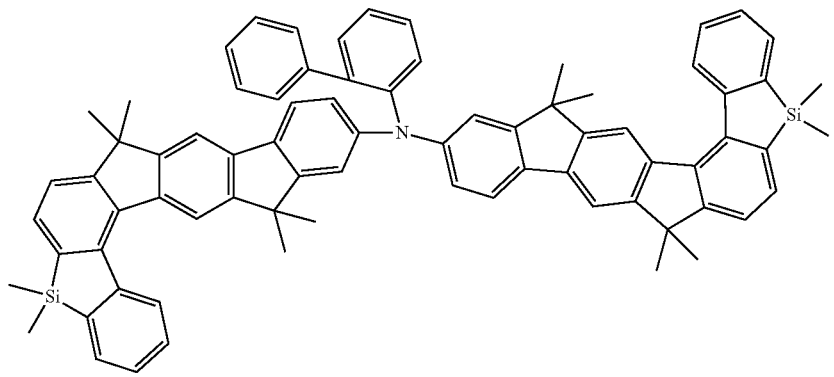
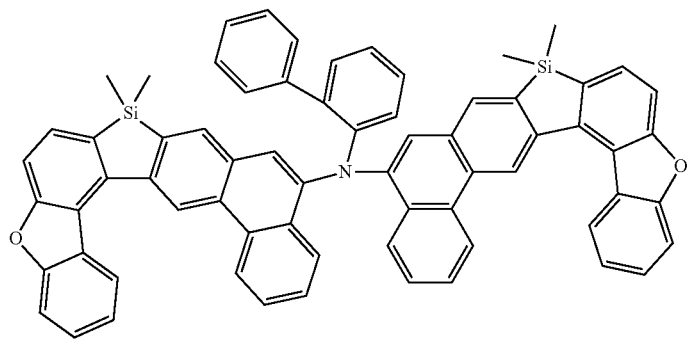
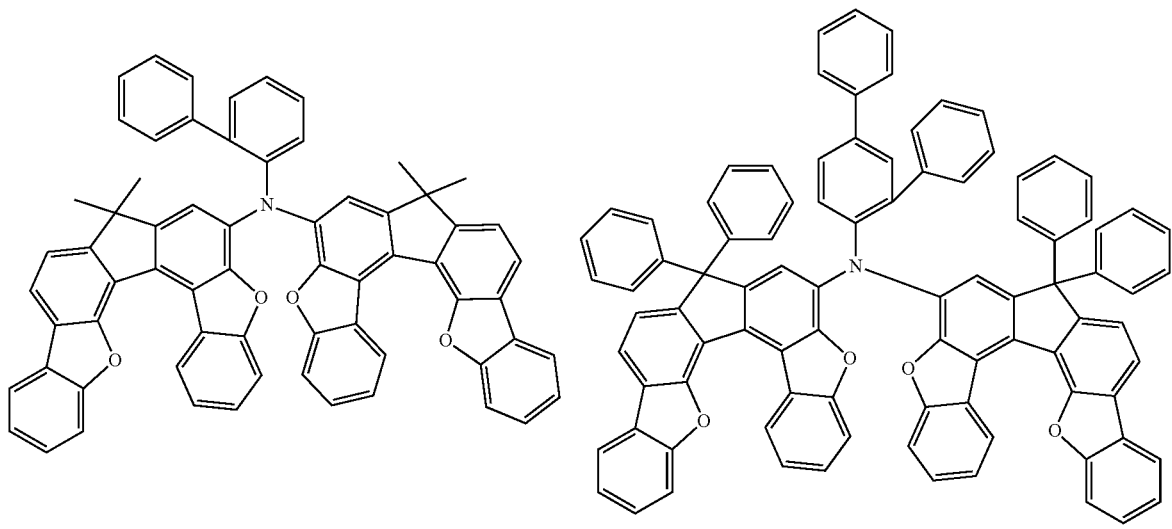
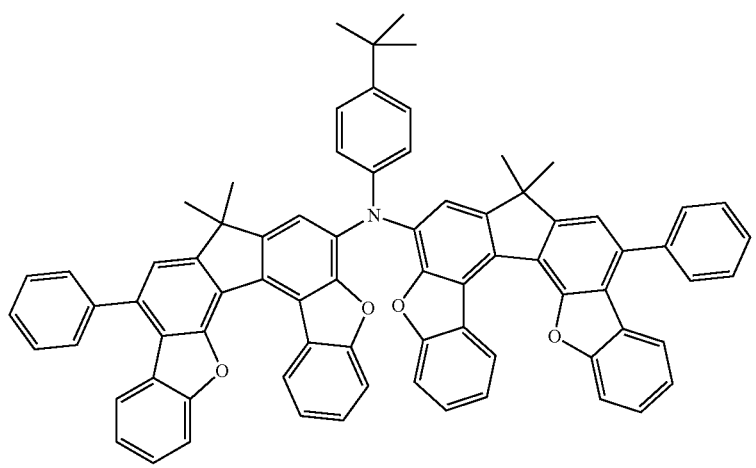

-continued
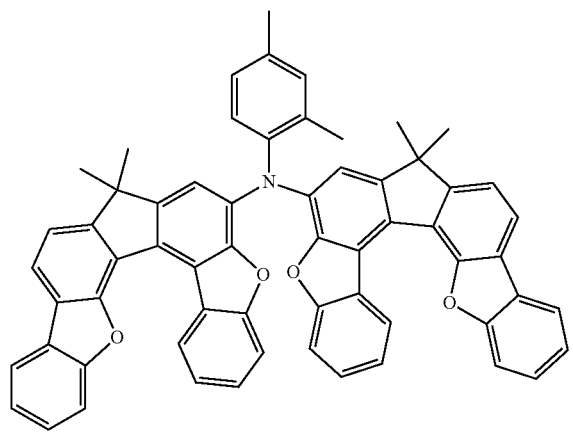
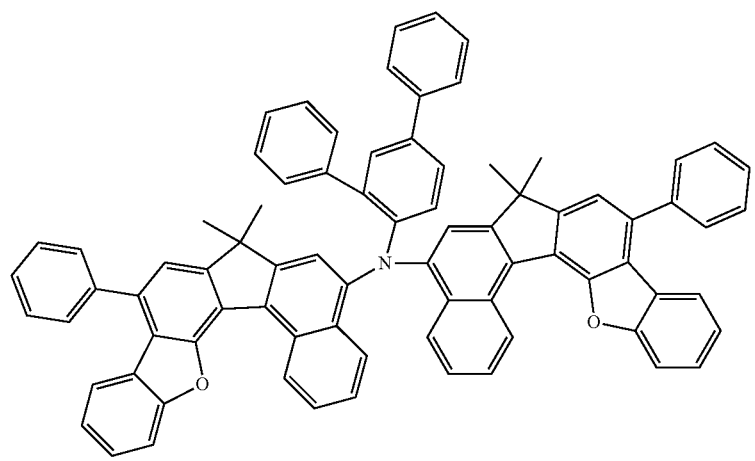
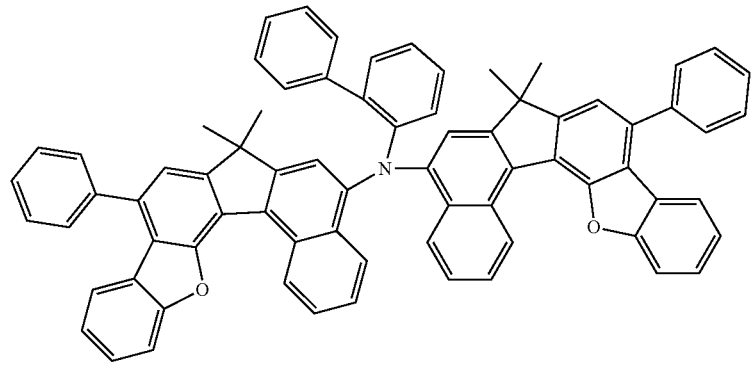
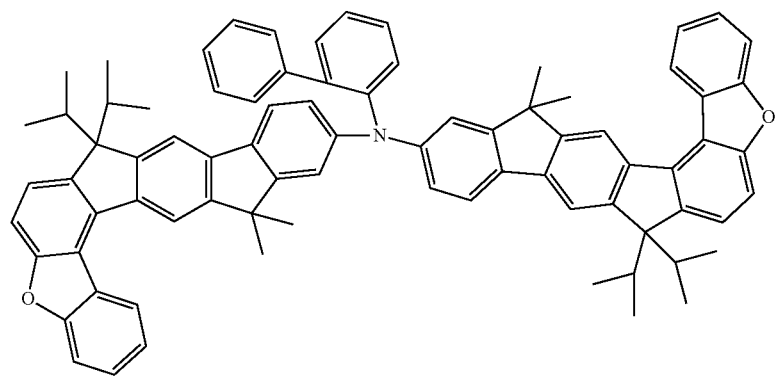

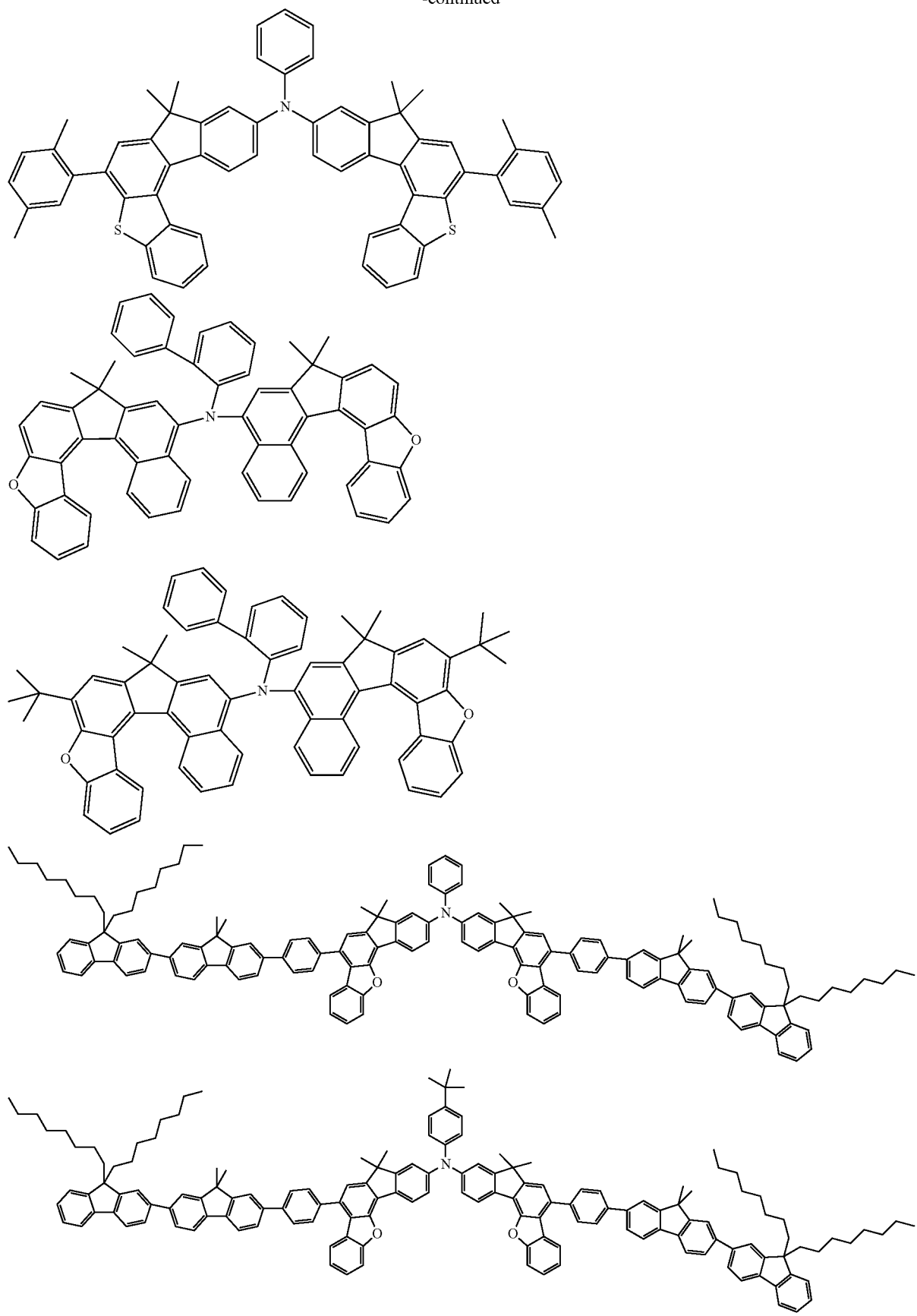

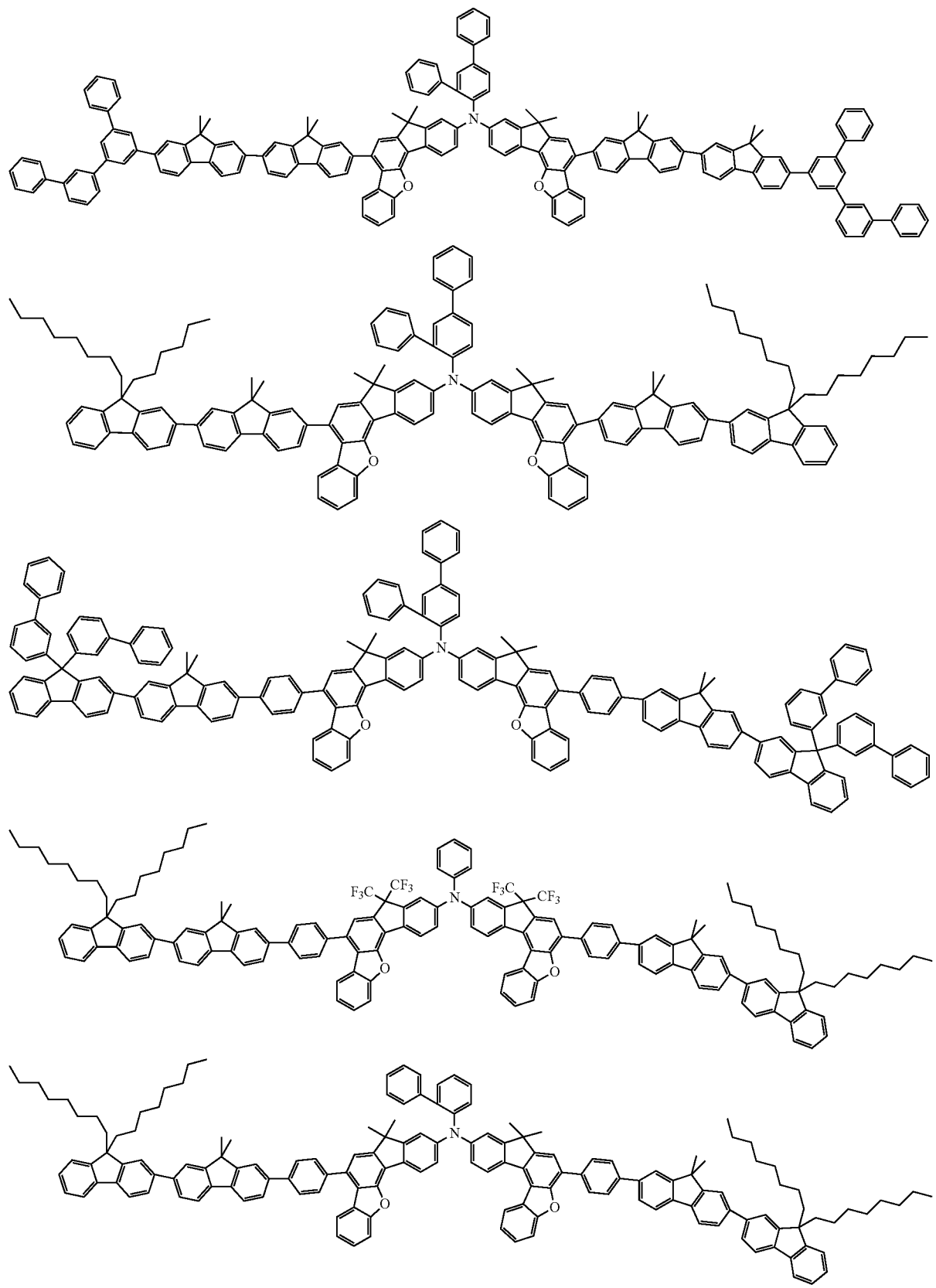

-continued
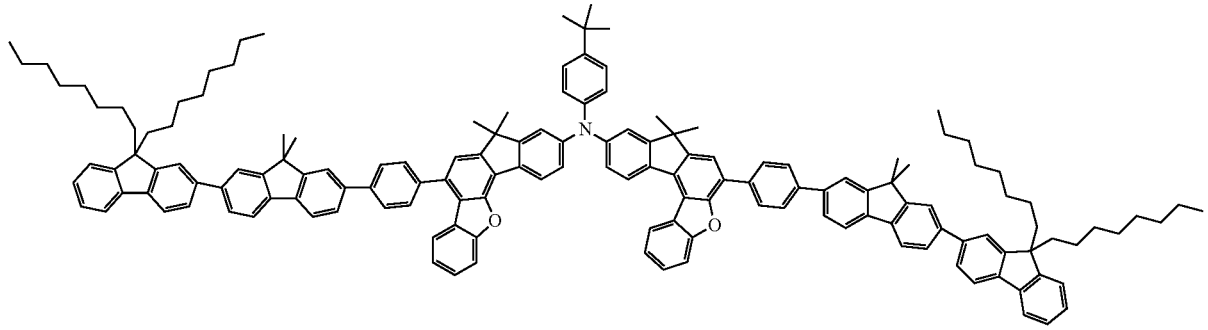
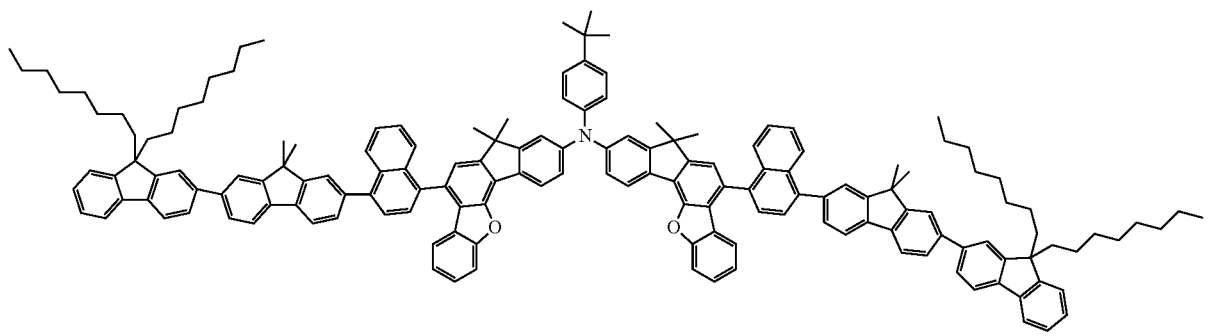
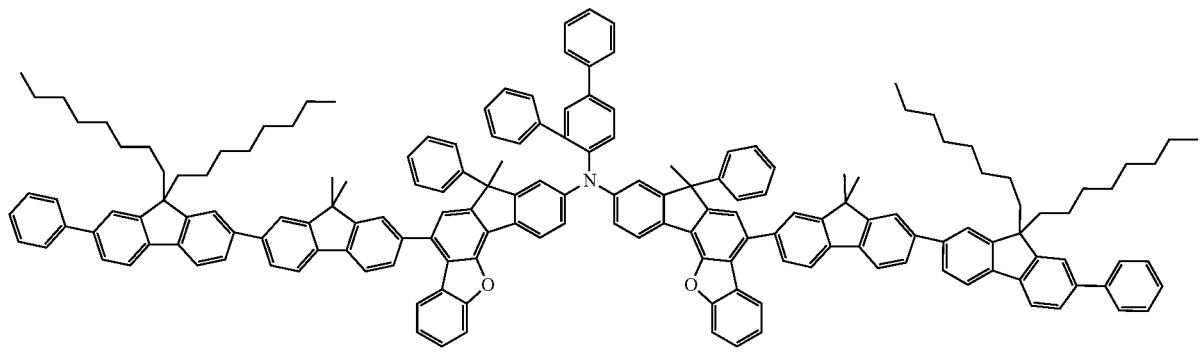
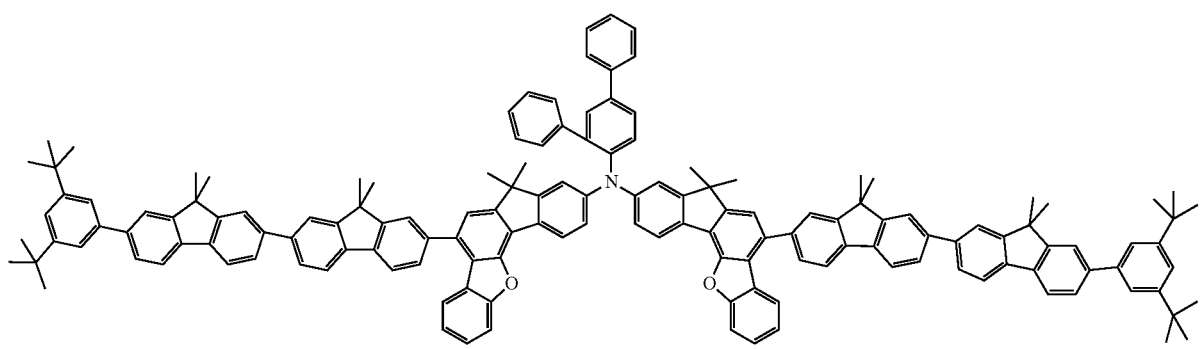
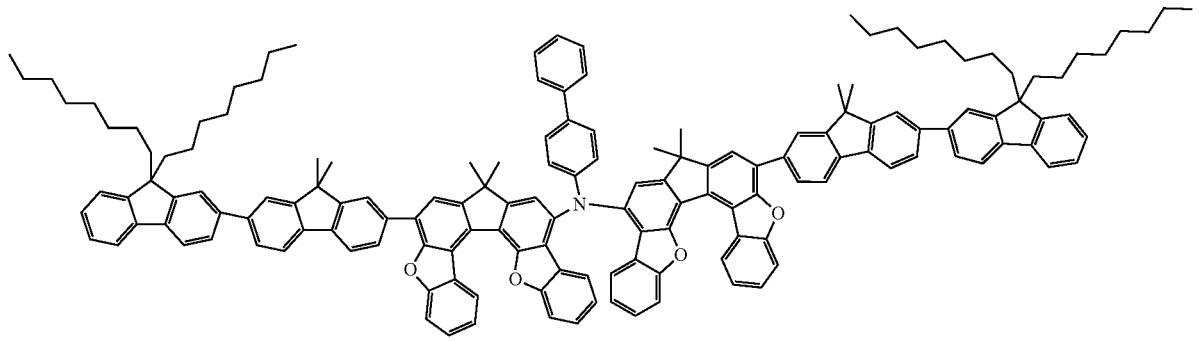

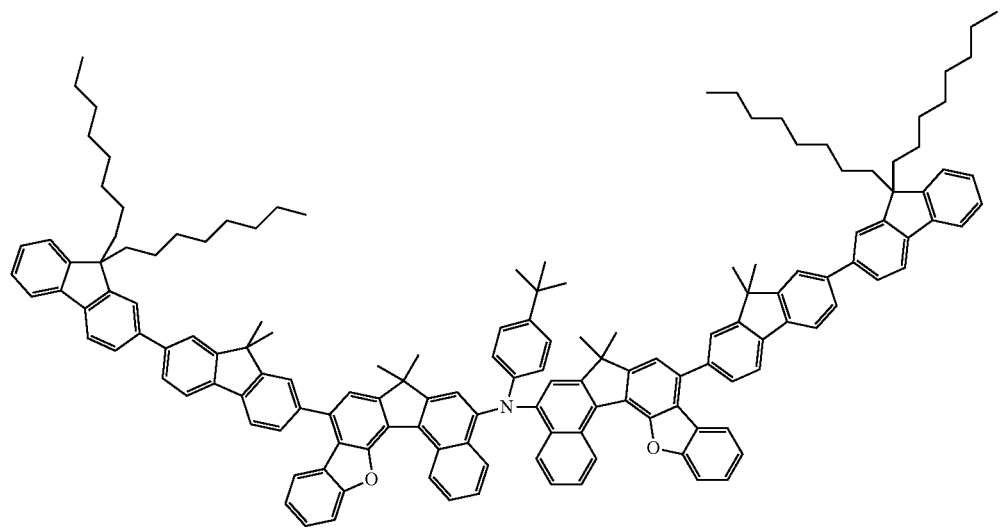
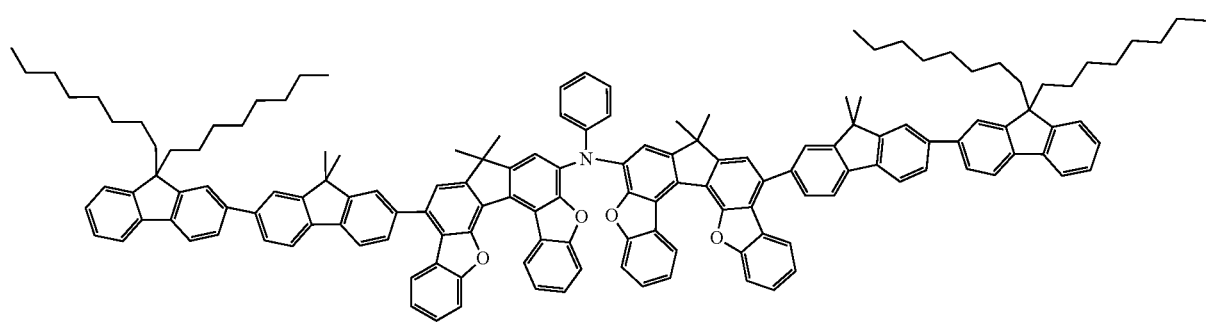
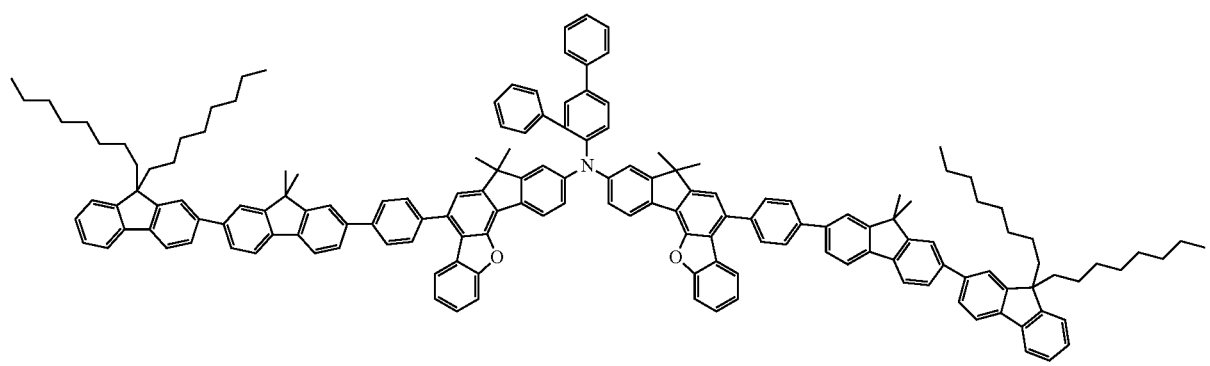
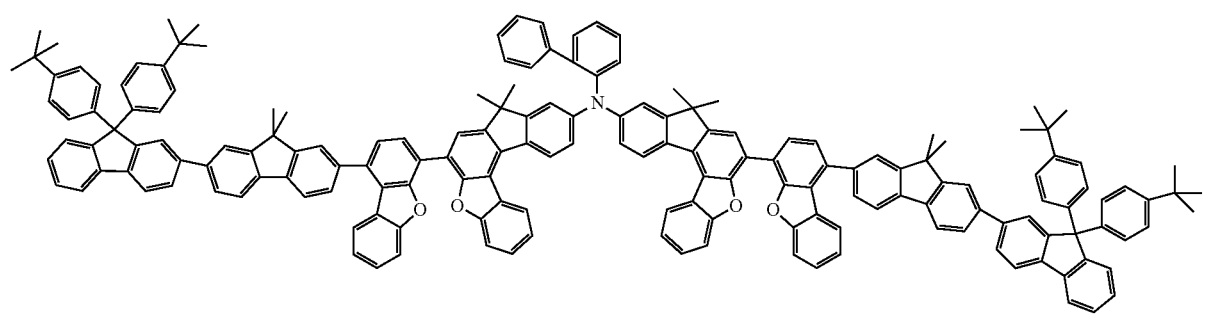

-continued
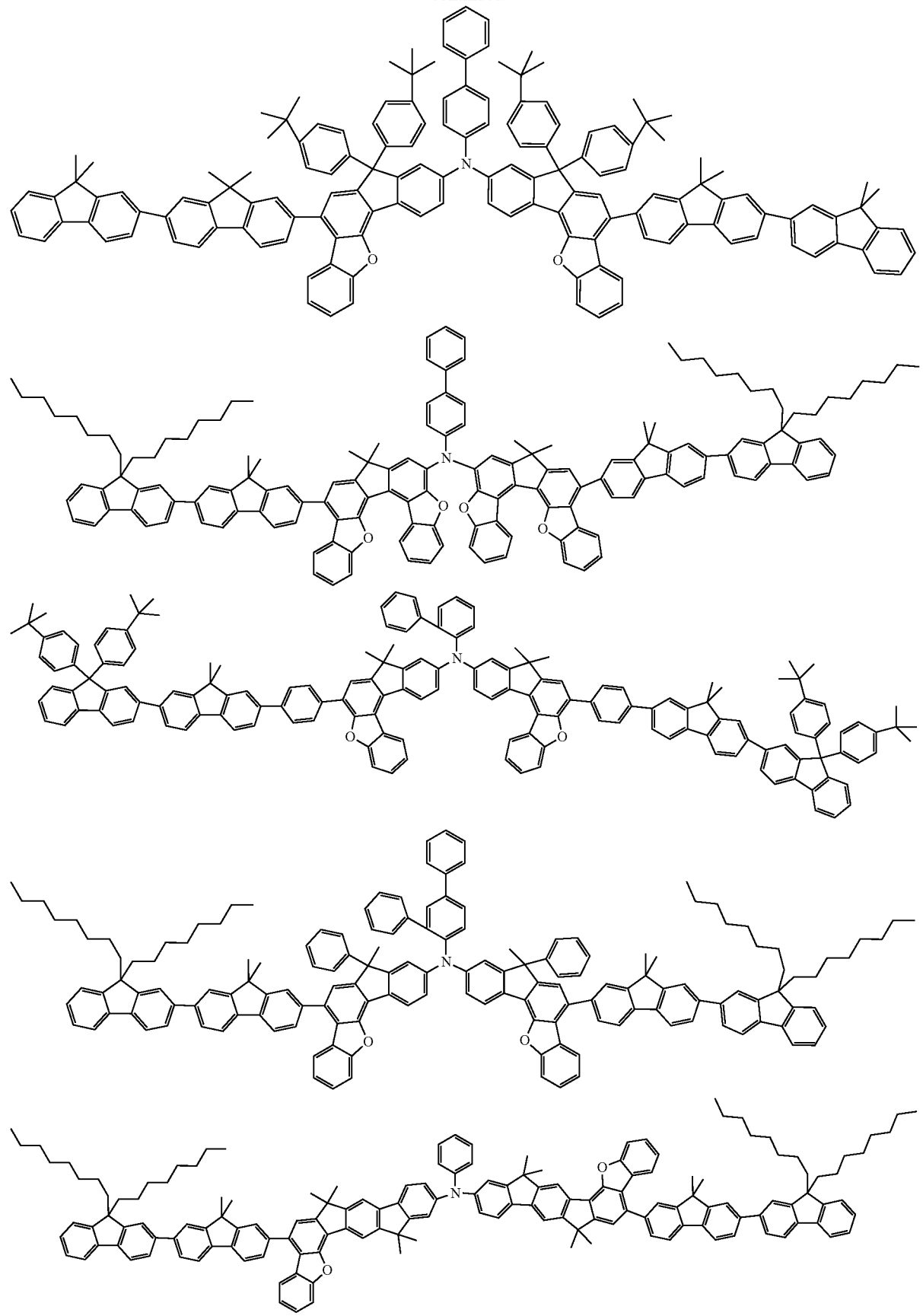

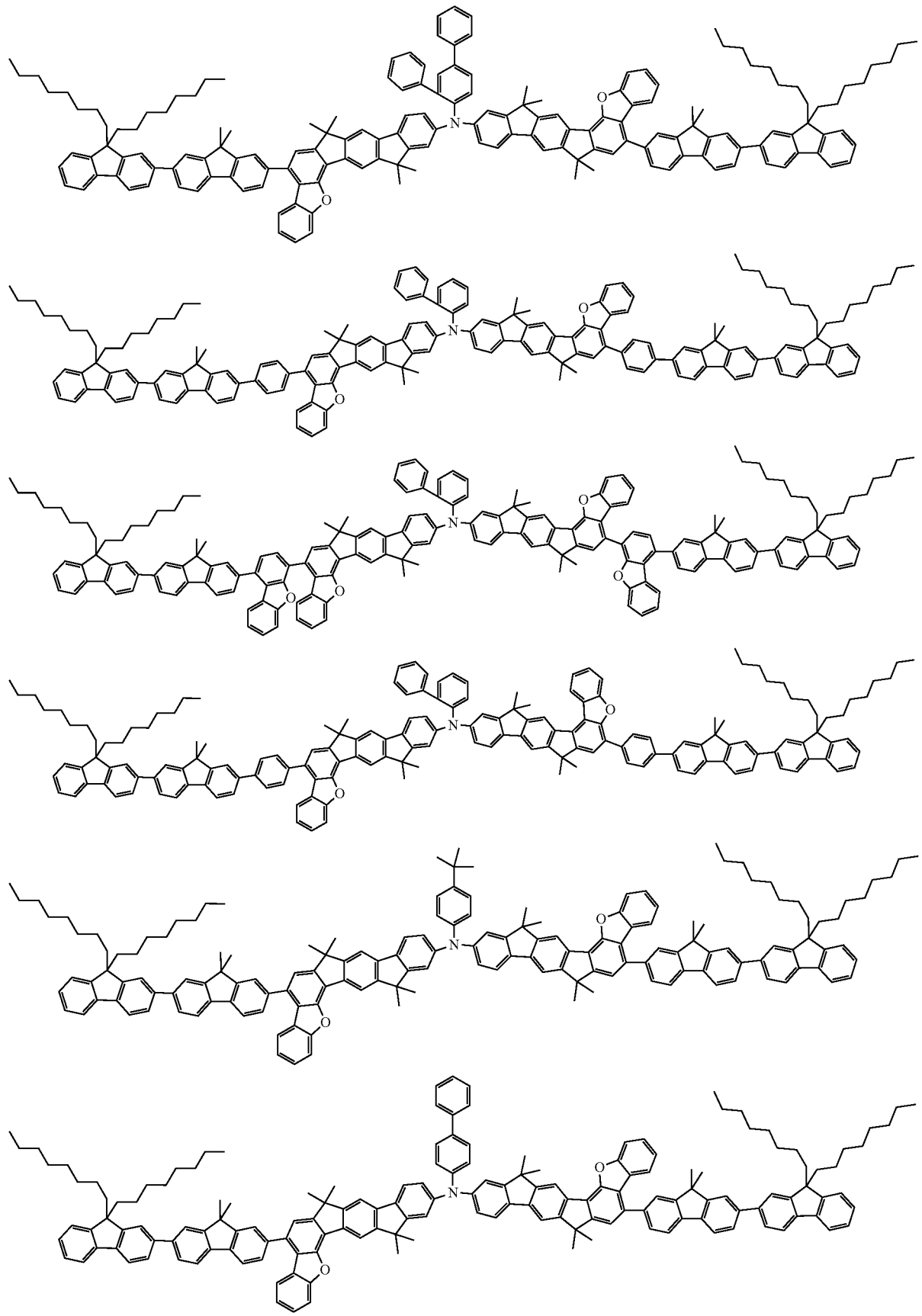

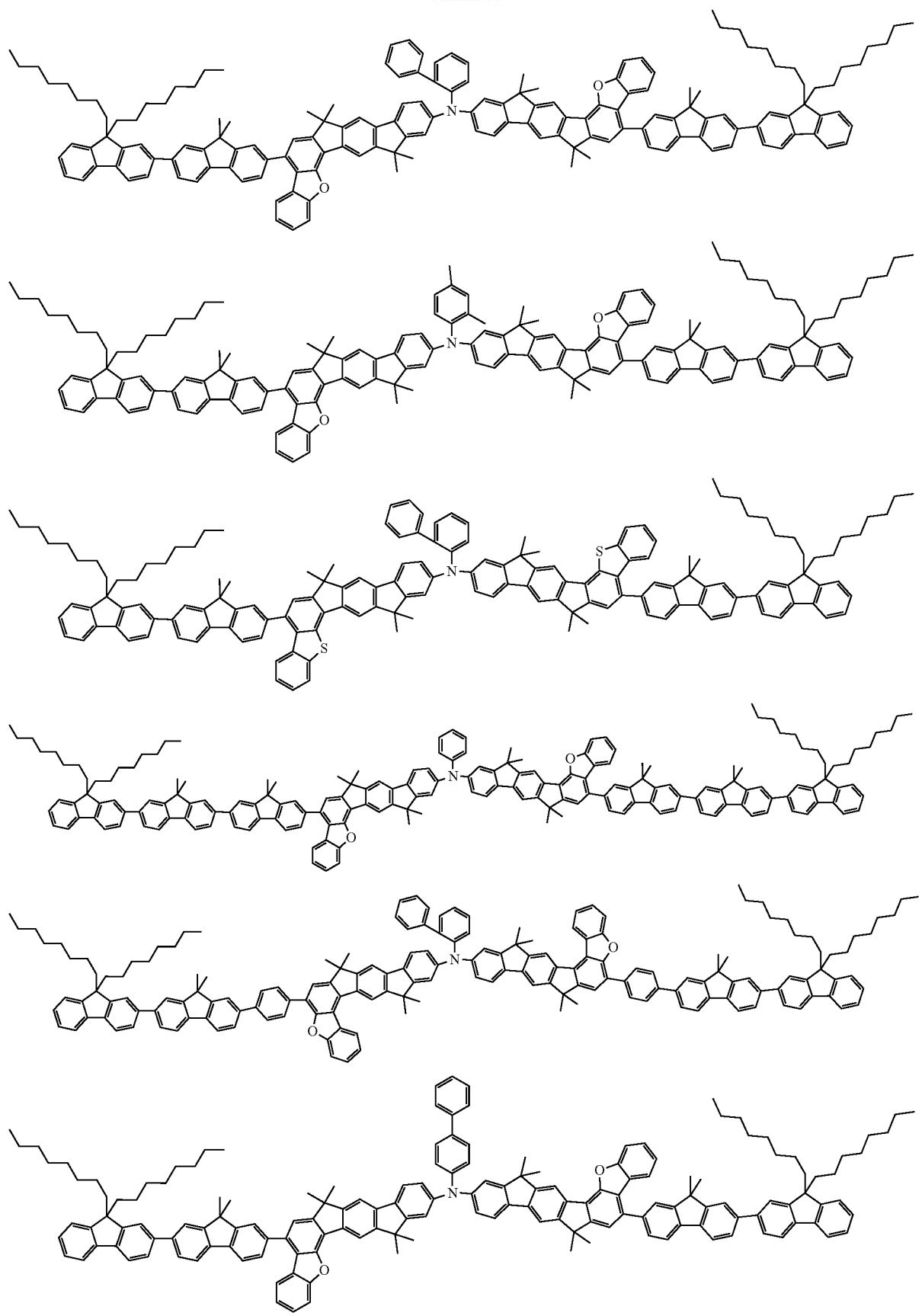

-continued
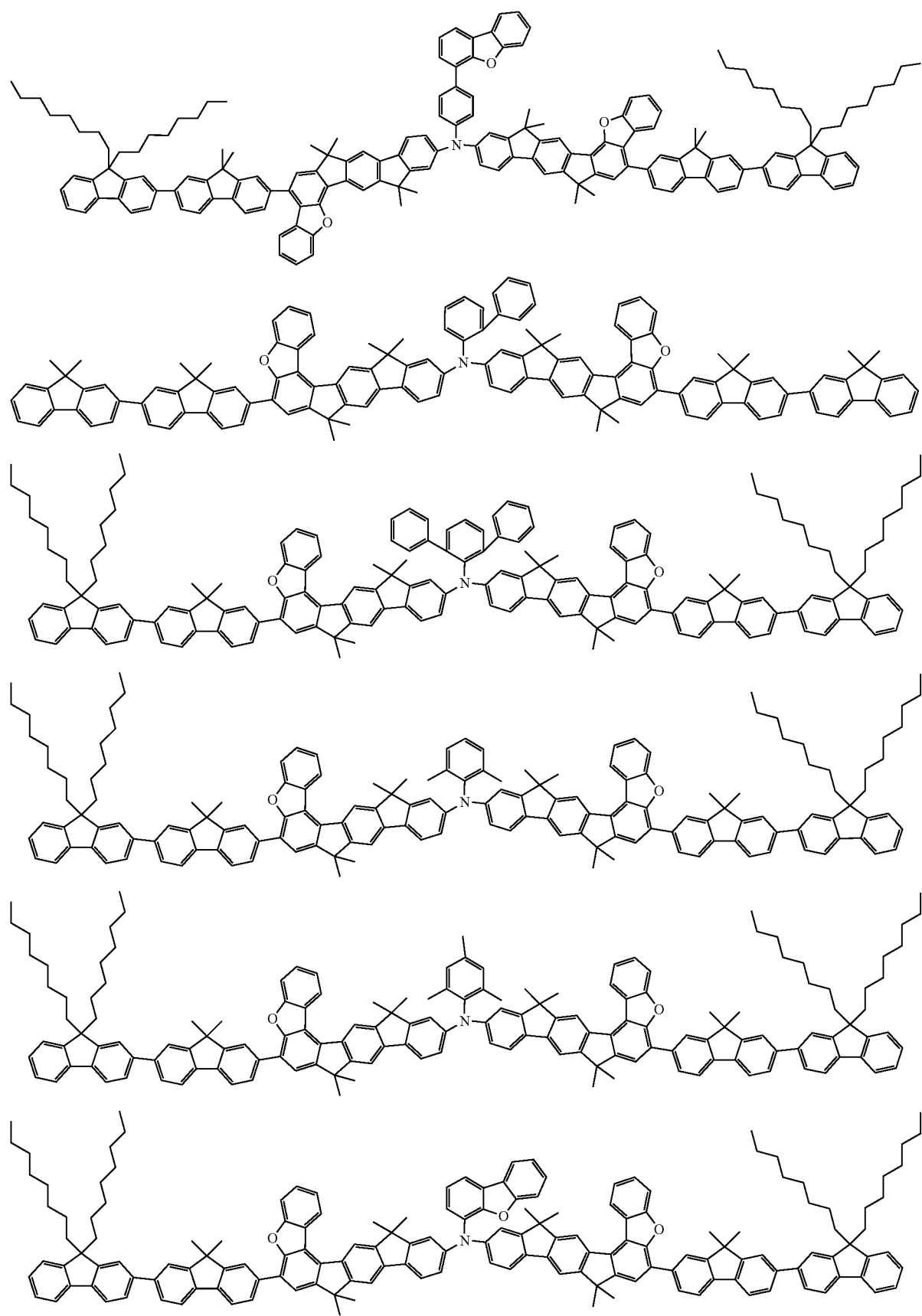

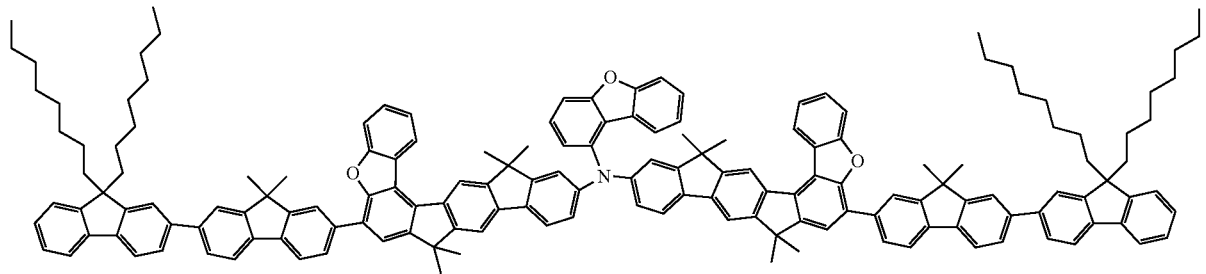
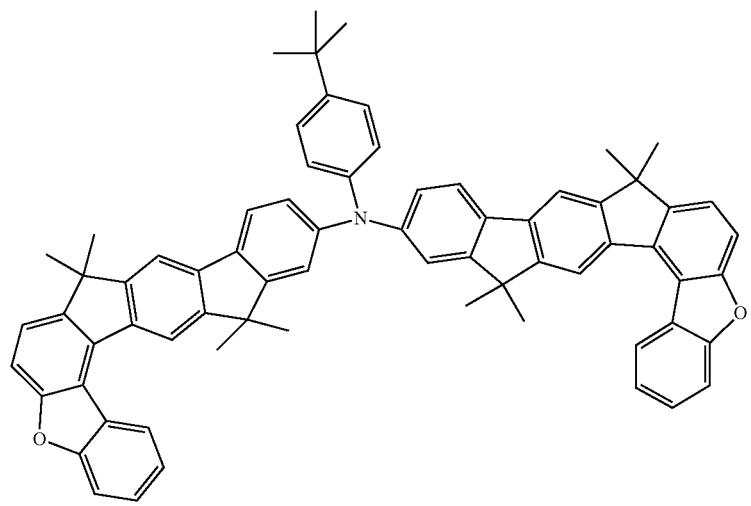
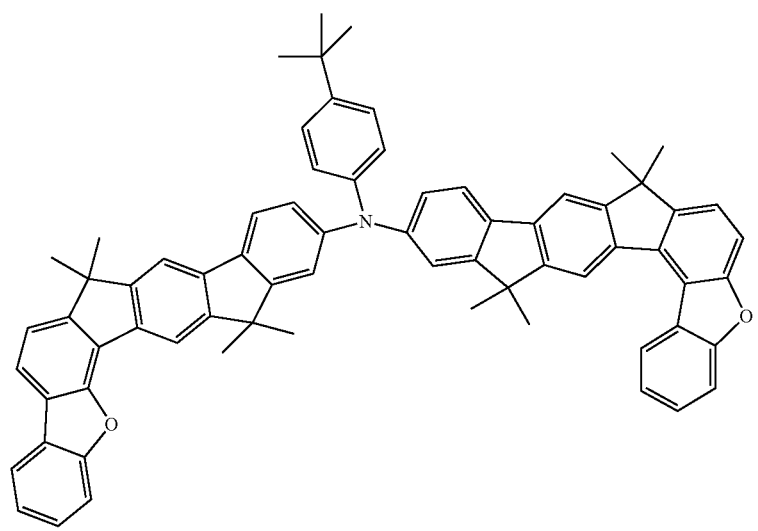

-continued
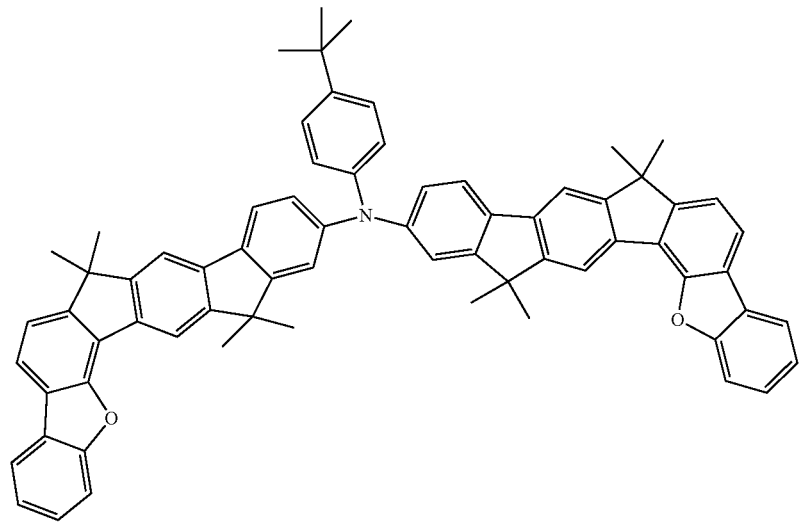
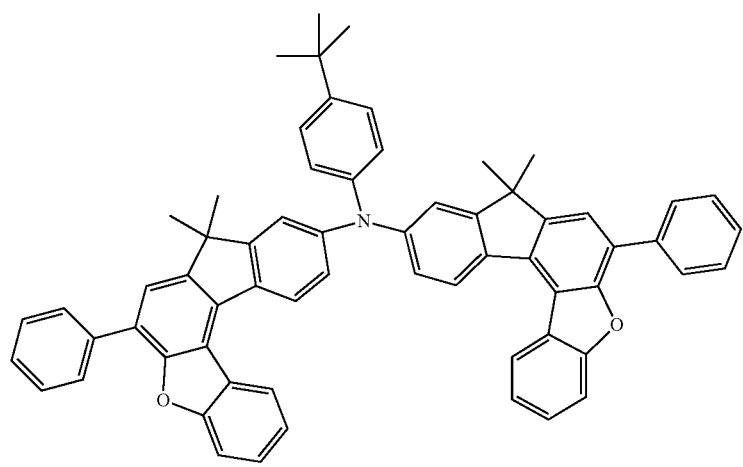
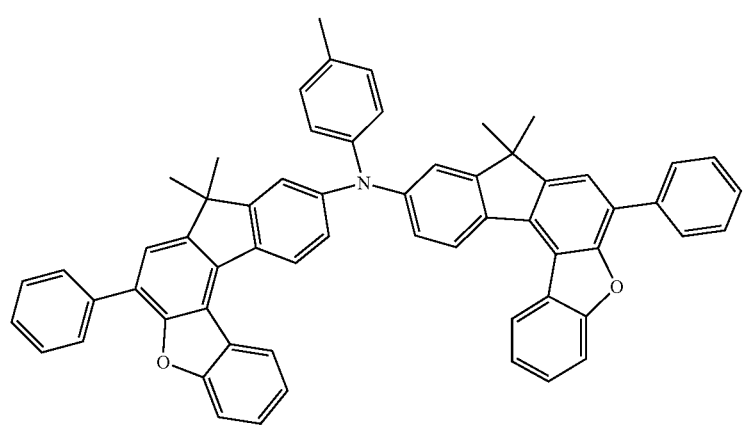

-continued
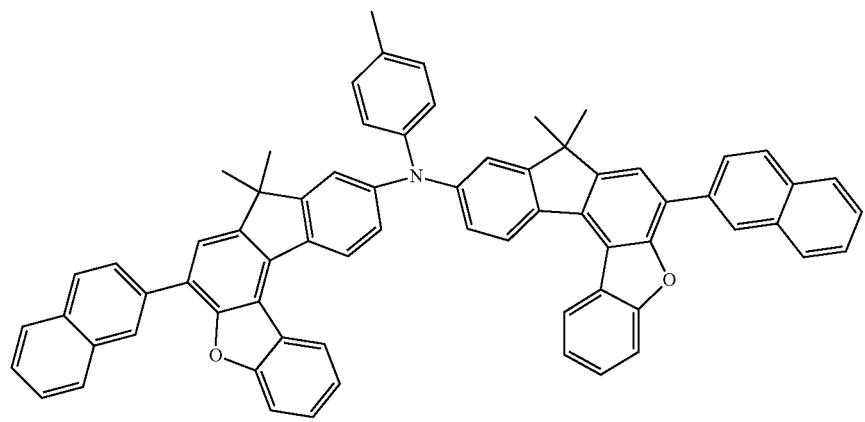
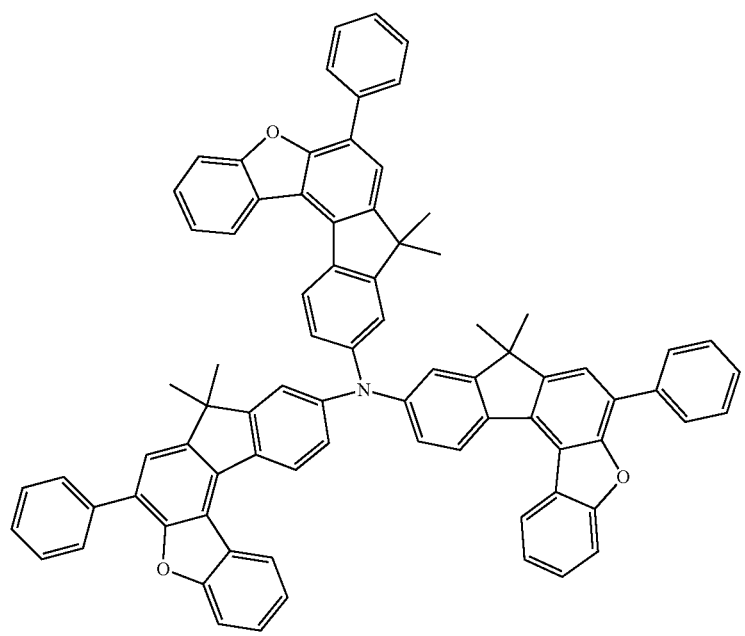
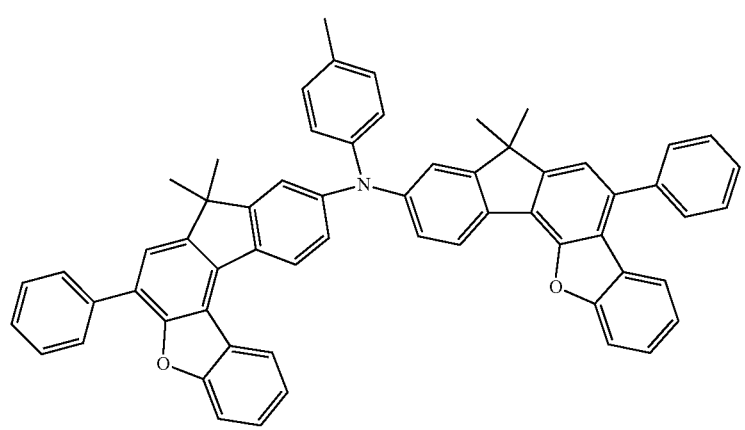

-continued
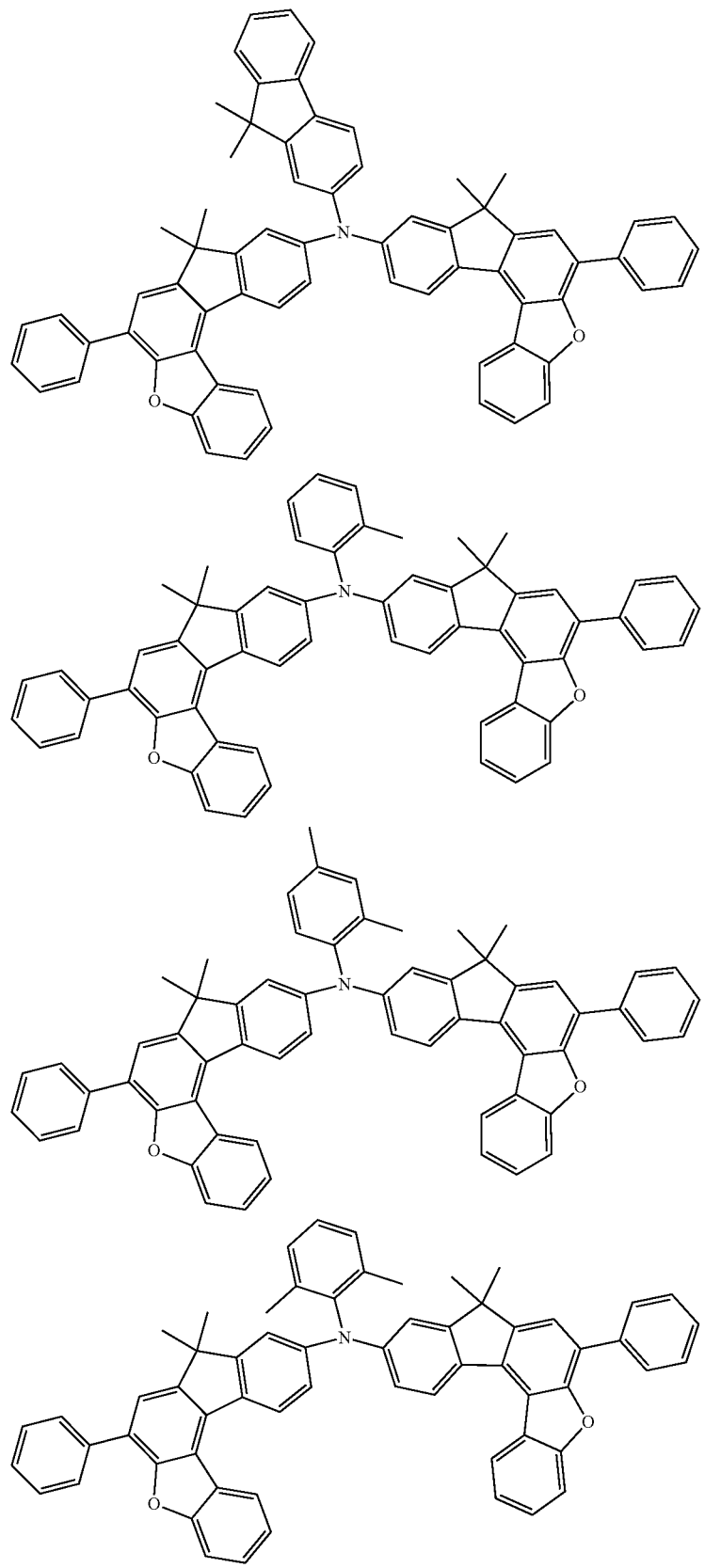

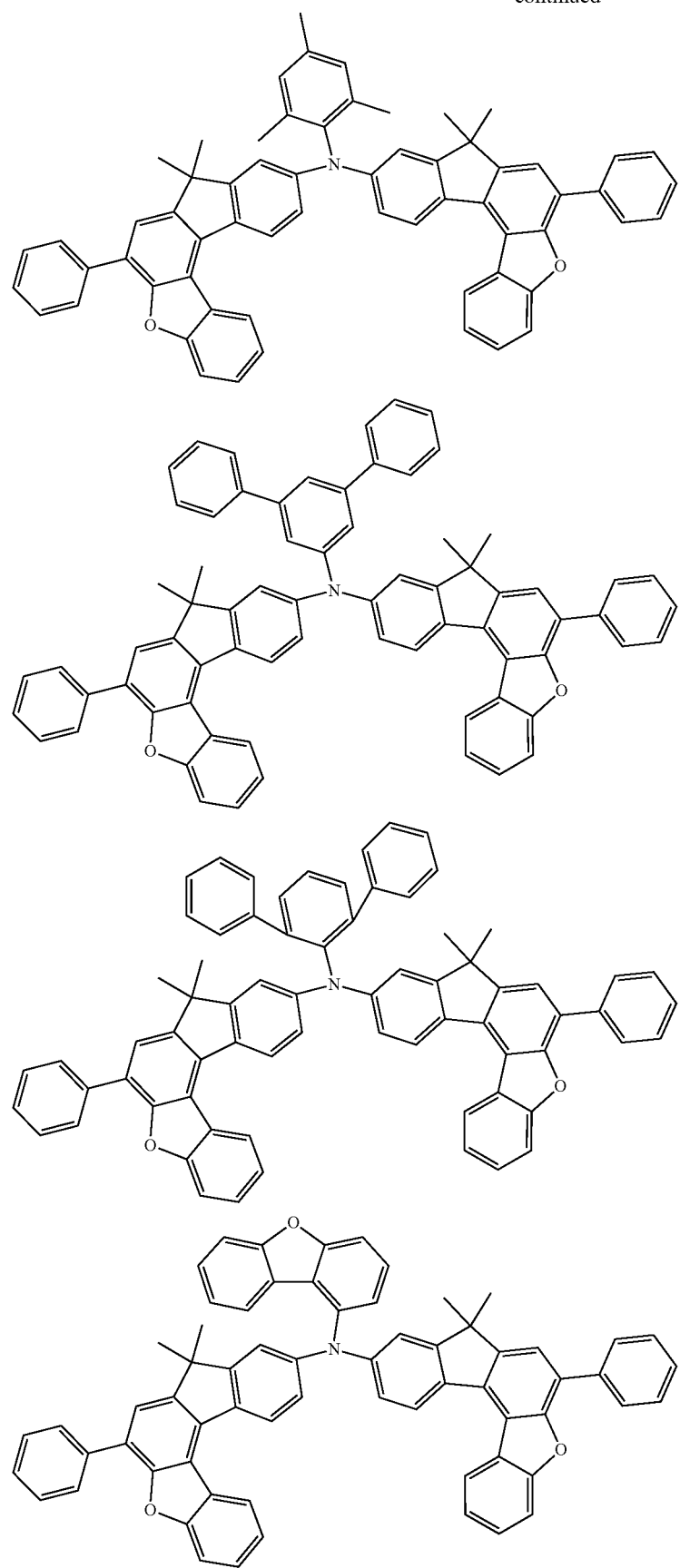

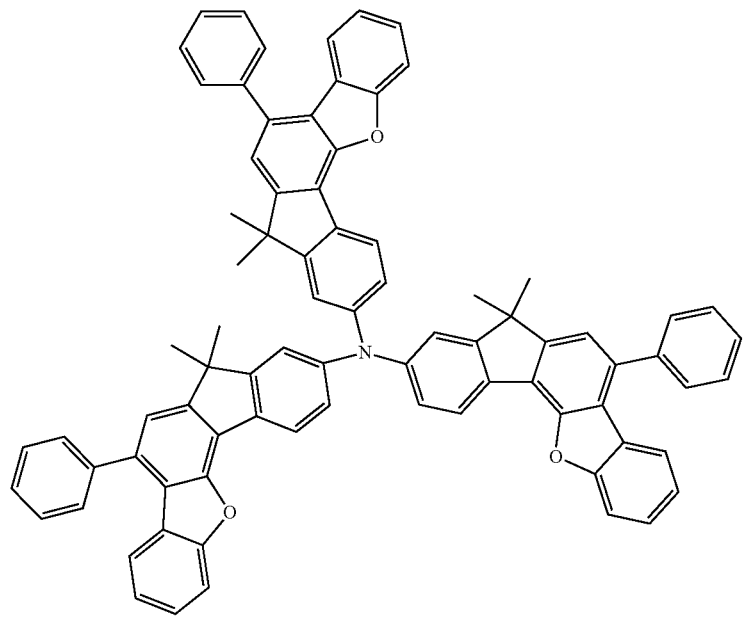
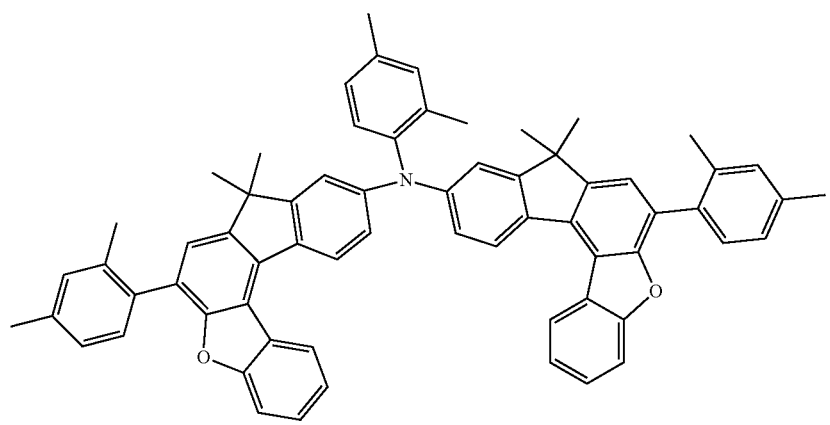
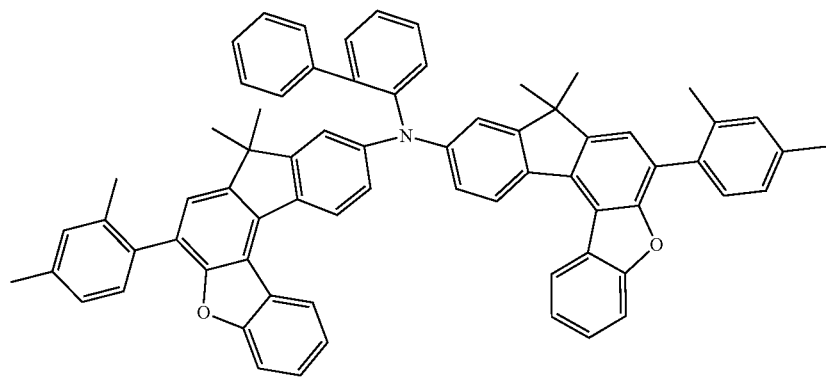

-continued
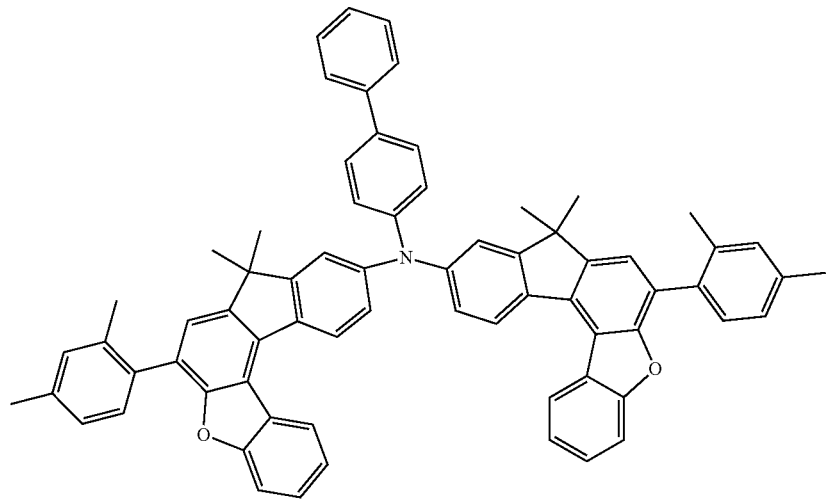
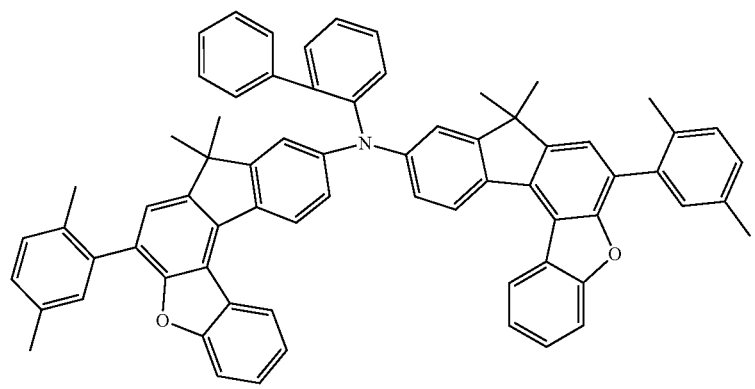
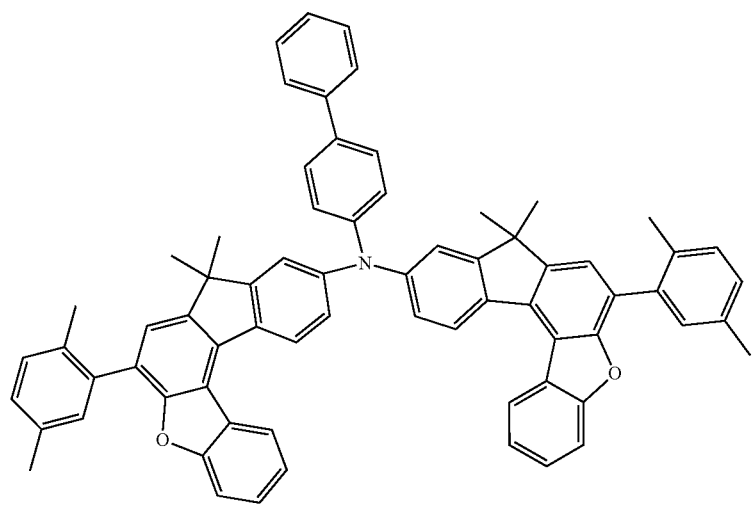

-continued
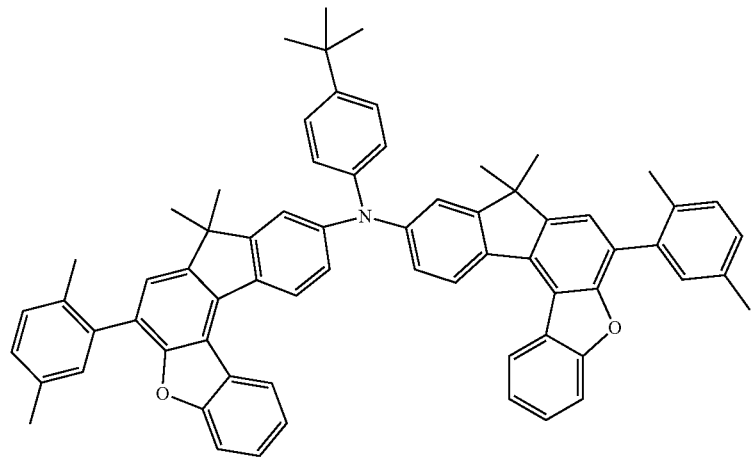
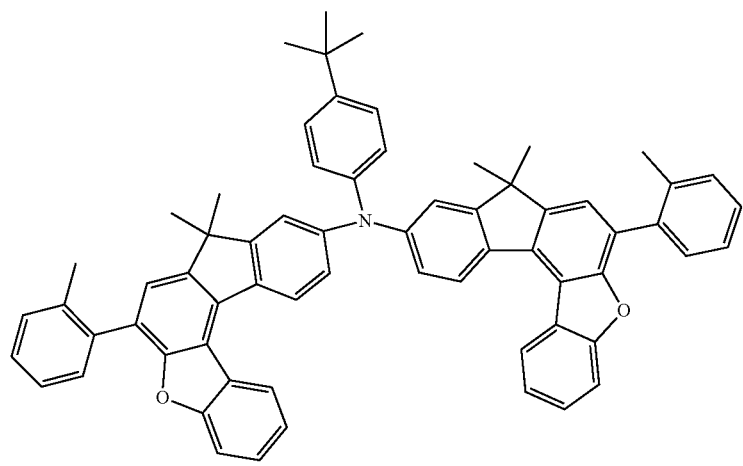
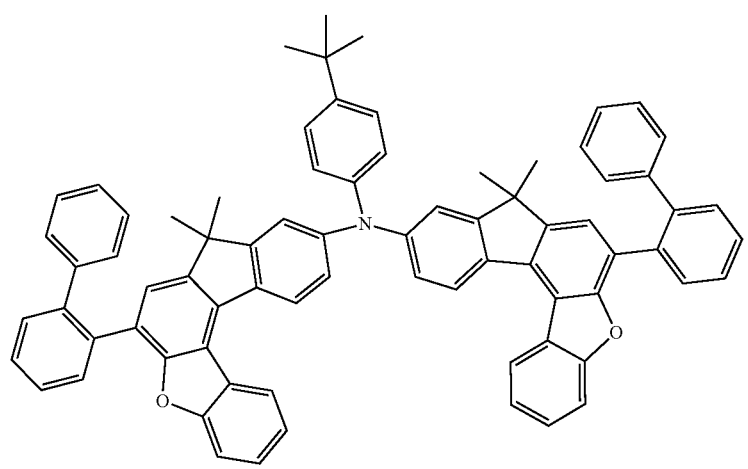

-continued
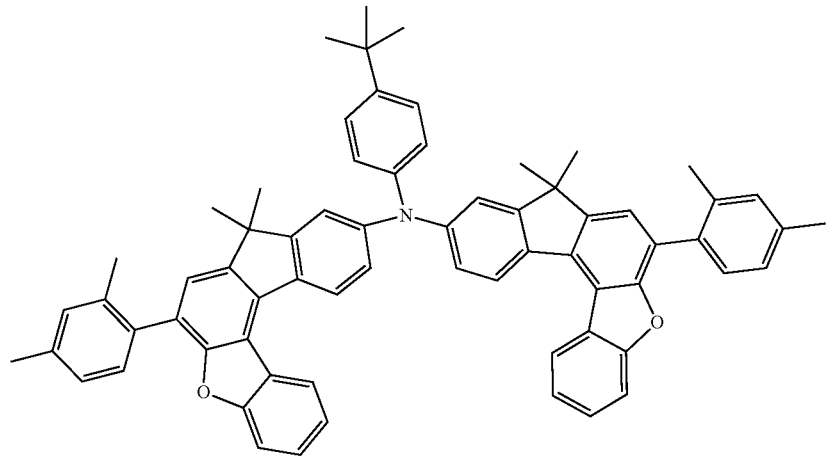
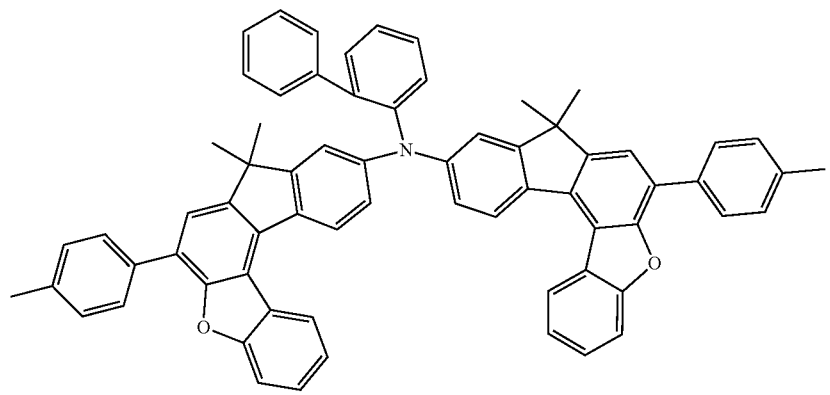
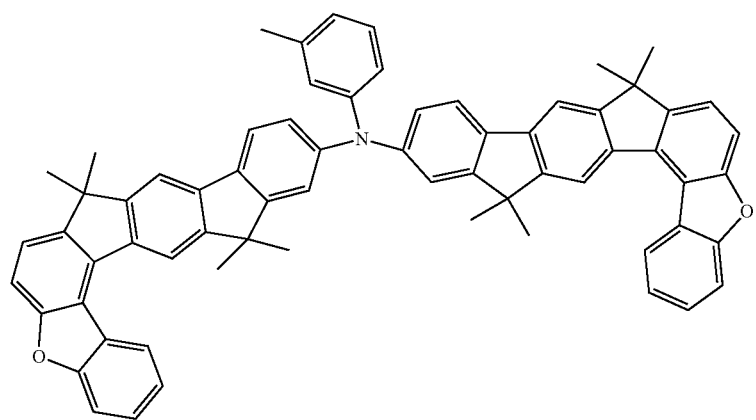

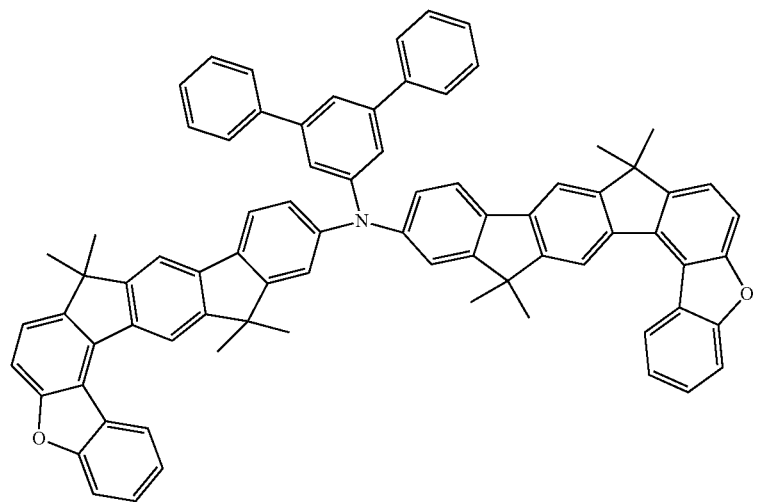
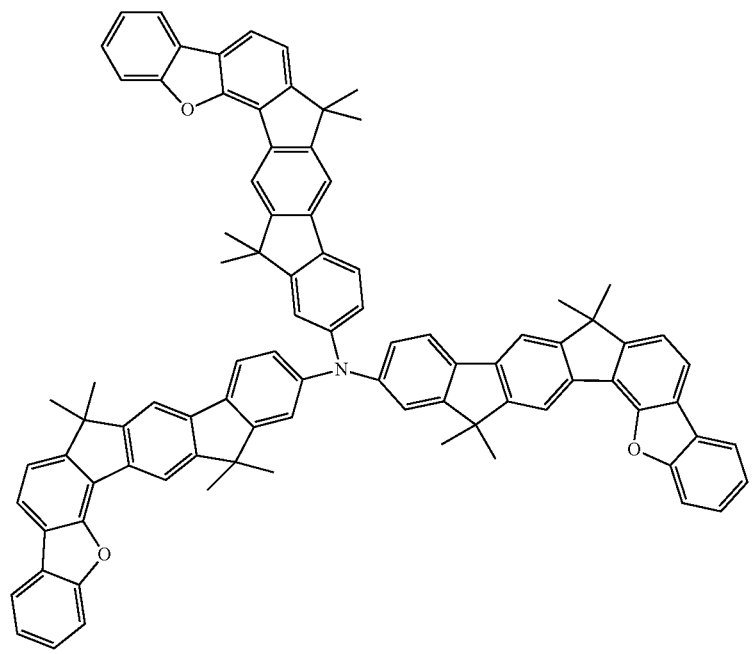
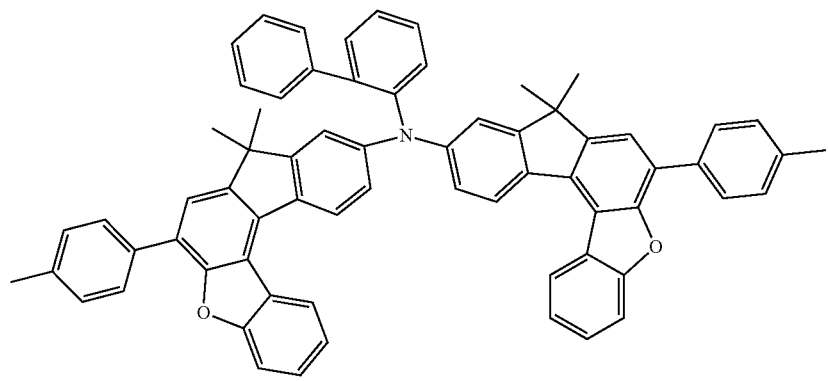

-continued
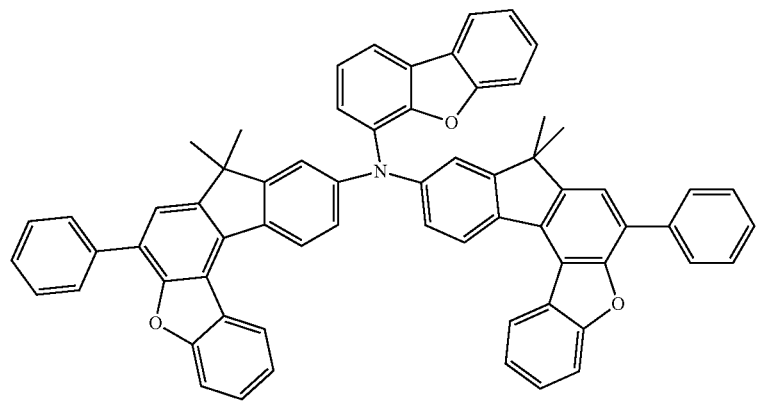
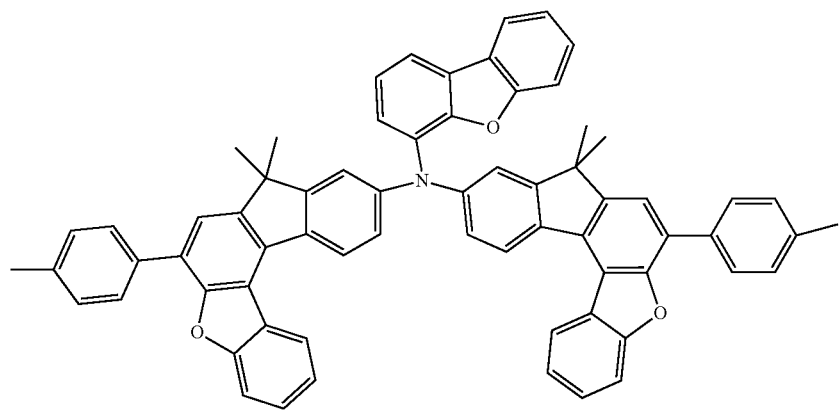
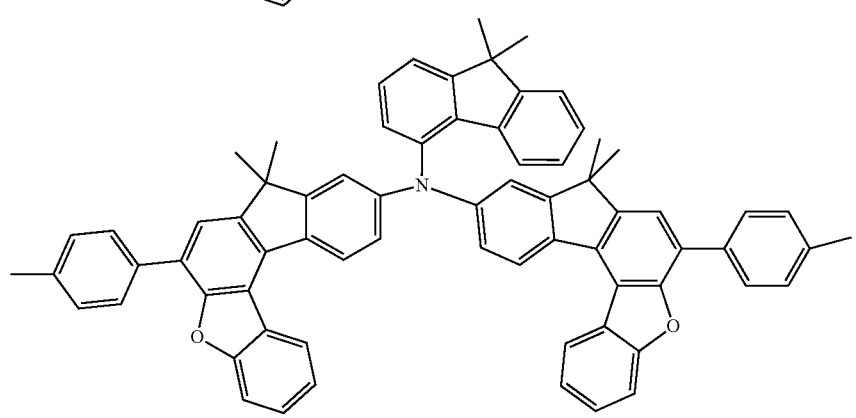
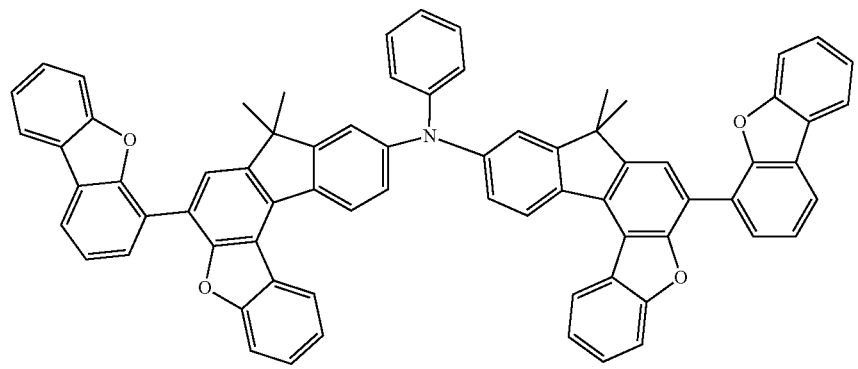

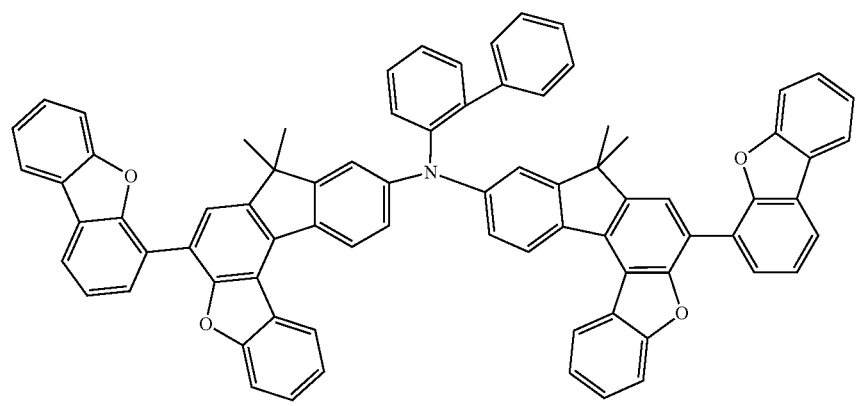
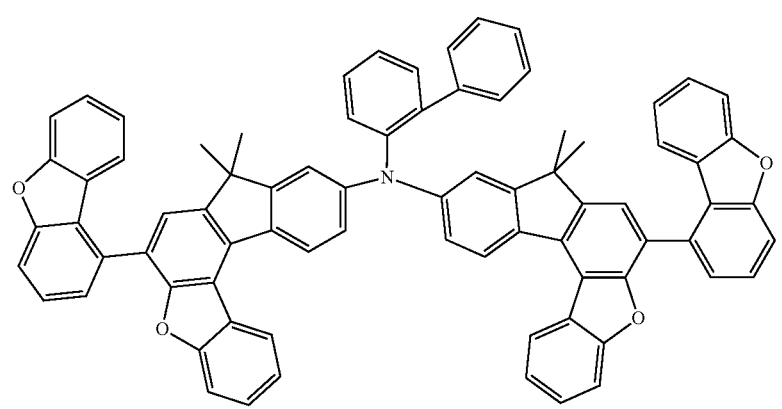
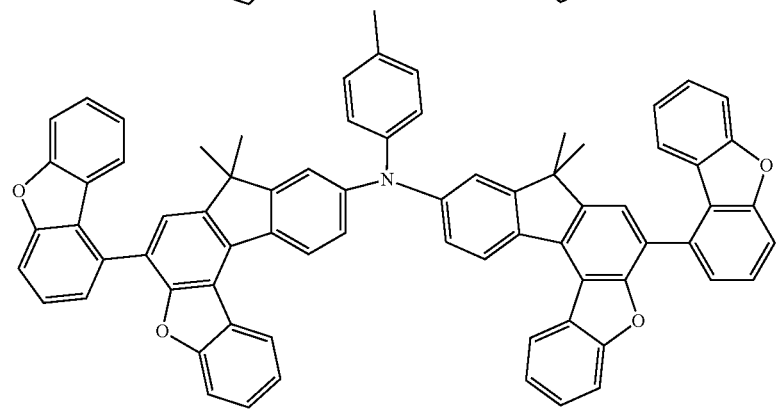
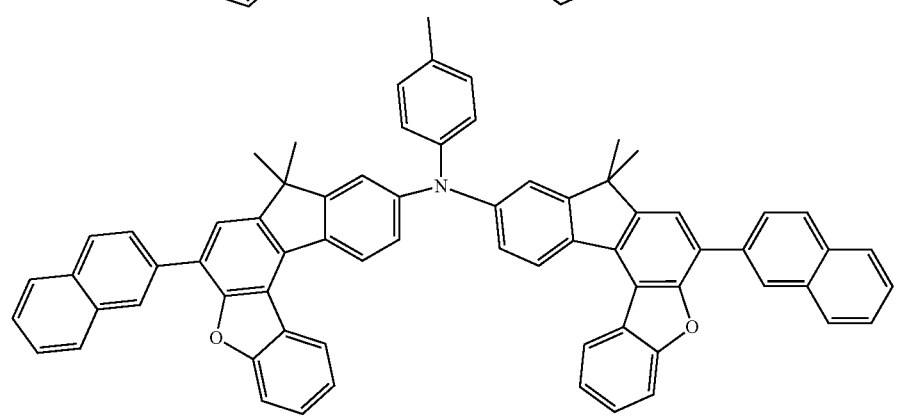

-continued
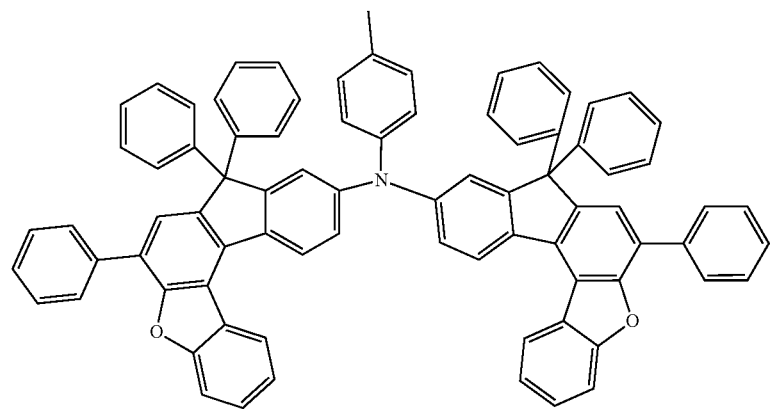
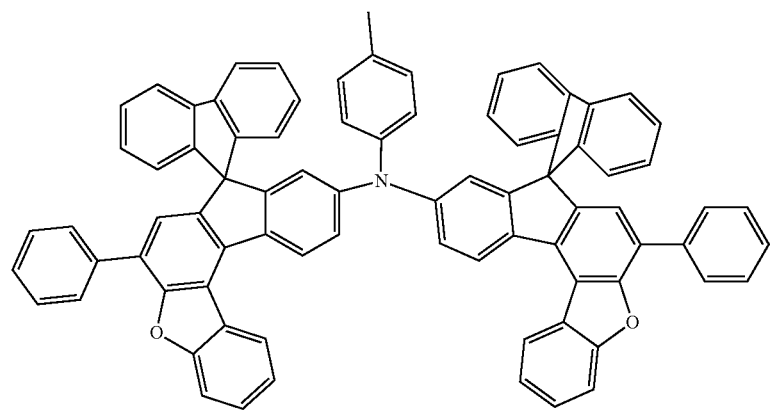
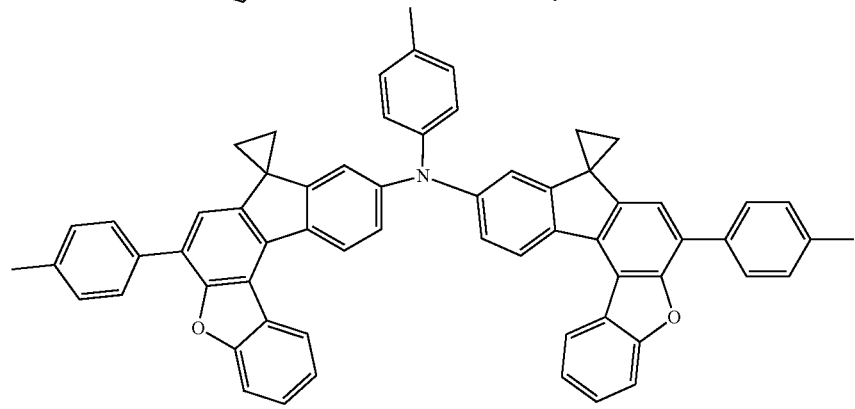
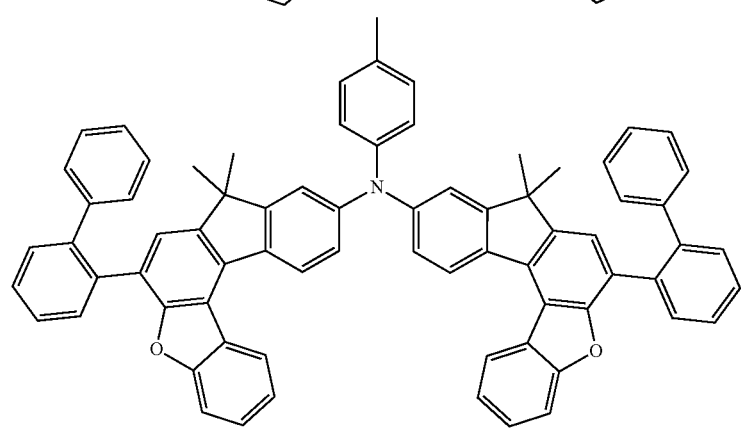

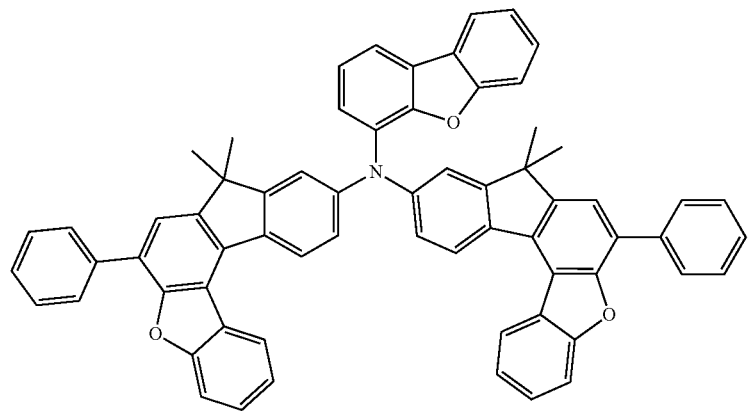
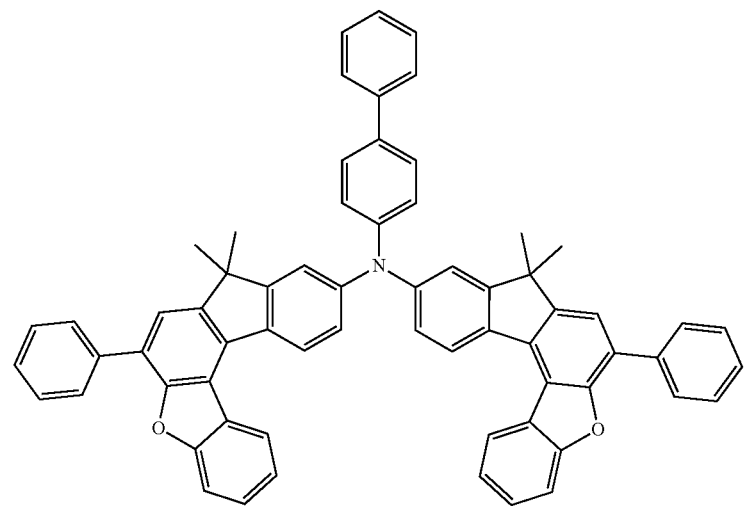
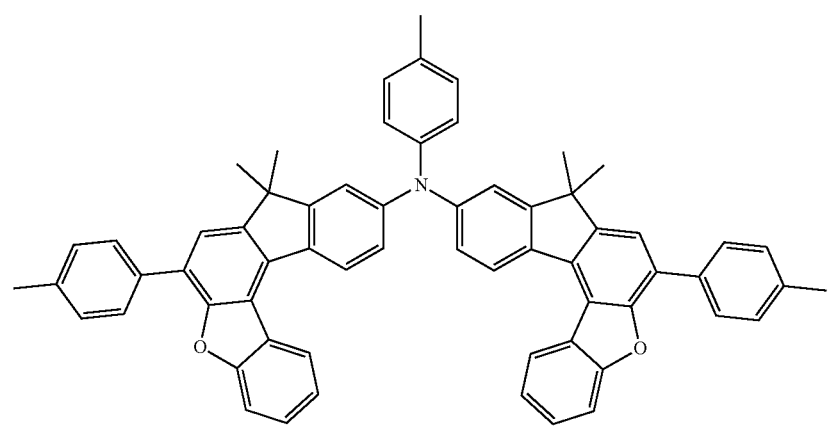

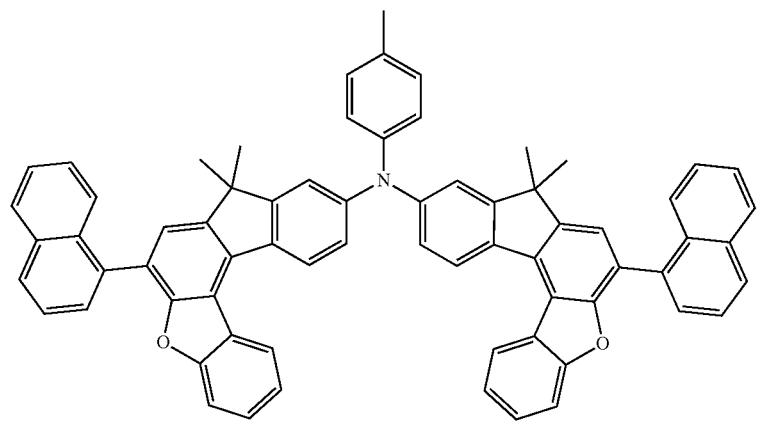
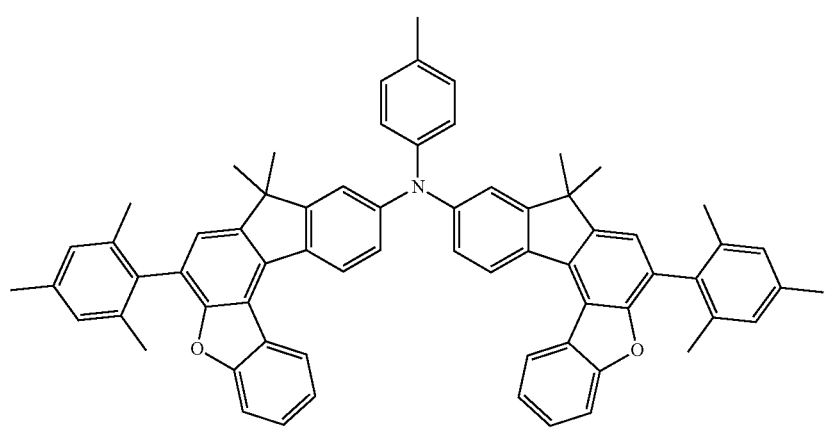
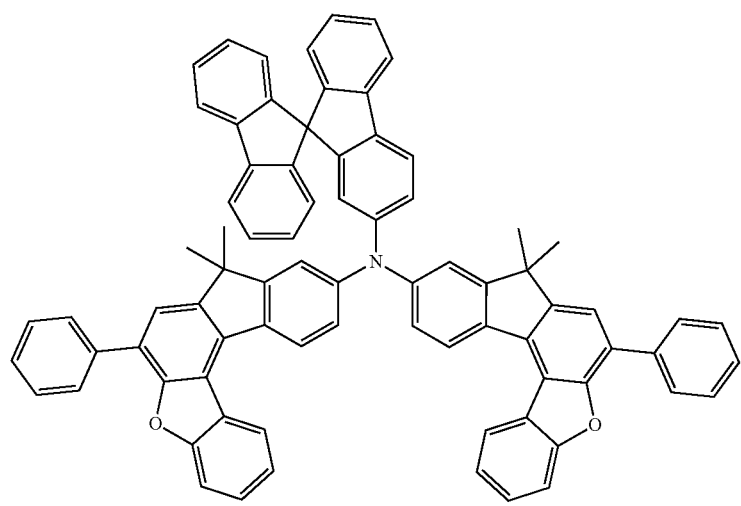

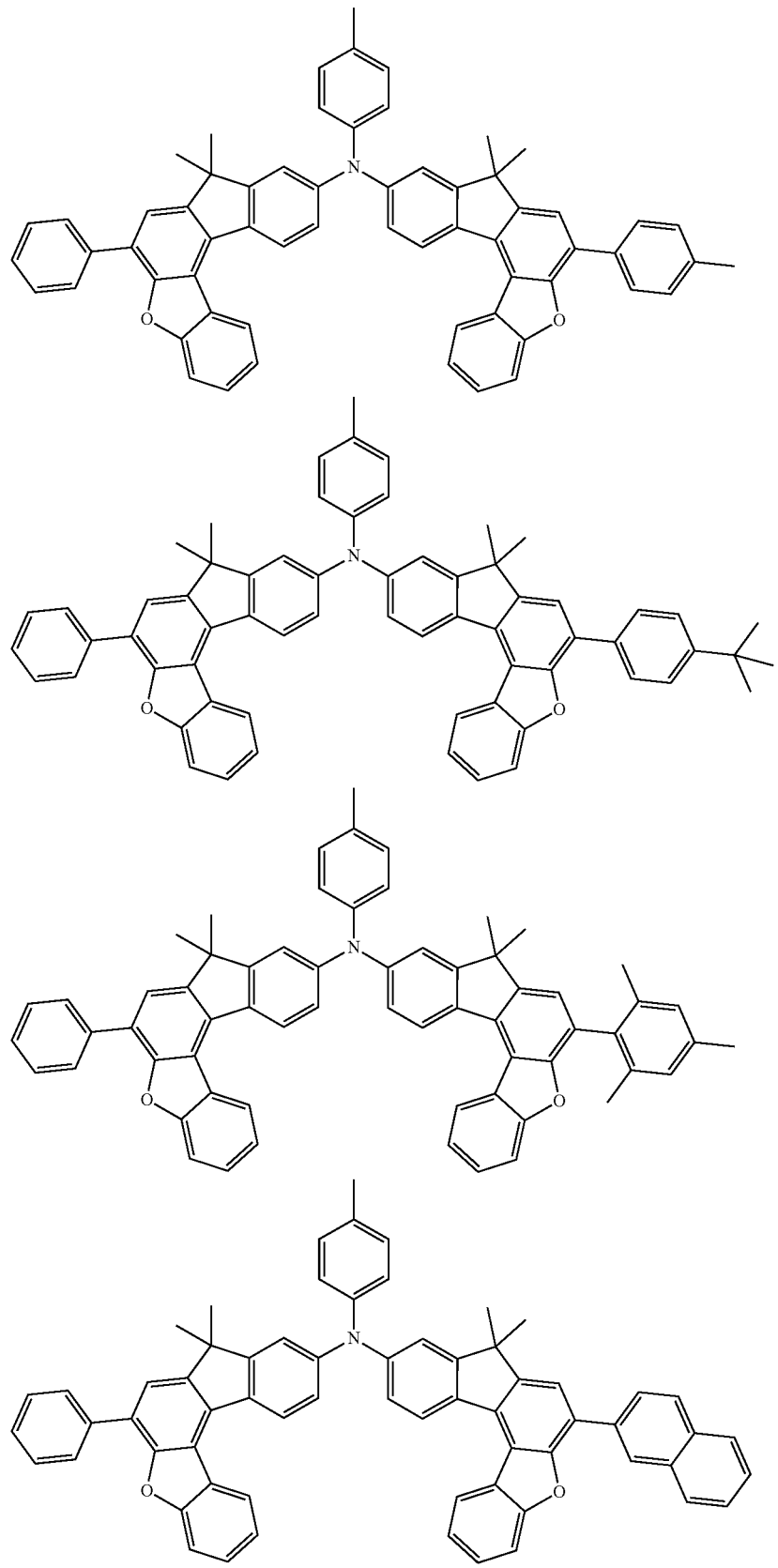

-continued
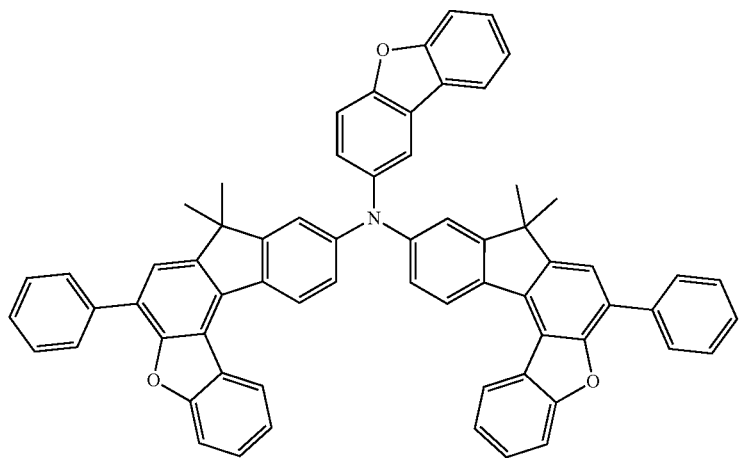
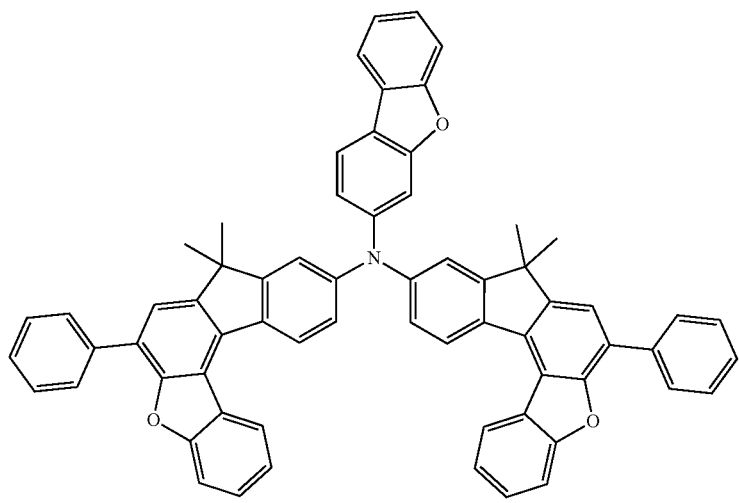
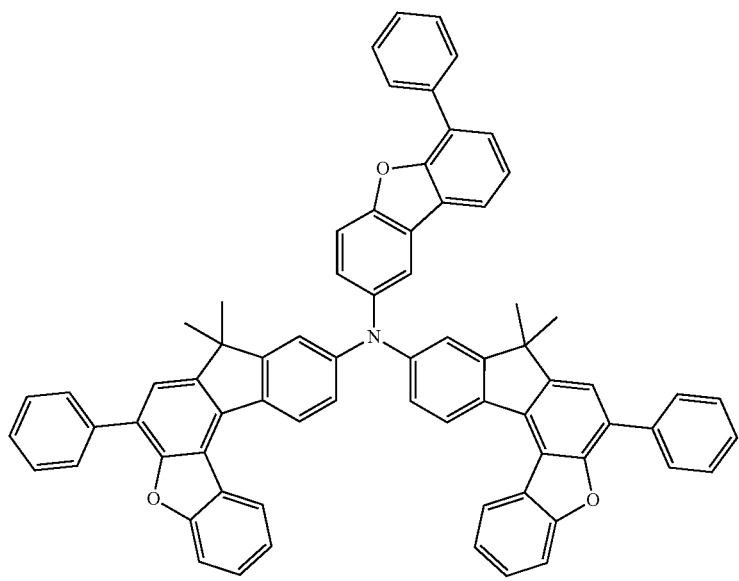

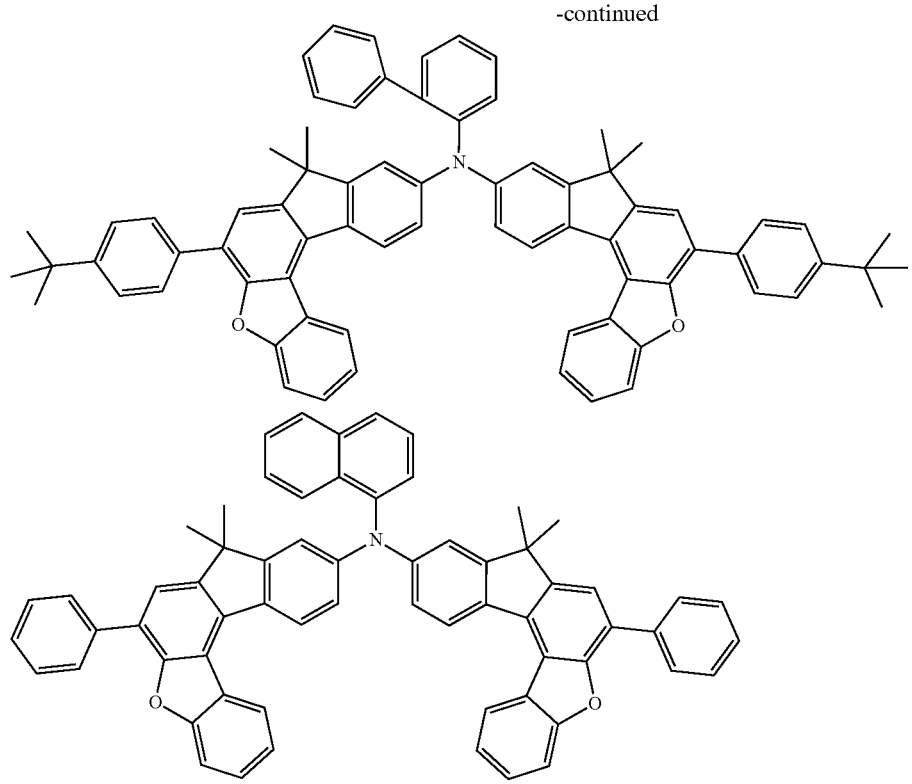
The compounds according to the invention can be prepared by synthesis steps known to the person skilled in the art, such as, for example, bromination, Suzuki coupling, Ullmann coupling, Hartwig-Buchwald coupling, etc. An example of a suitable synthesis process is depicted in general terms in Schemes 1 to 3 below.
Scheme 1
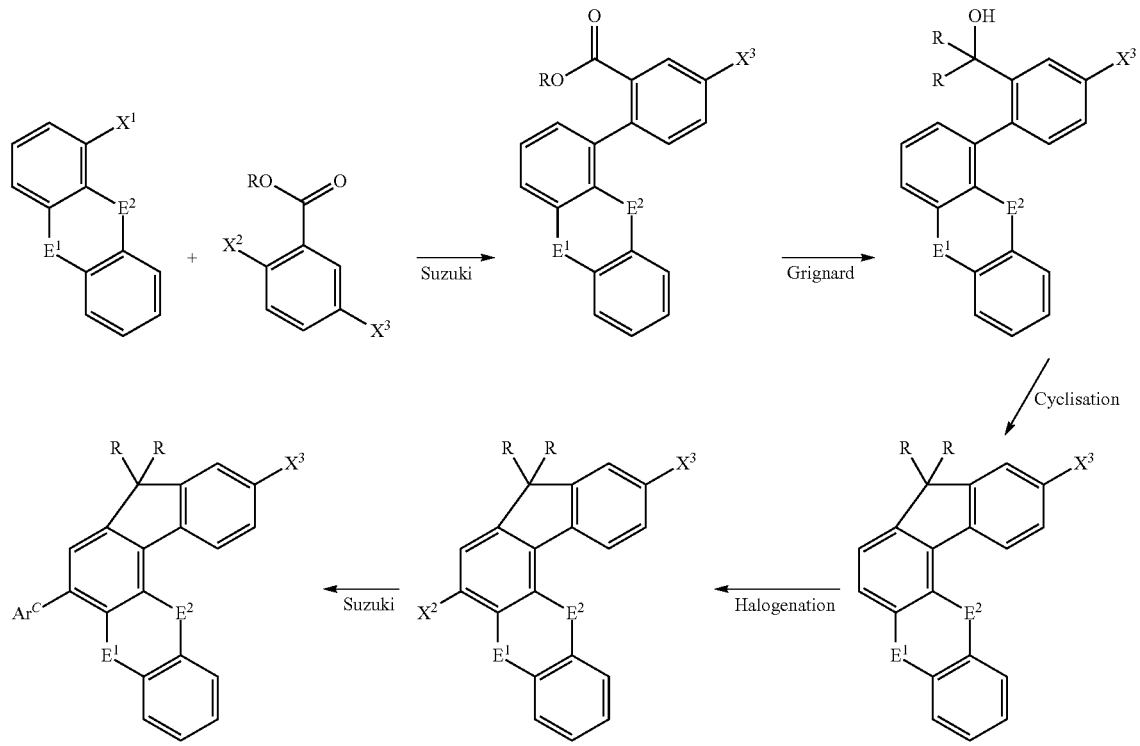

167
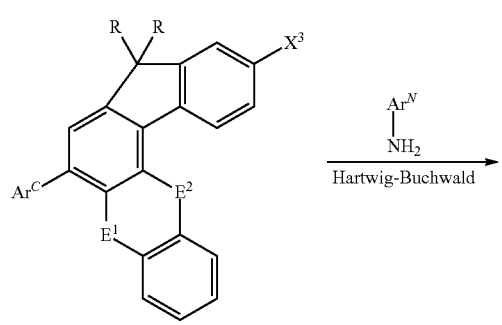
168
-continued
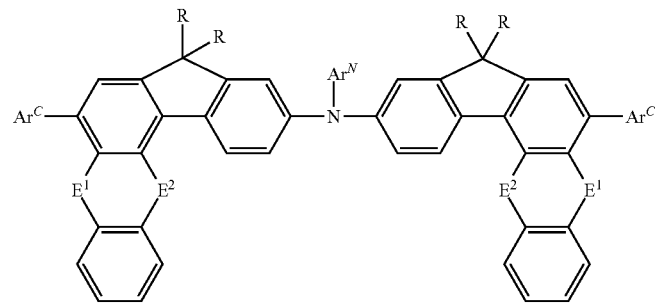
-continued
Scheme 2
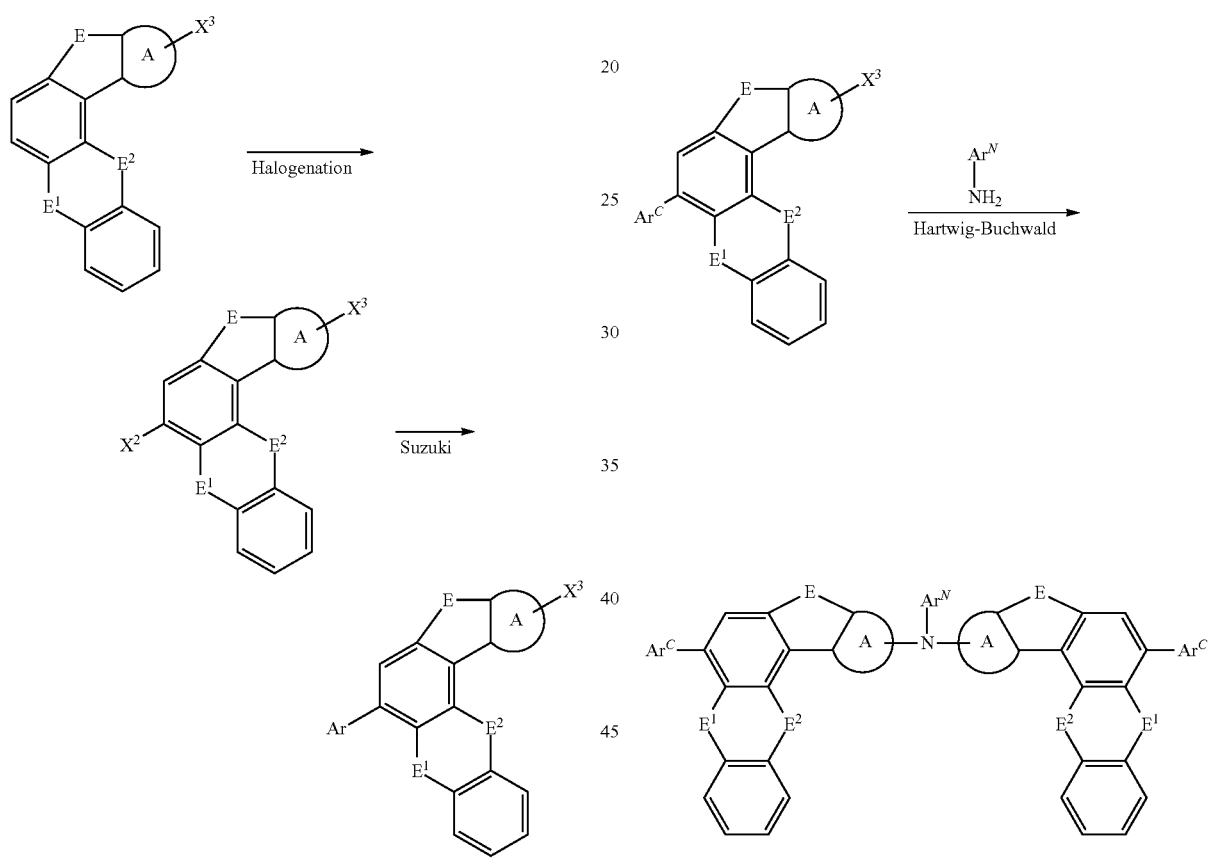
Scheme 3
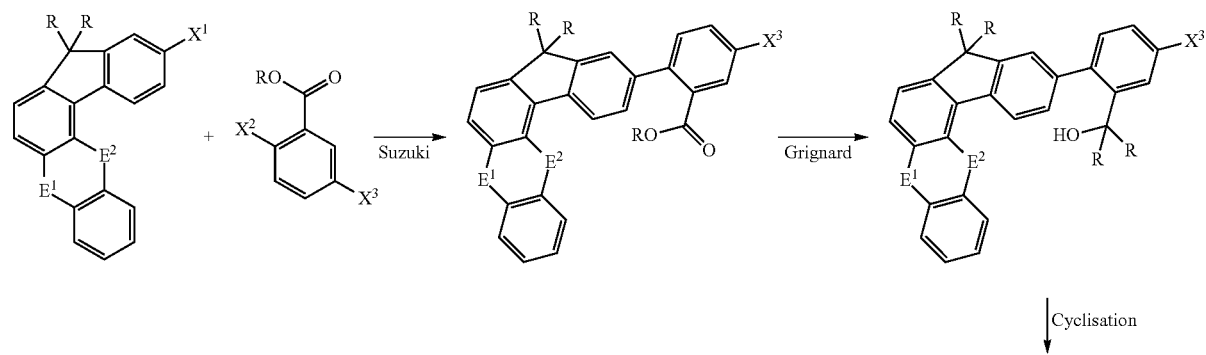

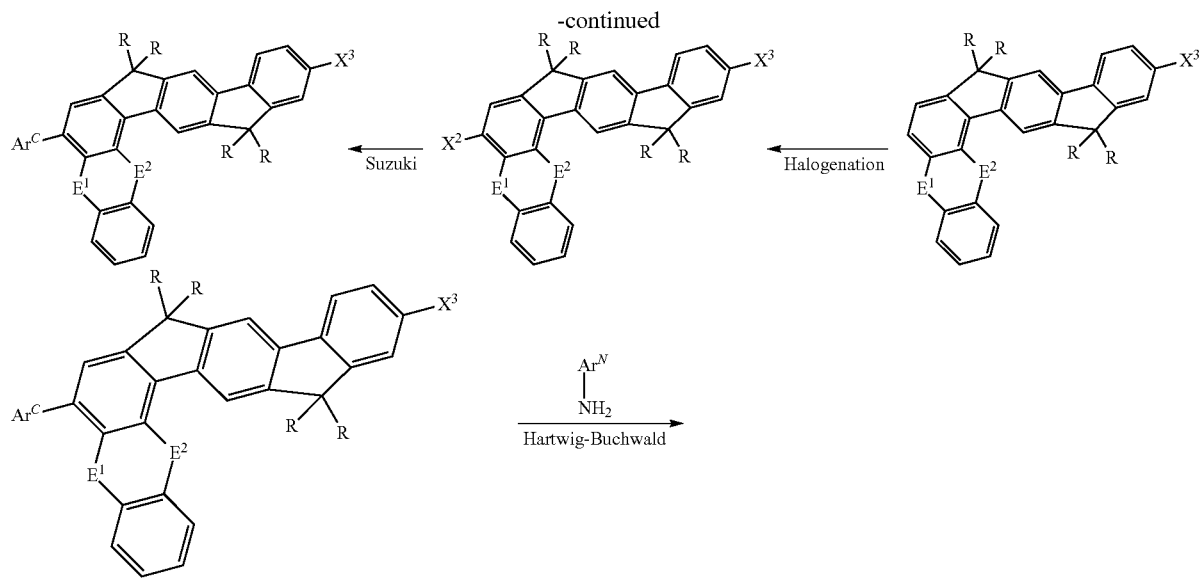

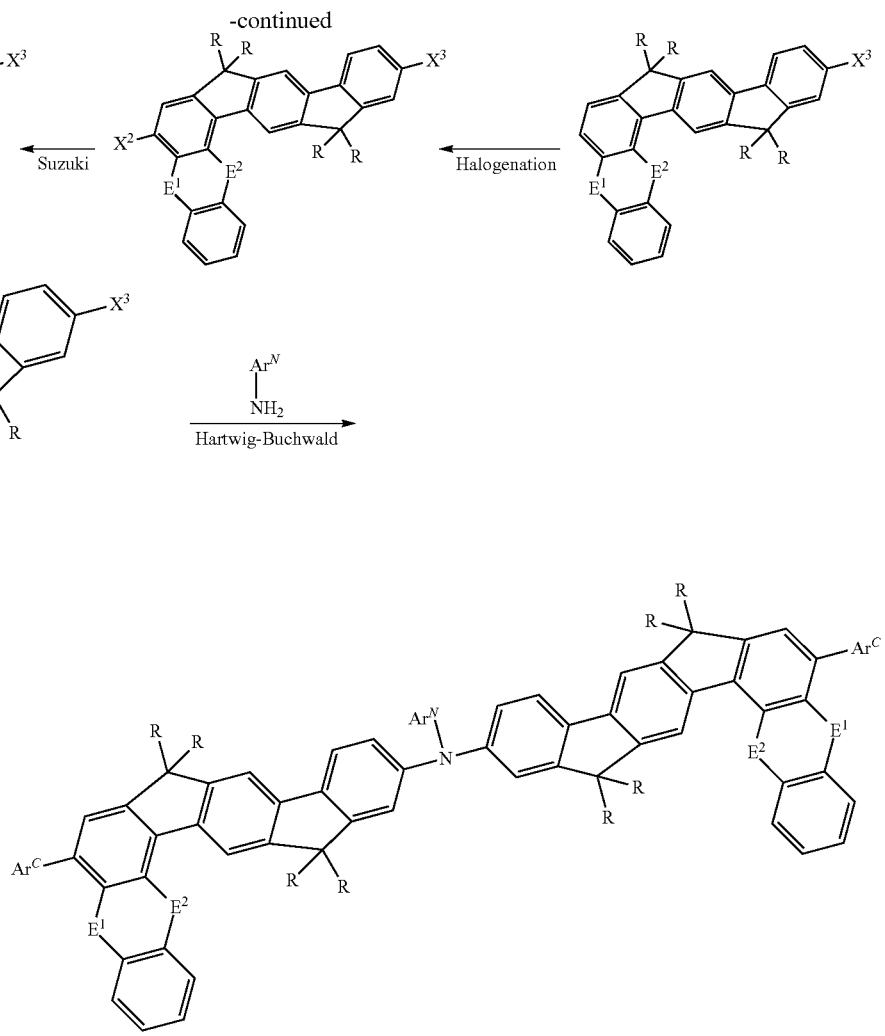

In Schemes 1 to 3, the symbols E, $E^1$, $E^2$, R and the ring A have the same meaning as above, the symbols $X^1$, $X^2$ and $X^3$ represent a leaving group (like an halogen or a boronic ester) and the symbols $Ar^N$ or $Ar^C$ represent aromatic or heteroaromatic ring systems.

The compounds of formula (1) may be synthesized as described above, where a group of formula (Int-1) reacts with an amine of formula $Ar^1$—$NH_2$ in order to obtain a group of formula (1):

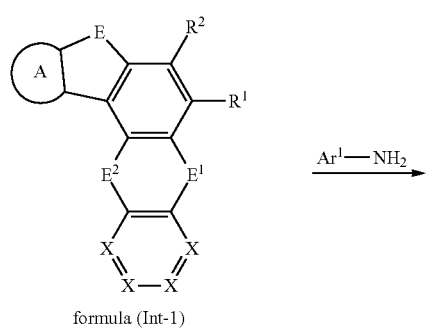

formula (Int-1)

-continued

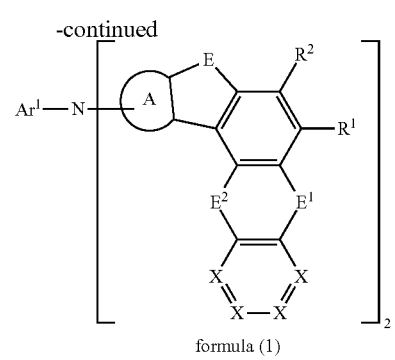

formula (1)

The present invention therefore relates to a process for the synthesis of the compounds according to the invention, comprising a step where a group of formula (Int-1) reacts with an amine of formula $Ar^1$—$NH_2$.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound, in particular a phosphorescent dopant, and/or a further matrix material. Suitable emitting compounds and further matrix materials are indicated below in connection with the organic electroluminescent device. This further compound may also be polymeric.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure and on the substitution. Preference is given to an organic electroluminescent device comprising a compound of the formula (1) or in accordance with the preferred embodiments as fluorescent emitters, emitters showing TADF (Thermally Activated Delayed Fluorescence), matrix material for fluorescent emitters. Particularly preferred is an organic electroluminescent device comprising a compound of the formula (1) or in accordance with the preferred embodiments as fluorescent emitters, more particularly blue-emitting fluorescent compound.

The compounds of formula (1) can also be employed in an electron-transport layer and/or in an electron-blocking or exciton-blocking layer and/or in a hole-transport layer, depending on the precise substitution. The preferred embodiments indicated above also apply to the use of the materials in organic electronic devices.

The compound according to the invention is particularly suitable for use as blue-emitting emitter compound. The electronic device concerned may comprise a single emitting layer comprising the compound according to the invention or it may comprise two or more emitting layers. The further emitting layers here may comprise one or more compounds according to the invention or alternatively other compounds.

If the compound according to the invention is employed as a fluorescent emitting compound in an emitting layer, it is preferably employed in combination with one or more matrix materials. A matrix material here is taken to mean a material which is present in the emitting layer, preferably as the principal component, and which does not emit light on operation of the device.

The proportion of the emitting compound in the mixture of the emitting layer is between 0.1 and 50.0%, preferably between 0.5 and 20.0%, particularly preferably between 1.0 and 10.0%. Correspondingly, the proportion of the matrix material or matrix materials is between 50.0 and 99.9%, preferably between 80.0 and 99.5%, particularly preferably between 90.0 and 99.0%.

The specifications of the proportions in % are, for the purposes of the present application, taken to mean % by vol. if the compounds are applied from the gas phase and % by weight if the compounds are applied from solution.

Preferred matrix materials for use in combination with fluorescent emitting compounds are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiroDPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Particularly preferred matrix materials for use in combination with the compounds of the formula (1) in the emitting layer are depicted in the following table.

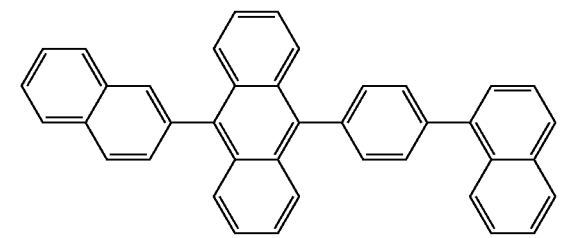 [SMILES: c1ccc2cc(-c3c4ccccc4c(-c4ccc(-c5cccc6ccccc56)cc4)c4ccccc34)ccc2c1]

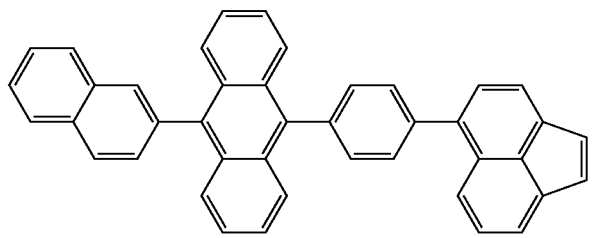 [SMILES: C1=Cc2ccc(-c3ccc(-c4c5ccccc5c(-c5ccc6ccccc6c5)c5ccccc45)cc3)c3cccc1c23]

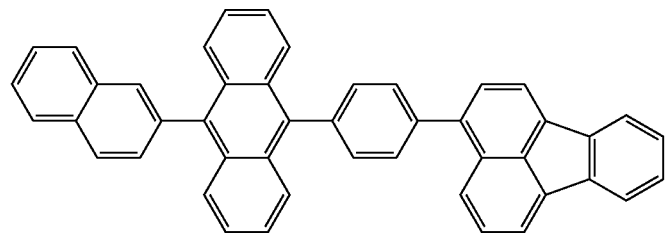 [SMILES: c1ccc2c(c1)-c1cccc3c(-c4ccc(-c5c6ccccc6c(-c6ccc7ccccc7c6)c6ccccc56)cc4)ccc-2c13]

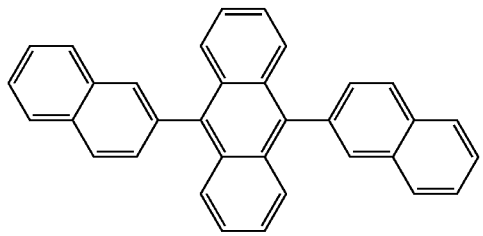 [SMILES: c1ccc2cc(-c3c4ccccc4c(-c4ccc5ccccc5c4)c4ccccc34)ccc2c1]

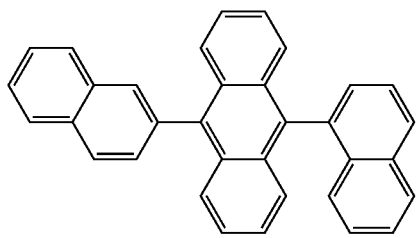 [SMILES: c1ccc2cc(-c3c4ccccc4c(-c4cccc5ccccc45)c4ccccc34)ccc2c1]

-continued
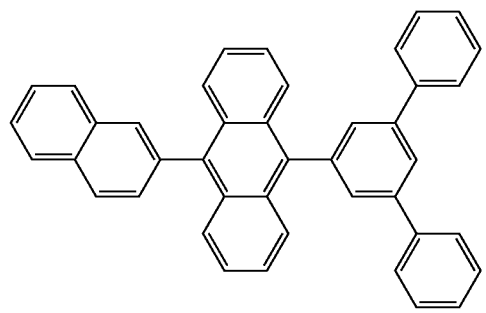 [SMILES: c1ccc(-c2cc(-c3ccccc3)cc(-c3c4ccccc4c(-c4ccc5ccccc5c4)c4ccccc34)c2)cc1]
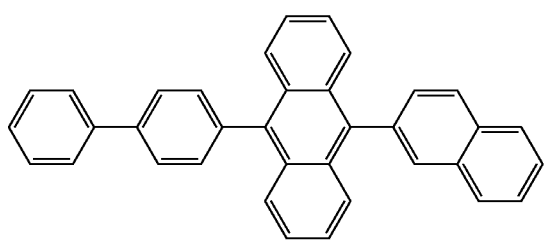 [SMILES: c1ccc(-c2ccc(-c3c4ccccc4c(-c4ccc5ccccc5c4)c4ccccc34)cc2)cc1]
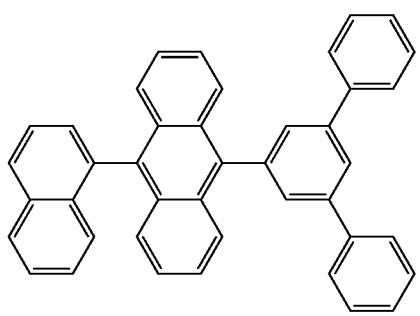 [SMILES: c1ccc(-c2cc(-c3ccccc3)cc(-c3c4ccccc4c(-c4cccc5ccccc45)c4ccccc34)c2)cc1]
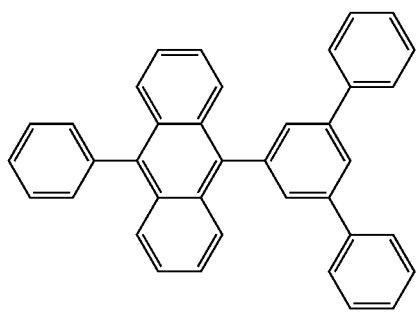 [SMILES: c1ccc(-c2cc(-c3ccccc3)cc(-c3c4ccccc4c(-c4ccccc4)c4ccccc34)c2)cc1]
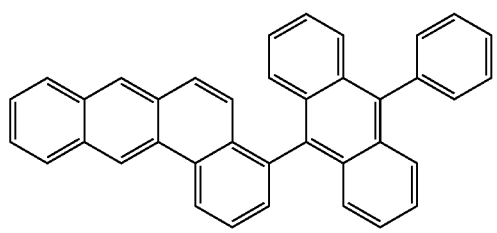 [SMILES: c1ccc(-c2c3ccccc3c(-c3cccc4c3ccc3cc5ccccc5cc34)c3ccccc23)cc1]

-continued
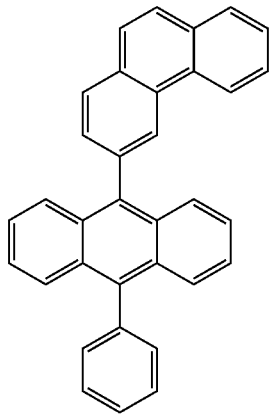 [SMILES: c1ccc(-c2c3ccccc3c(-c3ccc4ccc5ccccc5c4c3)c3ccccc23)cc1]
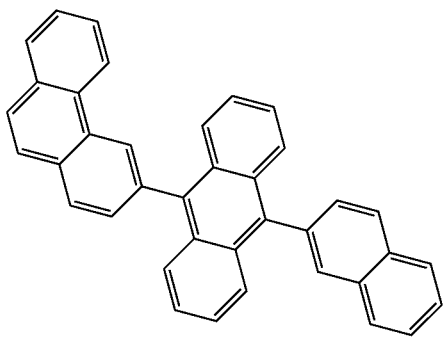 [SMILES: c1ccc2cc(-c3c4ccccc4c(-c4ccc5ccc6ccccc6c5c4)c4ccccc34)ccc2c1]
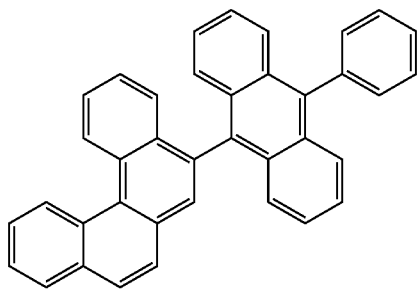 [SMILES: c1ccc(-c2c3ccccc3c(-c3cc4ccc5ccccc5c4c4ccccc34)c3ccccc23)cc1]
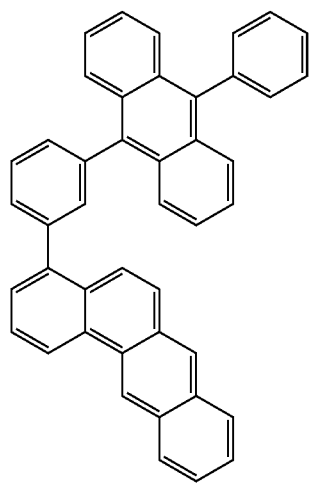 [SMILES: c1ccc(-c2c3ccccc3c(-c3cccc(-c4cccc5c4ccc4cc6ccccc6cc45)c3)c3ccccc23)cc1]

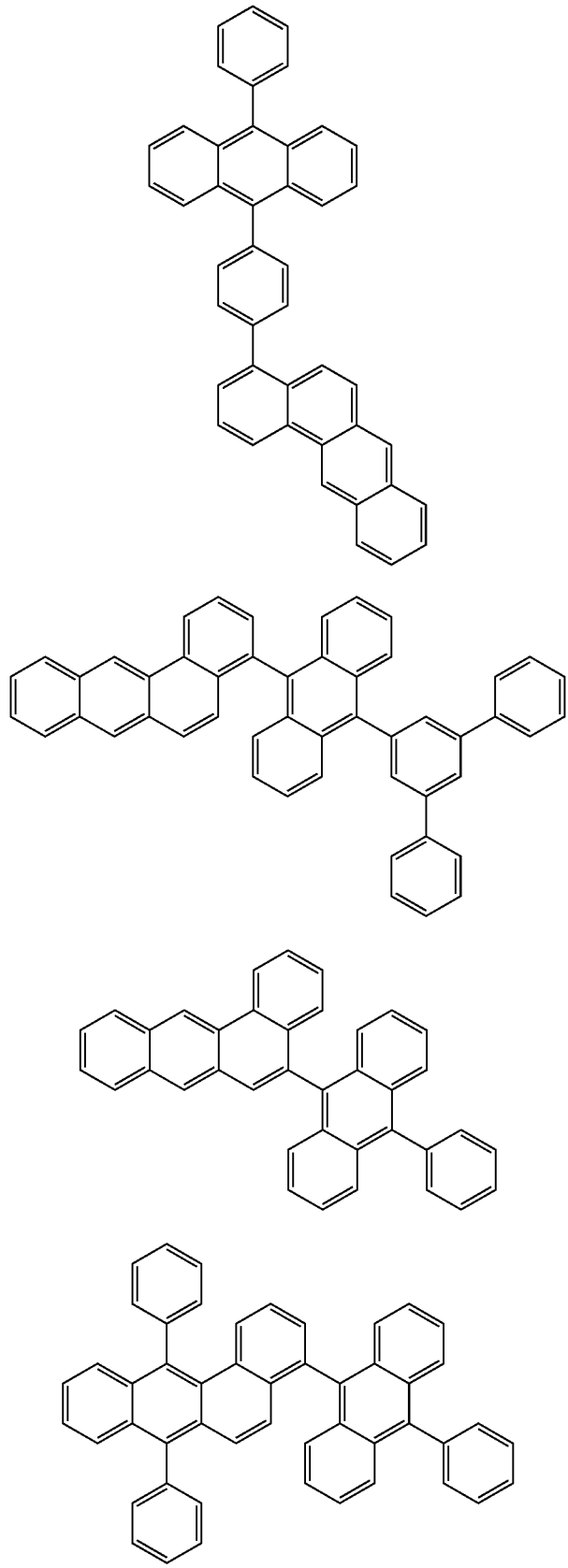

-continued
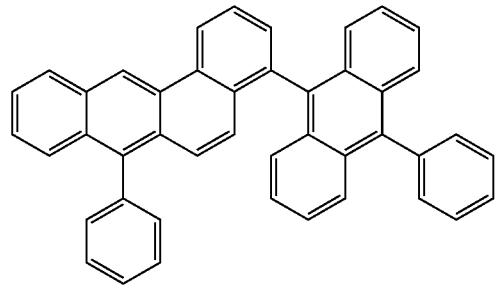 [SMILES: c1ccc(-c2c3ccccc3c(-c3cccc4c3ccc3c(-c5ccccc5)c5ccccc5cc34)c3ccccc23)cc1]
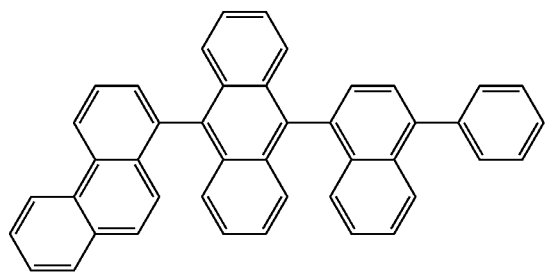 [SMILES: c1ccc(-c2ccc(-c3c4ccccc4c(-c4cccc5c4ccc4ccccc45)c4ccccc34)c3ccccc23)cc1]
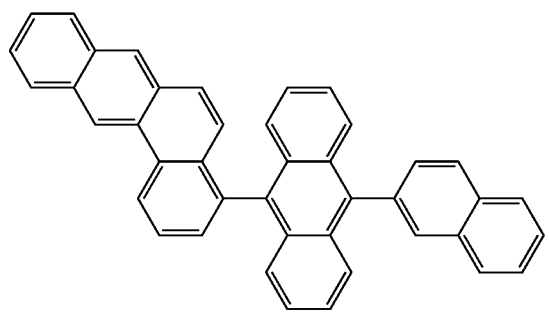 [SMILES: c1ccc2cc(-c3c4ccccc4c(-c4cccc5c4ccc4cc6ccccc6cc45)c4ccccc34)ccc2c1]
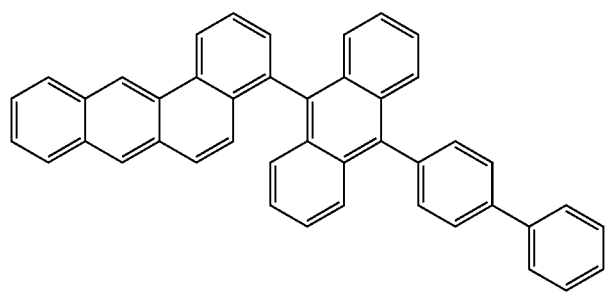 [SMILES: c1ccc(-c2ccc(-c3c4ccccc4c(-c4cccc5c4ccc4cc6ccccc6cc45)c4ccccc34)cc2)cc1]

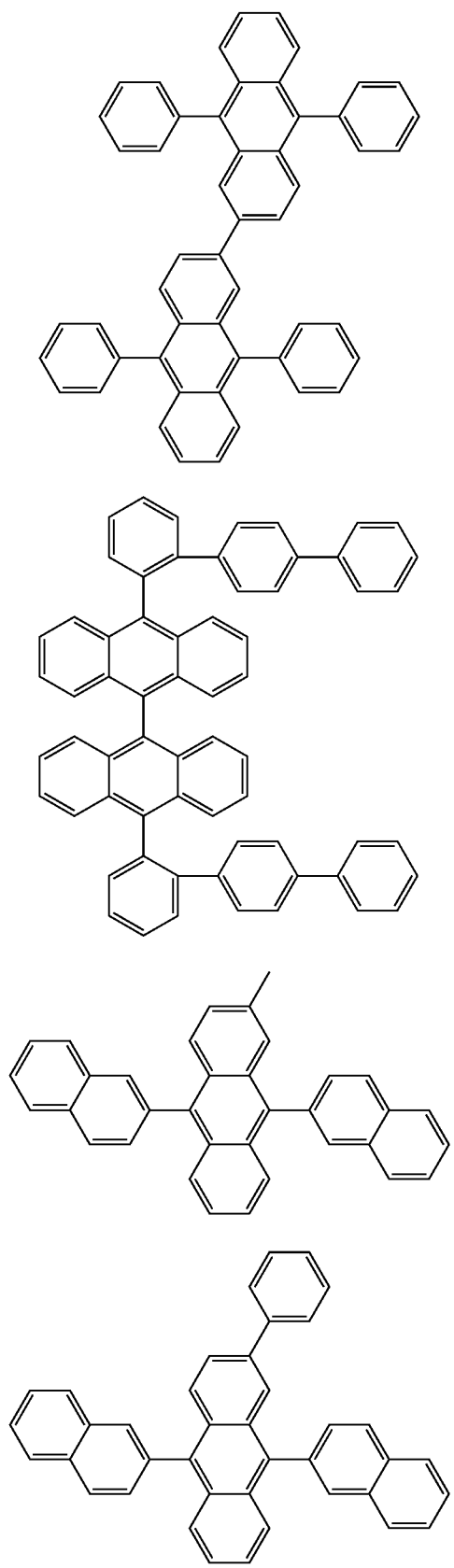

-continued
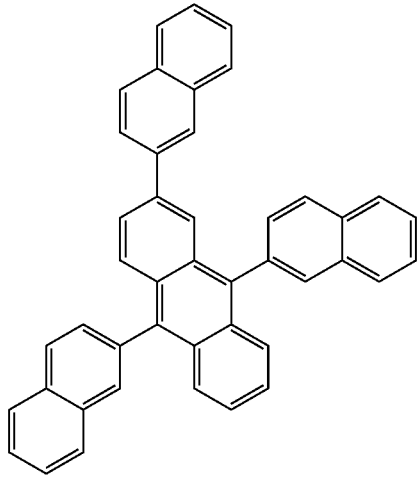 [SMILES: c1ccc2cc(-c3ccc4c(-c5ccc6ccccc6c5)c5ccccc5c(-c5ccc6ccccc6c5)c4c3)ccc2c1]
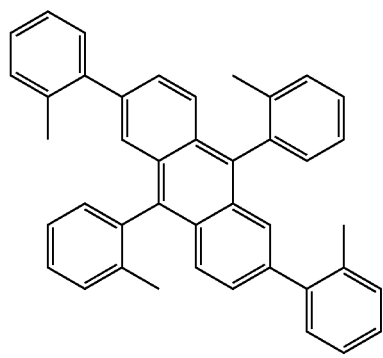 [SMILES: Cc1ccccc1-c1ccc2c(-c3ccccc3C)c3cc(-c4ccccc4C)ccc3c(-c3ccccc3C)c2c1]
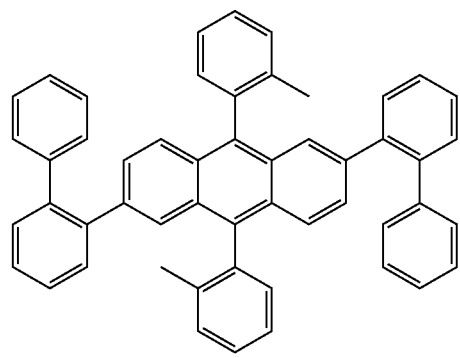 [SMILES: Cc1ccccc1-c1c2ccc(-c3ccccc3-c3ccccc3)cc2c(-c2ccccc2C)c2ccc(-c3ccccc3-c3ccccc3)cc12]

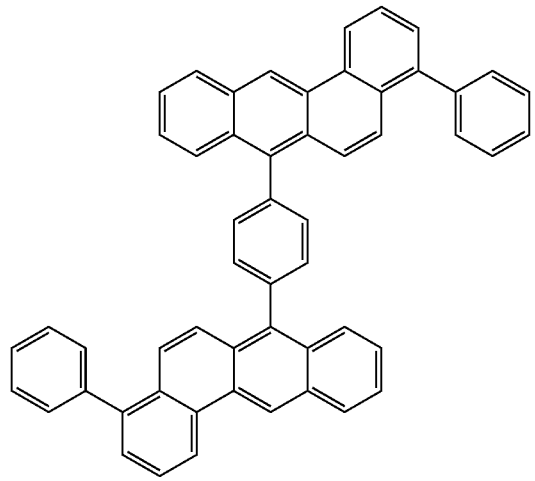 [SMILES: c1ccc(-c2cccc3c2ccc2c(-c4ccc(-c5c6ccccc6cc6c5ccc5c(-c7ccccc7)cccc56)cc4)c4ccccc4cc23)cc1]
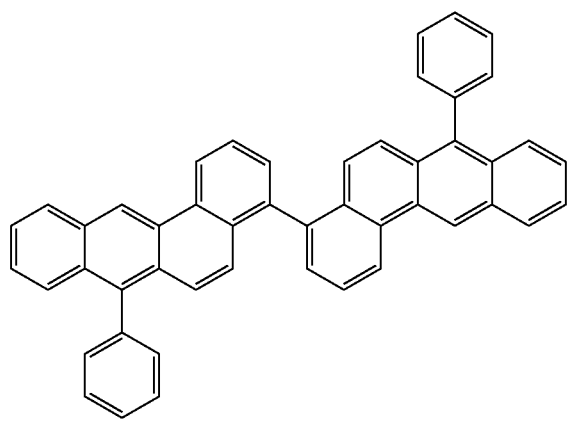 [SMILES: c1ccc(-c2c3ccccc3cc3c2ccc2c(-c4cccc5c4ccc4c(-c6ccccc6)c6ccccc6cc45)cccc23)cc1]
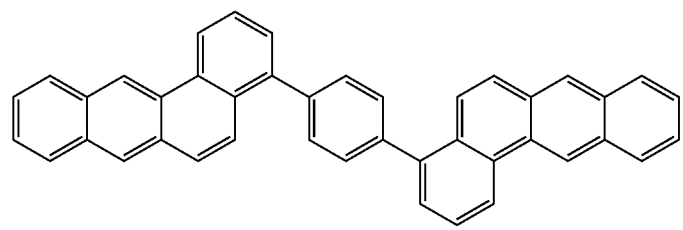 [SMILES: c1ccc2cc3c(ccc4c(-c5ccc(-c6cccc7c6ccc6cc8ccccc8cc67)cc5)cccc43)cc2c1]

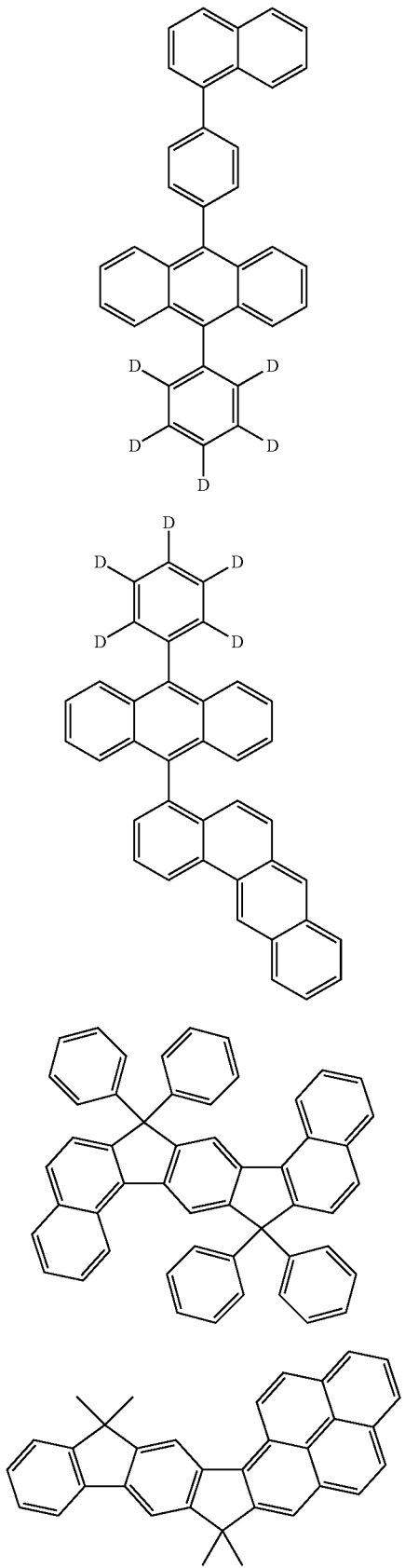

-continued
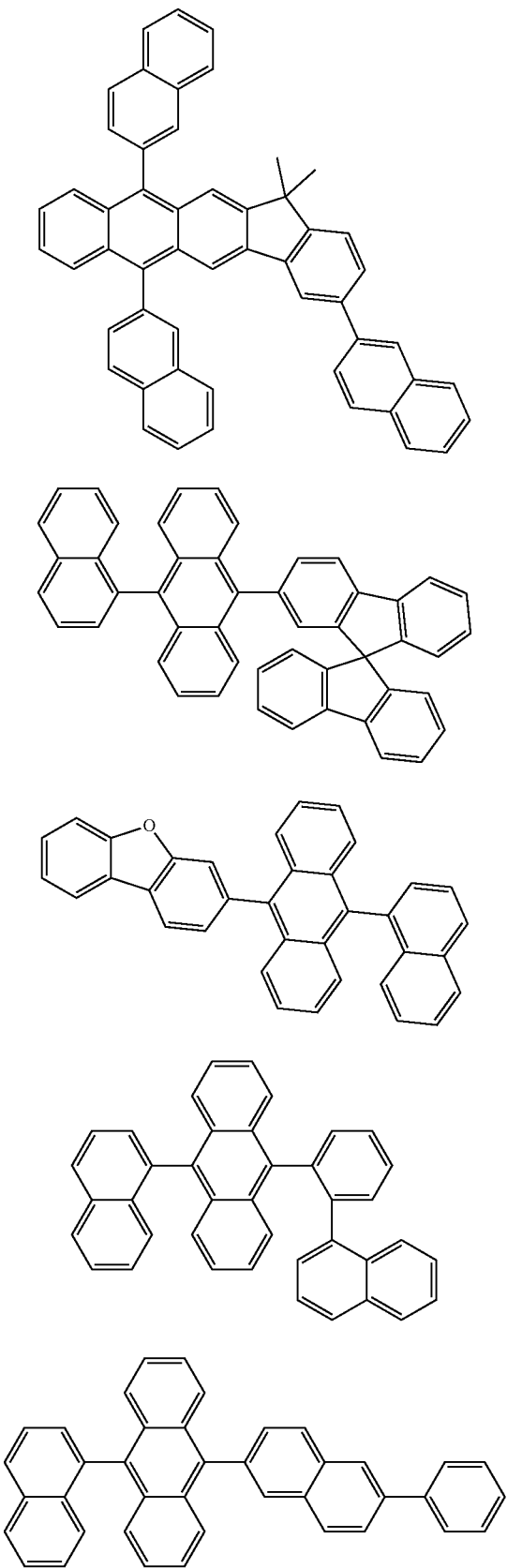

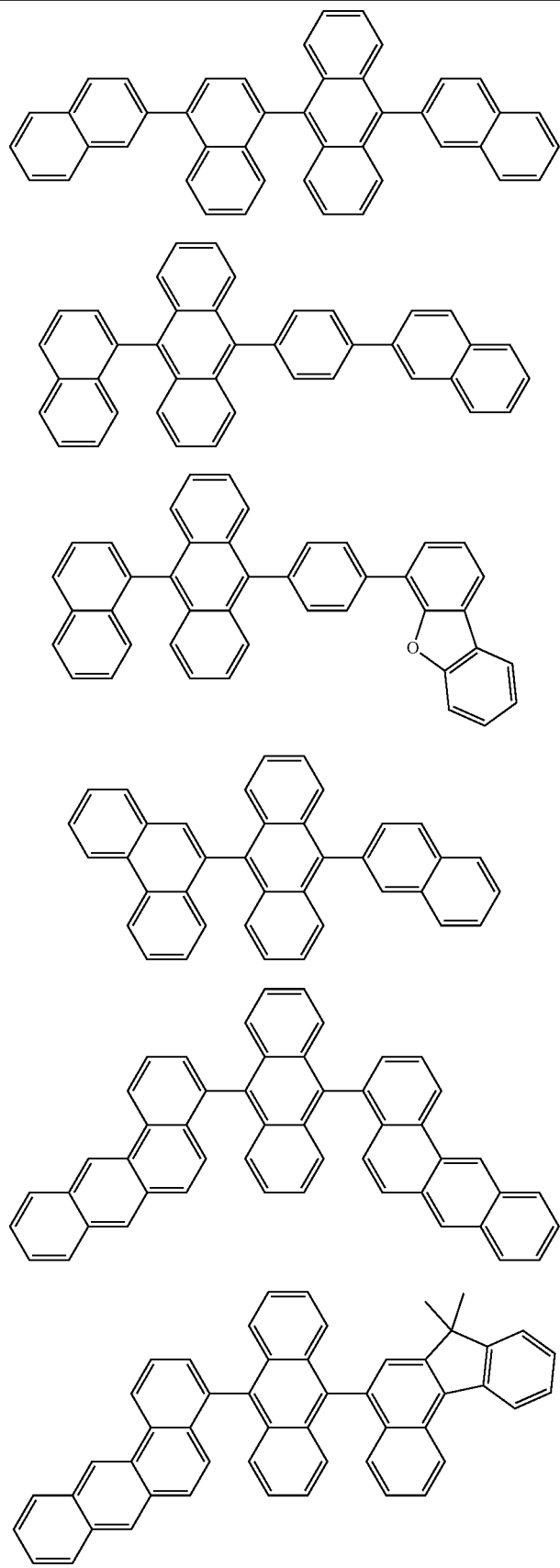

-continued
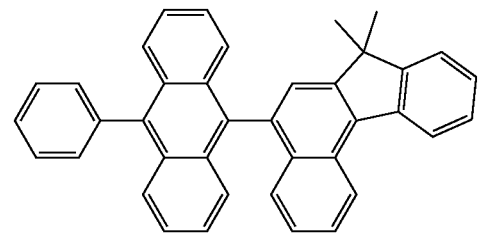 [SMILES: CC1(C)c2ccccc2-c2c1cc(-c1c3ccccc3c(-c3ccccc3)c3ccccc13)c1ccccc21]
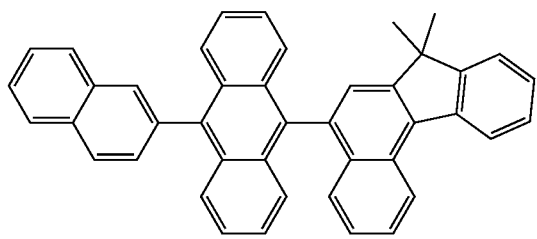 [SMILES: CC1(C)c2ccccc2-c2c1cc(-c1c3ccccc3c(-c3ccc4ccccc4c3)c3ccccc13)c1ccccc21]
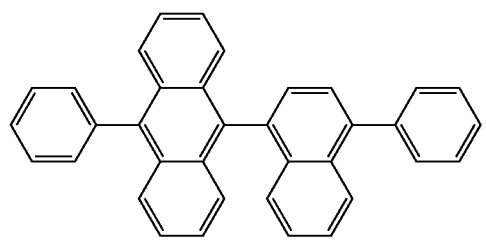 [SMILES: c1ccc(-c2ccc(-c3c4ccccc4c(-c4ccccc4)c4ccccc34)c3ccccc23)cc1]
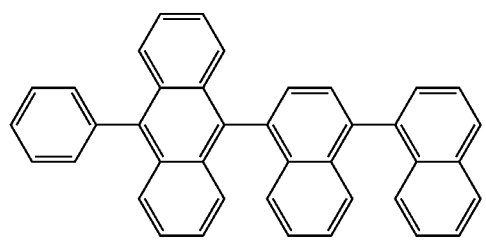 [SMILES: c1ccc(-c2c3ccccc3c(-c3ccc(-c4cccc5ccccc45)c4ccccc34)c3ccccc23)cc1]
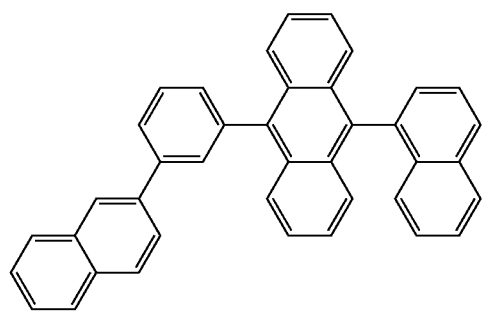 [SMILES: c1cc(-c2ccc3ccccc3c2)cc(-c2c3ccccc3c(-c3cccc4ccccc34)c3ccccc23)c1]
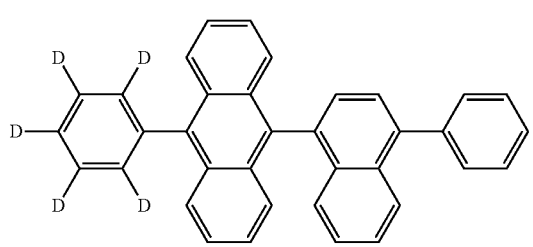 [SMILES: [2H]c1c([2H])c([2H])c(-c2c3ccccc3c(-c3ccc(-c4ccccc4)c4ccccc34)c3ccccc23)c([2H])c1[2H]]

-continued
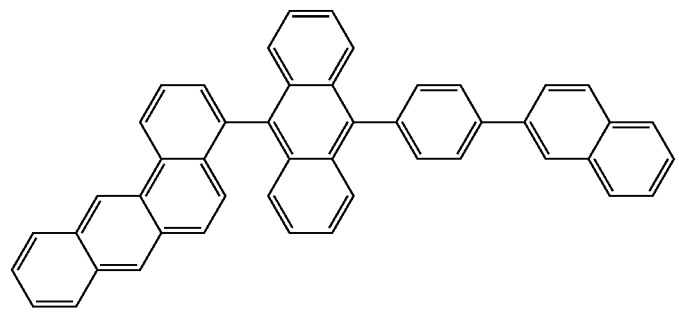 [SMILES: c1ccc2cc(-c3ccc(-c4c5ccccc5c(-c5cccc6c5ccc5cc7ccccc7cc56)c5ccccc45)cc3)ccc2c1]
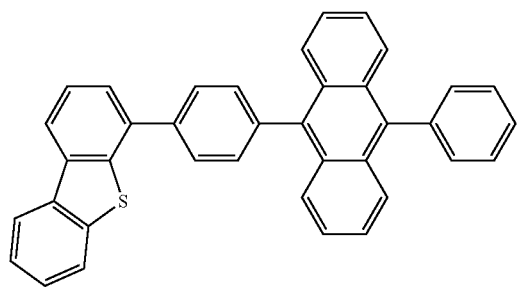 [SMILES: c1ccc(-c2c3ccccc3c(-c3ccc(-c4cccc5c4sc4ccccc45)cc3)c3ccccc23)cc1]
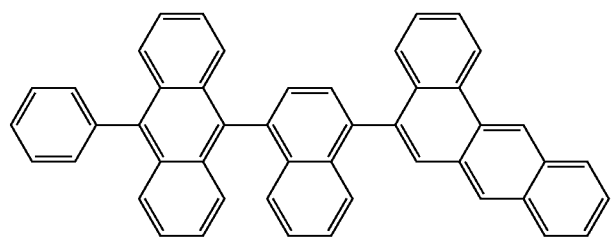 [SMILES: c1ccc(-c2c3ccccc3c(-c3ccc(-c4cc5cc6ccccc6cc5c5ccccc45)c4ccccc34)c3ccccc23)cc1]
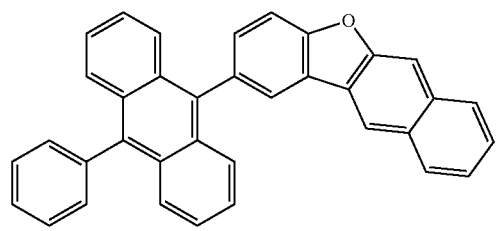 [SMILES: c1ccc(-c2c3ccccc3c(-c3ccc4oc5cc6ccccc6cc5c4c3)c3ccccc23)cc1]
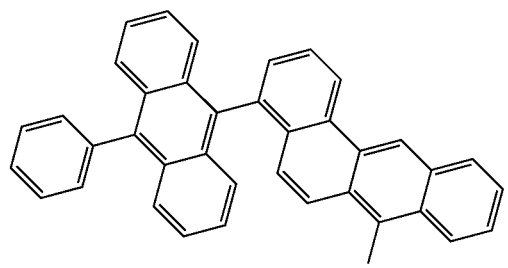 [SMILES: Cc1c2ccccc2cc2c1ccc1c(-c3c4ccccc4c(-c4ccccc4)c4ccccc34)cccc12]

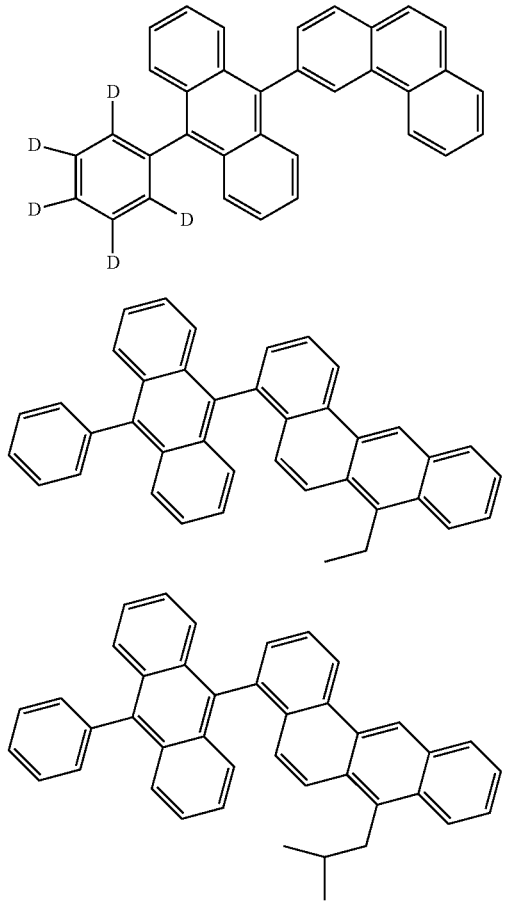

If the compound according to the invention is employed as a fluorescent emitting compound in an emitting layer, it may be employed in combination with one or more other fluorescent emitting compounds.

Preferred fluorescent emitters, besides the compounds according to the invention, are selected from the class of the arylamines. An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Still further preferred emitters are benzanthracene derivatives as disclosed in WO 2015/158409, anthracene derivatives as disclosed in WO 2017/036573, fluorene dimers like in WO 2016/150544 or phenoxazine derivatives as disclosed in WO 2017/028940 and WO 2017/028941. Preference is likewise given to the pyrenarylamines disclosed in WO 2012/048780 and WO 2013/185871. Preference is likewise given to the benzoindenofluorenamines disclosed in WO 2014/037077, the benzofluorenamines disclosed in WO 2014/106522 and the indenofluorenes disclosed in WO 2014/111269 or WO 2017/036574.

Examples of preferred fluorescent emitting compounds, besides the compounds according to the invention, which can be used in combination with the compounds of the invention in an emitting layer or which can be used in another emitting layer of the same device are depicted in the following table:

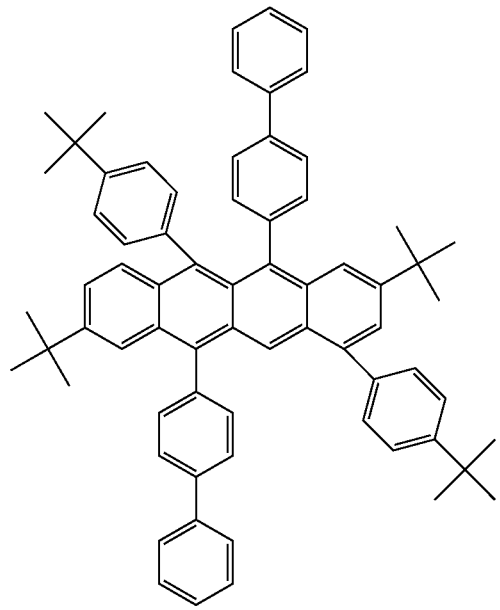 [SMILES: CC(C)(C)c1ccc(-c2cc(C(C)(C)C)cc3c(-c4ccc(-c5ccccc5)cc4)c4c(-c5ccc(C(C)(C)C)cc5)c5ccc(C(C)(C)C)cc5c(-c5ccc(-c6ccccc6)cc5)c4cc23)cc1]
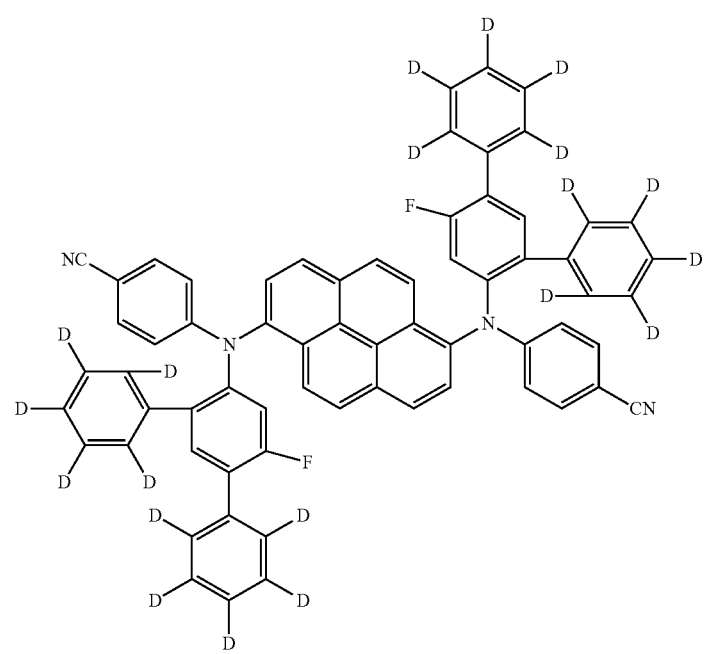 [SMILES: [2H]c1c([2H])c([2H])c(-c2cc(-c3c([2H])c([2H])c([2H])c([2H])c3[2H])c(N(c3ccc(C#N)cc3)c3ccc4ccc5c(N(c6ccc(C#N)cc6)c6cc(F)c(-c7c([2H])c([2H])c([2H])c([2H])c7[2H])cc6-c6c([2H])c([2H])c([2H])c([2H])c6[2H])ccc6ccc3c4c65)cc2F)c([2H])c1[2H]]

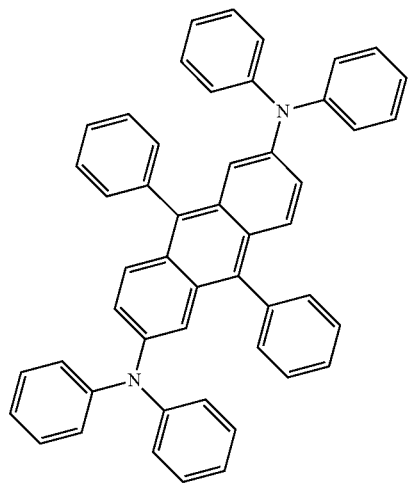 [SMILES: c1ccc(-c2c3ccc(N(c4ccccc4)c4ccccc4)cc3c(-c3ccccc3)c3ccc(N(c4ccccc4)c4ccccc4)cc23)cc1]
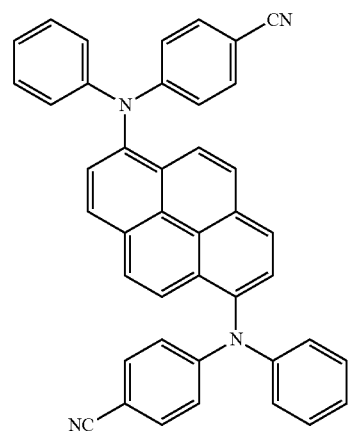 [SMILES: N#Cc1ccc(N(c2ccccc2)c2ccc3ccc4c(N(c5ccccc5)c5ccc(C#N)cc5)ccc5ccc2c3c54)cc1]
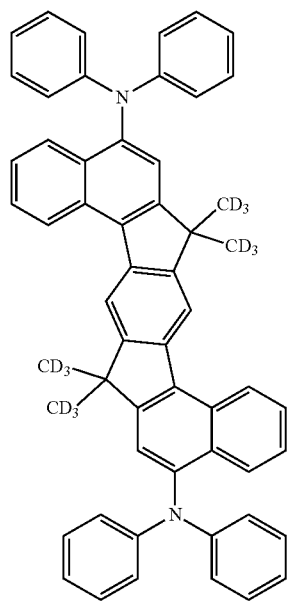 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]

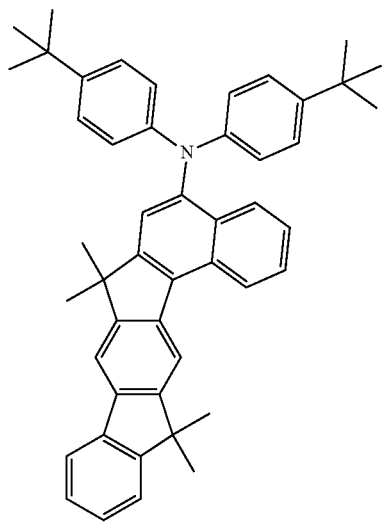 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
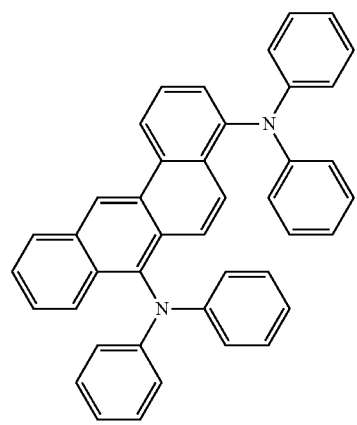 [SMILES: c1ccc(N(c2ccccc2)c2cccc3c2ccc2c(N(c4ccccc4)c4ccccc4)c4ccccc4cc23)cc1]
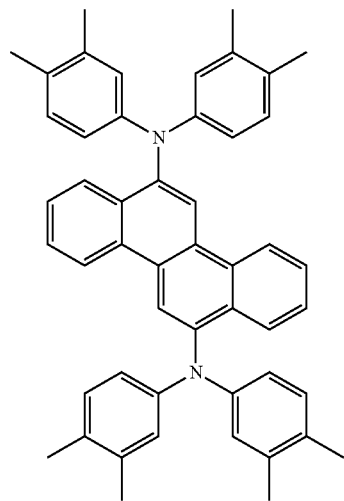

-continued
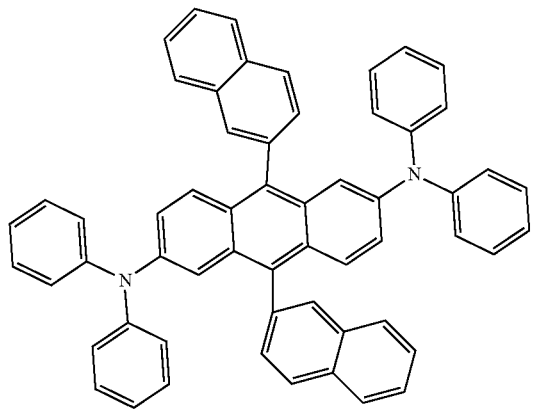 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
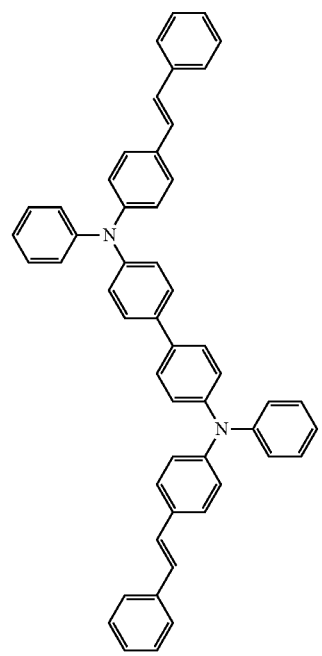 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
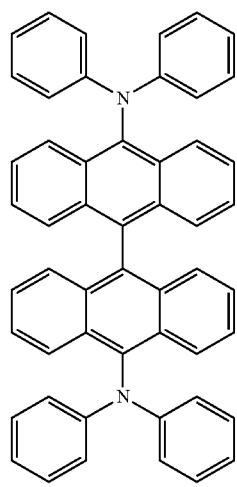 [SMILES: c1ccc(N(c2ccccc2)c2c3ccccc3c(-c3c4ccccc4c(N(c4ccccc4)c4ccccc4)c4ccccc34)c3ccccc23)cc1]

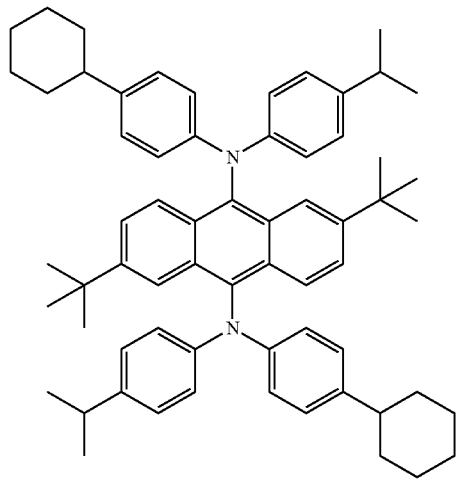 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
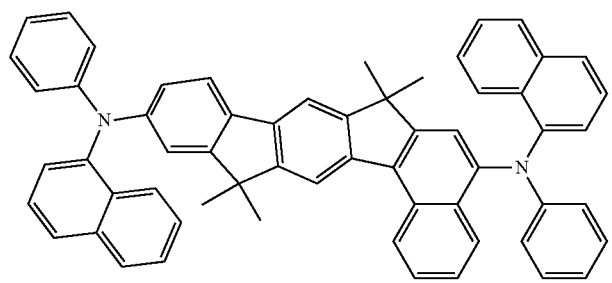 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
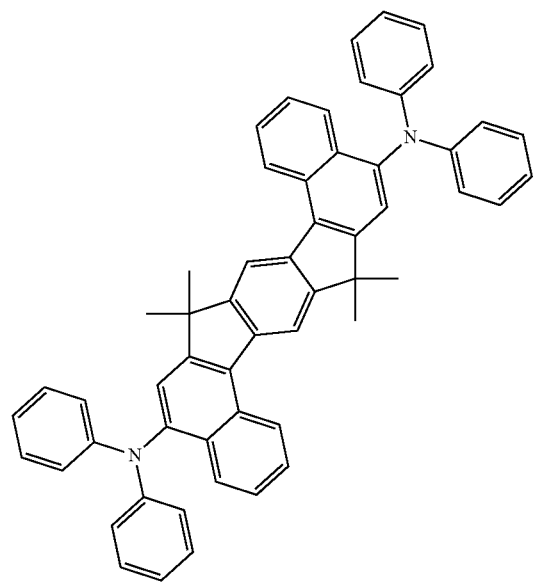 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]

-continued
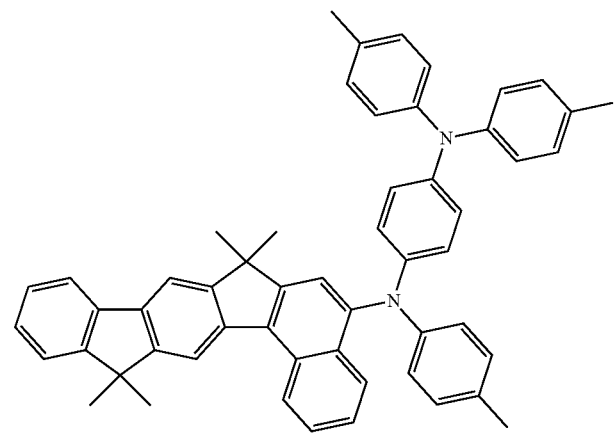 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
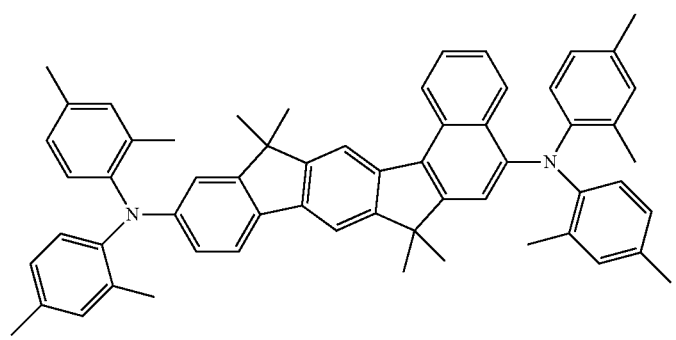
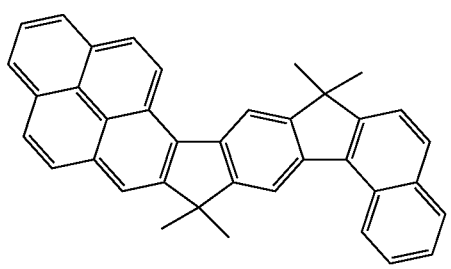 [SMILES: CC1(C)c2cc3c(cc2-c2c1ccc1ccccc21)C(C)(C)c1cc2ccc4cccc5ccc(c1-3)c2c45]
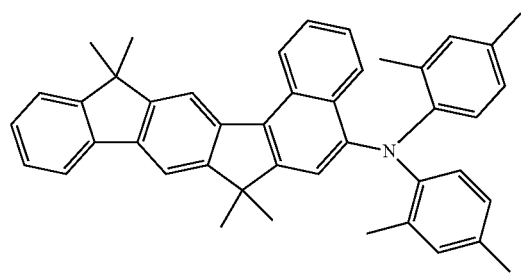 [SMILES: Cc1ccc(N(c2ccc(C)cc2C)c2cc3c(c4ccccc24)-c2cc4c(cc2C3(C)C)-c2ccccc2C4(C)C)c(C)c1]

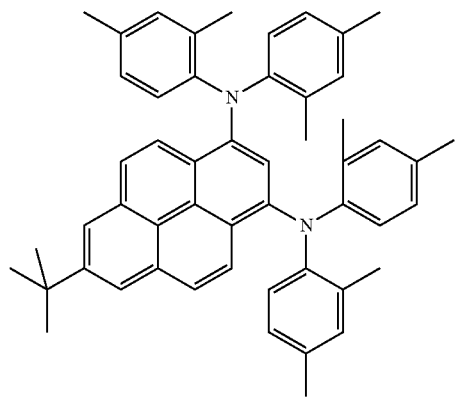 [SMILES: Cc1ccc(N(c2ccc(C)cc2C)c2cc(N(c3ccc(C)cc3C)c3ccc(C)cc3C)c3ccc4cc(C(C)(C)C)cc5ccc2c3c54)c(C)c1]
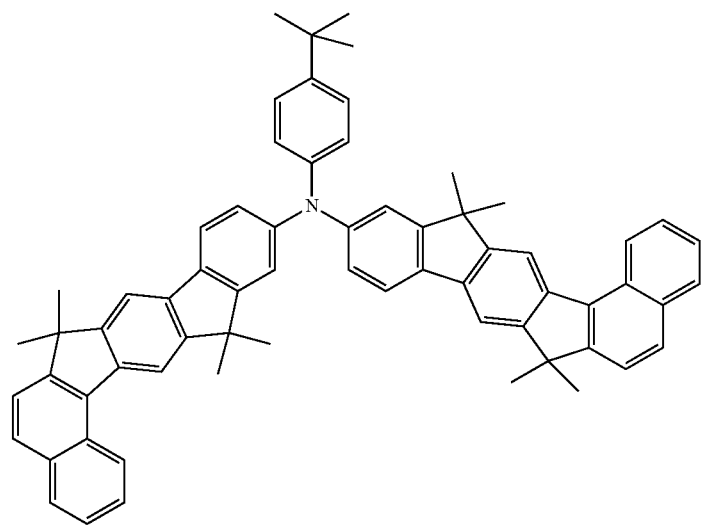 [SMILES: CC(C)(C)c1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)cc1]
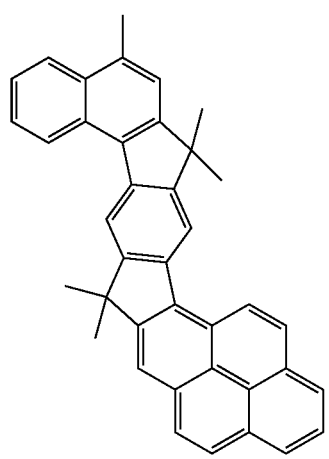 [SMILES: Cc1cc2c(c3ccccc13)-c1cc3c(cc1C2(C)C)-c1c(cc2ccc4cccc5ccc1c2c45)C3(C)C]

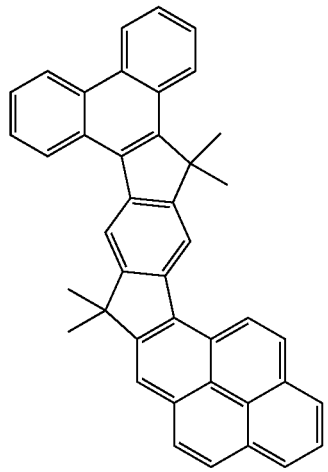 [SMILES: CC1(C)c2cc3c(cc2-c2c1cc1ccc4cccc5ccc2c1c45)C(C)(C)c1c-3c2ccccc2c2ccccc12]
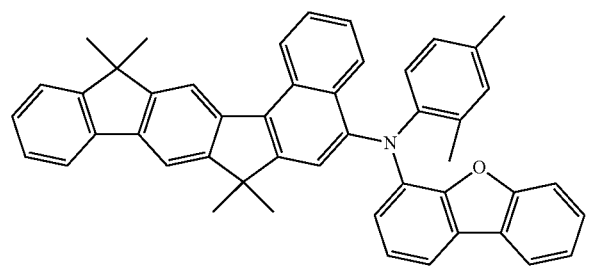 [SMILES: Cc1ccc(N(c2cc3c(c4ccccc24)-c2cc4c(cc2C3(C)C)-c2ccccc2C4(C)C)c2cccc3c2oc2ccccc23)c(C)c1]
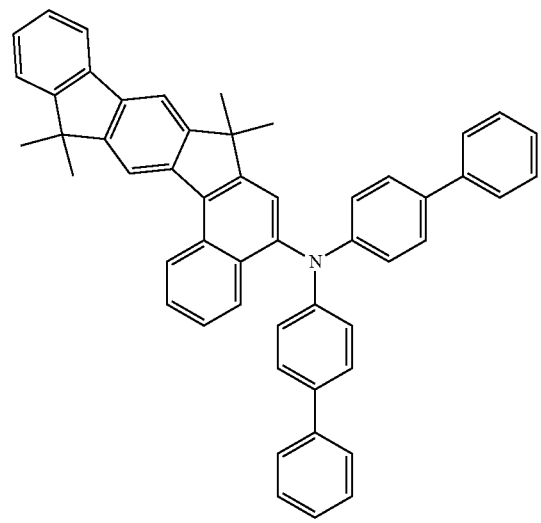 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]

-continued
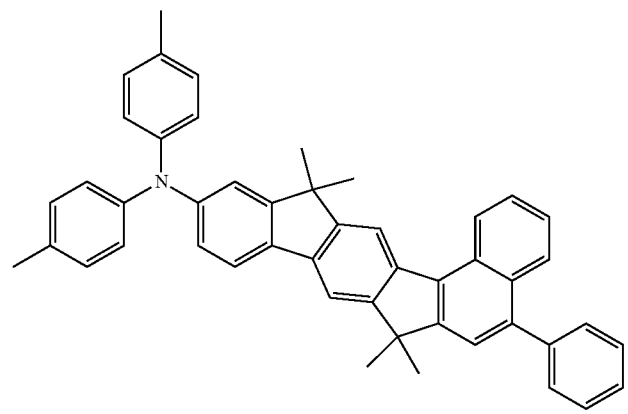 [SMILES: Cc1ccc(N(c2ccc(C)cc2)c2ccc3c(c2)C(C)(C)c2cc4c(cc2-3)C(C)(C)c2cc(-c3ccccc3)c3ccccc3c2-4)cc1]
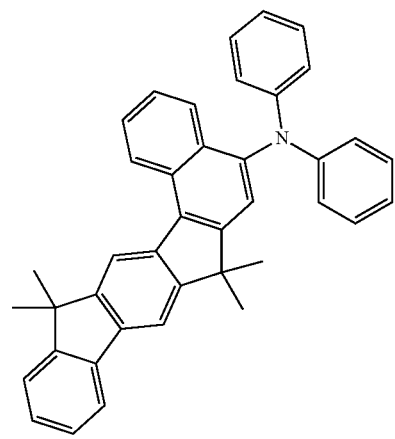 [SMILES: CC1(C)c2ccccc2-c2cc3c(cc21)-c1c(cc(N(c2ccccc2)c2ccccc2)c2ccccc12)C3(C)C]
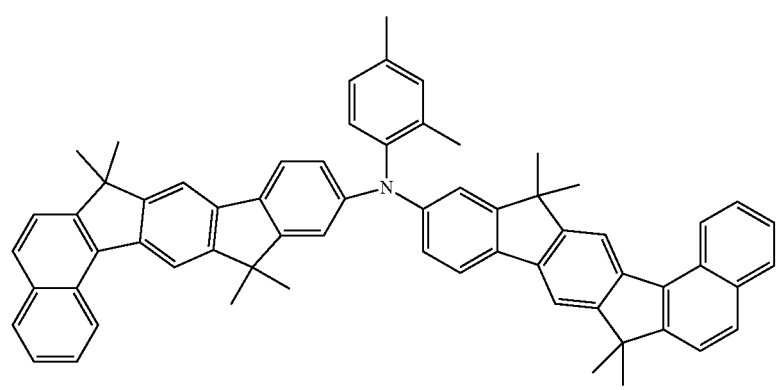 [SMILES: Cc1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)c(C)c1]

-continued
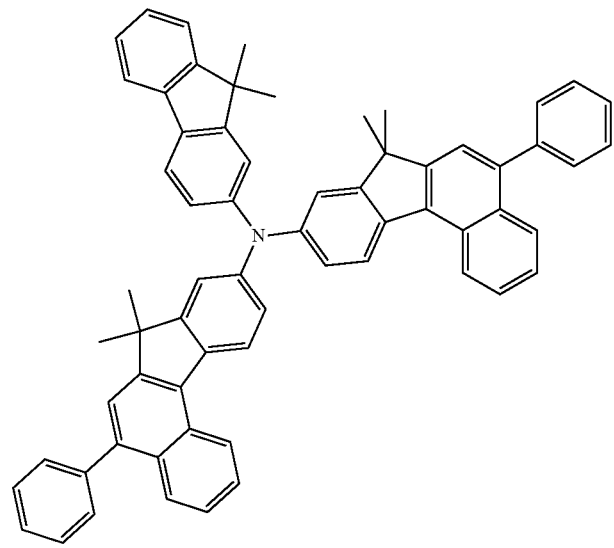 [SMILES: CC1(C)c2ccccc2-c2ccc(N(c3ccc4c(c3)C(C)(C)c3cc(-c5ccccc5)c5ccccc5c3-4)c3ccc4c(c3)C(C)(C)c3cc(-c5ccccc5)c5ccccc5c3-4)cc21]
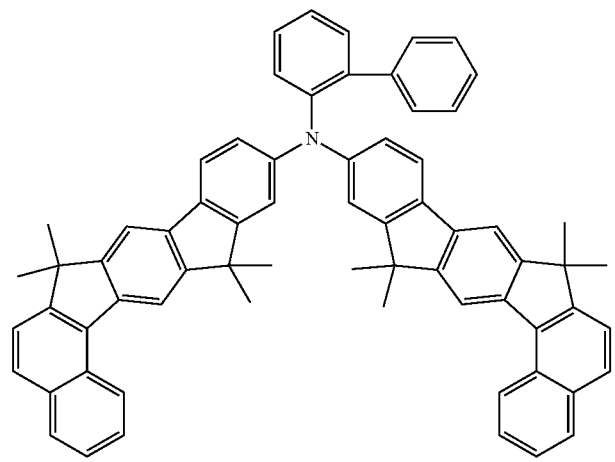 [SMILES: CC1(C)c2cc(N(c3ccc4c(c3)C(C)(C)c3cc5c(cc3-4)C(C)(C)c3ccc4ccccc4c3-5)c3ccccc3-c3ccccc3)ccc2-c2cc3c(cc21)-c1c(ccc2ccccc12)C3(C)C]
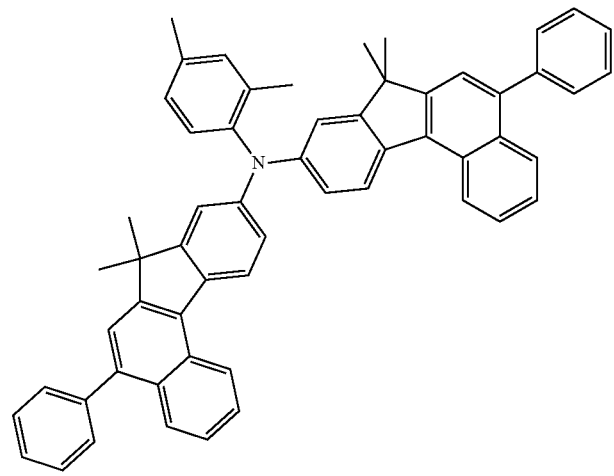 [SMILES: Cc1ccc(N(c2ccc3c(c2)C(C)(C)c2cc(-c4ccccc4)c4ccccc4c2-3)c2ccc3c(c2)C(C)(C)c2cc(-c4ccccc4)c4ccccc4c2-3)c(C)c1]

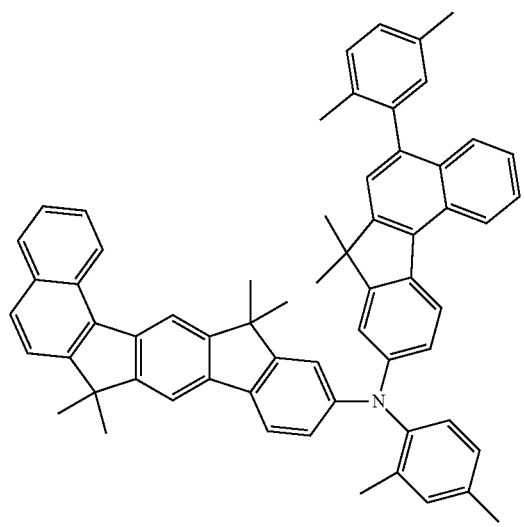 [SMILES: Cc1ccc(N(c2ccc3c(c2)C(C)(C)c2cc4c(cc2-3)C(C)(C)c2ccc3ccccc3c2-4)c2ccc3c(c2)C(C)(C)c2cc(-c4cc(C)ccc4C)c4ccccc4c2-3)c(C)c1]
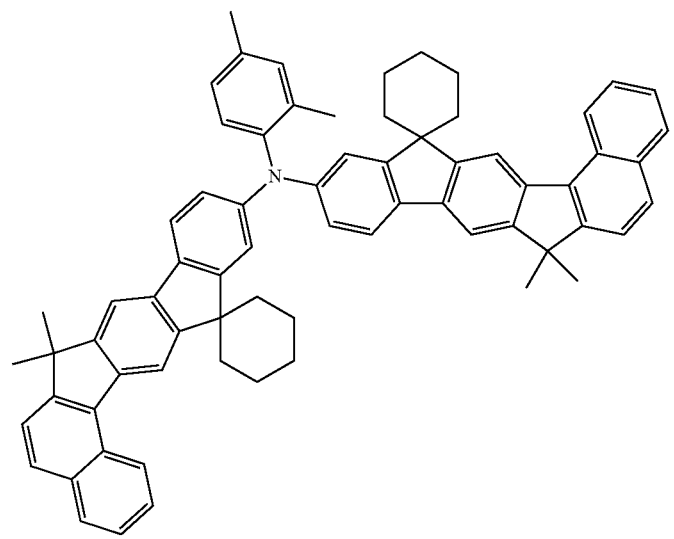 [SMILES: Cc1ccc(N(c2ccc3c(c2)C2(CCCCC2)c2cc4c(cc2-3)C(C)(C)c2ccc3ccccc3c2-4)c2ccc3c(c2)C2(CCCCC2)c2cc4c(cc2-3)C(C)(C)c2ccc3ccccc3c2-4)c(C)c1]
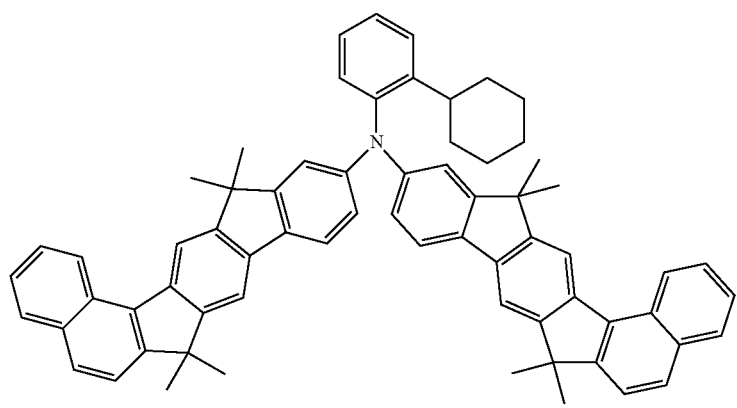 [SMILES: CC1(C)c2cc(N(c3ccc4c(c3)C(C)(C)c3cc5c(cc3-4)C(C)(C)c3ccc4ccccc4c3-5)c3ccccc3C3CCCCC3)ccc2-c2cc3c(cc21)-c1c(ccc2ccccc12)C3(C)C]

-continued
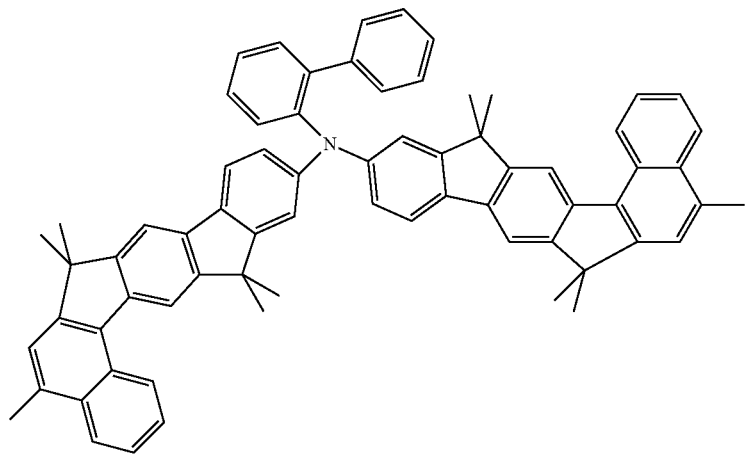
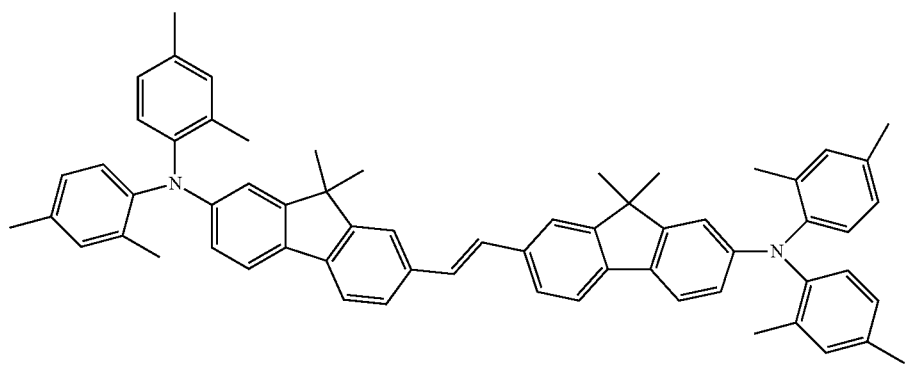
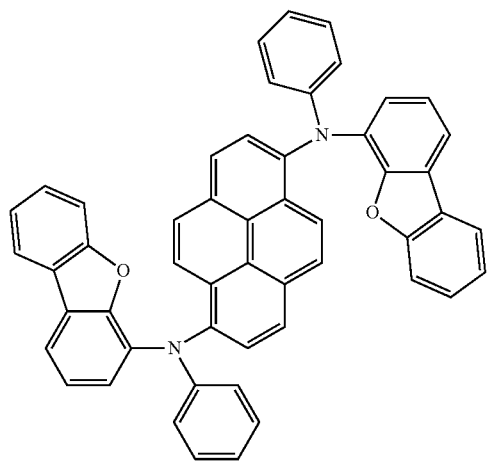 [SMILES: c1ccc(N(c2ccc3ccc4c(N(c5ccccc5)c5cccc6c5oc5ccccc56)ccc5ccc2c3c54)c2cccc3c2oc2ccccc23)cc1]

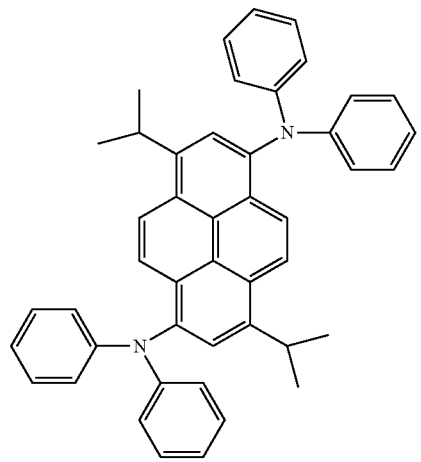 [SMILES: CC(C)c1cc(N(c2ccccc2)c2ccccc2)c2ccc3c(C(C)C)cc(N(c4ccccc4)c4ccccc4)c4ccc1c2c34]
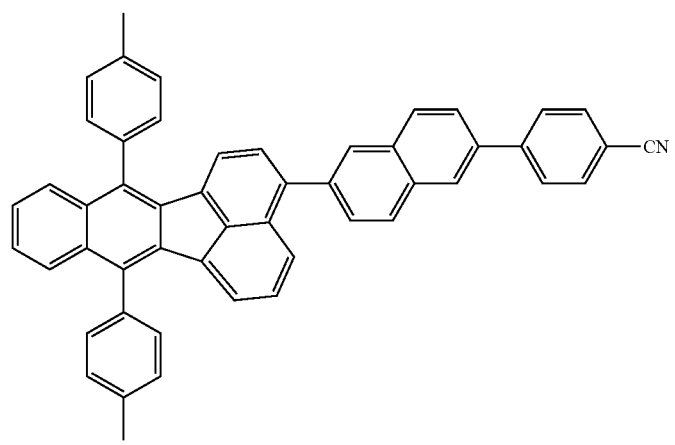 [SMILES: Cc1ccc(-c2c3c(c(-c4ccc(C)cc4)c4ccccc24)-c2ccc(-c4ccc5cc(-c6ccc(C#N)cc6)ccc5c4)c4cccc-3c24)cc1]
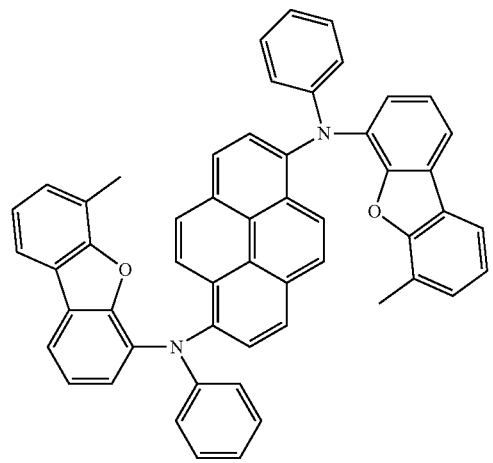 [SMILES: Cc1cccc2c1oc1c(N(c3ccccc3)c3ccc4ccc5c(N(c6ccccc6)c6cccc7c6oc6c(C)cccc67)ccc6ccc3c4c65)cccc12]

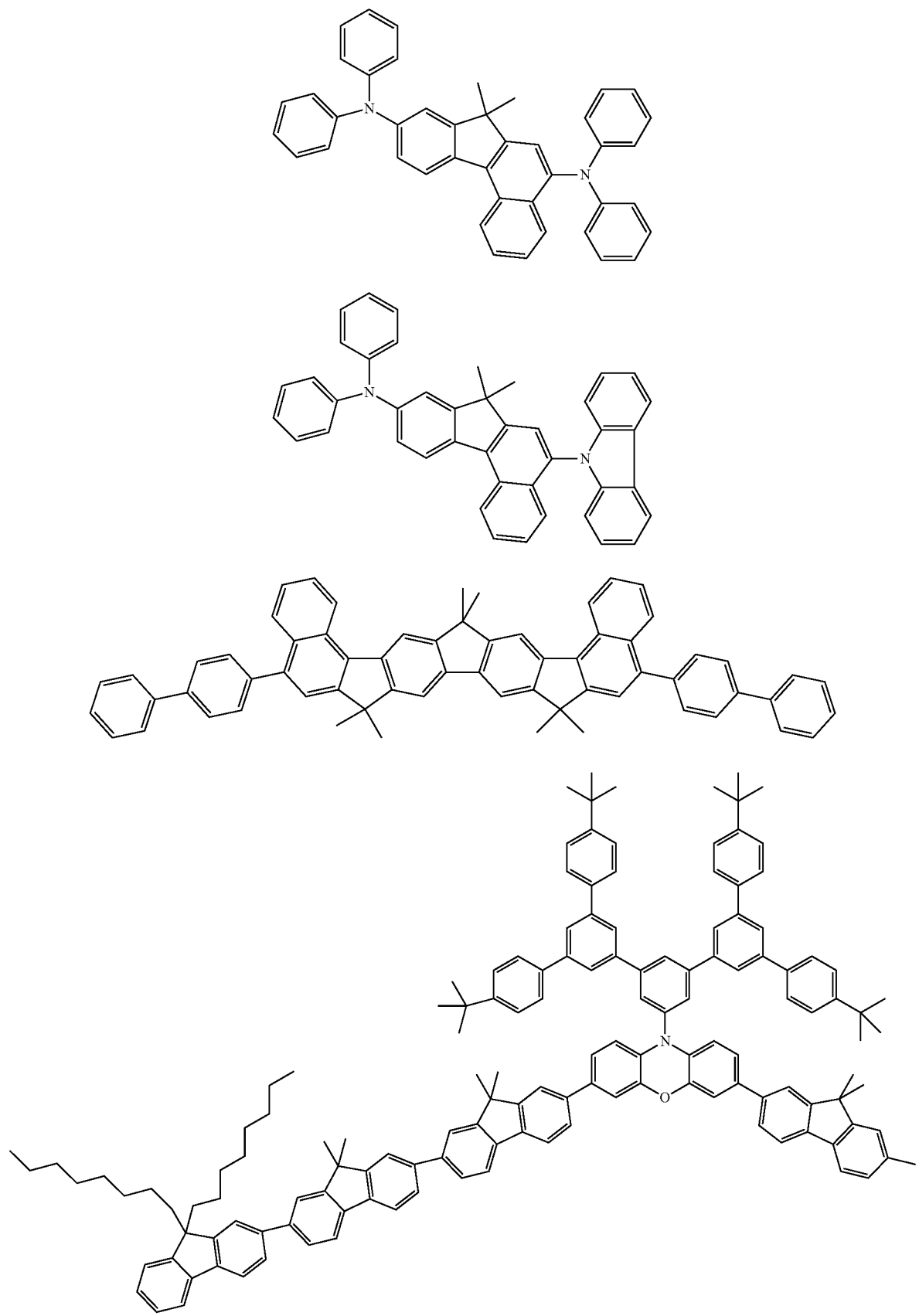

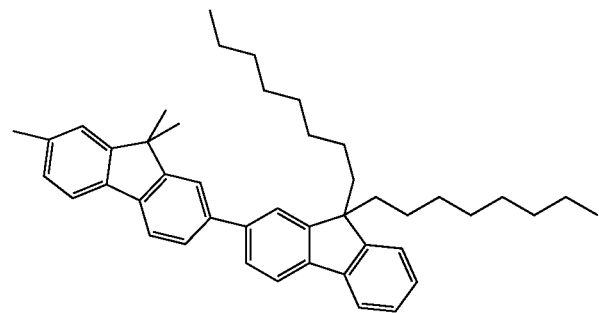
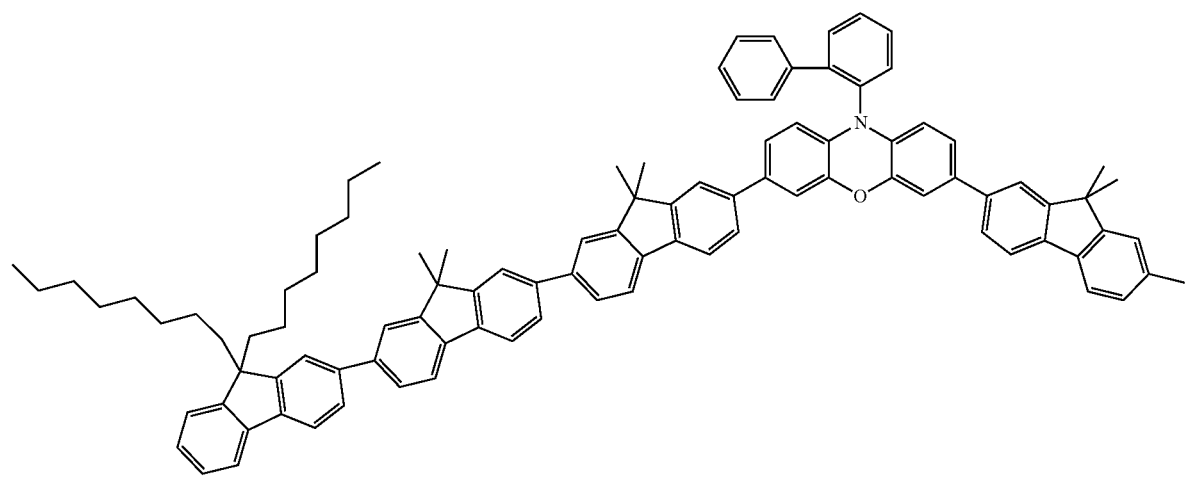
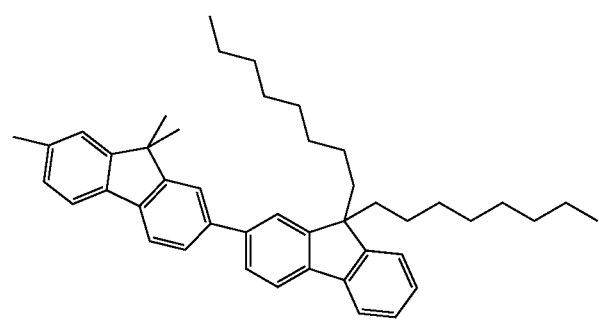

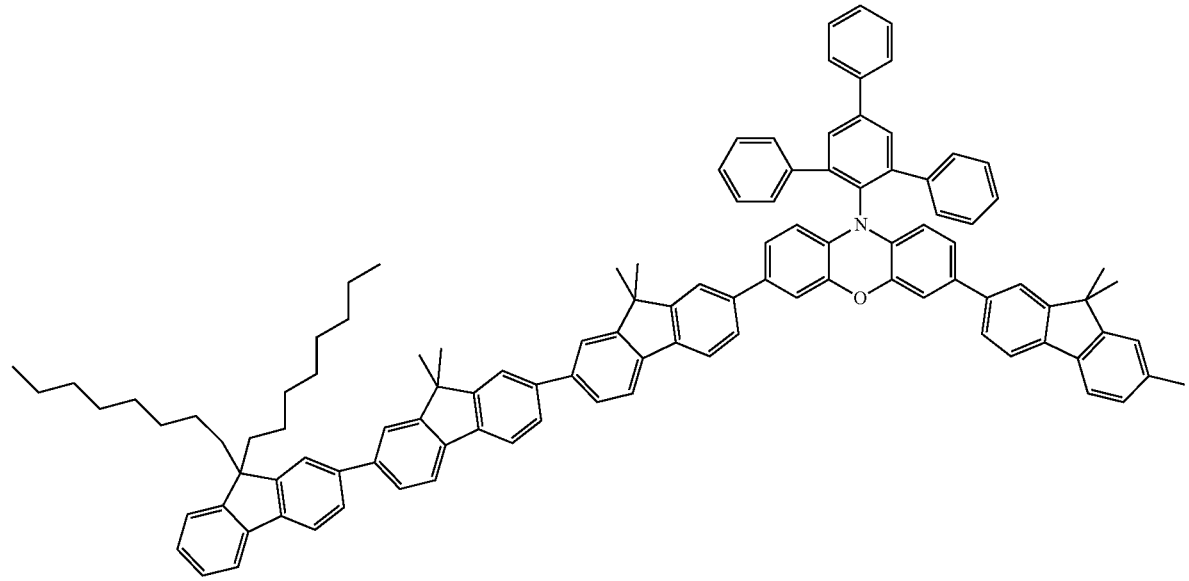
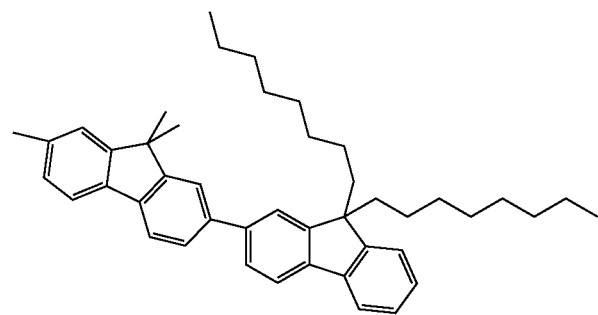
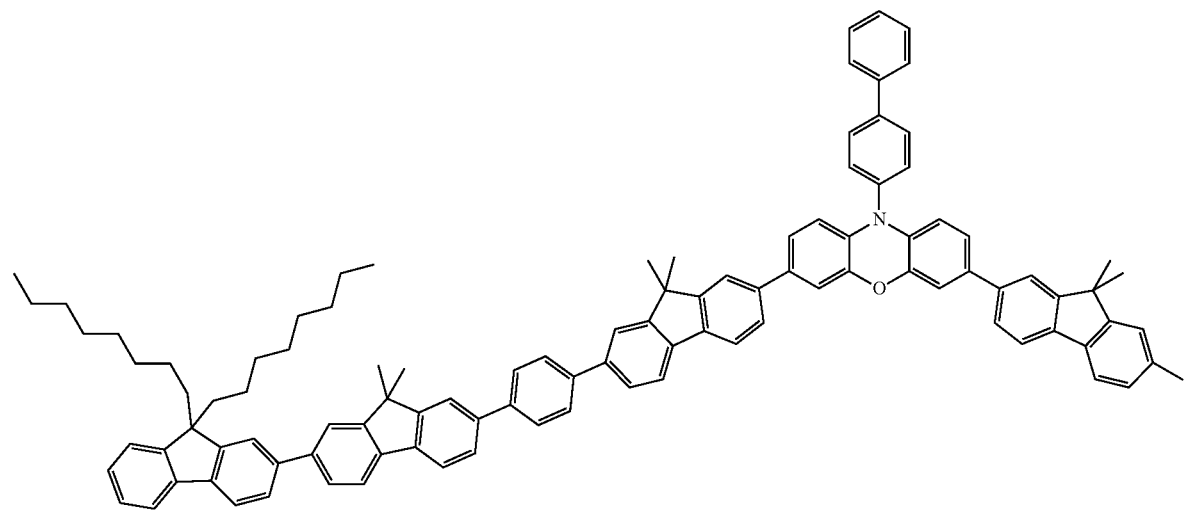

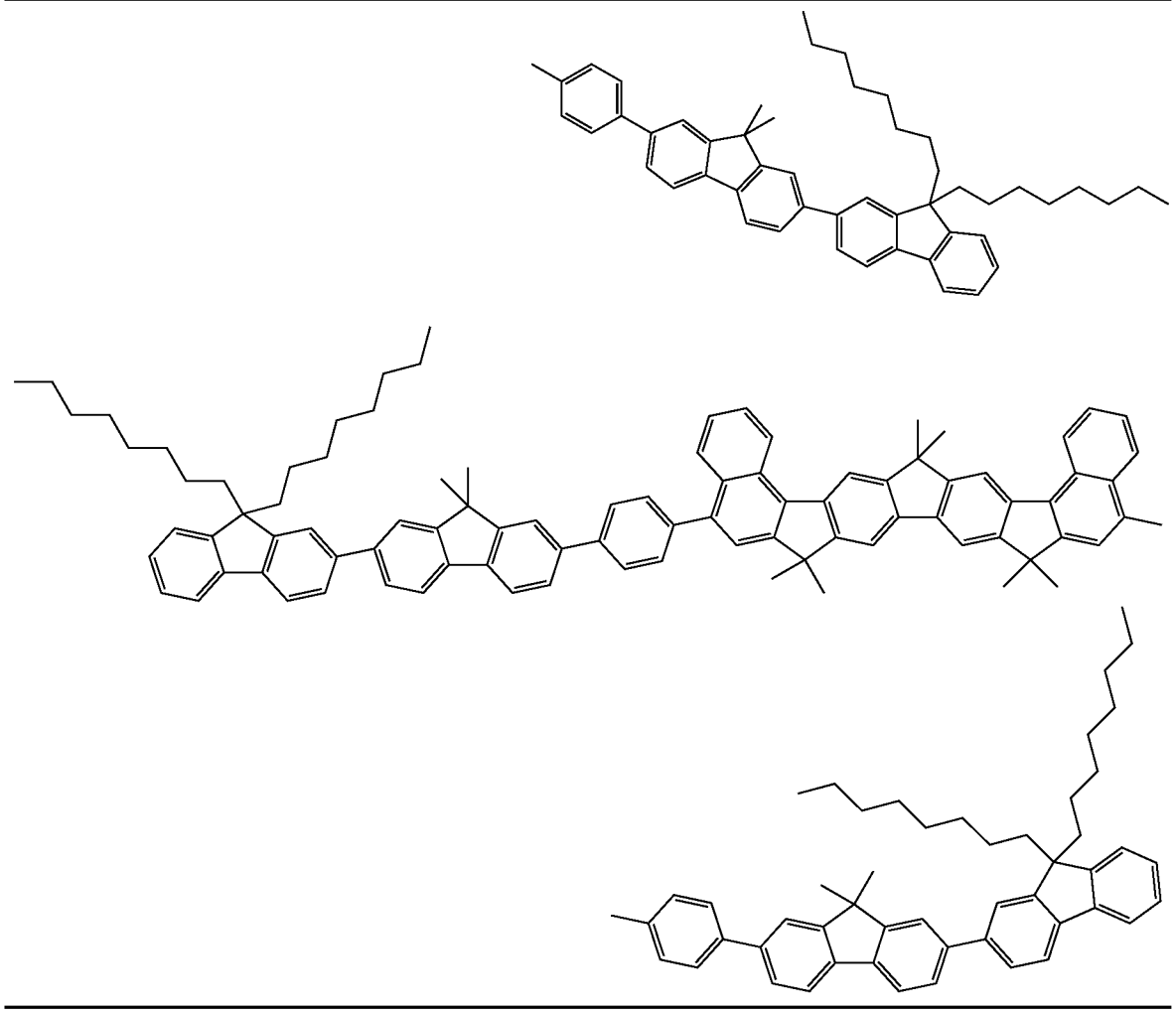

The compounds according to the invention can also be employed in other layers, for example as hole-transport materials in a hole-injection or holetransport layer or electron-blocking layer or as matrix materials in an emitting layer, preferably as matrix materials for phosphorescent emitters.

If the compound of the formula (I) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) then additionally comprises one or more p-dopants. The p-dopants employed in accordance with the present invention are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

If the compound of the formula (I) is employed as matrix material in combination with a phosphorescent emitter in an emitting layer, the phosphorescent emitter is preferably selected from the classes and embodiments of phosphorescent emitters indicated below. Furthermore, one or more further matrix materials are preferably present in the emitting layer in this case.

So-called mixed-matrix systems of this type preferably comprise two or three different matrix materials, particularly preferably two different matrix materials. It is preferred here for one of the two materials to be a material having hole-transporting properties and for the other material to be a material having electron-transporting properties. The compound of the formula (I) is preferably the material having hole-transporting properties.

However, the desired electron-transporting and hole-transporting properties of the mixed-matrix components may also be combined mainly or completely in a single mixed-matrix component, where the further mixed-matrix component or components satisfy other functions. The two different matrix materials may be present here in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. Further details on mixed-matrix systems are contained, inter alia, in the application WO 2010/108579.

Particularly suitable matrix materials which can be used as matrix components of a mixed-matrix system in combination with the compounds according to the invention are selected from the preferred matrix materials for phosphorescent emitters indicated below or the preferred matrix materials for fluorescent emitters, depending on what type of emitter compound is employed in the mixed-matrix system.

Generally preferred classes of material for use as corresponding functional materials in the organic electroluminescent devices according to the invention are indicated below.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent emitters described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs. Preferred matrix materials for phosphorescent emitters are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Besides the compounds according to the invention, suitable charge-transport materials, as can be used in the hole-injection or hole-transport layer or electron-blocking layer or in the electron-transport layer of the electronic device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001). The compounds according to the invention can also be used as hole-transport materials.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

In accordance with the invention, the electronic devices comprising one or more compounds according to the invention can be employed in displays, as light sources in lighting applications and as light sources in medical and/or cosmetic applications (for example light therapy).

The invention will now be explained in greater detail by the following examples, without wishing to restrict it thereby.

A) Syntheses Examples

Scheme Synthesis Example Compound 1

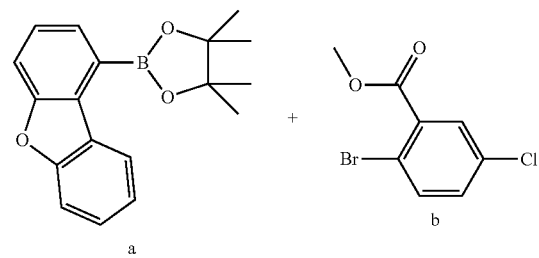 + 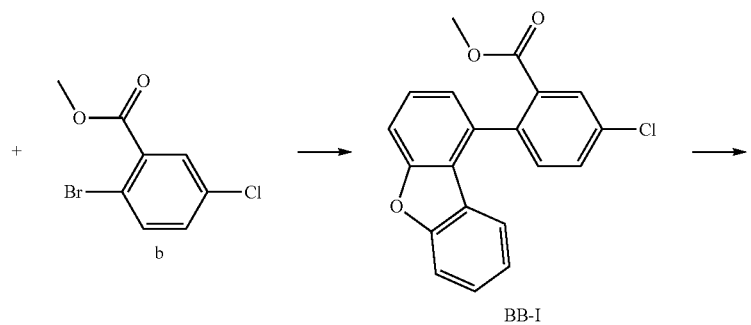

BB-I

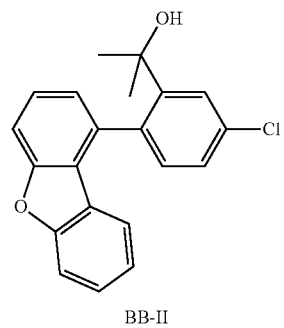

BB-II

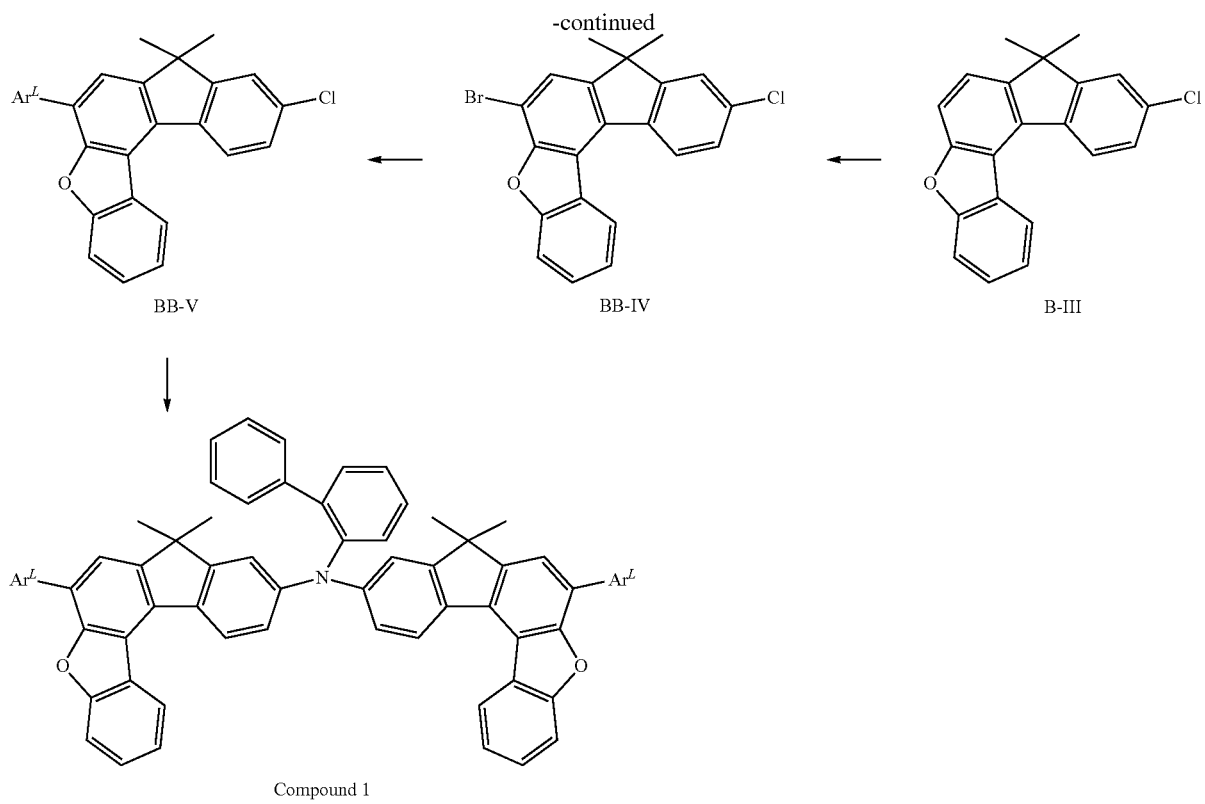

Synthesis of the Group ArL

Synthesis of Compound Int1.1

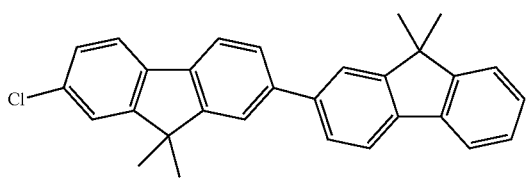 [SMILES: CC1(C)c2ccccc2-c2ccc(-c3ccc4c(c3)C(C)(C)c3cc(Cl)ccc3-4)cc21]

30 g (97.5 mmol) 2-Bromo-7-Chloro-9,9-dimethyl-9H-fluorene (see JP 2003277305 A), 25.5 g (107.3 mmol) (9,9-dimethylfluoren-2-yl)boronic acid 90 g (390 mmol), 0.9 g (4 mmol) palladium(II)acetate and 3.6 g (11.7 mmol) tri(o-tolyl)-phosphine are mixed in 1 L toluene, dioxane, water (1:1:1) and stirred at reflux overnight. After cooling down to room temperature, 200 mL toluene are added and the organic phase is separated and washed with water (2×200 mL), the combined organic phases are concentrated under reduced pressure. The residue is purified by recrystallization from toluene/heptane.

Yield: 39.1 g (93 mmol; 96%).

Following compounds can be synthesized in an analogous manner:

| Comp. | Starting material | Starting material | Product |
|---|---|---|---|
| Int1.2 | | | |

-continued

| Comp. | Starting material | Starting material | Product |
|---|---|---|---|
| Int1.3 | 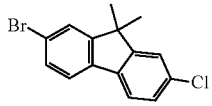 [SMILES: CC1(C)c2cc(Cl)ccc2-c2ccc(Br)cc21] | ArL2 (see below)  | 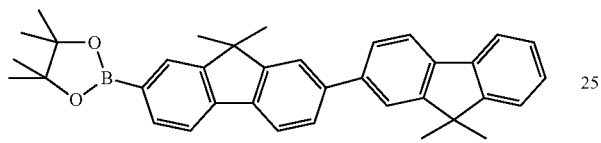 |

Synthesis of ArL1

40 g (95 mmol) Int1.1, 38.6 g (152 mmol) bis-(pinacolato)-diboron, 4.2 g (5.7 mmol) trans-dichloro(tricyclohexylphosphine)palladium(II) and 28 g (285 mmol) potassium acetate are mixed in 400 mL dioxane and stirred for 16 h at reflux. The reaction mixture is allowed to cool to room temperature and 400 mL toluene are added. The organic phase is separated, washed with water (2×200 mL) and filtered through Celite. The solution is concentrated to dryness under reduced pressure. The residue is purified by recrystallization from toluene/heptane.

Yield: 36 g (70 mmol; 74%).

Following compounds can be synthesized in an analogous manner:

| Compound | Starting material | Product |
|---|---|---|
| ArL2 | Int1.2 | 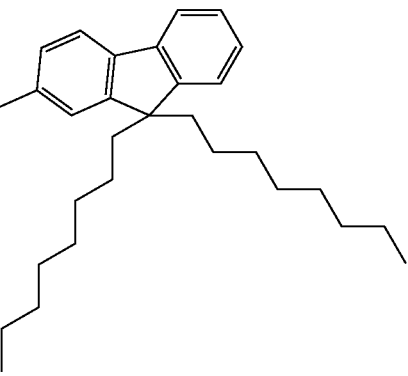 |

Synthesis of Int1.4

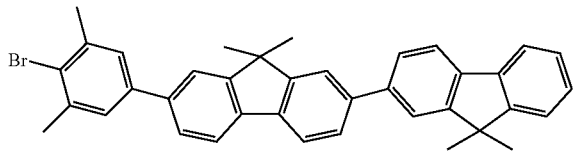 [SMILES: Cc1cc(-c2ccc3c(c2)C(C)(C)c2cc(-c4ccc5c(c4)C(C)(C)c4ccccc4-5)ccc2-3)cc(C)c1Br]

5.5 g (17.8 mmol) 2-Bromo-5-iodo-1,3-dimethylbenzene, 6.5 g (12.7 mmol) ArL1, 366 mg (0.3 mmol) tetrakis(triphenylphosphine)-palladium(0) and 2.7 g (13 mmol) sodium carbonate are mixed in 200 mL toluene, ethanol and water (2:1:1) and stirred for 16 hours at 90° C. After cooling down to room temperature, 100 mL toluene are added, the organic phase is separated and washed with water (2×50 mL). The organic phase is concentrated to dryness under reduced pressure. The residue is purified by recrystallization from toluene/heptane.

Yield: 6.2 g (11 mmol; 86%).

The following compounds can be synthesized in an analogous manner:

| Compound | Starting material | Starting material | Product |
|---|---|---|---|
| Int1.5 | ArL2 | CAS 106-93-8 | |
| Int1.6 | ArL2 | JP 2003277305 A | |
| Int1.7 | CAS 1679-18-1 | Int1.4 | |
| Int1.8 | ArL2 | CAS 14495-51-3 | |

Synthesis of ArL3 to ArL6
Compounds ArL3 to ArL6 can be synthesized in an analogous manner to ArL1:
| Compound | Starting material | Product |
|---|---|---|
| ArL3 | Int1.7 | 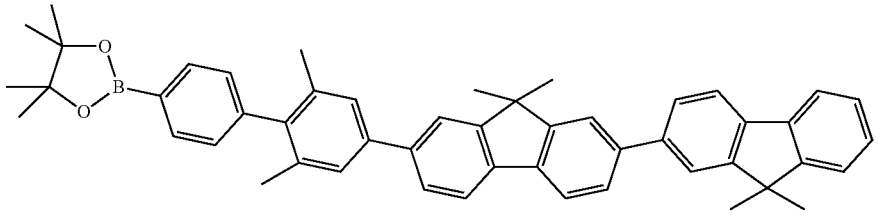 |
| ArL4 | Int1.6 | 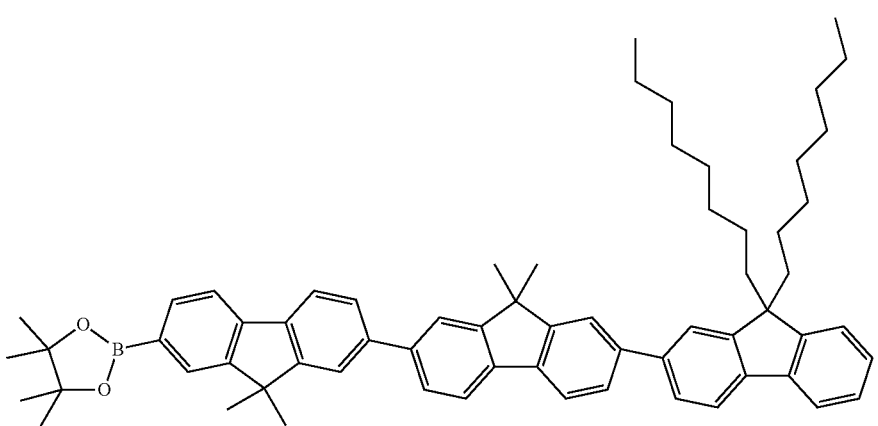 |
| ArL5 | Int1.5 | 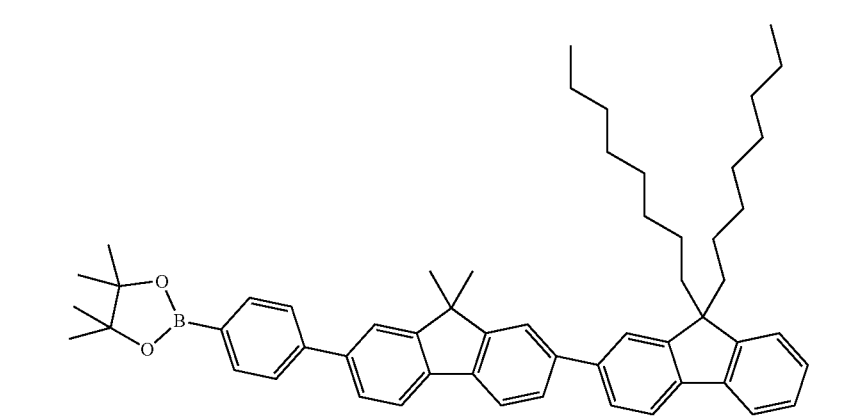 |
| ArL6 | Int1.8 | 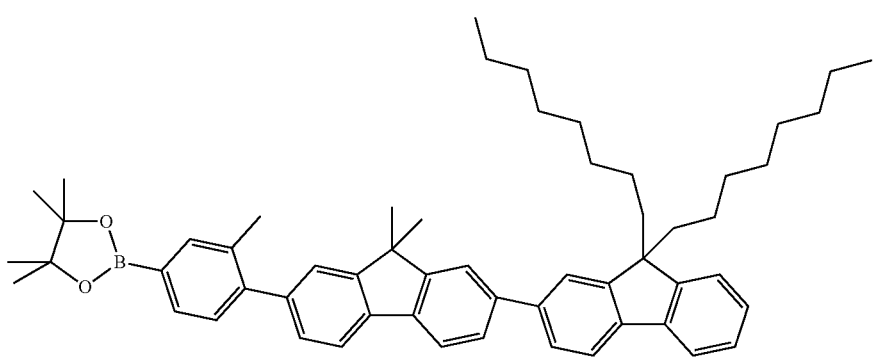 |

Synthesis Building Block BB-I

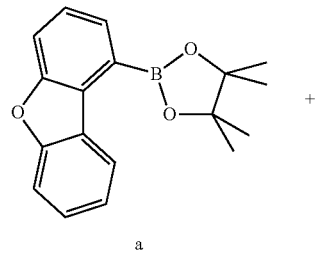

a +

117.9 g (401 mmol) starting material a, 100 g (401 mmol) starting material b and 203.1 g (882 mmol) potassium phosphate monohydrate are mixed in 1.6 L toluene/water/dioxane (2:1:1) and degassed. To the mixture, palladium acetate (0.9 g, 4 mmol) and tri-ortho-tolylphosphine (2.44 g, 8 mmol) are added and the mixture is stirred at reflux for 16 h. After cooling the mixture to room temperature, the phases are separated. The aqueous phase is further extracted with ethyl acetate (2×300 mL). The combined organic phases are washed multiple times with water, dried over sodium sulfate and finally removed in vacuum. The crude is filtered over a plug of $SiO_2/Al_2O_3$ using ethyl acetate as solvent. After removing the solvent in vacuum, an oil is obtained in quantitative yield.

The following compounds can be synthesized in an analogous manner:

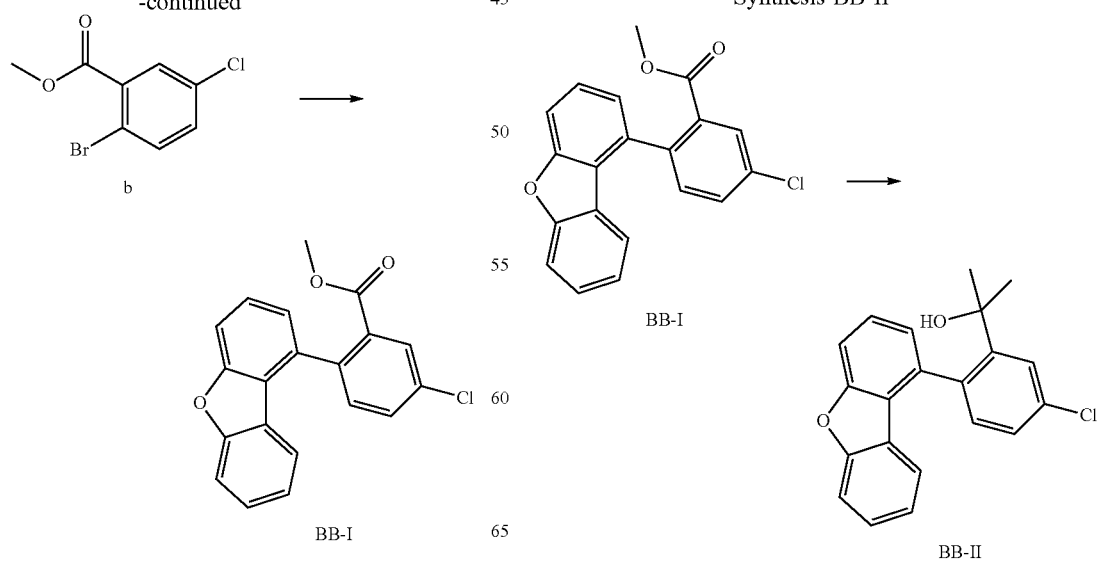

MeMgCl (461 mL, 3 M in THF, 1.38 mol) is added dropwise to a pre-cooled THF suspension (0° C., 1.5 L) of compound BB-I (135 g, 0.4 mol) and CeCl$_3$ (199 g, 0.8 mol). After completion of the reaction, a saturated aqueous solution of NH$_4$Cl is added to quench the excess of MeMgCl, and the organic phase is extracted three times with ethyl acetate. The organic fractions are combined and washed with water and brine, successively. The volatiles were removed in vacuum to yield the desired product. 129 g (96%).

The following compounds can be synthesized in an analogous manner:

To a solution of compound BB-II (129 g, 383 mmol) in toluene (1 L), 50 g of Amberlyst-15 are added. The mixture is stirred at reflux overnight. The mixture is cooled down to room temperature and the Amberlyst-15 filtered off. The solvent is removed in vacuum and the crude product is purified by column chromatography (SiO$_2$, heptane). Yield: 106.2 g (87%).

The following compounds can be synthesized in an analogous manner:

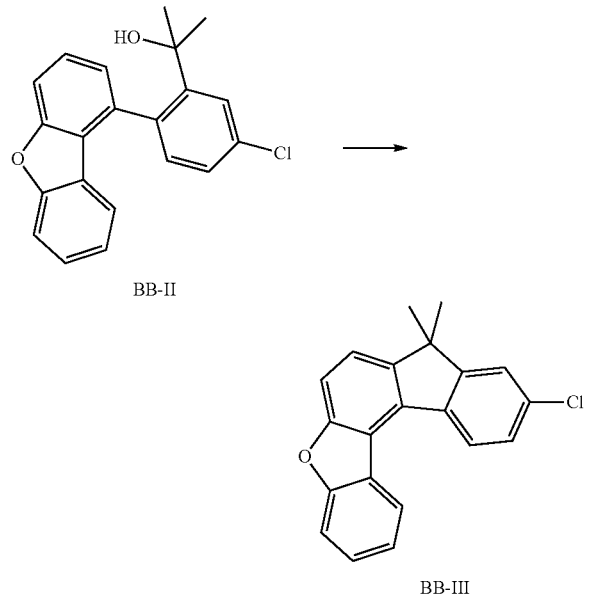

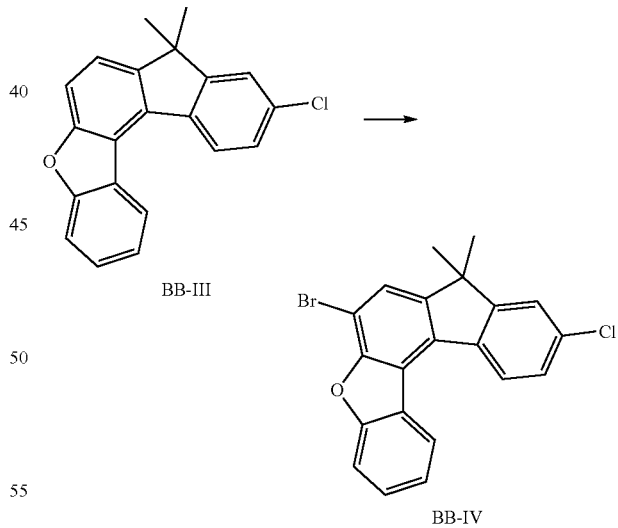

Synthesis BB-III

Synthesis Ba-IV

To a solution of compound BB-III (100 g, 314 mmol) in CH$_2$Cl$_2$ (1.2 L), N-bromosuccinimide (55.83 g, 314 mmol) and HBr (32% solution in acetic acid, 0.5 mL) are added. The reaction is heated at 30° C. for 4 days. After completion of the reaction, Na$_2$S$_2$O$_3$ (300 mL, saturated aqueous solution) is added and the mixture is stirred vigorously for 30 minutes. The phases are separated and the organic phase is washed several times with water. The solvent is removed in vacuum and the crude product vigorously stirred with ethanol to yield a white solid. Yield: 119.8 g (96%).

The following compounds can be synthesized in an analogous manner:

| Compound | Starting material | Product |
|---|---|---|
| BB-IV.a | | |
| BB-IV.b | | |

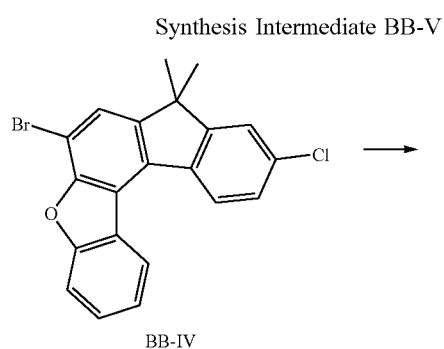

Synthesis Intermediate BB-V

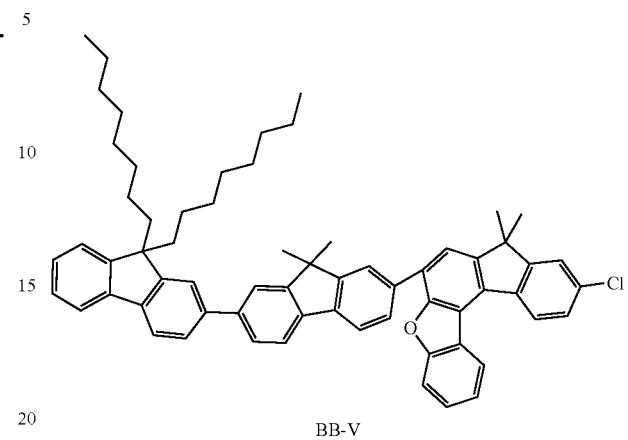

BB-V 30.0 g (75.4 mmol) BB-IV, 53.7 g (75.4 mmol) ArL2 and 16.0 g (151 mmol) sodium carbonate are mixed in 600 mL toluene/dioxane/water (2:1:2) and degassed. To the mixture, Tetrakis(triphenylphosphine)palladium (2.2 g, 1.9 mmol) is added and the mixture is stirred at reflux for 4 h. After cooling the mixture to room temperature, 400 mL of ethyl acetate is added and the phases are separated. The organic phase is washed multiple times with water and the solvent is removed in vacuum. Afterwards, the organic phase is filtrated over a plug of silica using ethyl acetate as solvent. The solvent is removed in vacuum and the crude product vigorously stirred with ethanol to yield a white solid. Yield: 64.4 g (95%).

The following compounds can be synthesized in an analogous manner:

| Comp. | Starting material | Starting material | Product |
|---|---|---|---|
| BB-V.a | BB-IV | ArL1 | |
| BB-V.b | BB-IV | ArL5 | |
| BB-V.c | BB-IV | ArL3 | |

| Comp. | Starting material | Starting material | Product |
|---|---|---|---|
| BB-V.d | BB-IV.a | ArL2 | 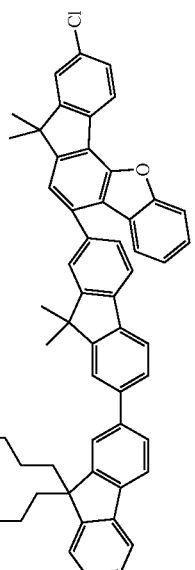 |
| BB-V.e | BB-IV.a | ArL4 | 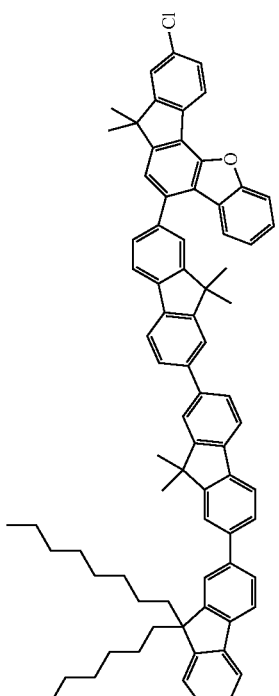 |
| BB-V.f | BB-IV.a | 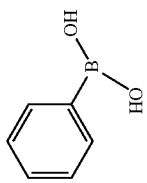 | |

-continued

| Comp. | Starting material | Starting material | Product |
|---|---|---|---|
| BB-V.g | [structure with Br, 1831917-17-9] | phenylboronic acid | [product structure] |
| BB-V.h | BB-IV.a | naphthalen-1-ylboronic acid | [product structure with Cl] |
| BB-V.i | BB-IV | phenylboronic acid | [product structure with Cl] |

-continued

| Comp. | Starting material | Starting material | Product |
|---|---|---|---|
| BB-V.j | BB-IV | 3-biphenylboronic acid | chloro-dimethyl-fluorene-benzofuran with 3-biphenyl substituent |
| BB-V.k | BB-IV | 2-biphenylboronic acid | chloro-dimethyl-fluorene-benzofuran with 2-biphenyl substituent |
| BB-V.l | BB-IV | 2-methylphenylboronic acid | chloro-dimethyl-fluorene-benzofuran with 2-tolyl substituent |

| Comp. | Starting material | Starting material | Product |
|---|---|---|---|
| BB-V.m | BB-IV | ArL6 | |
| BB-V.n | BB-IV | (4-methylphenyl)boronic acid | |
| BB-V.o | BB-IV | (4-tert-butylphenyl)boronic acid | |

| Comp. | Starting material | Starting material | Product |
|---|---|---|---|
| BB-V.p. | BB-IV | 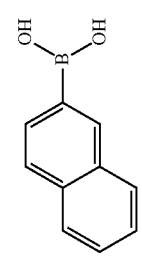 | 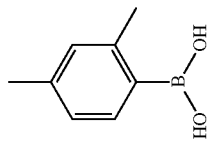 |
| BB-V.q. | BB-IV | 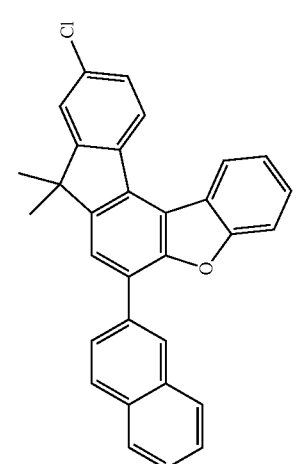 | 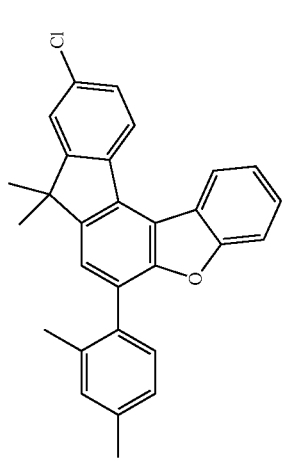 |

The following compound can be synthesized in an analogous manner like compound BB-IV:

| Starting material | Product |
|---|---|
| BB-VI.g | |

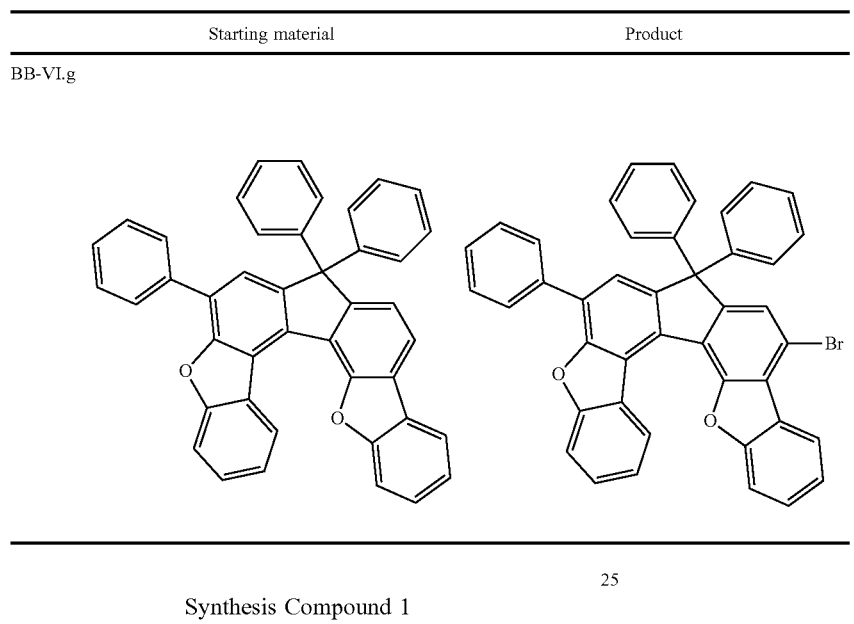

Synthesis Compound 1

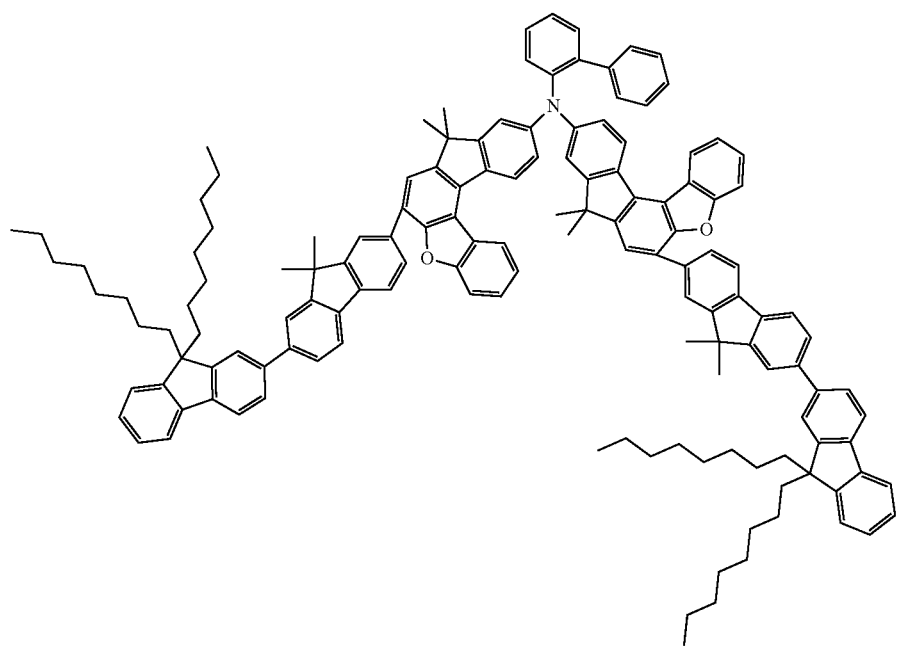 [SMILES: CCCCCCCCC1(CCCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7cc(-c9ccc%10c(c9)C(C)(C)c9cc(-c%11ccc%12c(c%11)C(CCCCCCCC)(CCCCCCCC)c%11ccccc%11-%12)ccc9-%10)c9oc%10ccccc%10c9c7-8)c7ccccc7-c7ccccc7)cc5C6(C)C)ccc3-4)cc21]

2.28 g (13.5 mmol) biphenyl-2-ylamine, 24.2 g (27.0 mmol) BB-V and 7.75 g (80.6 mmol) sodium tertbutylate are mixed in 300 mL toluene and degassed. Afterwards, 563 mg (1.4 mmol)S-Phos and 151 mg (0.7 mmol) palladium acetate are added and the mixture is stirred at reflux for 16 h. After cooling the mixture at room temperature, 200 mL of water is added and the phases are separated. The crude product is filtrate over a plug of aluminium oxide using toluene as solvent. The product is further purified by several recrystallizations from toluene/heptane. Yield: 7.7 g (45%).

The following compounds can be synthesized in an analogous manner:

| Comp | Starting material | Starting material | Product |
|---|---|---|---|
| 2 | BB-V.a | 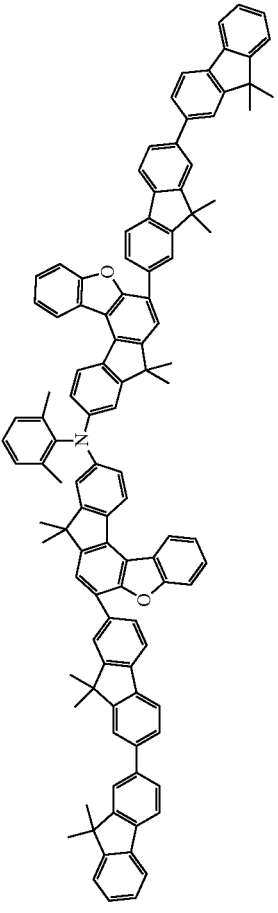 | 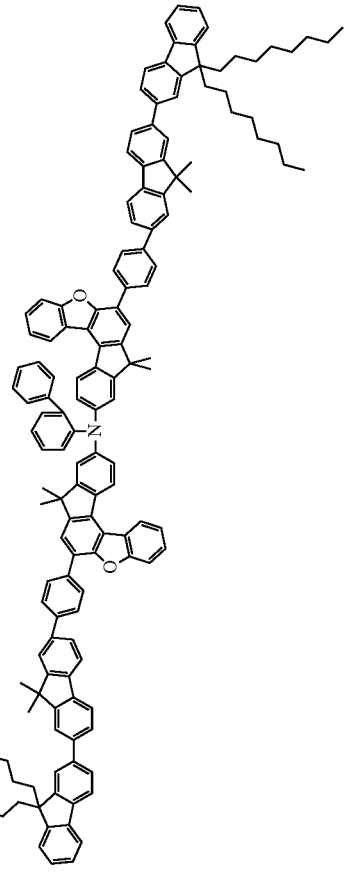 |
| 3 | BB-V.b | 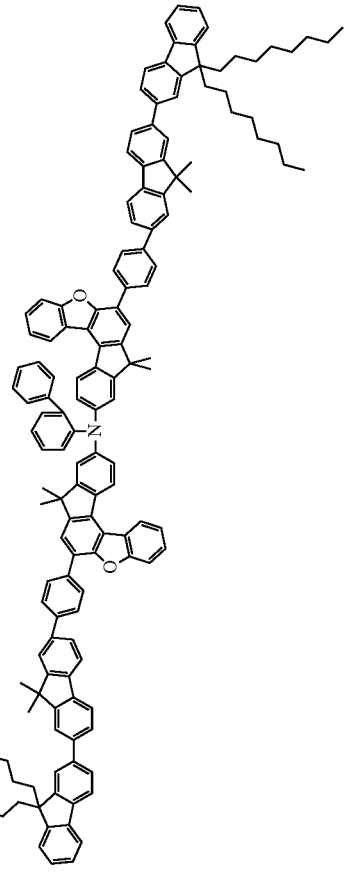 | 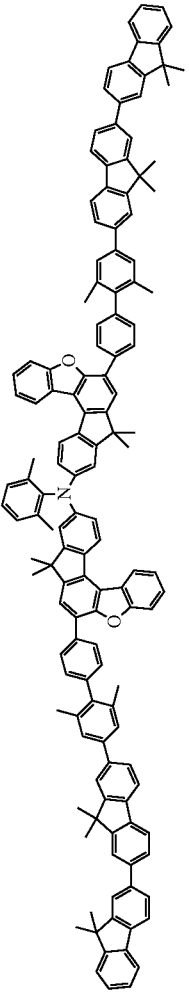 |
| 4 | BB-V.c | 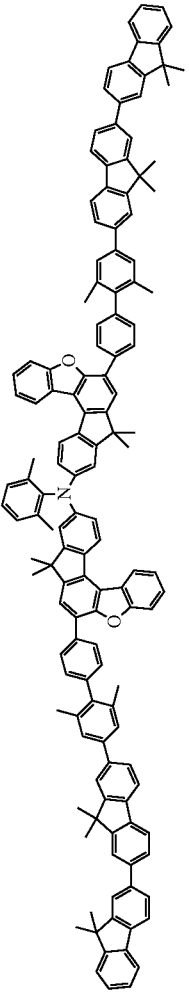 | 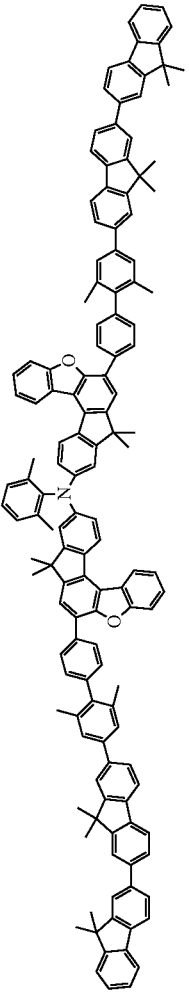 |

| Comp | Starting material | Starting material | Product |
|---|---|---|---|
| 5 | BB-V.d | 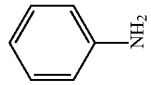 | 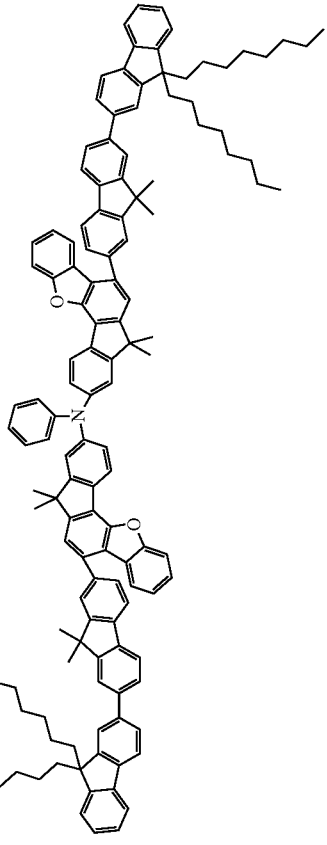 |
| 6 | BB-V.e | 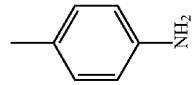 | 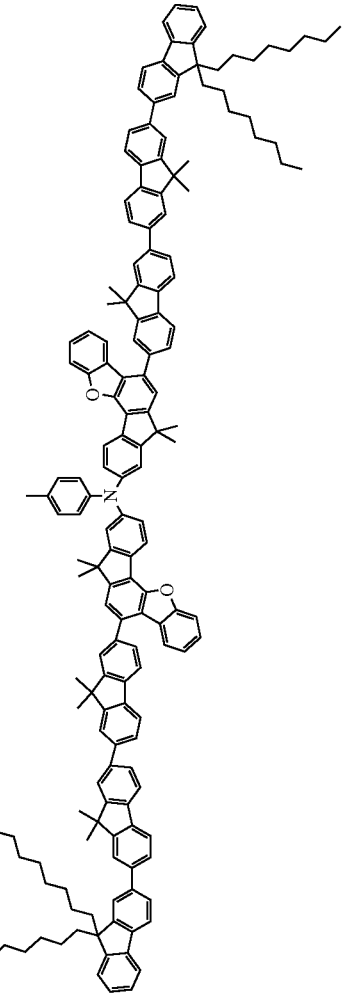 |

| Comp | Starting material | Starting material | Product |
|---|---|---|---|
| 7 | BB-V.f | 4-tert-butylaniline | (structure shown) |
| 8 | BB-VI.g | 4-tert-butylaniline | (structure shown) |

| Comp | Starting material | Starting material | Product |
|---|---|---|---|
| 9 | BB-IV.b | 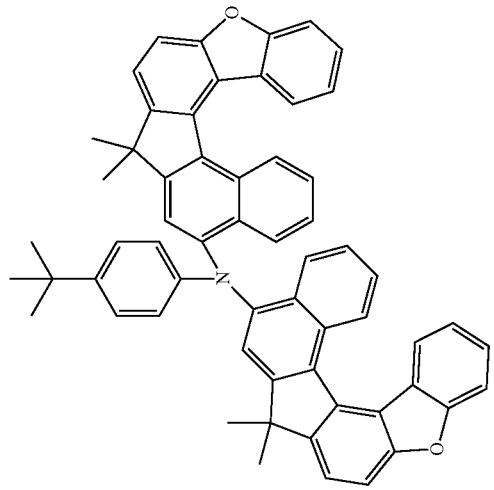 | |

| Comp. | Starting material | Starting material | Product |
|---|---|---|---|
| 10 | BB-V.f | 4-aminobiphenyl | |
| 11 | BB-V.f | 2,4-dimethylaniline | |

| Comp | Starting material | Starting material | Product |
|---|---|---|---|
| 12 | 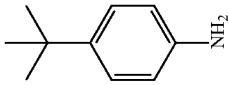 CAS 1831917-17-9 | 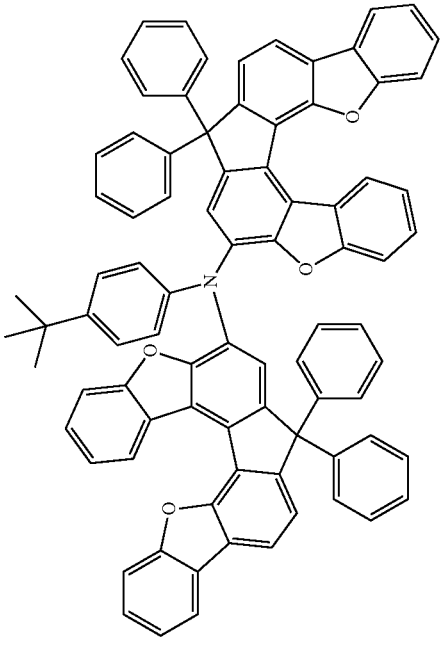 | 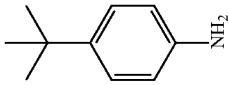 |
| 13 | | BB-V.h | 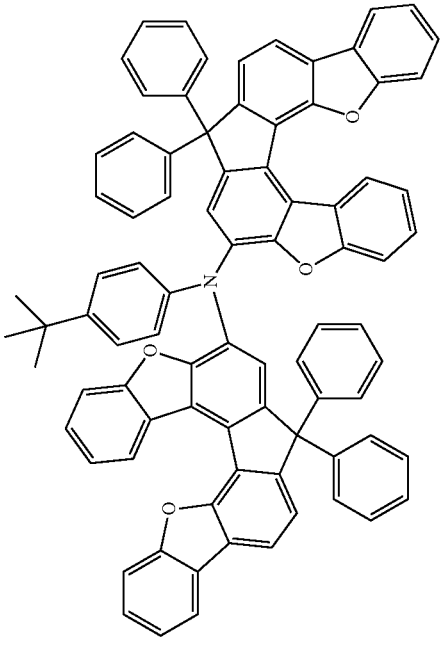 |

-continued

| Comp | Starting material | Starting material | Product |
|---|---|---|---|
| 14 | BB-V.i | 4-tert-butylaniline | (structure) |
| 15 | BB-V.i | 2,4-dimethylaniline | (structure) |

-continued

| Comp. | Starting material | Starting material | Product |
|---|---|---|---|
| 16 | BB-V.i | 4-aminobiphenyl | (structure) |
| 17 | BB-V.i | 2-aminobiphenyl | (structure) |

-continued

| Comp | Starting material | Starting material | Product |
|---|---|---|---|
| 18 | BB-V.i | [3-aminobiphenyl structure] | [product structure] |
| 19 | BB-V.j | [3-aminobiphenyl structure] | [product structure] |

| Comp | Starting material | Starting material | Product |
|---|---|---|---|
| 20 | BB-V.k | 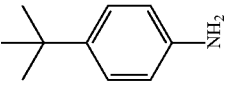 | 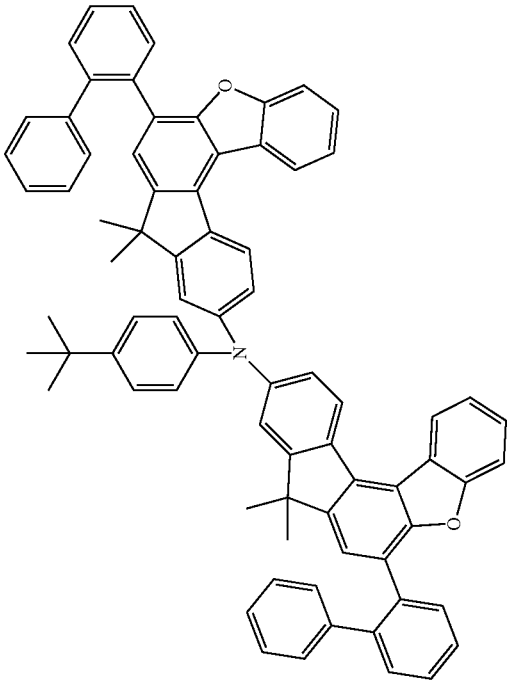 |
| 21 | BB-V.l | 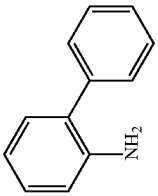 | 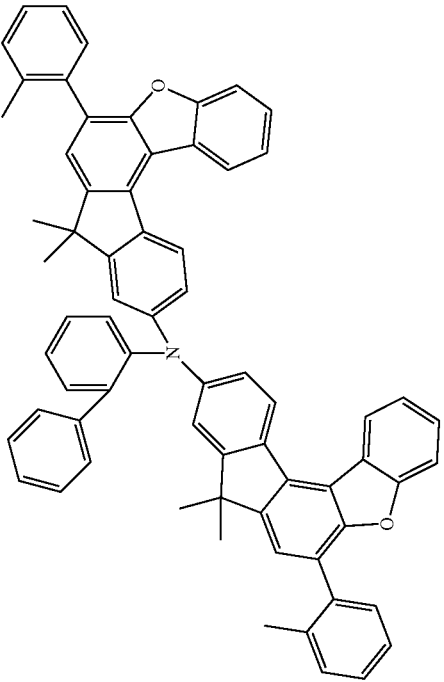 |

| Comp. | Starting material | Starting material | Product |
|---|---|---|---|
| 22 | BB-V.q | biphenyl-2-amine | (structure with two dimethylfluoreno-benzofuran units linked via N, each bearing a 2-naphthyl substituent; N also bears a biphenyl group) |
| 23 | BB-V.p | biphenyl-2-amine | (structure with two dimethylfluoreno-benzofuran units linked via N, each bearing a 2,4-dimethylphenyl substituent; N also bears a biphenyl group) |

| Comp. | Starting material | Starting material | Product |
|---|---|---|---|
| 24 | BB-V.n | ![biphenyl-2-amine] | [structure with two dibenzofuran-fluorene units linked by N-phenyl, with p-tolyl substituents] |
| 25 | BB-V.o | ![aniline] | [structure with two dibenzofuran-fluorene units linked by N-phenyl, with 4-tert-butylphenyl substituents] |

-continued
| Comp | Starting material | Starting material | Product |
|---|---|---|---|
| 26 | BB-V.o | 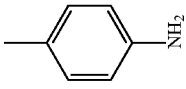 | 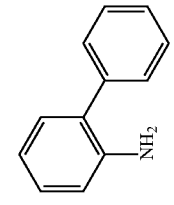 |
| 27 | BB-V.o | 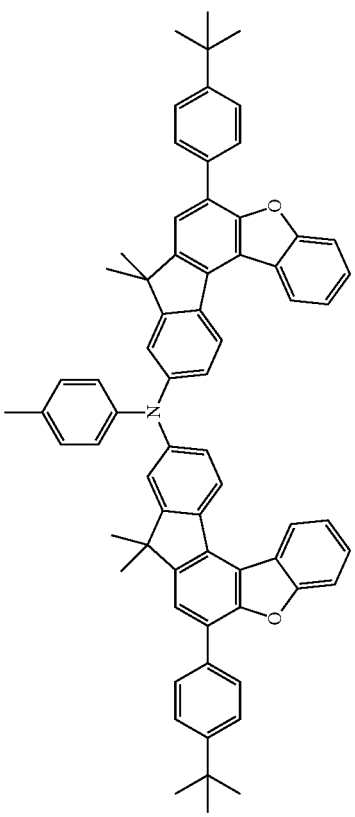 | 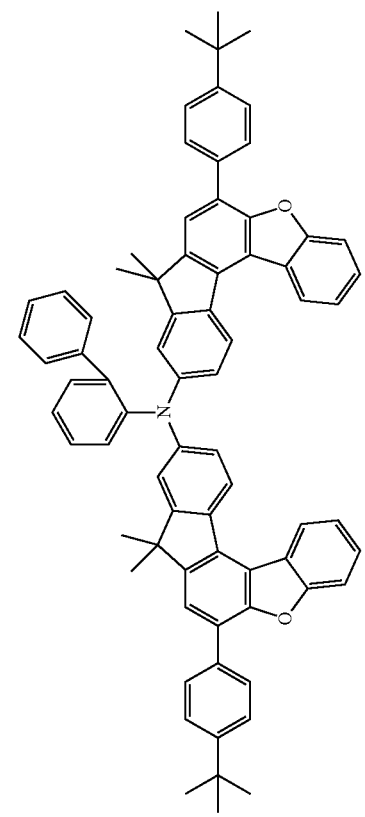 |

-continued

| Comp. | Starting material | Starting material | Product |
|---|---|---|---|
| 28 | BB-V.o | (3-phenylphenyl)-substituted biphenyl-4-amine | structure |
| 29 | BB-V.o | 2,4-dimethylaniline | structure |

| Comp | Starting material | Starting material | Product |
|---|---|---|---|
| 30 | BB-V.o | 2-methylaniline | (structure) |
| 31 | BB-V.i | 2-methylaniline | (structure) |

-continued

| Comp. | Starting material | Starting material | Product |
|---|---|---|---|
| 32 | BB-V.i | 4-methylaniline | *(structure)* |
| 33 | BB-V.i | [1,1':3',1''-terphenyl]-4'-amine | *(structure)* |

| Comp. | Starting material | Starting material | Product |
|---|---|---|---|
| 34 | BB-V.n | ![p-toluidine] | (structure) |
| 35 | BB-V.p | ![p-toluidine] | (structure) |

-continued
| Comp. | Starting material | Starting material | Product |
|---|---|---|---|
| 36 | BB-V.q | 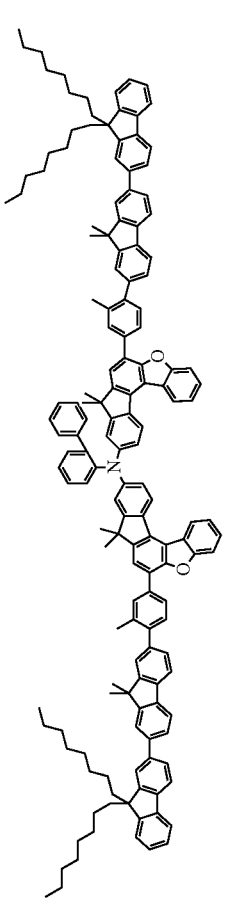 | 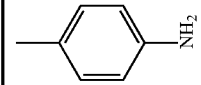 |
| 37 | BB-V.m | 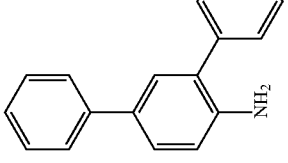 | 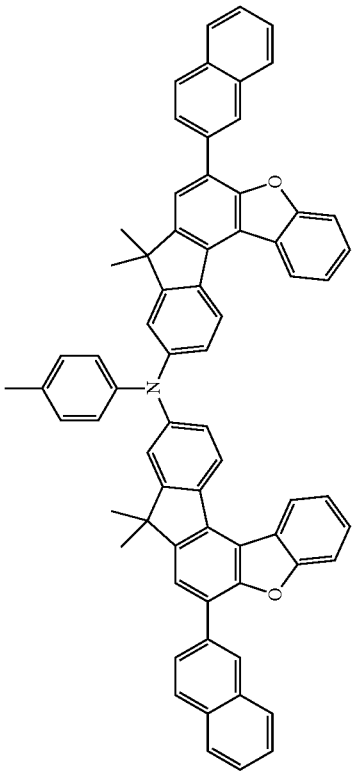 |
| 38 | BB-V.m | 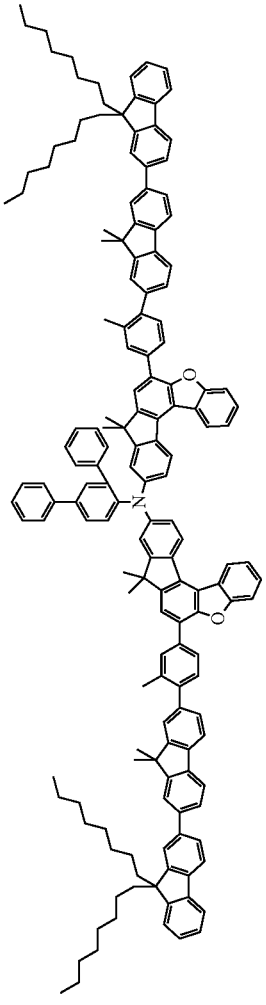 | 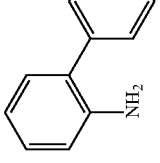 |

-continued

| Comp | Starting material | Starting material | Product |
|---|---|---|---|
| 39 | BB-V.m | | |
| 40 | BB-V.b | | |
| 41 | BB-V.b | | |

| Comp. | Starting material | Starting material | Product |
|---|---|---|---|
| 42 | BB-V.i | 2-aminonaphthalene | (structure) |
| 43 | BB-V.i | 1-aminonaphthalene | (structure) |

| Comp | Starting material | Starting material | Product |
|---|---|---|---|
| 44 | BB-V.n | 2-naphthylamine (NH₂) | [structure] |

| Comp | Starting material | Starting material | Product |
|---|---|---|---|
| 45 | BB-V | aniline (PhNH$_2$) | Step 1 with 0.95 eq of BB-V and purified by column; Step 2 with 1.1 eq of BB-V.d |

311
Synthesis Examples Part 2
Scheme Synthesis Example Compound 1.1
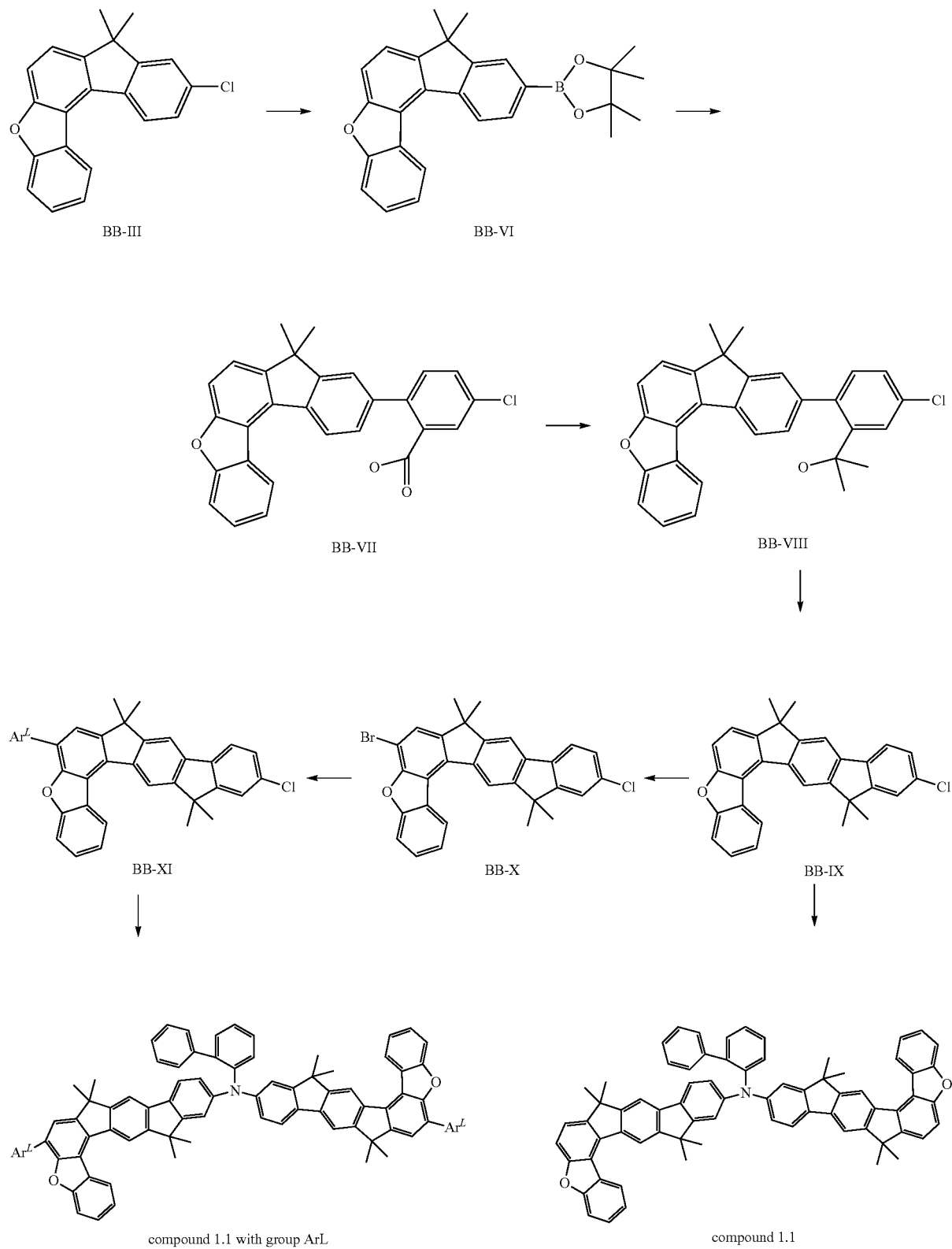
compound 1.1 with group ArL
compound 1.1

313
Synthesis BB-VI

314
Synthesis of BB-VII

Synthesis of BB-VII is Done Analog to BB-I

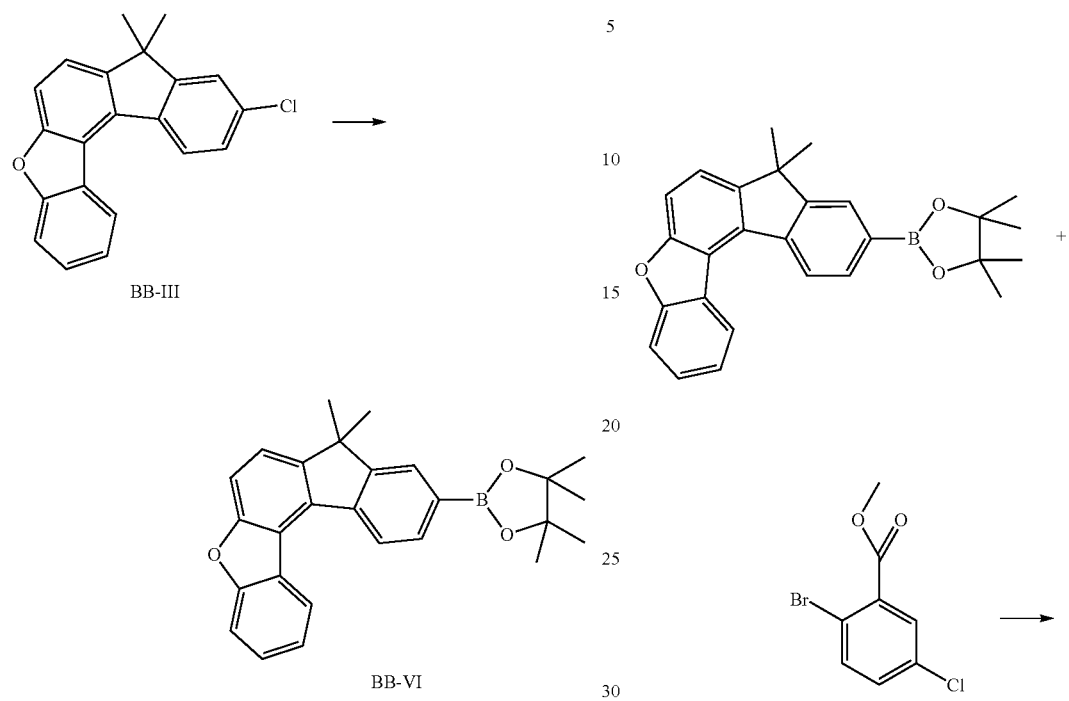

BB-III

BB-VI

10-Chloro-8,8-dimethyl-8H-5-oxa-indeno[2,1-c]fluorene (30.00 g; 94.1 mmol), bis-(pinacolato)-diboron (28.68 g; 112.9 mmol) and potassium acetate (18.47 g; 188.2 mmol) are dissolved in 800 mL 1,4-dioxane.

XPhos Palladacycle Gen 3 (CAS:1445085-55-1; 1.59 g; 1.882 mmol) and bis(pinacolato)-diboron (28.68 g; 112.9 mmol) are added and the reaction mixture is stirred at 100° C. overnight. After complete conversion, the reaction mixture is cooled down to room temperature and water and toluene are added. The phases are separated and the organic phase is washed several times with water. The combined organic phases are filtrated over silica with toluene as eluent. The solvent is removed in vacuum and the crude product vigorously stirred with ethanol to yield a white solid.

Yield: 34.2 g (83.4 mmol; 88%)

The following compound can be synthesized in an analogous manner:

Yield 93%

| Compound | Starting material | Product |
|---|---|---|
| BB-VI.a | 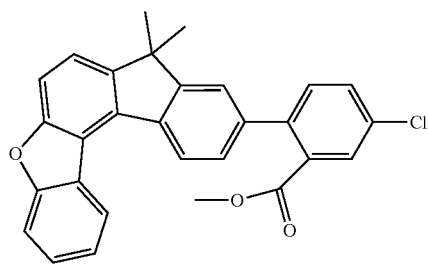 | |

The following compound can be synthesized in an analogous manner:
| Compound | Starting material | Product |
|---|---|---|
| BB-VII.a | 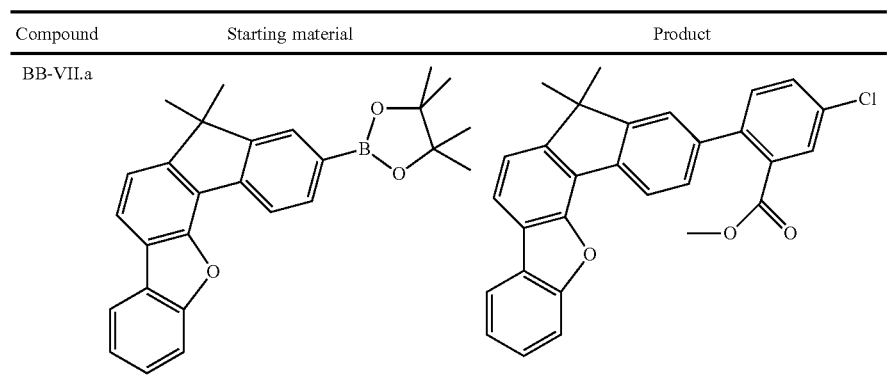 | |
Synthesis of BB-VIII
Synthesis of BB-VIII is Done Analog to BB-II
Synthesis of BB-IX
Synthesis of BB-IX is Done Analog to BB-III
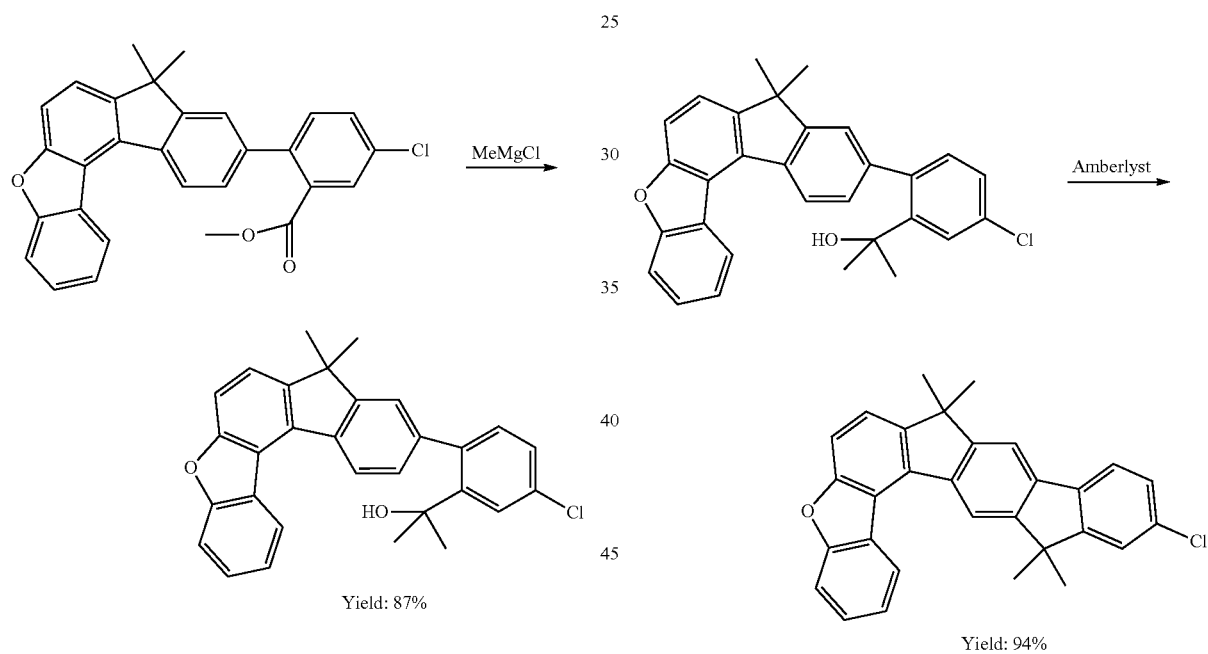
Yield: 87%
Yield: 94%
The following compound can be synthesized in an analogous manner:
| Compound | Starting material | Product |
|---|---|---|
| BB-VIII.a | 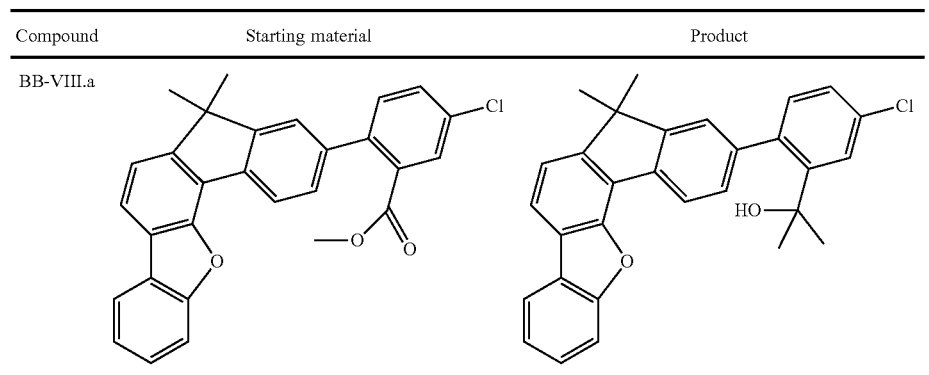 | |

| Compound | Starting material | Product |
|---|---|---|
| BB-IX.a | | |

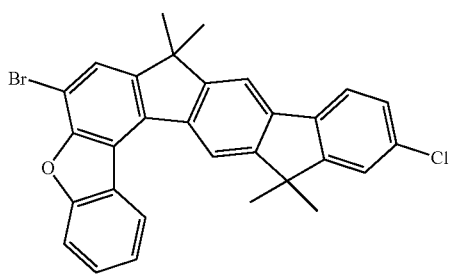 [SMILES: CC1(C)c2cc(Cl)ccc2-c2cc3c(cc21)-c1c(cc(Br)c2oc4ccccc4c12)C3(C)C]

Synthesis of BB-X

To a solution of compound BB-IX (100 g, 229 mmol) in $CH_2Cl_2$ (1.2 L), N-bromosuccinimide (40.71 g, 314 mmol) and HBr (32% solution in acetic acid, 0.5 mL) are added. The reaction is heated at 30° C. for 4 days. After completion of the reaction, $Na_2S_2O_3$ (300 mL, saturated aqueous solution) is added and the mixture is stirred vigorously for 30 minutes. The phases are separated and the organic phase is washed several times with water. The solvent is removed in vacuum and the crude product vigorously stirred with ethanol to yield a white solid. Yield: 101.2 g (86%).

The following compound can be synthesized in an analogous manner:

| Compound | Starting material | Product |
|---|---|---|
| BB-X.a | | |

Synthesis of BB-XI

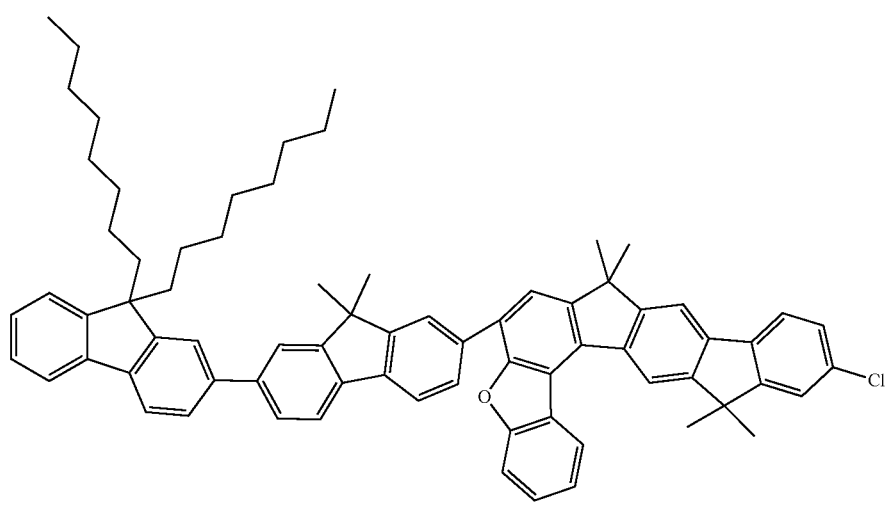 [SMILES: CCCCCCCCC1(CCCCCCCC)c2ccccc2-c2ccc(-c3ccc4c(c3)C(C)(C)c3cc(-c5cc6c(c7c5oc5ccccc57)-c5cc7c(cc5C6(C)C)-c5ccc(Cl)cc5C7(C)C)ccc3-4)cc21]

30.0 g (58.4 mmol) BB-X, 42.5 g (60.0 mmol) ArL2 and 16.0 g (151 mmol) sodium carbonate are mixed in 600 mL toluene/dioxane/water (2:1:2) and degassed. To the mixture, tetrakis(triphenylphosphine)palladium (2.2 g, 1.9 mmol) is added and the mixture is stirred at reflux for 4 h. After cooling the mixture to room temperature, 400 mL of ethyl acetate is added and the phases are separated. The organic phase is washed multiple times with water and the solvent is removed in vacuum. Afterwards, the organic phase is filtrated over a plug of silica using ethyl acetate as solvent. The solvent is removed in vacuum and the crude product vigorously stirred with ethanol to yield a white solid. Yield: 48.1 g (84%).

The following compounds can be synthesized in an analogous manner:

| Comp. | Starting Material | Starting Material | Product |
|---|---|---|---|
| BB-XI.a | BB-X.a | ArL2 | |
| BB-XI.b | BB-X.a | ArL1 | |
| BB-XI.c | BB-X | ArL5 | |

Synthesis of Compound 1.1

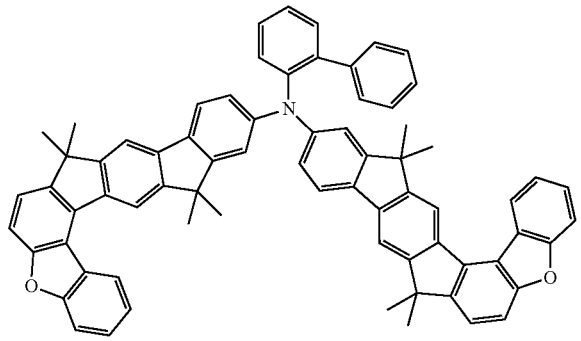 [SMILES: CC1(C)c2cc(N(c3ccc4c(c3)C(C)(C)c3cc5c(cc3-4)C(C)(C)c3ccc4oc6ccccc6c4c3-5)c3ccccc3-c3ccccc3)ccc2-c2cc3c(cc21)-c1c(ccc2oc4ccccc4c12)C3(C)C]

2.00 g (11.8 mmol) biphenyl-2-ylamine, 11.31 g (26.0 mmol) BB-IX and 6.82 g (70.9 mmol) sodium tertbutylate are mixed in 300 mL toluene and degassed. Afterwards, 563 mg (1.4 mmol)S-Phos and 151 mg (0.7 mmol) palladium acetate are added and the mixture is stirred at reflux for 16 h. After cooling the mixture at room temperature, 200 mL of water is added and the phases are separated. The crude product is filtrate over a plug of aluminium oxide using toluene as solvent. The product is further purified by several recrystallizations from toluene/heptane. Yield: 6.7 g (59%).

The following compounds can be synthesized in an analogous manner:

| Comp. | SM | SM | Product |
|---|---|---|---|
| 1.2 | BB-IX | 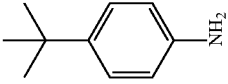 | 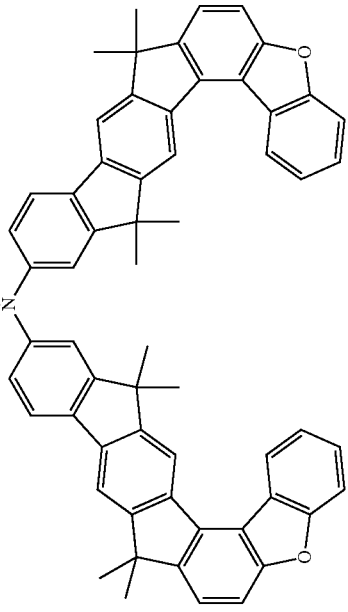 |
| 1.3 | BB-IX | 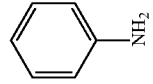 | 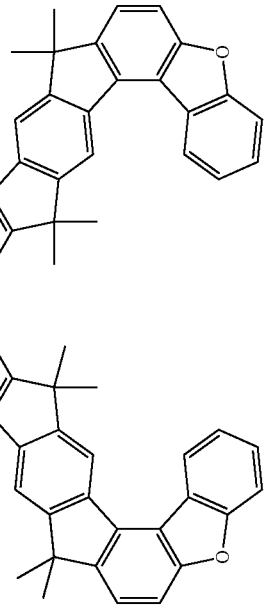 |

-continued
| Comp. | SM | SM | Product |
|---|---|---|---|
| 1.4 | BB-IX | 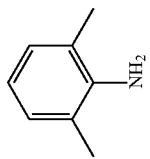 | 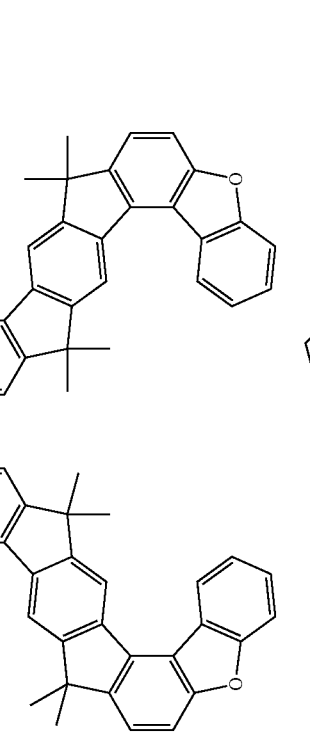 |
| 1.5 | BB-IX.a | 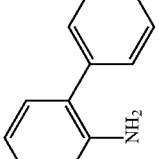 | 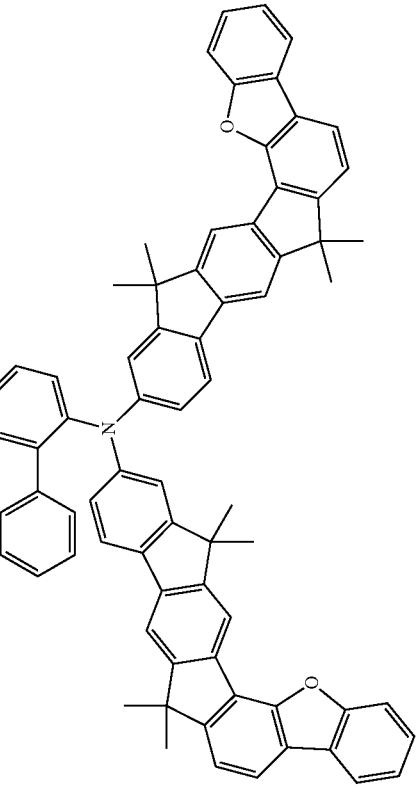 |

-continued
| Comp. | SM | SM | Product |
|---|---|---|---|
| 1.6 | BB-IX.a | 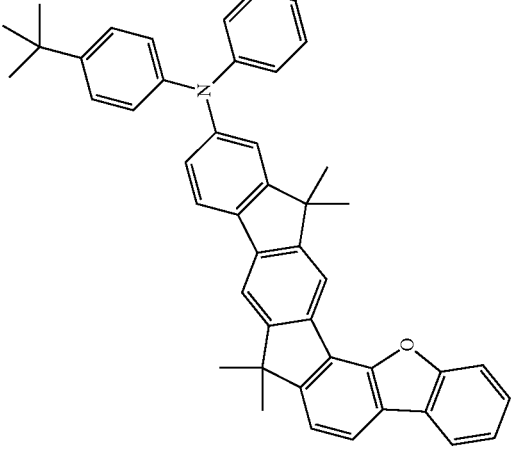 | 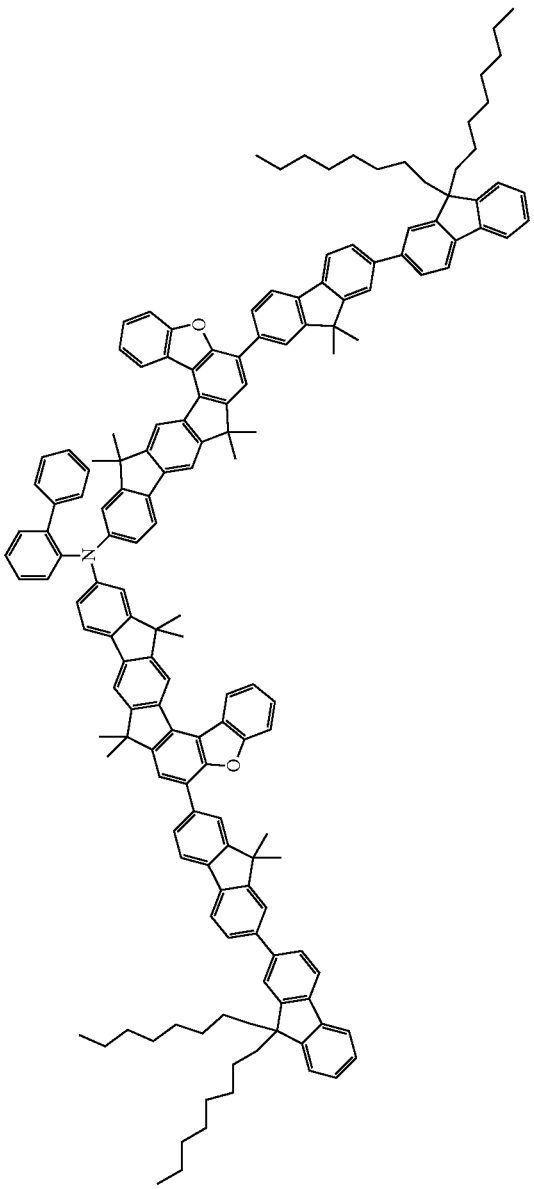 |
| 1.7 | BB-XI |  | 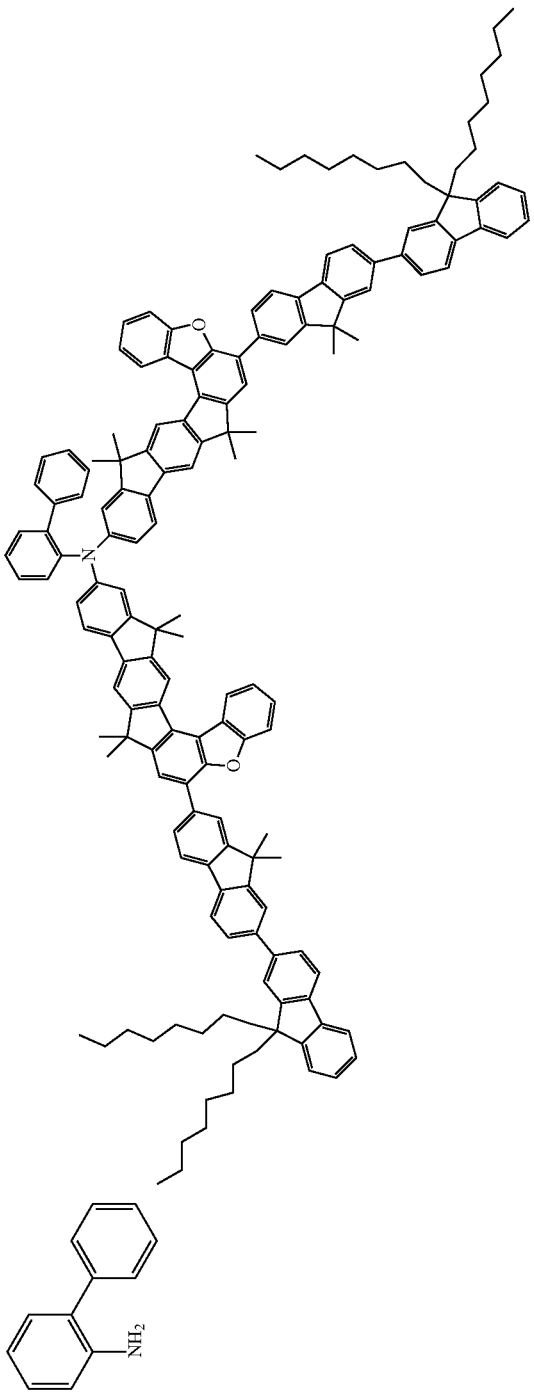 |

-continued
| Comp. | SM | SM | Product |
|---|---|---|---|
| 1.8 | BB-XI.a | | |
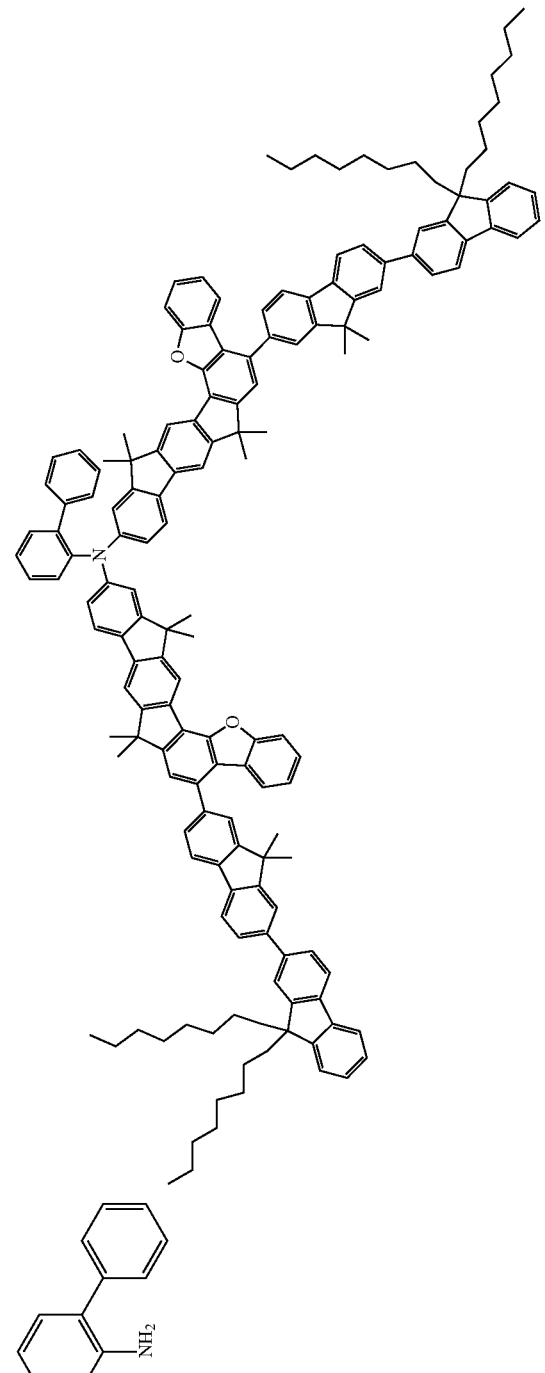

-continued

| Comp. | SM | SM | Product |
|---|---|---|---|
| 1.9 | BB-XI.b | 4-tert-butylaniline | (structure) |
| 1.10 | BB-XI.c | 2-aminobiphenyl | (structure) |

| Comp. | SM | SM | Product |
|---|---|---|---|
| 1.11 | BB-IX | 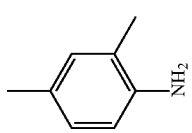 | 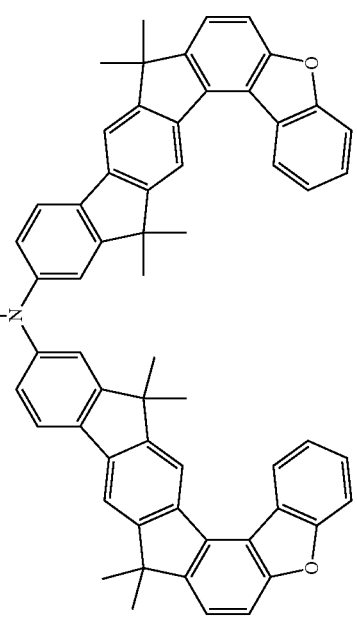 |

-continued

| Comp. | SM | SM | Product |
|---|---|---|---|
| 1.12 | BB-IX | 4-tert-butylaniline | (structures shown; Step 1 with 0.95 eq of BB-IX and purified by column; Step 2 with 1.1 eq of BB-Ix.a) |

B) Fabrication of Oleds

The manufacturing of the OLED devices is performed accordingly to WO 04/05891 with adapted film thicknesses and layer sequences. The following examples V1, E1 to E9 show data of various OLED devices.

Substrate Pre-Treatment of Examples V1, E1 to E9

Glass plates with structured ITO (50 nm, indium tin oxide) are coated with a buffer of 20 nm PEDOT:PSS (Poly(3,4-ethylenedioxythiophene) poly(styrene-sulfonate, CLEVIOS™ P VP Al 4083 from Heraeus Precious Metals GmbH Germany, spin-coated from a water-based solution) to form the substrates on which the OLED devices are fabricated.

The OLED devices have in principle the following layer structure:
Substrate,
ITO (50 nm),
Buffer (20 nm),
Hole transporting layer (HTL),
Optional interlayer (IL)
Emissive layer (EML),
Optional hole blocking layer (HBL),
Electron transporting layer (ETL),
Electron injection layer (EIL),
Cathode.

The cathode is formed by an aluminium layer with a thickness of 100 nm.

The detailed stack sequence is shown in table A. The materials used for the OLED fabrication are presented in table C.

All materials are applied by thermal vapour deposition in a vacuum chamber. The emission layer here always consists of at least one matrix material (host material=H) and an emitting dopant (emitter=D), which is mixed with the matrix material or matrix materials in a certain proportion by volume by co-evaporation. An expression such as H1:D1 (97%:3%) here means that material H1 is present in the layer in a proportion by volume of 97%, whereas D1 is present in the layer in a proportion of 3%. Analogously, the electron-transport layer may also consist of a mixture of two or more materials.

The OLED devices are characterised by standard methods. For this purpose, the electroluminescence spectra, the current efficiency (measured in cd/A), power efficiency (lm/W) and the external quantum efficiency (EQE, measured in % at 1000 $cd/m^2$) are determined from current/voltage/luminance characteristic lines (IUL characteristic lines) assuming a Lambertian emission profile. The electroluminescence (EL) spectra are recorded at a luminous density of 1000 $cd/m^2$ and the CIE 1931 x an y coordinates are then calculated from the EL spectrum. U1000 is defined as the voltage at luminous density of 1000 $cd/m^2$. SE1000 represents the current efficiency, LE1000 the power efficiency at 1000 $cd/m^2$. EQE1000 is defined as the external quantum efficiency at luminous density of 1000 $cd/m^2$. The device data of various OLED devices is summarized in table B. The example V1 represents the comparative example according to the state-of-the-art. The examples E1 to E9 show data of inventive OLED devices.

In the following section several examples are described in more detail to show the advantages of the inventive OLED devices.

Use of Inventive Compounds as Emitting Material in Fluorescent OLEDs

The inventive compounds are especially suitable as an emitter (dopant) when blended into a fluorescent blue matrix to form the emissive layer of a fluorescent blue OLED device. The representative examples are D1 to D9. Comparative compound for the state-of-the-art is represented by SdT1 (structures see table C). The use of the inventive compound as an emitter (dopant) in a fluorescent blue OLED device results in significantly improved device data (E1 to E9) (device data see table B).

TABLE A

Device stack of vapor processed OLEDs

| Ex. | HTL [nm] | IL [nm] | EBL [nm] | EML [nm] | HBL [nm] | ETL [nm] | EIL [nm] |
|---|---|---|---|---|---|---|---|
| V1 | SpA1 140 nm | HATCN 5 nm | SpMA1 20 nm | H1:SdT1 (97%:3%) 20nm | HBM 10 nm | ETM:LiQ (50%:50%) 20 nm | LiQ 1 nm |
| E1 | SpA1 140 nm | HATCN 5 nm | SpMA1 20 nm | H1:D1 (97%:3%) 20 nm | HBM 10 nm | ETM:LiQ (50%:50%) 20 nm | LiQ 1 nm |
| E2 | SpA1 140 nm | HATCN 5 nm | SpMA1 20 nm | H1:D2 (97%:3%) 20 nm | HBM 10 nm | ETM:LiQ (50%:50%) 20 nm | LiQ 1 nm |
| E3 | SpA1 140 nm | HATCN 5 nm | SpMA1 20 nm | H1:D3 (97%:3%) 20 nm | HBM 10 nm | ETM:LiQ (50%:50%) 20 nm | LiQ 1 nm |
| E4 | SpA1 140 nm | HATCN 5 nm | SpMA1 20 nm | H1:D4 (97%:3%) 20 nm | HBM 10 nm | ETM:LiQ (50%:50%) 20 nm | LiQ 1 nm |
| E5 | SpA1 140 nm | HATCN 5 nm | SpMA1 20 nm | H1:D5 (97%:3%) 20 nm | HBM 10 nm | ETM:LiQ (50%:50%) 20 nm | LiQ 1 nm |
| E6 | SpA1 140nm | HATCN 5 nm | SpMA1 20 nm | H1:D6 (97%:3%) 20 nm | HBM 10 nm | ETM:LiQ (50%:50%) 20 nm | LiQ 1 nm |
| E7 | SpA1 140 nm | HATCN 5 nm | SpMA1 20 nm | H1:D7 (97%:3%) 20 nm | HBM 10 nm | ETM:LiQ (50%:50%) 20 nm | LiQ 1 nm |
| E8 | SpA1 140 nm | HATCN 5 nm | SpMA1 20 nm | H1:D8 (97%:3%) 20 nm | HBM 10 nm | ETM:LiQ (50%:50%) 20 nm | LiQ 1 nm |

TABLE A-continued
Device stack of vapor processed OLEDs
| Ex. | HTL [nm] | IL [nm] | EBL [nm] | EML [nm] | HBL [nm] | ETL [nm] | EIL [nm] |
|---|---|---|---|---|---|---|---|
| E9 | SpA1 140 nm | HATCN 5 nm | SpMA1 20 nm | H1:D9 (97%:3%) 20 nm | HBM 10 nm | ETM:LiQ (50%:50%) 20 nm | LiQ 1 nm |
TABLE B
Device data of vapor processed OLEDs
| Ex. | U1000 (V) | SE1000 (cd/A) | LE1000 (lm/W) | EQE1000 (%) | CIE x/y @ 1000 cd/m$^2$ |
|---|---|---|---|---|---|
| V1 | 4.4 | 5.7 | 4.1 | 7.1 | 0.15/0.09 |
| E1 | 4.3 | 6.2 | 4.5 | 8.3 | 0.15/0.08 |
| E2 | 4.3 | 7.8 | 5.6 | 8.5 | 0.14/0.10 |
| E3 | 4.4 | 6.1 | 4.4 | 7.8 | 0.15/0.08 |
| E4 | 4.3 | 6.6 | 4.8 | 8.2 | 0.15/0.09 |
| E5 | 4.3 | 8.0 | 5.8 | 8.4 | 0.14/0.10 |
| E6 | 4.4 | 6.7 | 4.8 | 8.5 | 0.16/0.09 |
| E7 | 4.3 | 7.9 | 5.8 | 8.3 | 0.14/0.10 |
| E8 | 4.4 | 8.2 | 5.9 | 8.5 | 0.14/0.11 |
| E9 | 4.3 | 8.4 | 6.1 | 8.2 | 0.14/0.11 |
TABLE C
Structural formulae of vapor processed OLED materials
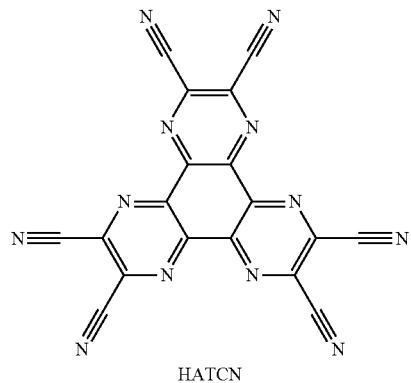
HATCN
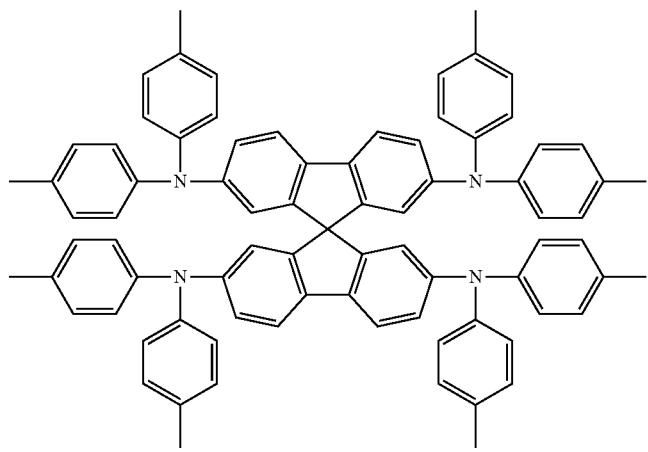
SpA1

TABLE C-continued
Structural formulae of vapor processed OLED materials
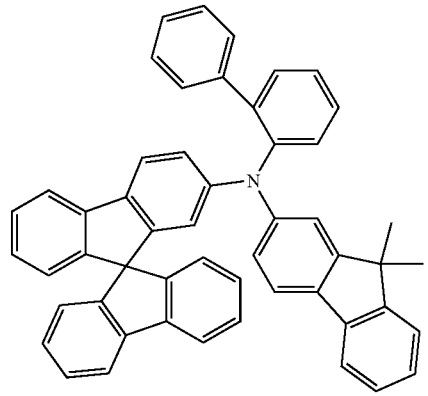
SpMA1
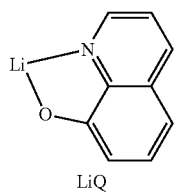
LiQ
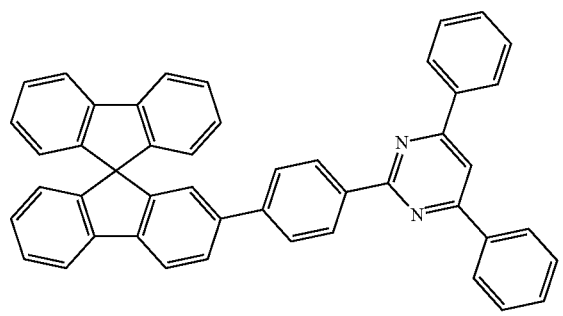
HBM
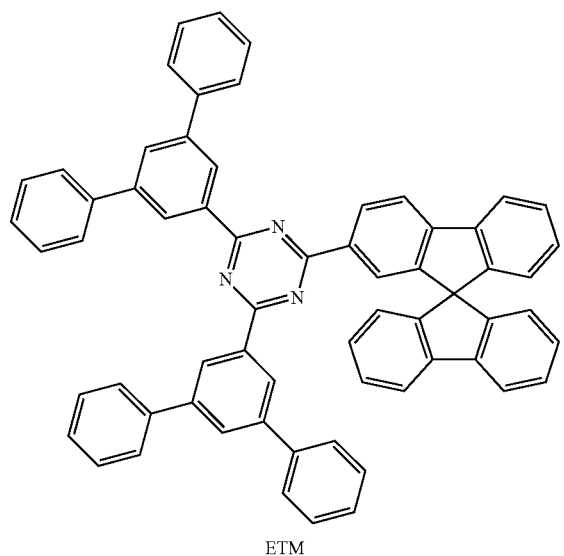 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM TABLE C-continued
Structural formulae of vapor processed OLED materials
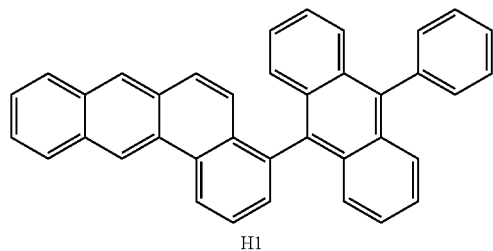
H1
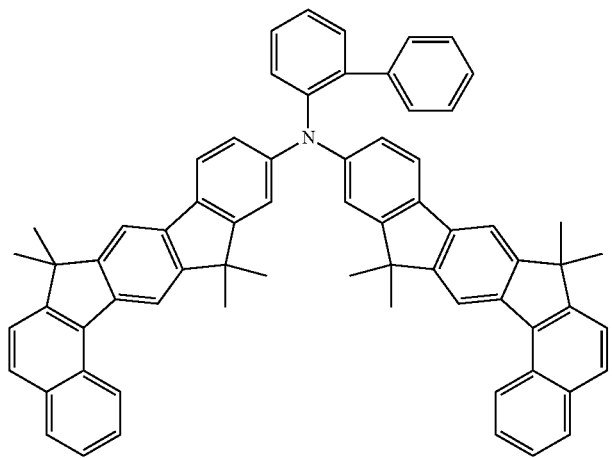
SdT1
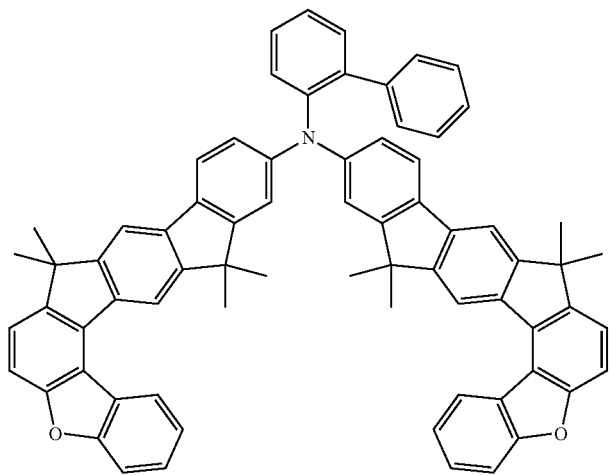
D1

TABLE C-continued
Structural formulae of vapor processed OLED materials
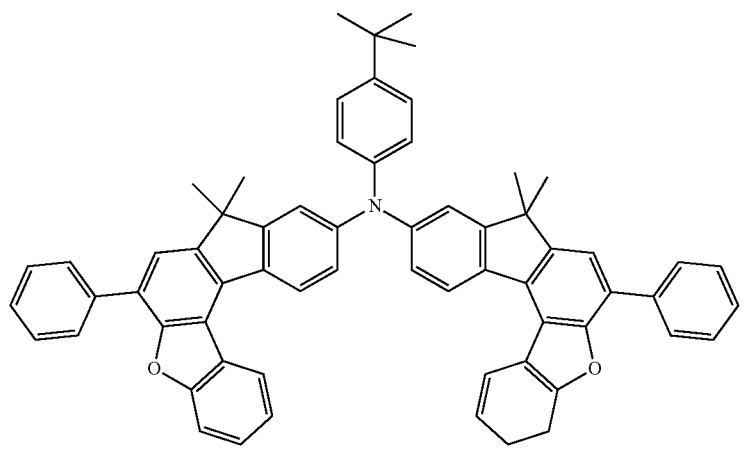
D2
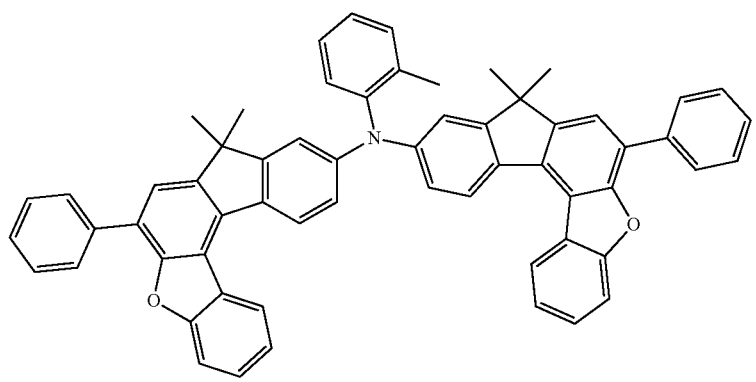
D3
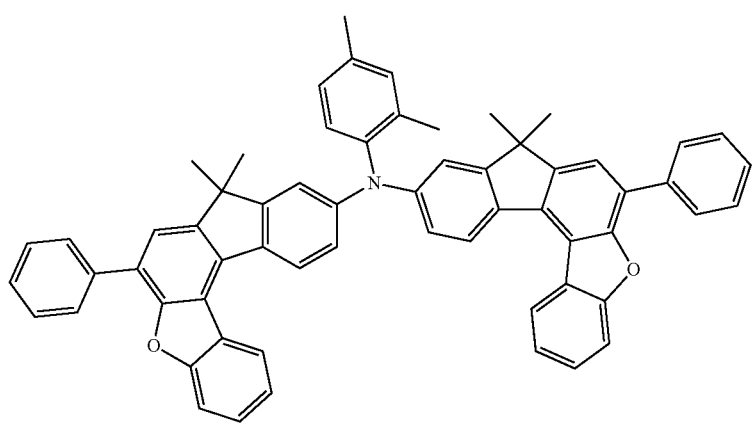
D4

TABLE C-continued
Structural formulae of vapor processed OLED materials
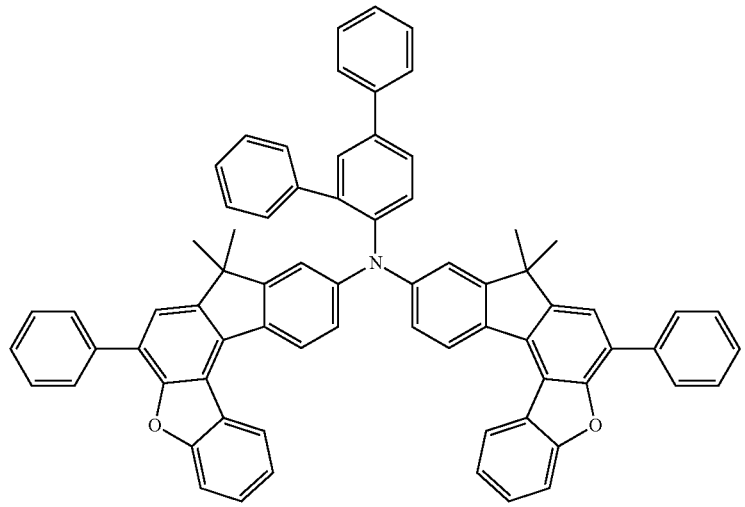
D5
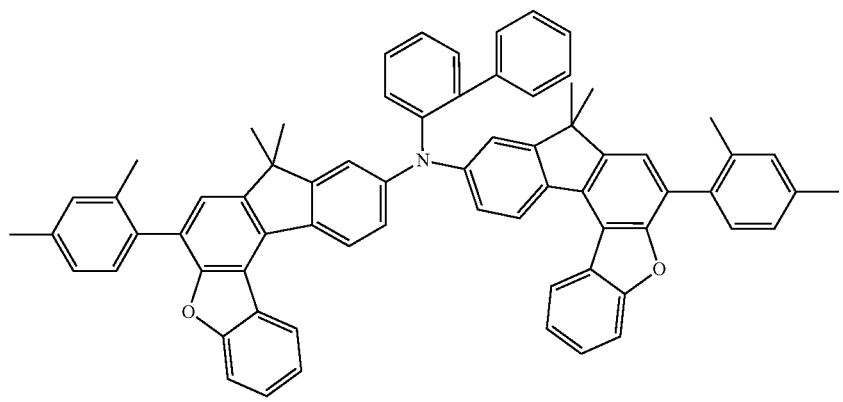
D6
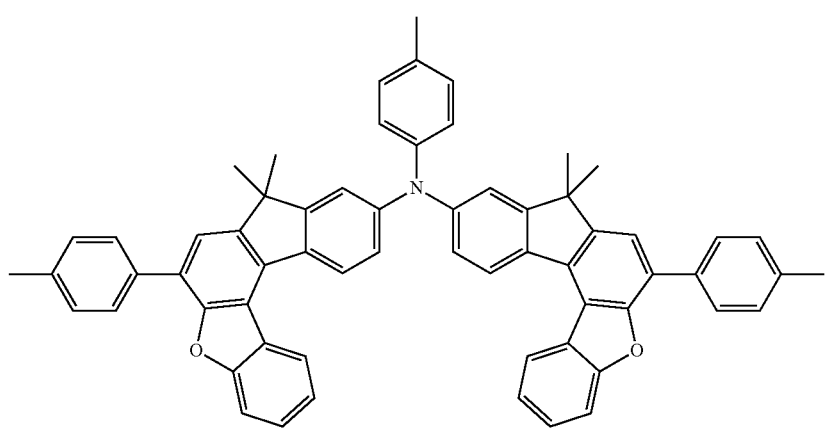
D7

TABLE C-continued

Structural formulae of vapor processed OLED materials

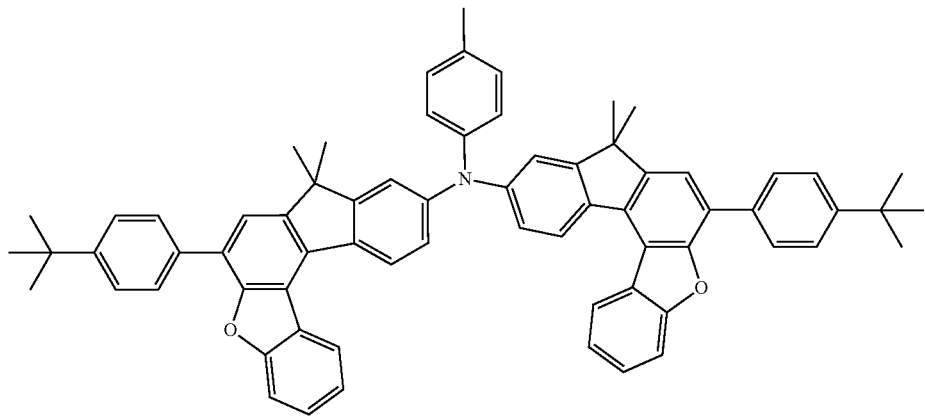

D8

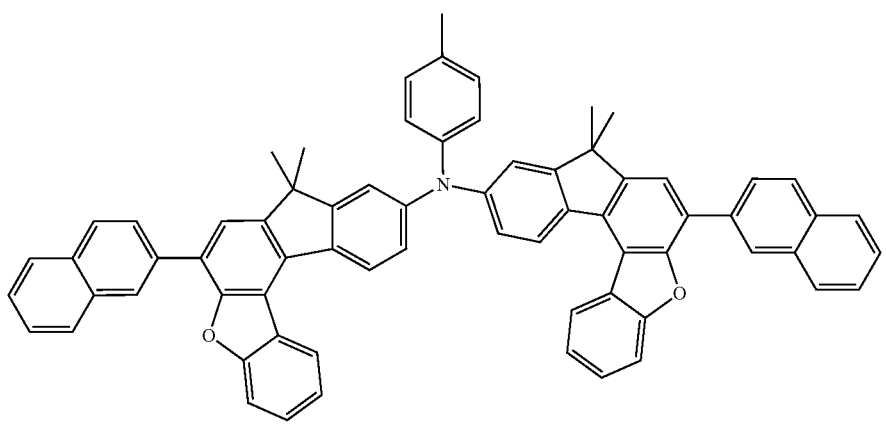

D9

Fabrication of Solution Processed OLED Devices

The production of solution-based OLEDs has already been described many times in the literature, for example in WO 2004/037887 and WO 2010/097155. The process is adapted to the circumstances described below (layer-thickness variation, materials).

The inventive material combinations are used in the following layer sequence:
substrate,
ITO (50 nm),
Buffer (40 nm),
emission layer (EML) (40 nm),
hole-blocking layer (HBL) (10 nm),
electron-transport layer (ETL) (30 nm),
cathode (Al) (100 nm).

Glass plates coated with structured ITO (indium tin oxide) in a thickness of 50 nm serve as substrate. These are coated with the buffer (PEDOT:PSS) Clevios P VP Al 4083 (Heraeus Clevios GmbH, Leverkusen). The spin coating of the buffer is carried out from water in air. The layer is subsequently dried by heating at 180° C. for 10 minutes. The emission layers are applied to the glass plates coated in this way.

The emission layer (EML) is composed of the matrix material (host material) H2 and the emitting dopant (emitter) D2. Both materials are present in the emission layer in a proportion of 97% by weight H2 and 3% by weight D2. The mixture for the emission layer is dissolved in toluene. The solids content of such solutions is about 9 mg/ml if, as here, the layer thickness of 40 nm which is typical for a device is to be achieved by means of spin coating. The layers are applied by spin coating in an inert-gas atmosphere and dried by heating at 120° C. for 10 minutes. The materials used in the present case are shown in table D.

TABLE D
Structural formulae of the solution processed materials in the EML
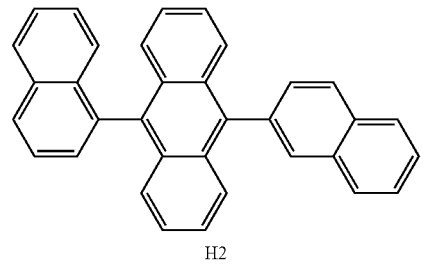
H2
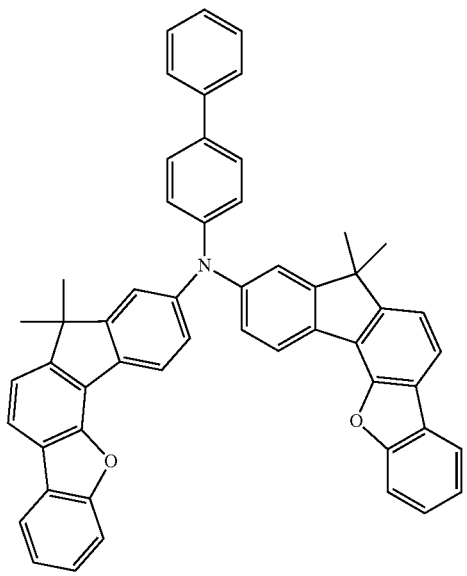
SdT2
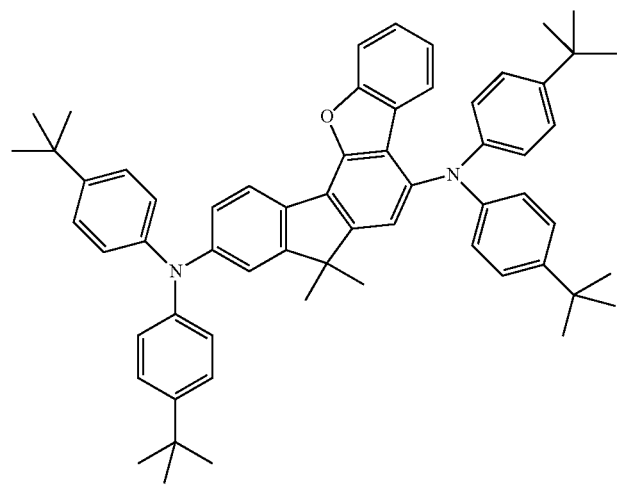
SdT3

TABLE D-continued
Structural formulae of the solution processed materials in the EML
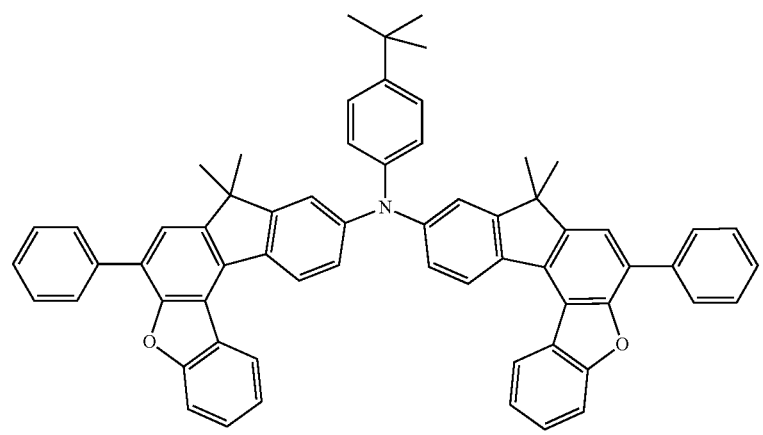
D2
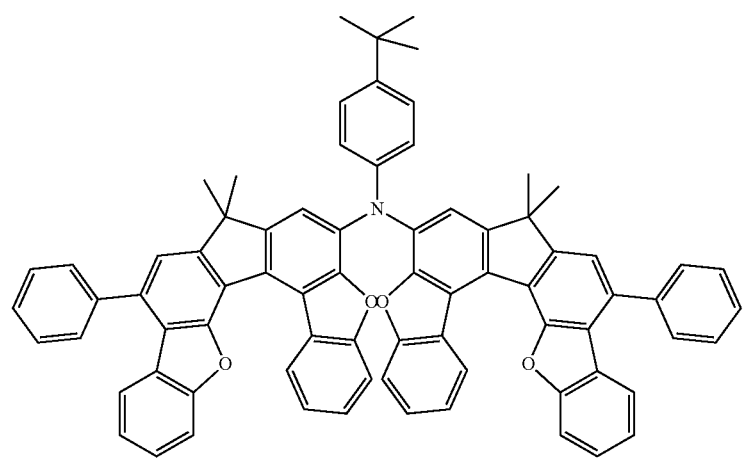
D10

TABLE D-continued
Structural formulae of the solution processed materials in the EML
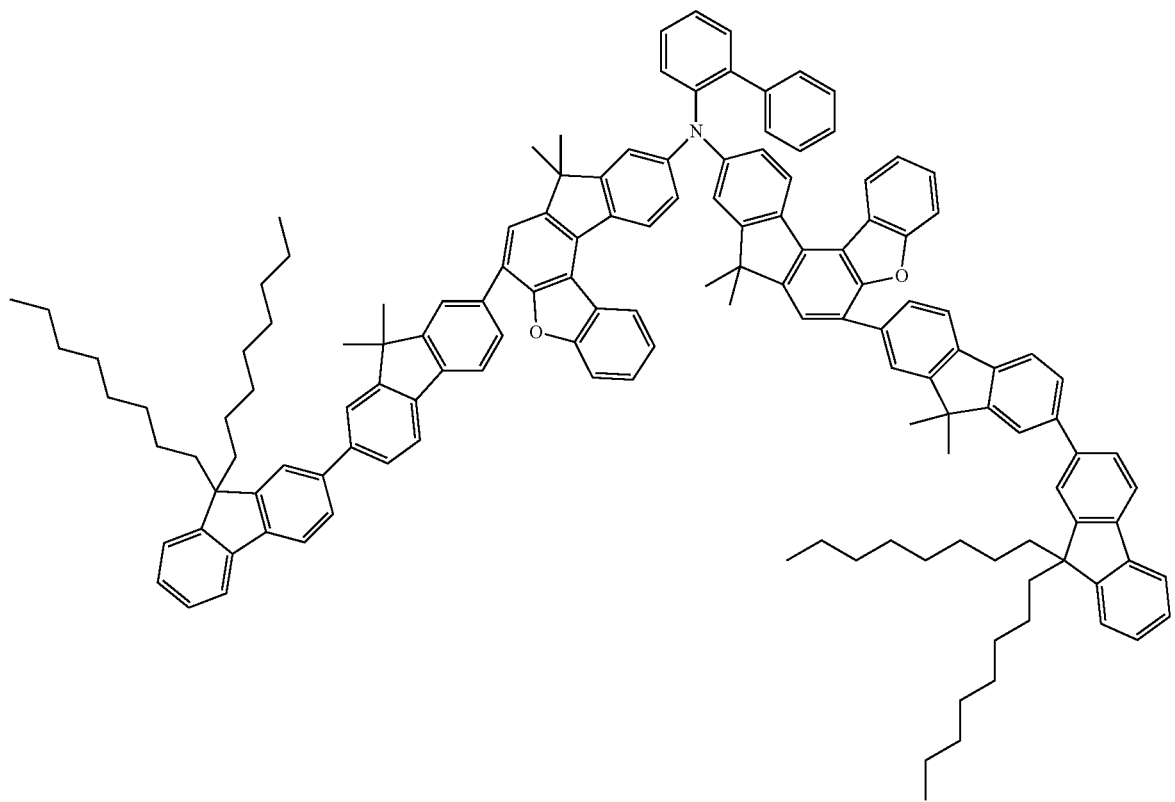
D11
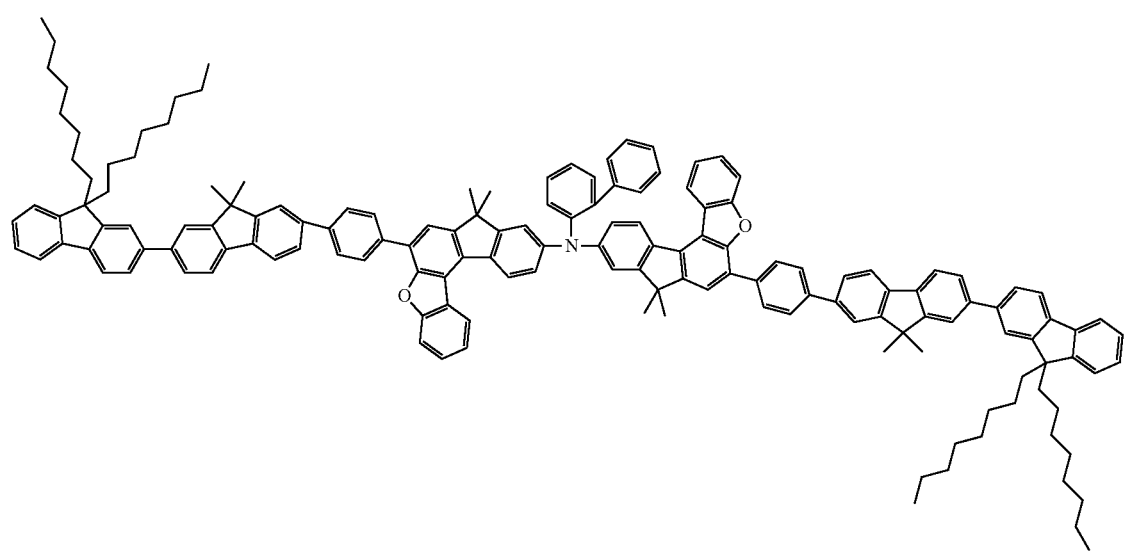
D12

TABLE D-continued
Structural formulae of the solution processed materials in the EML
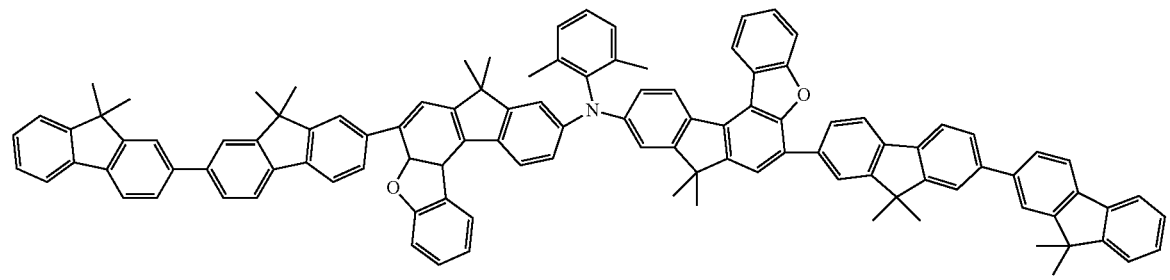
D13
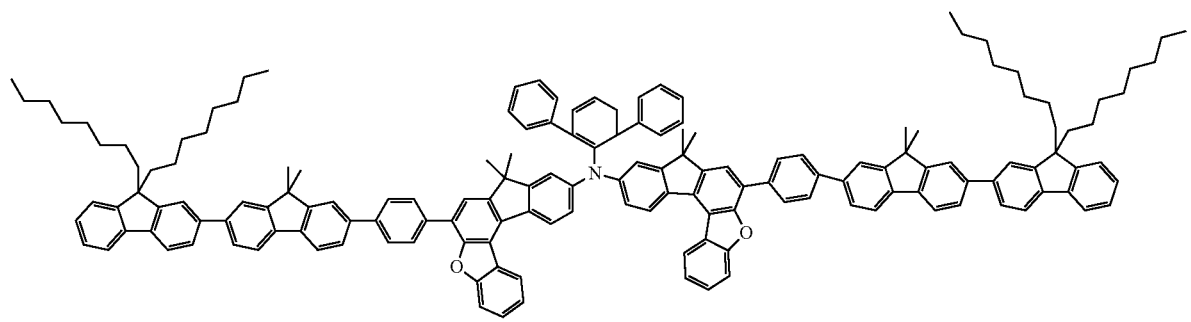
D14
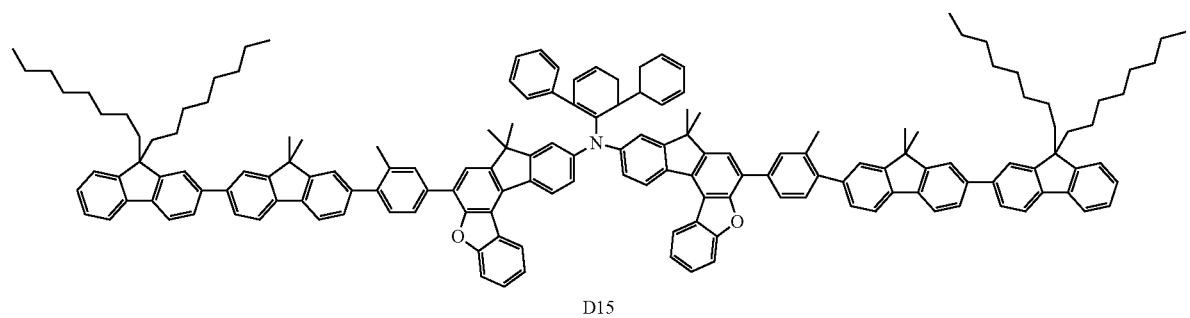 [SMILES: CCCCCCCCC1(CCCCCCCC)c2ccccc2-c2ccc(-c3ccc4c(c3)C(C)(C)c3cc(-c5ccc(-c6cc7c(c8c6oc6ccccc68)-c6ccc(N(C8=C(c9ccccc9)C=CCC8C8C=CC=CC8)c8ccc9c(c8)C(C)(C)c8cc(-c%10ccc(-c%11ccc%12c(c%11)C(C)(C)c%11cc(-c%13ccc%14c(c%13)C(CCCCCCCC)(CCCCCCCC)c%13ccccc%13-%14)ccc%11-%12)c(C)c%10)c%10oc%11ccccc%11c%10c8-9)cc6C7(C)C)cc5C)ccc3-4)cc21 ; "D15"]
D15
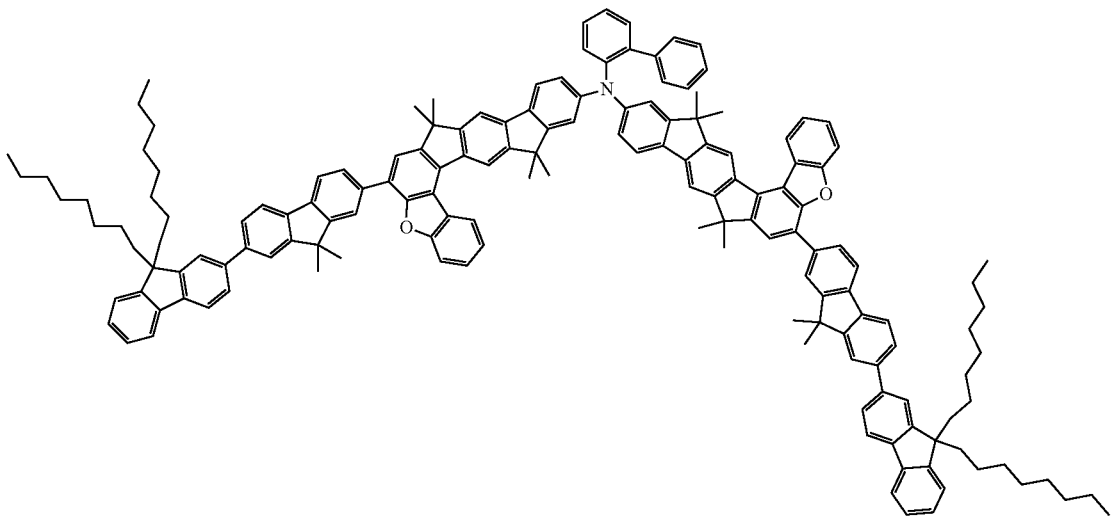
D16

The materials for the hole-blocking layer and electron-transport layer are likewise applied by thermal vapour deposition in a vacuum chamber and are shown in table C. The hole-blocking layer (HBL) consists of ETM. The electron-transport layer (ETL) consists of the two materials ETM and LiQ, which are mixed with one another in a proportion by volume of 50% each by co-evaporation. The cathode is formed by the thermal evaporation of an aluminium layer with a thickness of 100 nm.

The OLEDs are characterised by standard methods. For this purpose, the electroluminescence spectra are recorded, the current efficiency (measured in cd/A) and the external quantum efficiency (EQE, measured in percent) as a function of the luminous density assuming Lambert emission characteristics are calculated from current/voltage/luminous density characteristic lines (IUL characteristic lines). The electroluminescence spectra are recorded at a luminous density of 1000 cd/m², and the CIE 1931 x and y colour coordinates are calculated from this data. The term EQE1000 denotes the external quantum efficiency at an operating luminous density of 1000 cd/m².

The properties of the various OLEDs are summarized in table E. Examples V2 and V3 are the comparative examples, whereas E10 to E17 show properties of OLEDs containing materials of the present invention.

TABLE E

Device data of solution processed OLEDs

| Example | EML host | EML dopant | EQE1000 [%] | CIE x/y |
|---------|----------|------------|-------------|---------|
| V2 | H2 | SdT2 | 1.9 | 0.15/0.05 |
| V3 | H2 | SdT3 | 3.2 | 0.14/0.14 |
| E10 | H2 | D2 | 3.8 | 0.14/0.14 |
| E11 | H2 | D10 | 3.9 | 0.13/0.15 |
| E12 | H2 | D11 | 4.5 | 0.15/0.17 |
| E13 | H2 | D12 | 4.6 | 0.15/0.16 |
| E14 | H2 | D13 | 4.3 | 0.15/0.16 |
| E15 | H2 | D14 | 4.4 | 0.15/0.16 |
| E16 | H2 | D15 | 4.7 | 0.14/0.15 |
| E17 | H2 | D16 | 4.6 | 0.14/0.15 |

Table E shows that use of materials (D2, D10 to D16) according to the present invention give rise to improvements over the prior art (SdT2 and SdT3) when used as fluorescent blue emitters, in particular with respect to efficiency.

The invention claimed is:
1. A compound of formula (1):

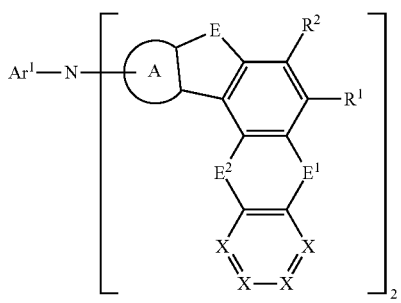

wherein
A is on each occurrence, identically or differently, an aromatic or heteroaromatic ring system having 5 to 60 aromatic ring atoms, which in each case is optionally substituted by one or more radicals R³; wherein the ring A is condensed on the five-membered ring comprising E via two adjacent carbon atoms;

Ar¹ is:
an aromatic or heteroaromatic ring system having 5 to 60 aromatic ring atoms, which in each case is optionally substituted by one or more radicals R⁴;

X is on each occurrence, identically or differently, CR³ or N;

E is on each occurrence, identically or differently, selected from the group consisting of —BR⁰—, —C(R⁰)₂—, —C(R⁰)₂—C(R⁰)₂—, —C(R⁰)₂—O—, —C(R⁰)₂—S—, —R⁰C=CR⁰—, —R⁰C=N—, —Si(R⁰)₂—, —Si(R⁰)₂—Si(R⁰)₂—, —C(=O)—, —C(=NR⁰)—, —C(=C(R⁰)₂)—, —O—, —S—, —S(=O)—, —SO₂—, —N(R⁰)—, —P(R⁰)—, and —P((=O)R⁰)—; or E is a group of formula (E-1):

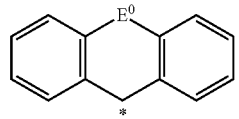

wherein the symbol * in formula (E-1) indicates the corresponding group E in formula (1);

E¹ and E²
are identically or differently on each occurrence, selected from the group consisting of a single bond, —C(R⁰)₂—, —Si(R⁰)₂—, —O—, and —S—; with the proviso that, in a ring comprising the groups E¹ and E², one of the groups E¹ and E², is a single bond, —C(R⁰)₂—, or —Si(R⁰)₂—, and the other group is O or S;

E⁰ is identically or differently on each occurrence, selected from the group consisting of a single bond, —BR⁰—, —C(R⁰)₂—, —C(R⁰)₂—C(R⁰)₂—, —C(R⁰)₂—O—, —C(R⁰)₂—S—, —R⁰C=CR⁰—, —R⁰C=N—, —Si(R⁰)₂—, —Si(R⁰)₂—Si(R⁰)₂—, —C(=O)—, —C(=NR⁰)—, —C(=C(R⁰)₂)—, —O—, —S—, —S(=O)—, —SO₂—, —N(R⁰)—, —P(R⁰)—, and —P((=O)R⁰)—;

R⁰, R¹, R², R³, and R⁴
are, identically or differently, on each occurrence:
H, deuterium (D), F, Cl, Br, I, CHO, CN, N(Ar)₂, C(=O)Ar, P(=O)(Ar)₂, S(=O)Ar, S(=O)₂Ar, NO₂, Si(R)₃, B(OR)₂, or OSO₂R;
a straight-chain alkyl, alkoxy, or thioalkyl group having 1 to 40 C atoms or a branched or a cyclic alkyl, alkoxy, or thioalkyl group having 3 to 40 C atoms, each of which is optionally substituted by one or more radicals R, wherein in each case one or more non-adjacent CH₂ groups is optionally replaced by RC=CR, C≡C, Si(R)₂, Ge(R)₂, Sn(R)₂, C=O, C=S, C=Se, P(=O)(R), SO, SO₂, O, S, or CONR and wherein one or more H atoms is optionally replaced by D, F, Cl, Br, I, CN, or NO₂;
an aromatic or heteroaromatic ring system having 5 to 60 aromatic ring atoms, which in each case is optionally substituted by one or more radicals R, or an aryl-oxy group having 5 to 40 aromatic ring atoms, which is optionally substituted by one or more radicals R; or
a group ArL, wherein ArL is a group of formula (ArL-1):

(ArL-1)

wherein the dashed bond in formula (ArL-1) indicates the bonding to the structure of formula (1), which is optionally substituted by one or more radicals R; and
wherein two adjacent substituents $R^0$, two adjacent substituents $R^1$ and $R^2$, two adjacent substituents $R^3$, and/or two adjacent substituents $R^4$ optionally define a mono- or polycyclic, aliphatic ring system or aromatic ring system, which is optionally substituted by one or more radicals R;
$Ar^2$ and $Ar^3$
are on each occurrence, identically or differently, an aromatic or heteroaromatic ring system having 5 to 60 aromatic ring atoms, which in each case is optionally substituted by one or more radicals R;
m is an integer selected from 1 to 10;
R is on each occurrence, identically or differently, H, D, F, Cl, Br, I, CHO, CN, N(Ar)$_2$, C(=O)Ar, P(=O)(Ar)$_2$, S(=O)Ar, S(=O)$_2$Ar, NO$_2$, Si(R')$_3$, B(OR')$_2$, OSO$_2$R, a straight-chain alkyl, alkoxy, or thioalkyl group having 1 to 40 C atoms or a branched or cyclic alkyl, alkoxy, or thioalkyl group having 3 to 40 C atoms, each of which is optionally substituted by one or more radicals R', wherein in each case one or more non-adjacent CH$_2$ groups are optionally replaced by R'C=CR', C≡C, Si(R')$_2$, Ge(R')$_2$, Sn(R')$_2$, C=O, C=S, C=Se, P(=O)(R'), SO, SO$_2$, O, S, or CONR' and wherein one or more H atoms is optionally replaced by D, F, Cl, Br, I, CN, or NO$_2$, an aromatic or heteroaromatic ring system having 5 to 60 aromatic ring atoms, which in each case is optionally substituted by one or more radicals R', or an aryloxy group having 5 to 60 aromatic ring atoms, which is optionally substituted by one or more radicals R', wherein two adjacent substituents R optionally define a mono- or polycyclic, aliphatic ring system or aromatic ring system, which is optionally substituted by one or more radicals R';
Ar is an aromatic or heteroaromatic ring system having 5 to 24 aromatic ring atoms, which in each case is optionally substituted by one or more radicals R';
R' is on each occurrence, identically or differently, H, D, F, Cl, Br, I, CN, a straight-chain alkyl, alkoxy, or thioalkyl group having 1 to 20 C atoms or a branched or cyclic alkyl, alkoxy, or thioalkyl group having 3 to 20 C atoms, wherein in each case one or more non-adjacent CH$_2$ groups are optionally replaced by SO, SO$_2$, O, or S and wherein one or more H atoms are optionally replaced by D, F, Cl, Br, or I, or an aromatic or heteroaromatic ring system having 5 to 24 C atoms;
with the proviso that, when the ring A is a benzene ring, then the group $R^1$ or the group $R^2$ is selected from an aromatic or heteroaromatic ring systems having 5 to 60 aromatic ring atoms, which optionally in each case be substituted by one or more radicals R.

2. The compound of claim 1, wherein the ring A is selected from the group consisting of phenyl, naphthyl, anthracene, phenanthrene, fluorene, dibenzothiophene, dibenzofurane, or carbazole, which in each case is optionally substituted by one or more radicals $R^3$.

3. The compound of claim 1, wherein $Ar^1$ is:
phenyl, biphenyl, fluorene, spirobifluorene, naphthalene, phenanthrene, dibenzofuran, dibenzothiophene, carbazole, pyridine, pyrimidine, pyrazine, pyridazine, triazine, benzopyridine, benzopyridazine, benzopyrimidine or quinazoline, or a combination of two or three of these groups, each of which is optionally substituted by one or more radicals $R^4$;
a group of formula (Ar 1-1)

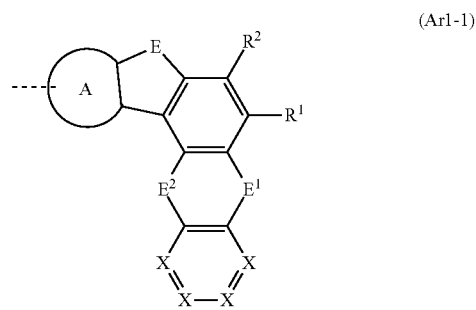
(Ar1-1)

wherein the dashed bond indicates the bonding to the nitrogen atom; or
a group ArL.

4. The compound of claim 1, wherein the compound is selected from the group consisting of compounds of formulae (2) through (41):

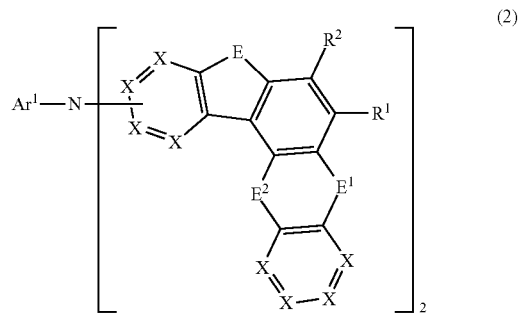
(2)

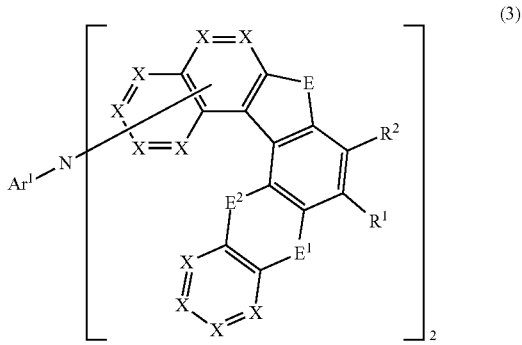
(3)

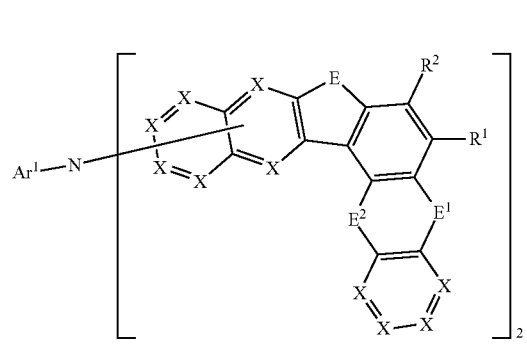
(4)
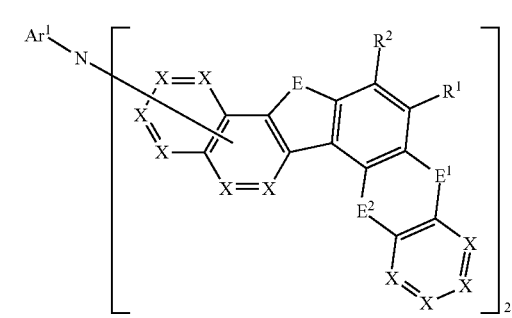
(5)
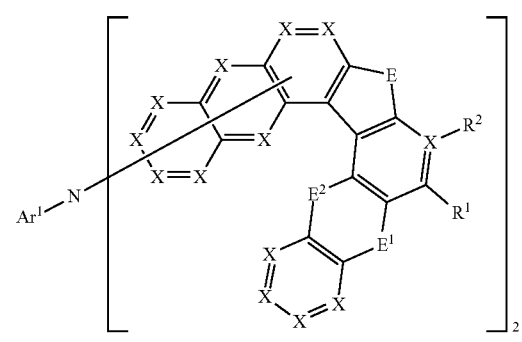
(6)
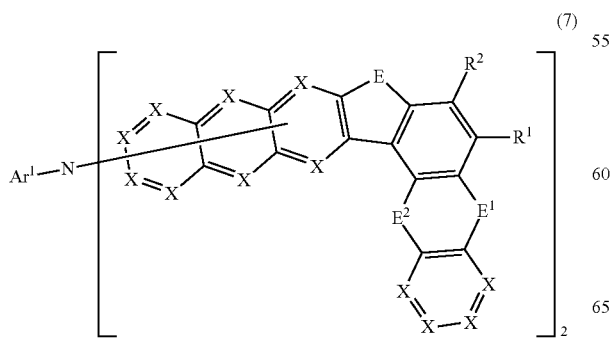
(7)
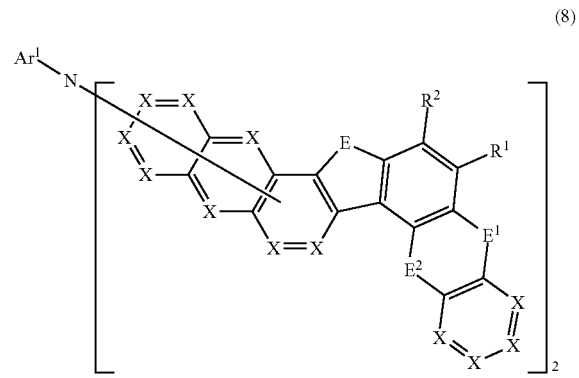
(8)
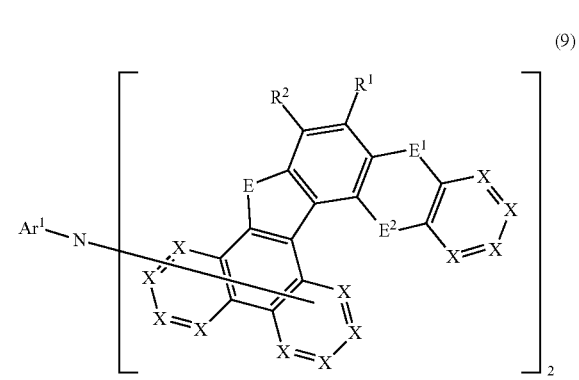
(9)
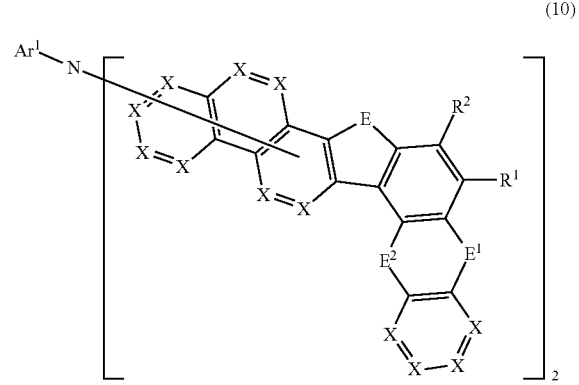
(10)
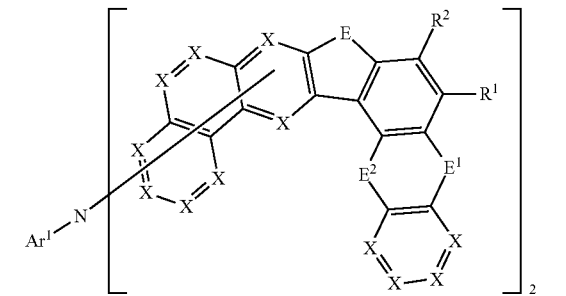
(11)

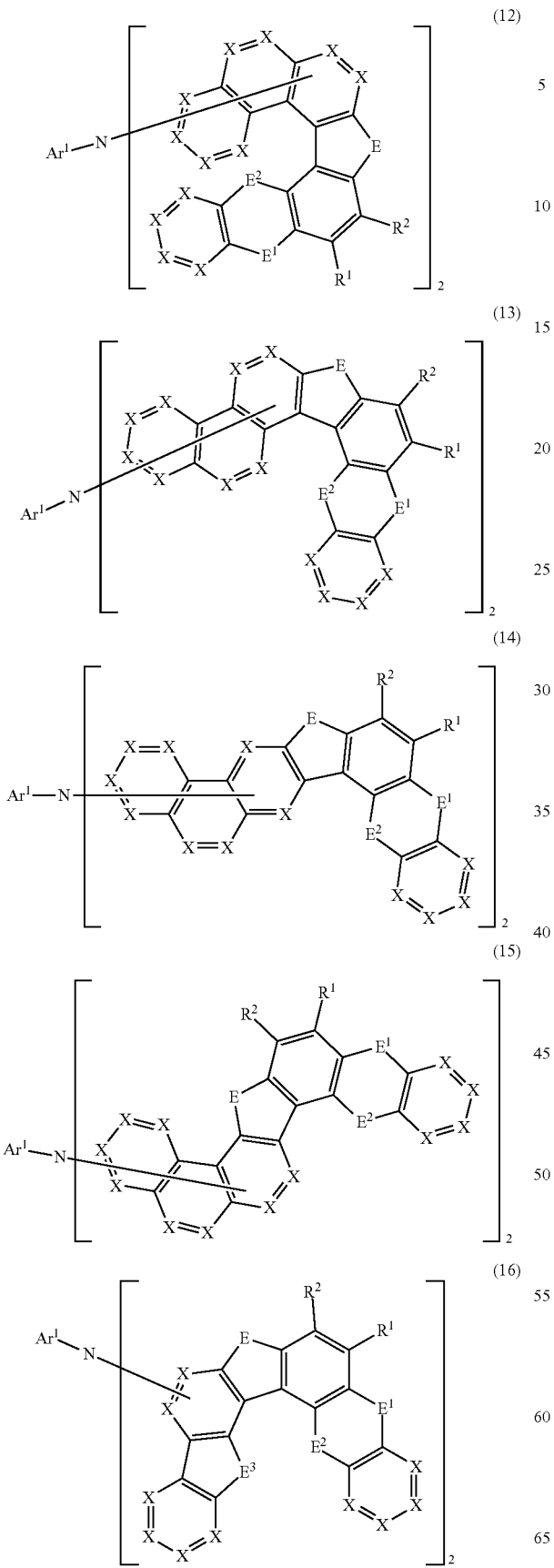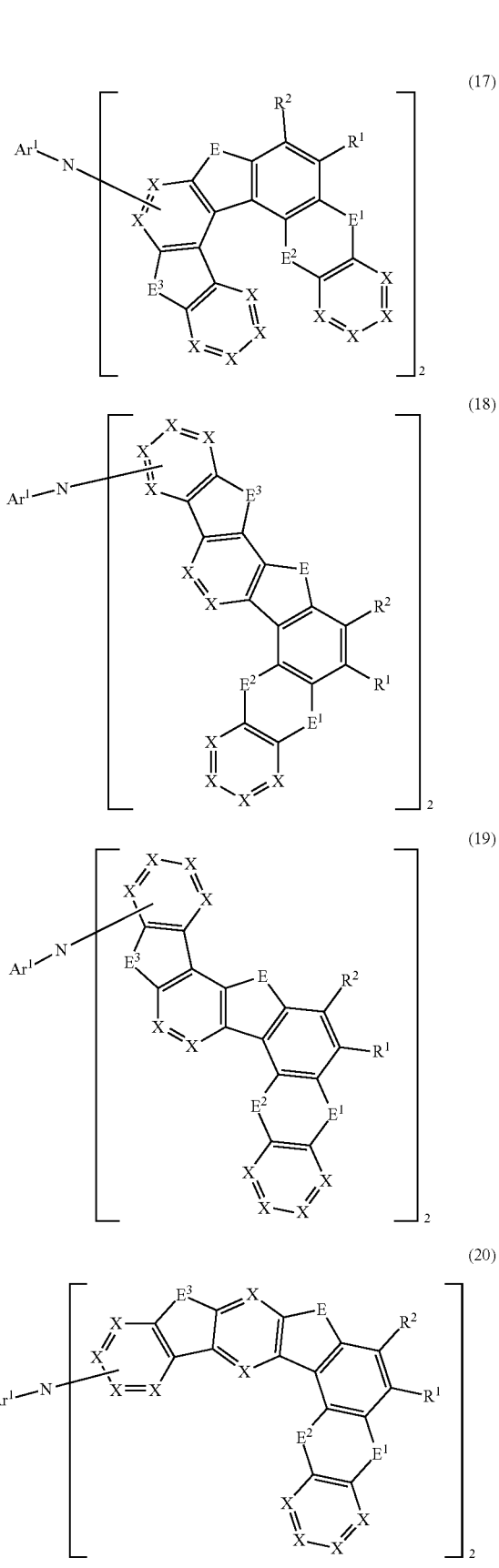

(21) 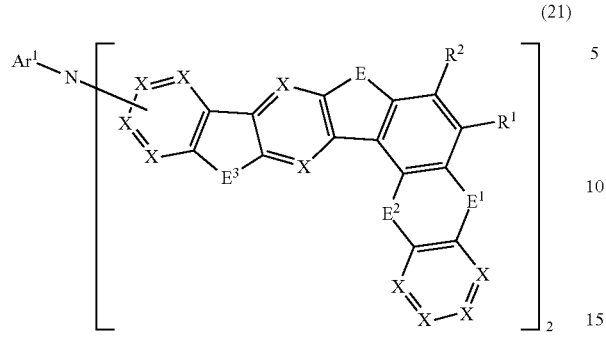
(22) 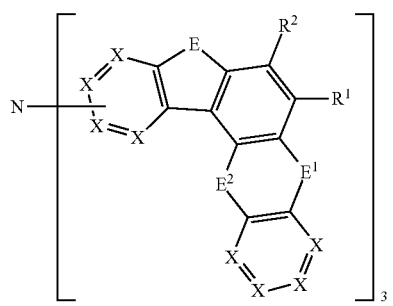
(23) 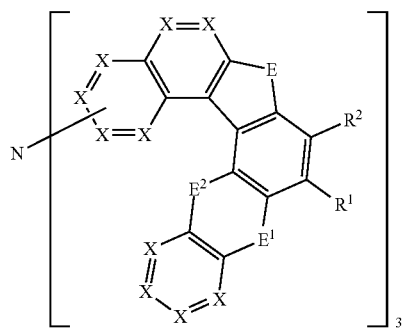
(24) 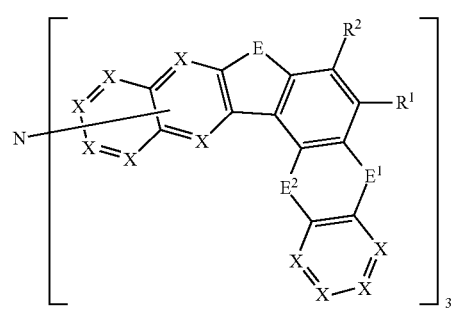
(25) 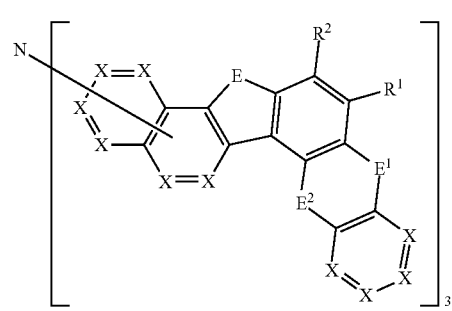
(26) 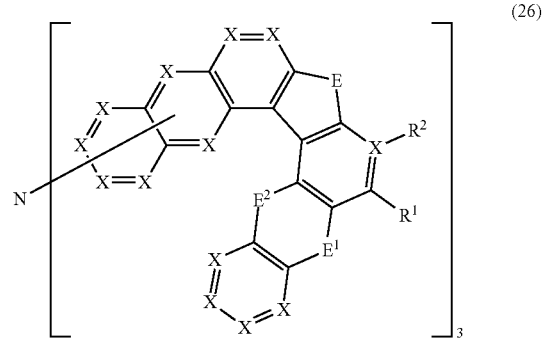
(27) 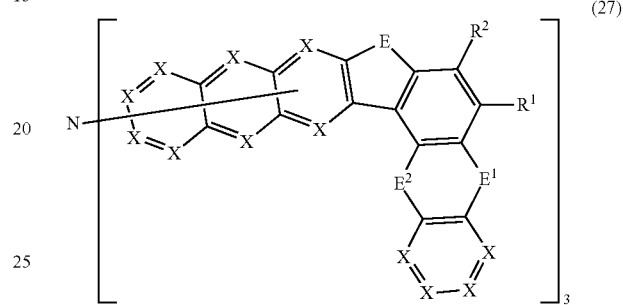
(28) 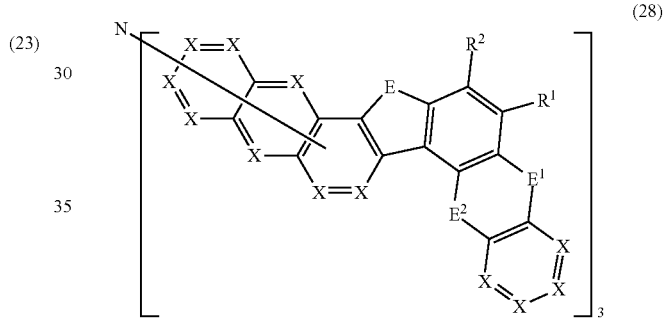
(29) 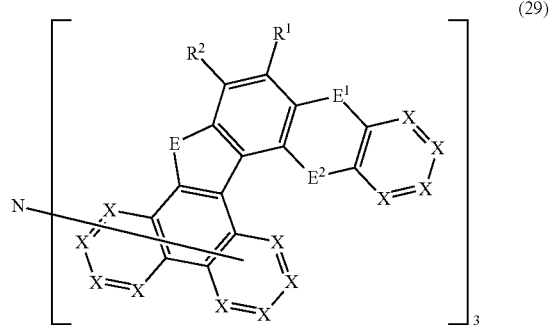
(30) 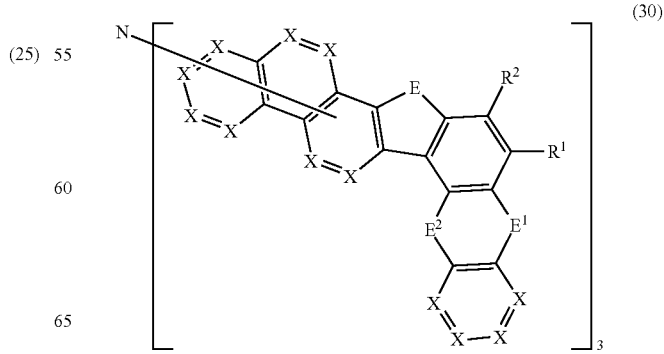

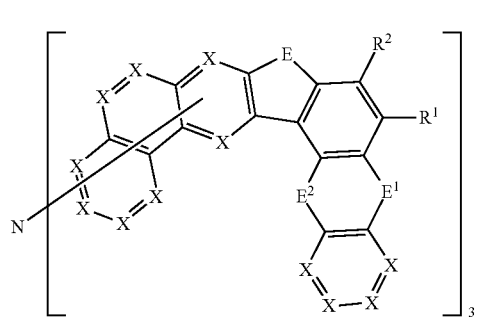 (31)
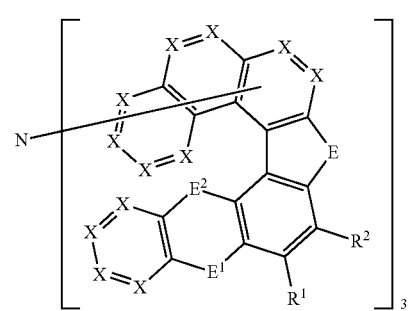 (32)
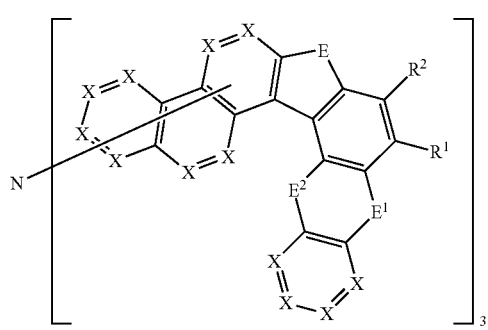 (33)
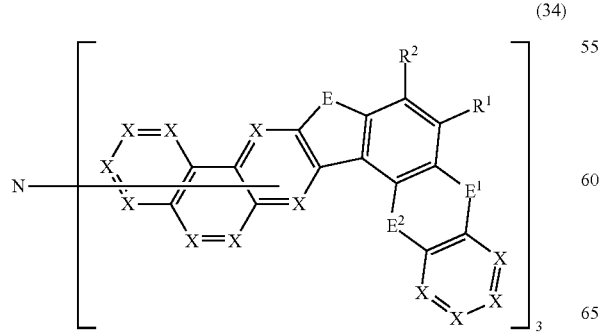 (34)
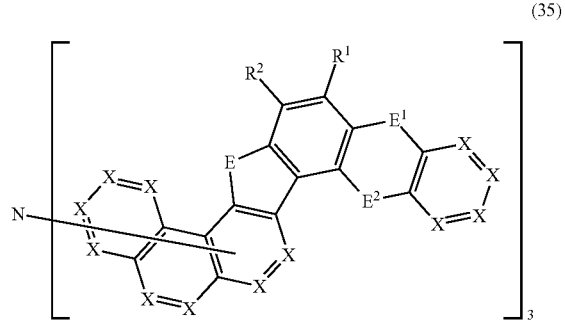 (35)
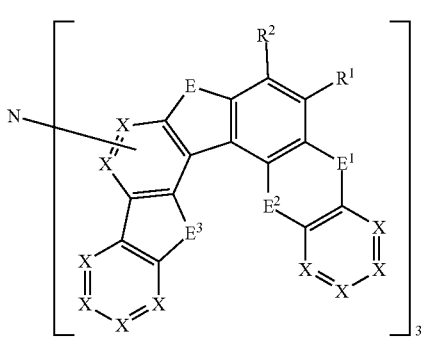 (36)
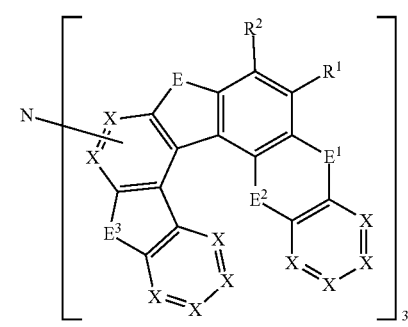 (37)
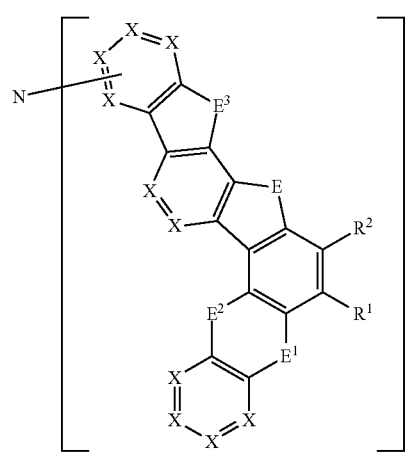 (38)

-continued
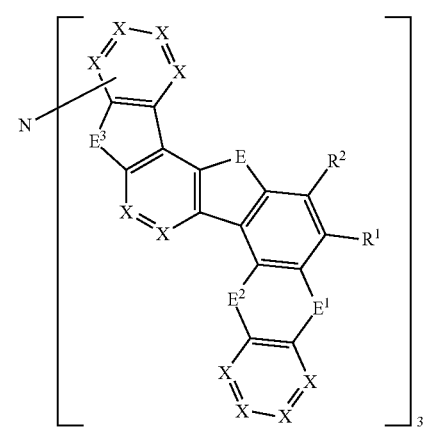
(39)
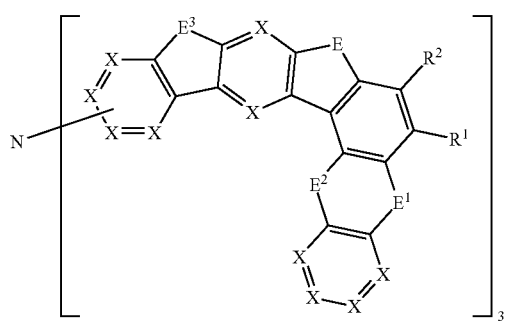
(40)
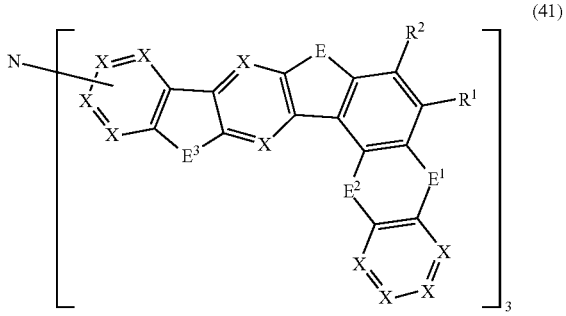
(41)
wherein
X is CR² or N; or X is C if a group —NAr¹ is bonded to X; and
E³ is on each occurrence, identically or differently, selected from the group consisting of —C(R⁰)₂—, —O—, —S—, and —N(R⁰)—.
5. The compound of claim 1, wherein the compound is selected from the group consisting of compounds of formulae (2-1) through (41-1):
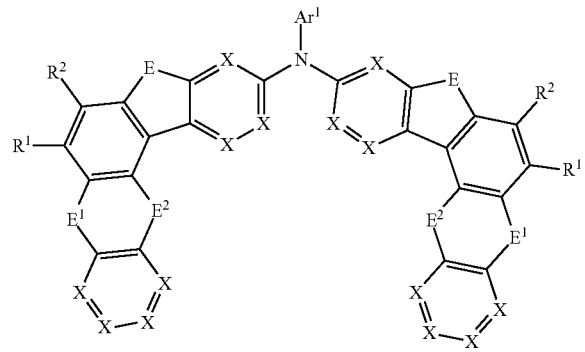
(2-1)
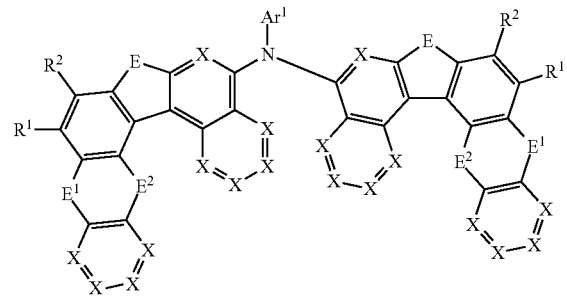
(3-1)
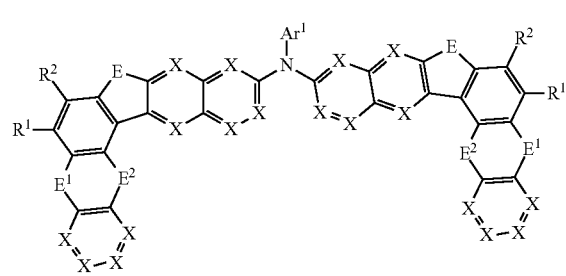
(4-1)
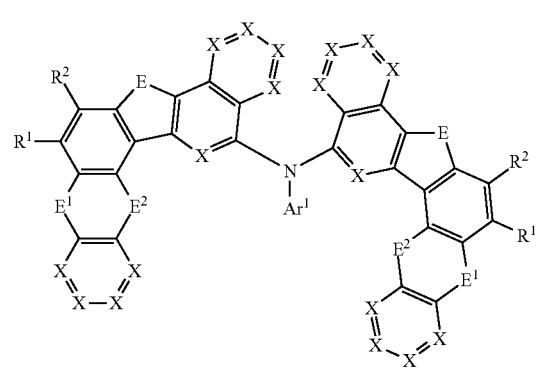
(5-1)

-continued
(6-1)
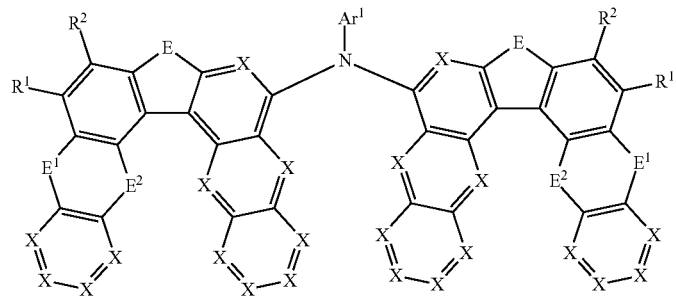
(7-1)
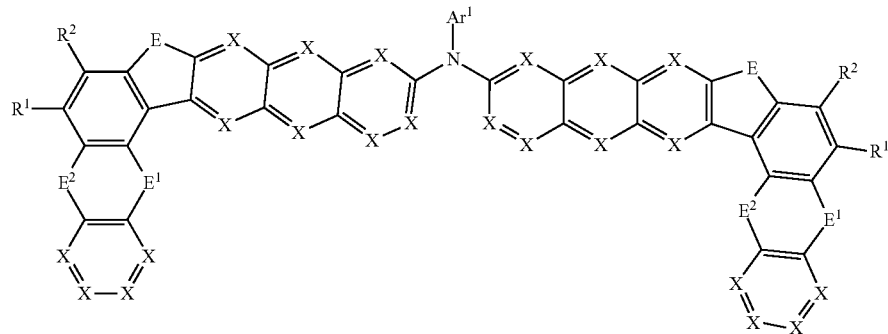
(8-1)
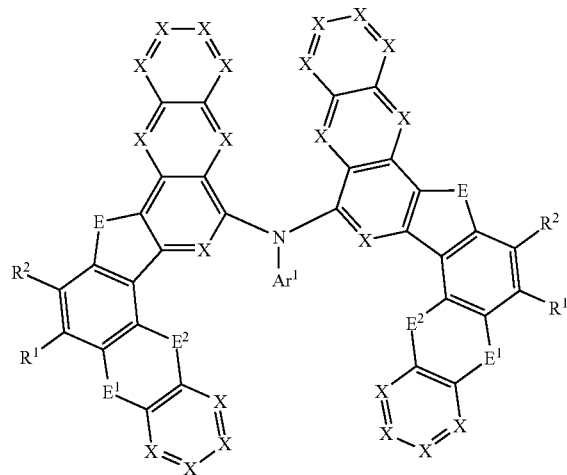
(9-1)
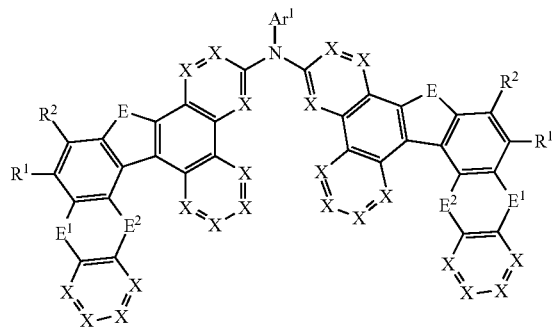
(10-1)
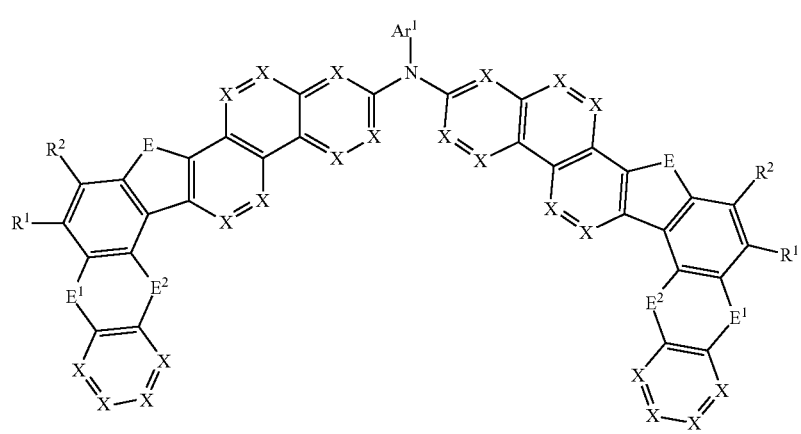

-continued
(11-1)
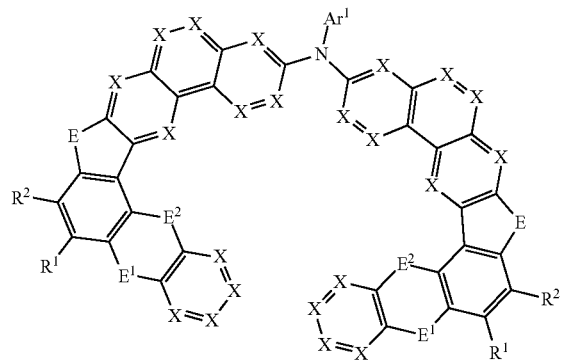
(12-1)
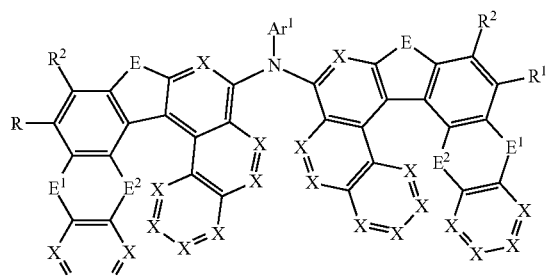
(13-1)
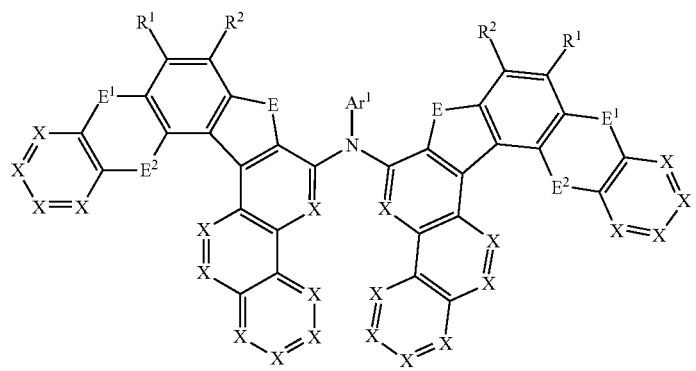
(14-1)
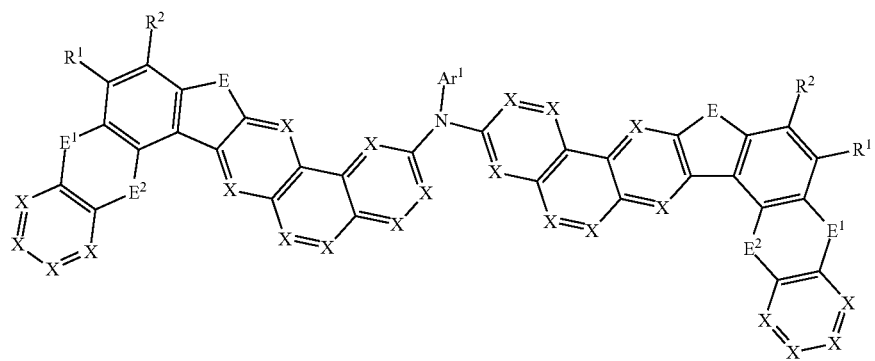
(15-1)
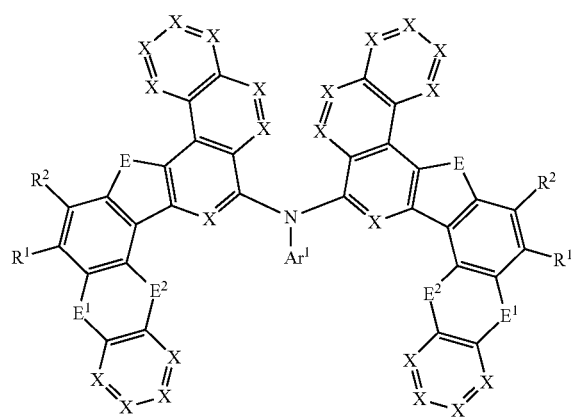
(16-1)
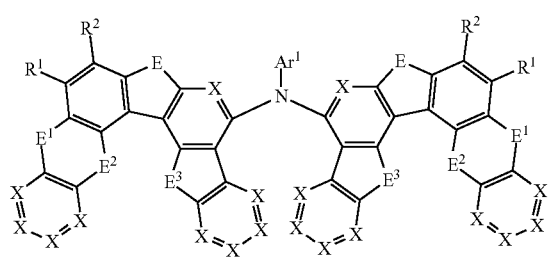

-continued
(17-1)
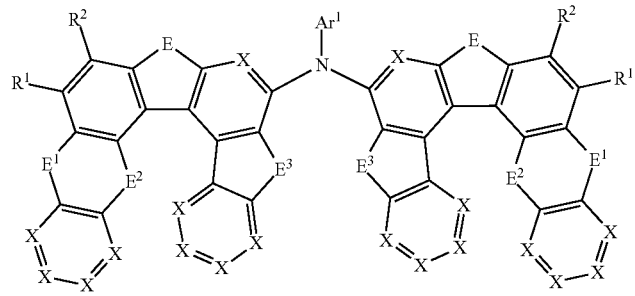
(18-1)
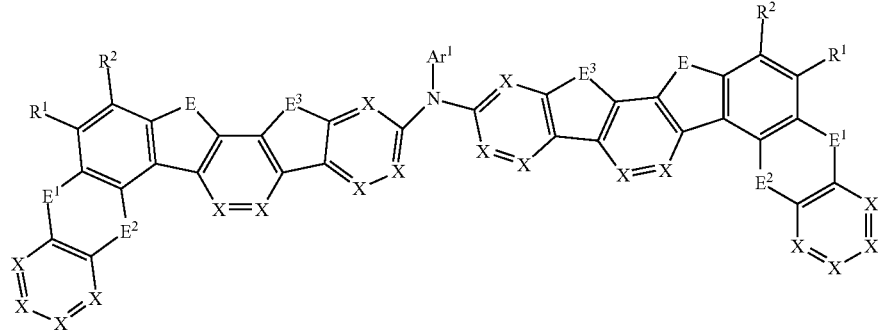
(19-1)
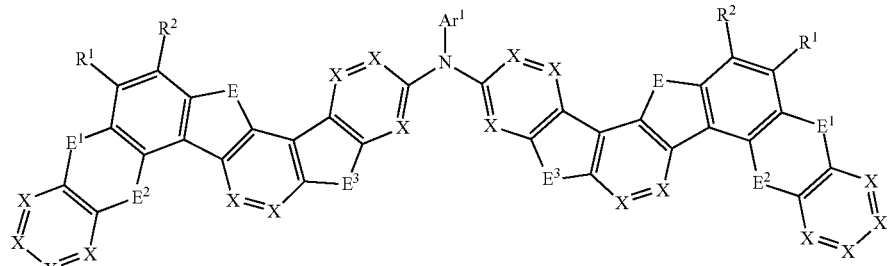
(20-1)
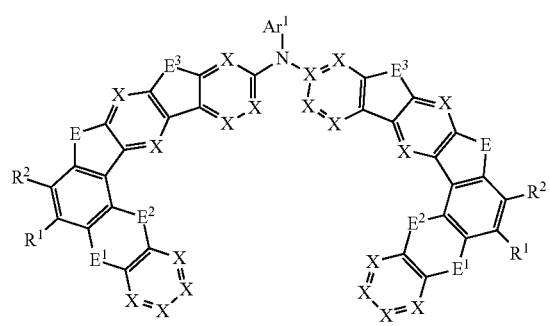
(21-1)
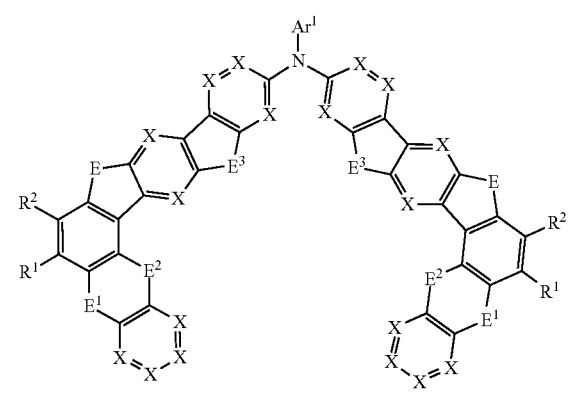
(22-1)
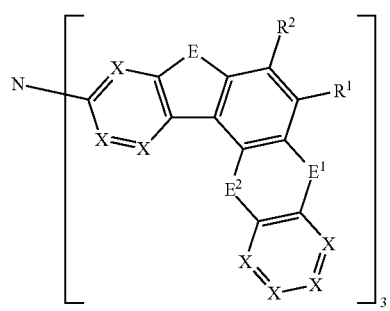
(23-1)
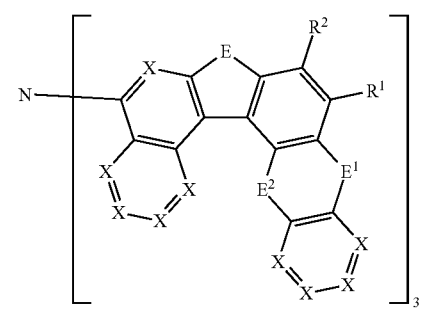

-continued
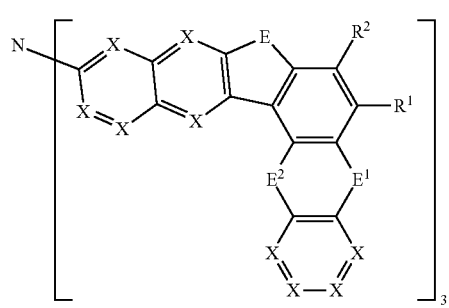
(24-1)
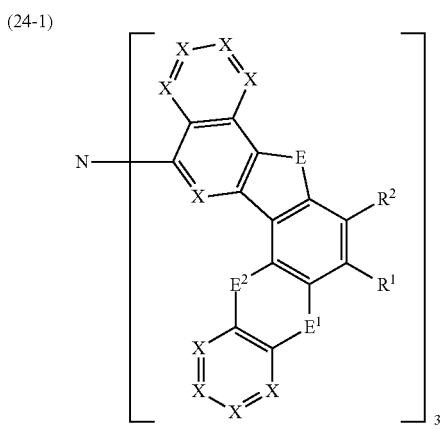
(25-1)
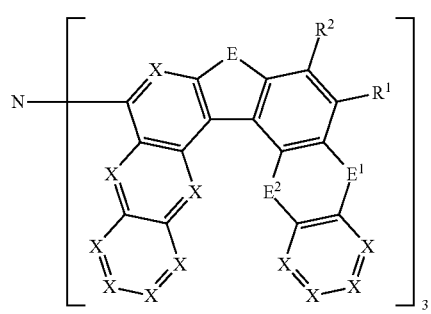
(26-1)
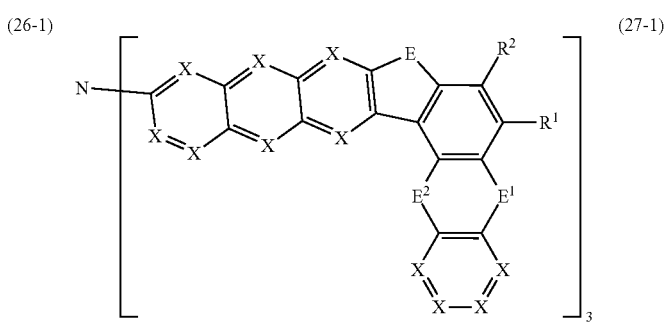
(27-1)
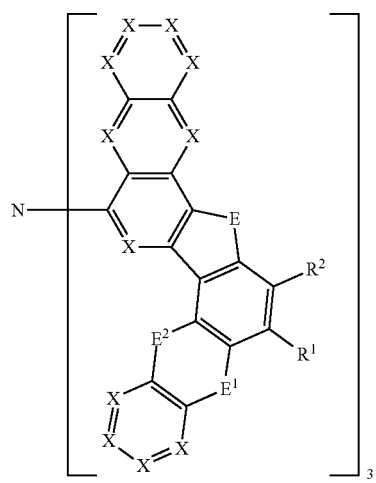
(28-1)
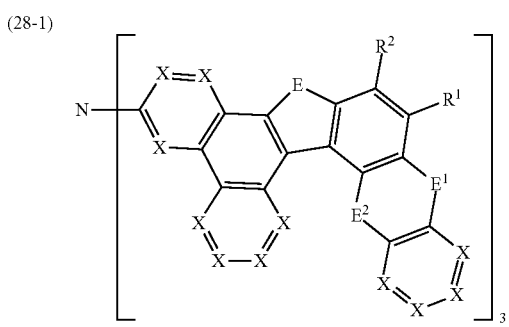
(29-1)
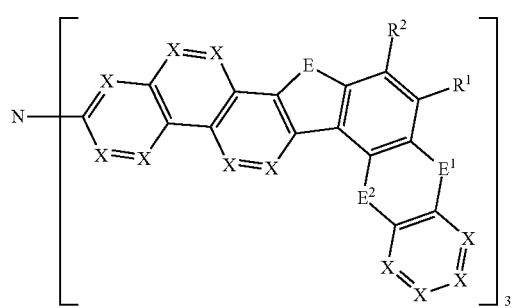
(30-1)
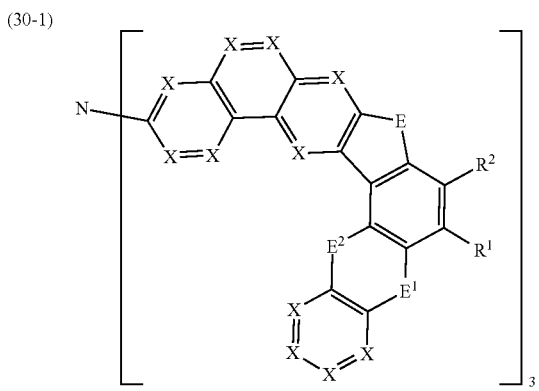
(31-1)

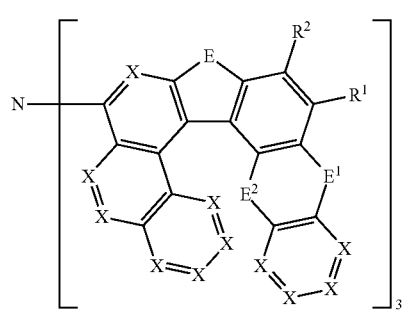
(32-1)
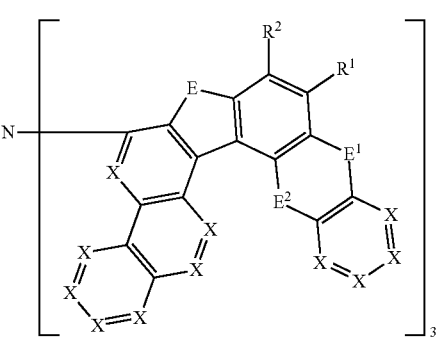
(33-1)
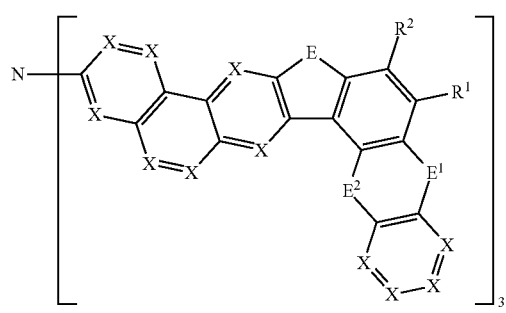
(34-1)
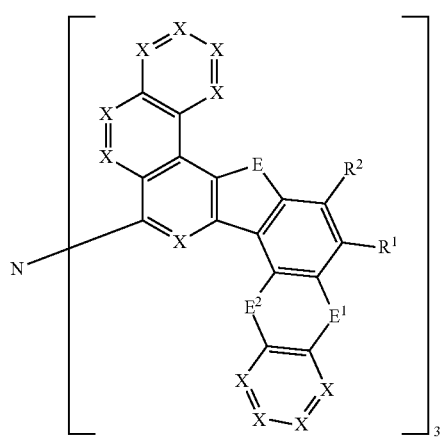
(35-1)
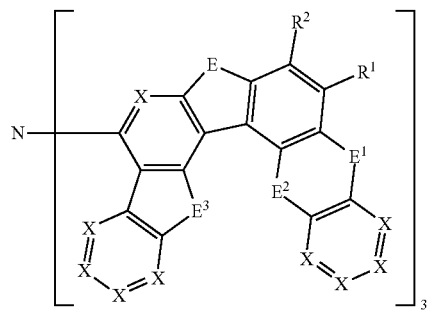
(36-1)
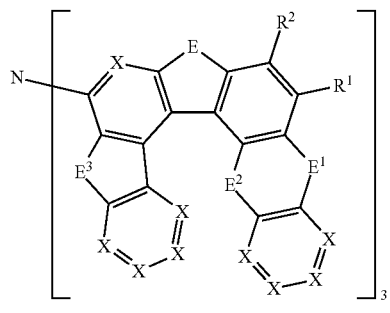
(37-1)
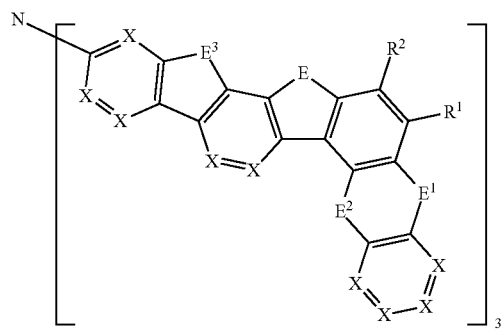
(38-1)
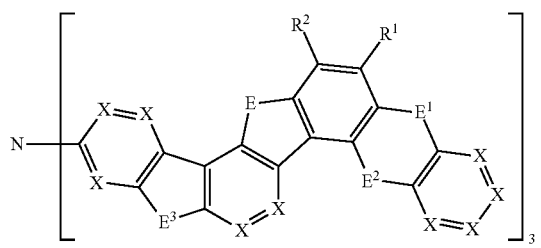
(39-1)

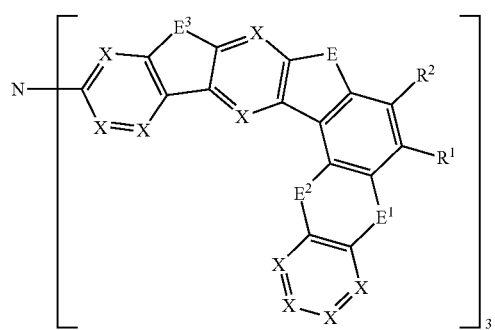

(40-1)

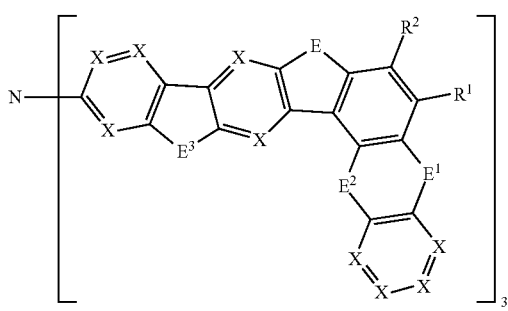

(41-1)

wherein
E³ is on each occurrence, identically or differently, selected from the group consisting of —C(R⁰)₂—, —O—, —S—, and —N(R⁰)—.

6. The compound of claim 1, wherein E¹ and E² are, identically or differently, on each occurrence, selected from the group consisting of a single bond, —O—, and —S—, with the proviso that, in a ring comprising the groups E¹ and E², one of the group E¹ and E² is a single bond, and the other group is O or S.

7. The compound of claim 1, wherein in a ring comprising the groups E¹ and E², E¹ is O and E² is a single bond or E¹ is a single bond and E² is O.

8. The compound of claim 1, wherein E is —C(R⁰)₂—.

9. The compound of claim 1, wherein Ar³ is on each occurrence, identically or differently, selected from the group consisting of groups of formulae (Ar³-1) through (Ar³-27):

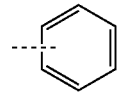
(Ar3-1)

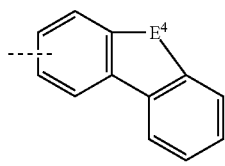
(Ar3-2)

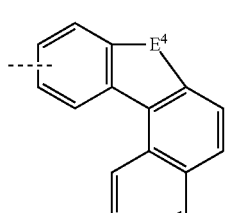
(Ar3-3)

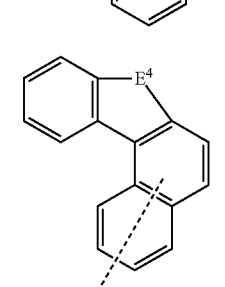
(Ar3-4)

-continued

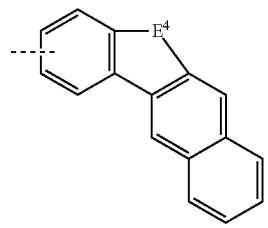
(Ar3-5)

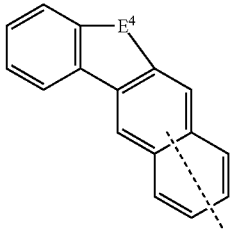
(Ar3-6)

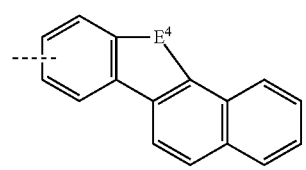
(Ar3-7)

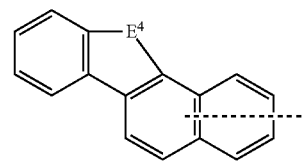
(Ar3-8)

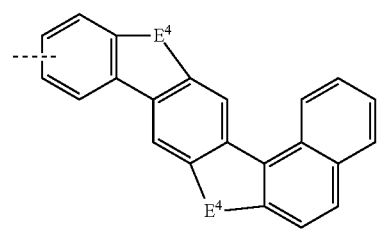
(Ar3-9)

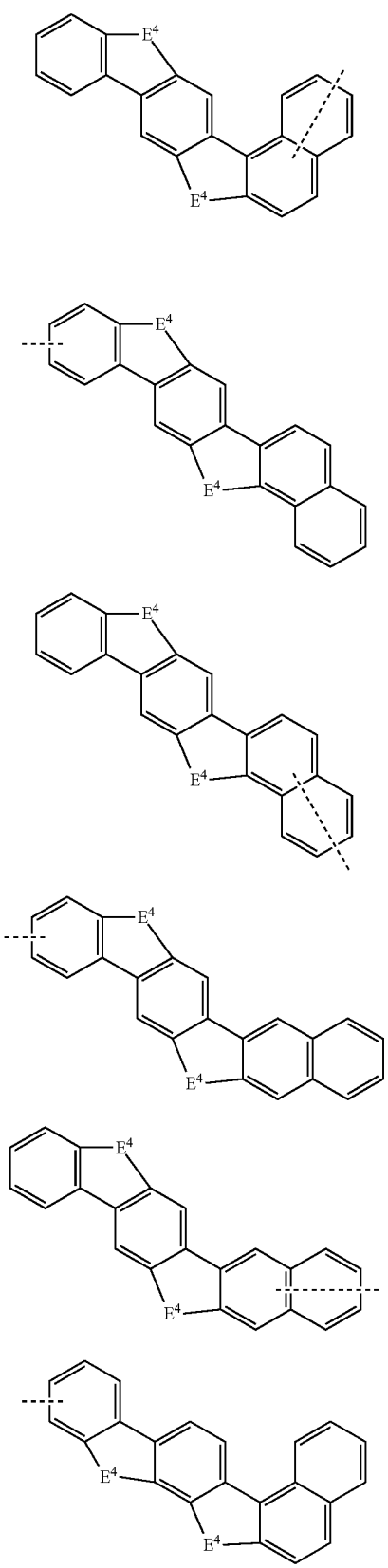
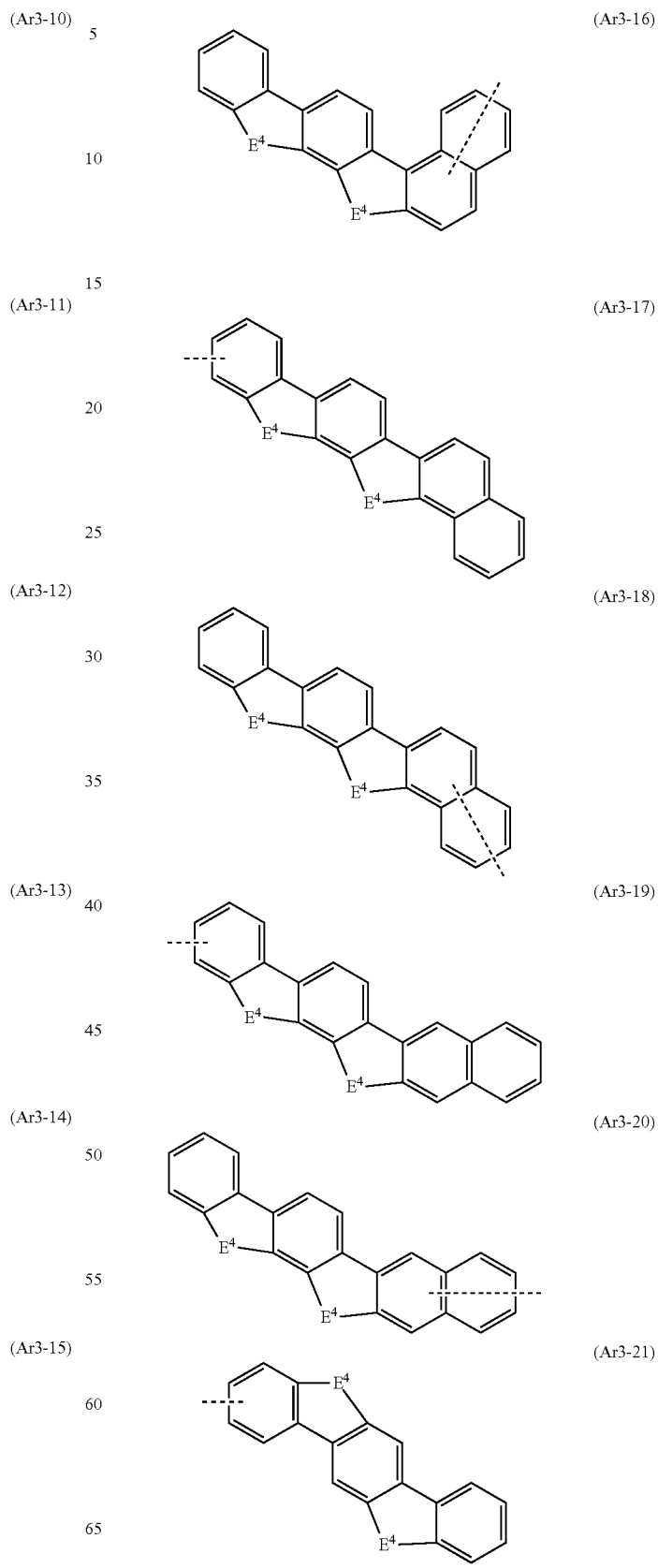

-continued (Ar3-22)
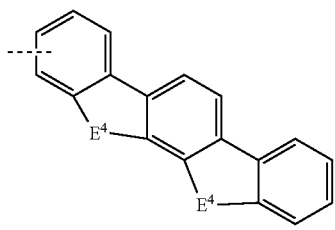

(Ar3-23)
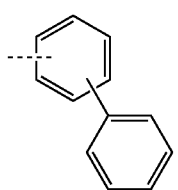

(Ar3-24)
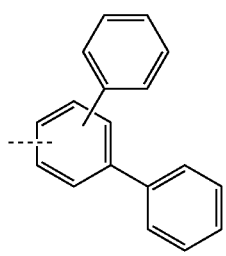

(Ar3-25)
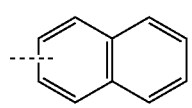

(Ar3-26)
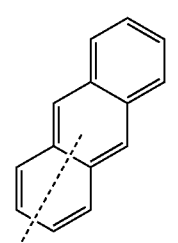

(Ar3-27)
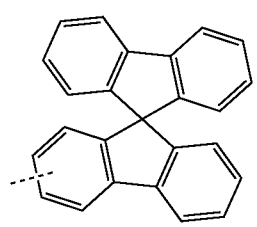

wherein
the dashed bond indicates the bonding to $Ar^2$;
$E^4$ is selected from the group consisting of —B(R$^0$)—, —C(R$^0$)$_2$—, —C(R$^0$)$_2$—C(R$^0$)$_2$—, —Si(R$^0$)$_2$—, —C(=O)—, —C(=NR$^0$)—, —C=(C(R$^0$))$_2$—, —O—, —S—, —S(=O)—, —SO$_2$—, —N(R$^0$)—, —P(R$^0$)—, and —P((=O)R$^0$)—; and
the groups of formulae (Ar$^3$-1) through (Ar$^3$-27) are optionally substituted at each free position by a group R.

10. A formulation comprising at least one compound of claim 1 and at least one solvent.

11. An electronic device comprising at least one compound of claim 1, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

12. The electronic device of claim 11, wherein the electronic device is an organic electroluminescent device and wherein the at least one compound is employed as a fluorescent emitter or as a matrix material for fluorescent emitters.

13. A compound of formula (1):

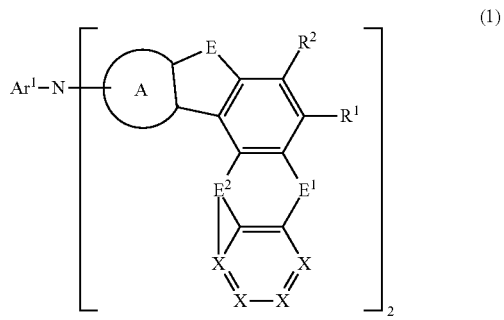

(1)

wherein
A is on each occurrence, identically or differently, an aromatic or heteroaromatic ring system having 5 to 60 aromatic ring atoms, which in each case is optionally substituted by one or more radicals $R^3$; wherein the ring A is condensed on the five-membered ring comprising E via two adjacent carbon atoms;
$Ar^1$ is:
a group of formula (Ar1-1):

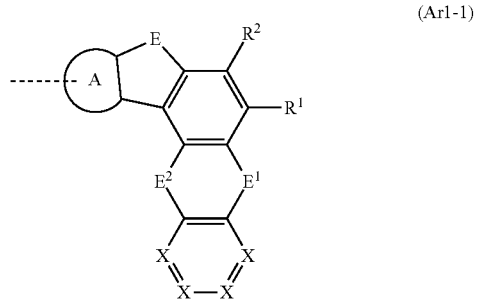

(Ar1-1)

wherein the dashed bond indicates the bonding to the nitrogen atom; or a group ArL, wherein ArL is a group of formula (ArL-1):

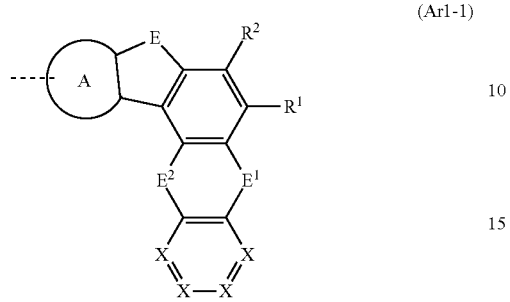

(ArL-1)

wherein the dashed bond in formula (ArL-1) indicates the bonding to the structure of formula (1), X is on each occurrence, identically or differently, $CR^3$ or N;

E is on each occurrence, identically or differently, selected from the group consisting of $—BR^0—$, $—C(R^0)_2—$, $—C(R^0)_2—C(R^0)_2—$, $—C(R^0)_2—O—$, $—C(R^0)_2—S—$, $—R^0C=CR^0—$, $—R^0C=N—$, $—Si(R^0)_2—$, $—Si(R^0)_2—Si(R^0)_2—$, $—C(=O)—$, $—C(=NR^0)—$, $—C(=C(R^0)_2)—$, $—O—$, $—S—$, $—S(=O)—$, $—SO_2—$, $—N(R^0)—$, $—P(R^0)—$, and $—P((=O)R^0)—$; or E is a group of formula (E-1):

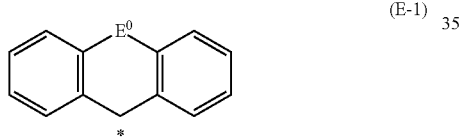

(E-1)

wherein the symbol * in formula (E-1) indicates the corresponding group E in formula (1);

$E^1$ and $E^2$ are identically or differently on each occurrence, selected from the group consisting of a single bond, $—C(R^0)_2—$, $—Si(R^0)_2—$, $—O—$, and $—S—$; with the proviso that, in a ring comprising the groups $E^1$ and $E^2$, one of the groups $E^1$ and $E^2$, is a single bond, $—C(R^0)_2—$, or $—Si(R^0)_2—$, and the other group is O or S;

$E^0$ is identically or differently on each occurrence, selected from the group consisting of a single bond, $—BR^0—$, $—C(R^0)_2—$, $—C(R^0)_2—C(R^0)_2—$, $—C(R^0)_2—O—$, $—C(R^0)_2—S—$, $—R^0C=CR^0—$, $—R^0C=N—$, $—Si(R^0)_2—$, $—Si(R^0)_2—Si(R^0)_2—$, $—C(=O)—$, $—C(=NR^0)—$, $—C(=C(R^0)_2)—$, $—O—$, $—S—$, $—S(=O)—$, $—SO_2—$, $—N(R^0)—$, $—P(R^0)—$, and $—P((=O)R^0)—$;

$R^0$, $R^1$, $R^2$, $R^3$, and $R^4$ are, identically or differently, on each occurrence:

H, deuterium (D), F, Cl, Br, I, CHO, CN, $N(Ar)_2$, $C(=O)Ar$, $P(=O)(Ar)_2$, $S(=O)Ar$, $S(=O)_2Ar$, $NO_2$, $Si(R)_3$, $B(OR)_2$, $OSO_2R$;

a straight-chain alkyl, alkoxy, or thioalkyl group having 1 to 40 C atoms or a branched or a cyclic alkyl, alkoxy, or thioalkyl group having 3 to 40 C atoms, each of which is optionally substituted by one or more radicals R, wherein in each case one or more non-adjacent $CH_2$ groups is optionally replaced by $RC=CR$, $C≡C$, $Si(R)_2$, $Ge(R)_2$, $Sn(R)_2$, $C=O$, $C=S$, $C=Se$, $P(=O)(R)$, SO, $SO_2$, O, S, or CONR and wherein one or more H atoms is optionally replaced by D, F, Cl, Br, I, CN, or $NO_2$;

an aromatic or heteroaromatic ring system having 5 to 60 aromatic ring atoms, which in each case is optionally substituted by one or more radicals R, or an aryl-oxy group having 5 to 40 aromatic ring atoms, which is optionally substituted by one or more radicals R; or a group ArL, which is optionally substituted by one or more radicals R; and wherein two adjacent substituents $R^0$, two adjacent substituents $R^1$ and $R^2$, two adjacent substituents $R^3$, and/or two adjacent substituents $R^4$ optionally define a mono- or polycyclic, aliphatic ring system or aromatic ring system, which is optionally substituted by one or more radicals R;

$Ar^2$ and $Ar^3$ are on each occurrence, identically or differently, an aromatic or heteroaromatic ring system having 5 to 60 aromatic ring atoms, which in each case is optionally substituted by one or more radicals R;

m is an integer selected from 1 to 10;

R is on each occurrence, identically or differently, H, D, F, Cl, Br, I, CHO, CN, $N(Ar)_2$, $C(=O)Ar$, $P(=O)(Ar)_2$, $S(=O)Ar$, $S(=O)_2Ar$, $NO_2$, $Si(R')_3$, $B(OR')_2$, $OSO_2R$, a straight-chain alkyl, alkoxy, or thioalkyl group having 1 to 40 C atoms or a branched or cyclic alkyl, alkoxy, or thioalkyl group having 3 to 40 C atoms, each of which is optionally substituted by one or more radicals R', wherein in each case one or more non-adjacent $CH_2$ groups are optionally replaced by $R'C=CR'$, $C≡C$, $Si(R')_2$, $Ge(R')_2$, $Sn(R')_2$, $C=O$, $C=S$, $C=Se$, $P(=O)(R')$, SO, $SO_2$, O, S, or CONR' and wherein one or more H atoms is optionally replaced by D, F, Cl, Br, I, CN, or $NO_2$, an aromatic or heteroaromatic ring system having 5 to 60 aromatic ring atoms, which in each case is optionally substituted by one or more radicals R', or an aryloxy group having 5 to 60 aromatic ring atoms, which is optionally substituted by one or more radicals R', wherein two adjacent substituents R optionally define a mono- or polycyclic, aliphatic ring system or aromatic ring system, which is optionally substituted by one or more radicals R';

Ar is an aromatic or heteroaromatic ring system having 5 to 24 aromatic ring atoms, which in each case is optionally substituted by one or more radicals R';

R' is on each occurrence, identically or differently, H, D, F, Cl, Br, I, CN, a straight-chain alkyl, alkoxy, or thioalkyl group having 1 to 20 C atoms or a branched or cyclic alkyl, alkoxy, or thioalkyl group having 3 to 20 C atoms, wherein in each case one or more non-adjacent $CH_2$ groups are optionally replaced by SO, $SO_2$, O, or S and wherein one or more H atoms are optionally replaced by D, F, Cl, Br, or I, or an aromatic or heteroaromatic ring system having 5 to 24 C atoms;

with the proviso that, when the ring A is a benzene ring, then the group $R^1$ or the group $R^2$ is selected from an aromatic or heteroaromatic ring systems having 5 to 60 aromatic ring atoms, which optionally in each case be substituted by one or more radicals R.

14. The compound of claim 13, wherein at least one of groups $R^1$ and $R^2$ present in the same ring corresponds to a group ArL.
15. The compound of claim 13, wherein the group $Ar^2$ in the group of formula (ArL-1) is selected from the group consisting of formulae (Ar2-1) through (Ar2-25):
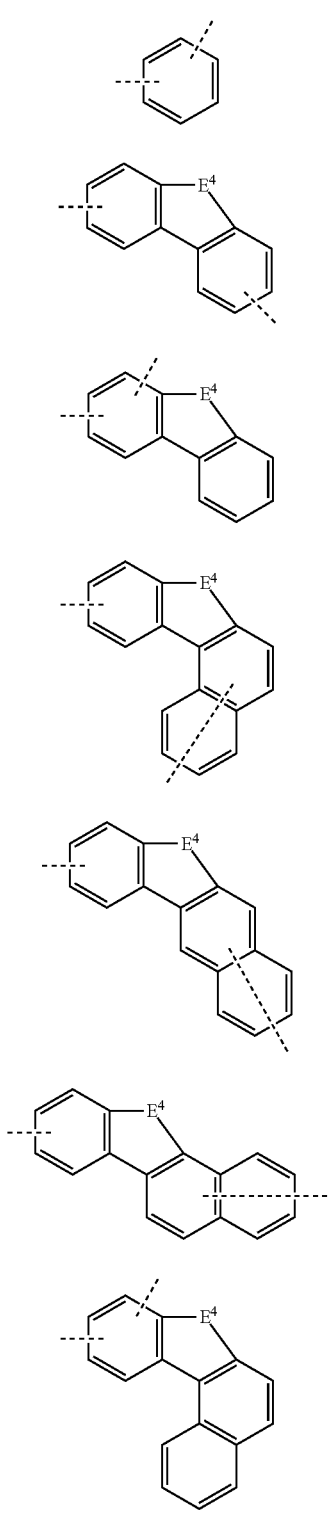
(Ar2-1)
(Ar2-2)
(Ar2-3)
(Ar2-4)
(Ar2-5)
(Ar2-6)
(Ar2-7)
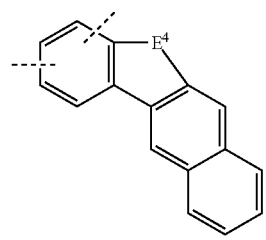
(Ar2-8)
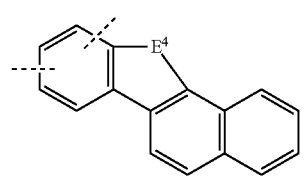
(Ar2-9)
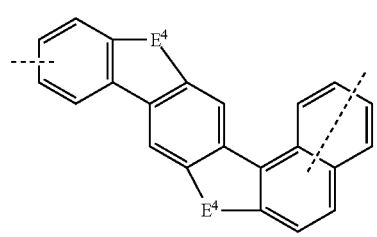
(Ar2-10)
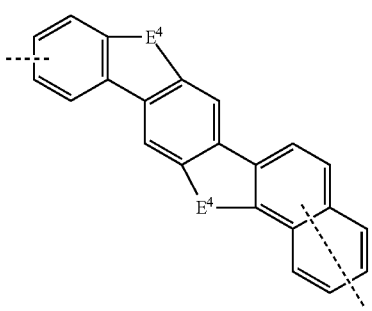
(Ar2-11)
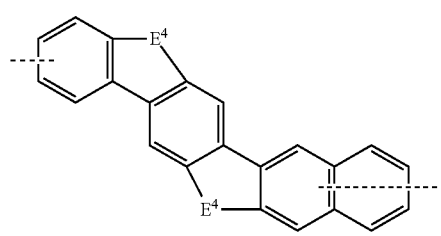
(Ar2-12)
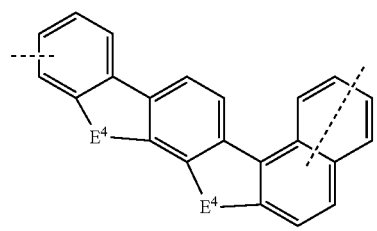
(Ar2-13)

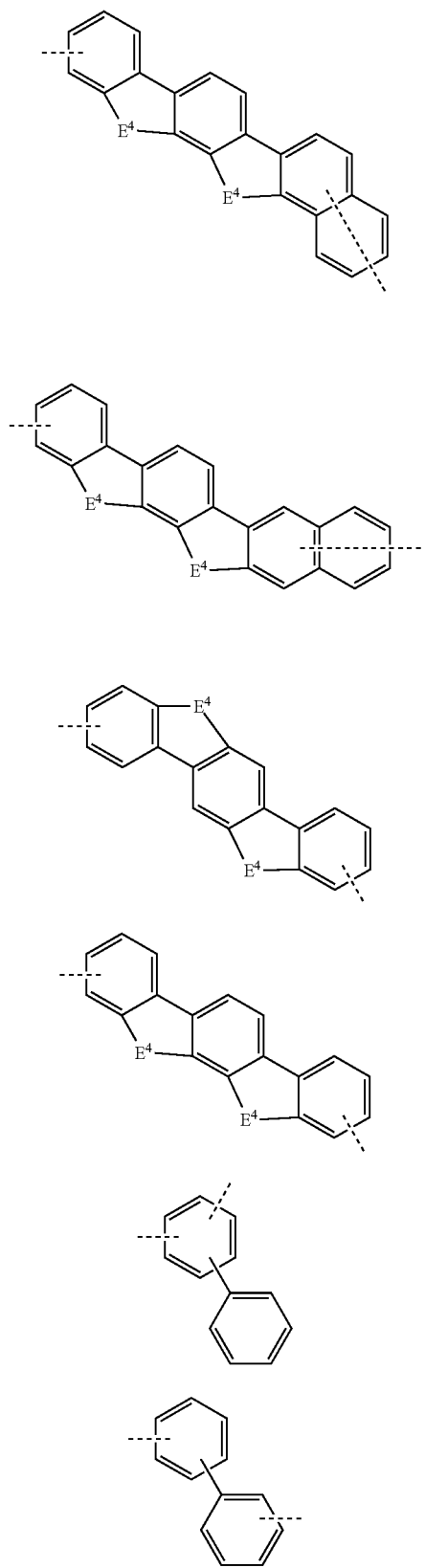
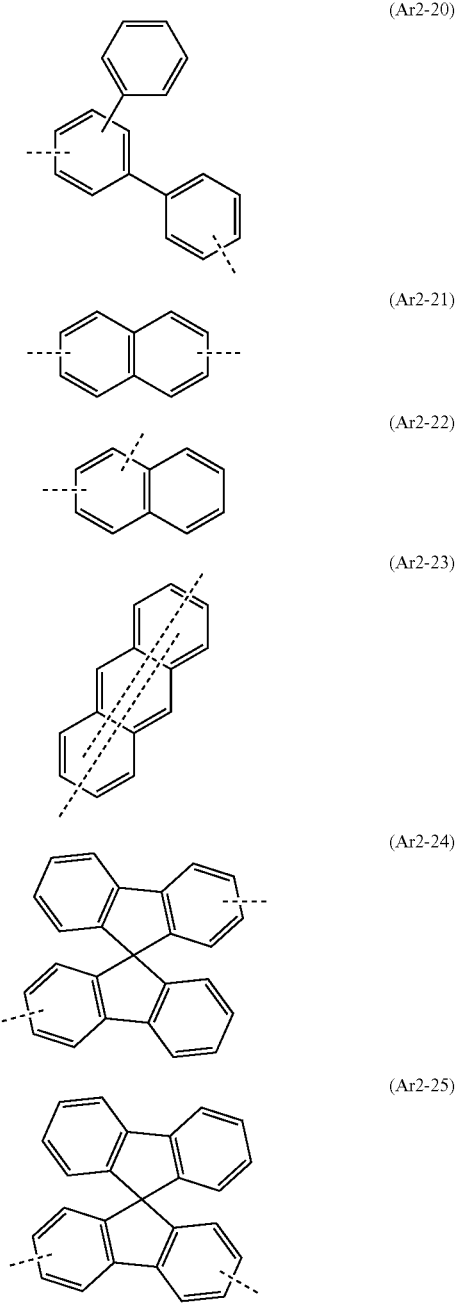

wherein the dashed bonds indicate the bonding to the structure of formula (1) and to a group Ar² or Ar³ and the groups of formulae (Ar2-1) through (Ar2-25) are optionally substituted at each free position by a group R; and $E^4$ is selected from the group consisting of —B(R°)—, —C(R°)$_2$—, —C(R°)$_2$—C(R°)$_2$—, —Si(R°)$_2$—, —C(=O)—, —C(=NR°)—, —C=(C(R°))$_2$—, —O—, —S—, —S(=O)—, —SO$_2$—, —N(R°)—, —P(R°)—, and —P((=O)R°)—.

16. The compound of claim 13, wherein, in formula (ArL-1), at least one group Ar² is a group of formula (Ar2-2) and/or at least one group Ar³ is a group of formula (Ar3-2):

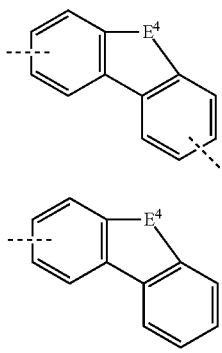

(Ar2-2)

(Ar3-2)

Wherein
the dashed bonds in formula (Ar2-2) indicate the bonding to the structure of formula (1) and to a group $Ar^2$ or $Ar^3$;
the dashed bond in formula (Ar3-2) indicates the bonding to $Ar^2$;
$E^4$ is selected from the group consisting of —B(R$^0$)—, —C(R$^0$)$_2$—, —C(R$^0$)$_2$—C(R$^0$)$_2$—, —Si(R$^0$)$_2$—, —C(=O)—, —C(=NR$^0$)—, —C=(C(R$^0$))$_2$—, —O—, —S—, —S(=O)—, —SO$_2$—, —N(R$^0$)—, —P(R$^0$)—, and —P((=O)R$^0$)—; and
the groups of formulae (Ar2-2) and (Ar3-2) are optionally substituted at each free position by a group R.

17. The compound of claim 13, wherein, in formula (ArL-1), at least one group $Ar^2$ is a group of formula (Ar2-2-1) and/or at least one group $Ar^3$ is a group of formula (Ar3-2-1):

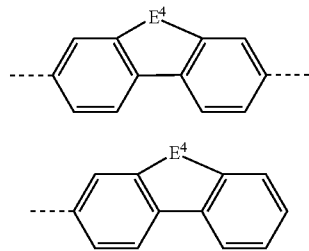

(Ar2-2-1)

(Ar3-2-1)

wherein
the dashed bonds in formula (Ar2-2-1) indicate the bonding to the structure of formula (1) and to a group $Ar^2$ or $Ar^3$;
the dashed bond in formula (Ar3-2-1) indicates the bonding to $Ar^2$;
$E^4$ is selected from the group consisting of —B(R$^0$)—, —C(R$^0$)$_2$—, —C(R$^0$)$_2$—C(R$^0$)$_2$—, —Si(R$^0$)$_2$—, —C(=O)—, —C(=NR$^0$)—, —C=(C(R$^0$))$_2$—, —O—, —S—, —S(=O)—, —SO$_2$—, —N(R$^0$)—, —P(R$^0$)—, and —P((=O)R$^0$)—; and
the groups of formulae (Ar2-2-1) and (Ar3-2-1) are optionally substituted at each free position by a group R.

18. The compound of claim 13, wherein, in formula (ArL-1), at least one group $Ar^2$ is a group of formula (Ar2-2-1b) and/or at least one group $Ar^3$ is a group of formula (Ar3-2-1b):

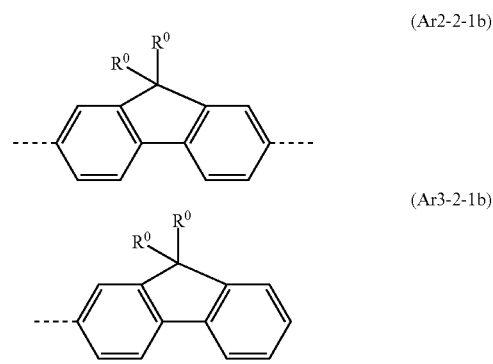

(Ar2-2-1b)

(Ar3-2-1b)

wherein
the dashed bonds in formula (Ar2-2-1b) indicate the bonding to the structure of formula (1) and to a group $Ar^2$ or $Ar^3$;
the dashed bond in formula (Ar3-2-1b) indicates the bonding to $Ar^2$; and
the groups of formulae (Ar2-2-1b) and (Ar3-2-1b) are optionally substituted at each free position by a group R.

* * * * *